United States Patent
Berthelot et al.

(10) Patent No.: US 10,898,504 B2
(45) Date of Patent: Jan. 26, 2021

(54) SUBSTITUTED NUCLEOSIDE ANALOGUES FOR USE AS PRMT5 INHIBITORS

(71) Applicant: Janssen Pharmaceutica NV, Beerse (BE)

(72) Inventors: Didier Jean-Claude Berthelot, La Neuville Chant d'Oisel (FR); Dirk Brehmer, Geel (BE); Lijs Beke, Antwerp (BE); An Boeckx, Herentals (BE); Gaston Stanislas Marcella Diels, Turnhout (BE); Ronaldus Arnodus Hendrika Joseph Gilissen, Kasterlee (BE); Edward Charles Lawson, Pipersville, PA (US); Vineet Pande, Vosselaar (BE); Marcus Cornelis Bernardus Catharina Parade, Eindhoven (NL); Wim Bert Griet Schepens, Sint Katelijne Waver (BE); Brian Christopher Shook, Holliston, MA (US); Johannes Wilhelmus John F. Thuring, Antwerp (BE); Marcel Viellevoye, Breda (NL); Weimei Sun, Lower Gwynedd, PA (US); Tongfei Wu, Boortmeerbeek (BE); Lieven Meerpoel, Beerse (BE)

(73) Assignee: Janssen Pharmaceutica NV, Beerse (BE)

(*) Notice: Subject to any disclaimer, the term of this patent is extended or adjusted under 35 U.S.C. 154(b) by 248 days.

(21) Appl. No.: 16/082,020

(22) PCT Filed: Feb. 24, 2017

(86) PCT No.: PCT/EP2017/054324
§ 371 (c)(1),
(2) Date: Sep. 4, 2018

(87) PCT Pub. No.: WO2017/153186
PCT Pub. Date: Sep. 14, 2017

(65) Prior Publication Data
US 2020/0289539 A1    Sep. 17, 2020

Related U.S. Application Data

(60) Provisional application No. 62/306,222, filed on Mar. 10, 2016.

(30) Foreign Application Priority Data

Mar. 30, 2016  (EP) .................................. 16162731

(51) Int. Cl.
| | | |
|---|---|---|
| A01N 43/04 | (2006.01) |
| A61K 31/70 | (2006.01) |
| A61K 31/7076 | (2006.01) |
| A61K 31/706 | (2006.01) |
| A61K 31/7064 | (2006.01) |

(52) U.S. Cl.
CPC ........ *A61K 31/7076* (2013.01); *A61K 31/706* (2013.01); *A61K 31/7064* (2013.01)

(58) Field of Classification Search
None
See application file for complete search history.

(56) References Cited

U.S. PATENT DOCUMENTS

| | | |
|---|---|---|
| 4,224,438 A | 9/1980 | Fauland et al. |
| 2003/0225205 A1 | 12/2003 | Epple et al. |
| 2008/0132525 A1 | 6/2008 | Wahhab et al. |
| 2014/0100184 A1 | 4/2014 | Song et al. |
| 2016/0244475 A1 | 8/2016 | Tatlock et al. |

FOREIGN PATENT DOCUMENTS

| | | |
|---|---|---|
| WO | WO 1996/040686 A1 | 12/1996 |
| WO | WO 2003/039523 A2 | 5/2003 |
| WO | WO 2003/039523 A3 | 5/2003 |

(Continued)

OTHER PUBLICATIONS

Andreu-Pérez, P. et al., "Protein Arginine Methyltransferase 5 Regulates ERL ½ Signal Transduction Amplitude and Cell Fate Through CRAF", Sci. Signal, (2011), p. ra58, vol. 4, No. 190.

Antonysamy, S., et al., "Crystal structure of the human PRMT5:MEP50 complex", Proc. Natl Acad Sci, (2012), pp. 17960-17965, vol. 109, No. 44.

Barbash, O., et al., "Abstract LB-248: Protein arginine methyltransferase 5 (PRMT5) inhibition as a therapeutic strategy in B-cell lymphoma", Cancer Research, (2015), see Abstract.

Bezzi, M., et al., "Regulation of constitutive and alternative splicing by PRMT5 reveals a role for Mdm4 pre-mRNA in sensing defects in the spliceosomal machinery", Genes & Development, (2013), pp. 1903-1916, vol. 27, No. 17.

(Continued)

*Primary Examiner* — Patrick T Lewis

(57) ABSTRACT

The present invention relates novel substituted nucleoside analogues of Formula (I)

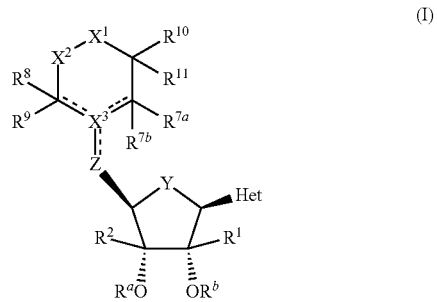

wherein the variables have the meaning defined in the claims. The compounds according to the present invention are useful as PRMT5 inhibitors. The invention further relates to pharmaceutical compositions comprising said compounds as an active ingredient as well as the use of said compounds as a medicament.

17 Claims, No Drawings

(56) References Cited

FOREIGN PATENT DOCUMENTS

| WO | WO 2003/070739 A1 | 8/2003 |
|---|---|---|
| WO | WO 2003/074083 A1 | 9/2003 |
| WO | WO 2005/065150 A2 | 7/2005 |
| WO | WO 2005/065150 A3 | 7/2005 |
| WO | WO 2006/078752 A2 | 7/2006 |
| WO | WO 2006/078752 A3 | 7/2006 |
| WO | WO 2010/039548 A2 | 4/2010 |
| WO | WO 2010/039548 A3 | 4/2010 |
| WO | WO 2011/075665 A2 | 6/2011 |
| WO | WO 2011/075665 A3 | 6/2011 |
| WO | WO 2012/075500 A2 | 6/2012 |
| WO | WO 2012/075500 A3 | 6/2012 |
| WO | WO 2012/082436 A2 | 6/2012 |
| WO | WO 2012/082436 A3 | 6/2012 |
| WO | WO 2012/083170 A1 | 6/2012 |
| WO | WO 2012/138530 A1 | 10/2012 |
| WO | WO 2013/151975 A1 | 10/2013 |
| WO | WO 2014/035140 A2 | 3/2014 |
| WO | WO 2014/035140 A3 | 3/2014 |
| WO | WO 2014/100695 A1 | 6/2014 |
| WO | WO 2014/100719 A2 | 6/2014 |
| WO | WO 2014/100730 A1 | 6/2014 |
| WO | WO 2017/100719 A3 | 6/2014 |
| WO | WO 2015/106025 A1 | 7/2015 |
| WO | WO 2015/200680 A2 | 12/2015 |
| WO | WO 2015/200680 A3 | 12/2015 |
| WO | WO 2015/200680 A8 | 12/2015 |
| WO | WO 2016/135582 A1 | 9/2016 |
| WO | WO 2017/153186 A1 | 9/2017 |
| WO | WO 2018/065365 A1 | 4/2018 |
| WO | WO 2018/154104 A1 | 8/2018 |

OTHER PUBLICATIONS

Braun, C.J., et al., "Coordinated Splicing of Regulatory Detained Introns within Oncogenic Transcripts Creates an Exploitable Vulnerability in Malignant Glioma", Cancer Cell, (2017), pp. 411-426, vol. 32, No. 4.

Bundegaard, H., "Design of Prodrugs", Elsevier, New York-Oxford, (1985), pp. 1-92.

Chan-Penebre, E., et al., "A selective inhibitor of PRMT5 with in vivo and in vitro potency in MCL models", Nature Chemical Biology, (2015), pp. 432-437, vol. 11, No. 6.

Devkota, K., et al., "Analogues of the Natural Product Sinefungin as Inhibitors of EHMT1 and EHMT2", ACS Med Chem Lett, (2014), pp. 293-297, vol. 5.

Di Lorenzo, A., et al., "Histone arginine methylation", FEBS Letters, (2011), pp. 2024-2031, vol. 585, No. 13.

Friesen, W.J., et al., "The Methylosome, a 20S Complex Containing JBP1 and plCln, Produces Dimethylarginine-Modifiied Sm Proteins", Molecular and Cellular Biology, (2001), pp. 8289-8300, vol. 21, No. 24.

Geoghegan, V., et al., "Comprehensive identification of arginine methylation in primary T cells reveals regulatory roles in cell signaling", Nature Communications, (2015), p. 6758, vol. 6.

Gu, Z., et al., "Protein arginine methyltransferase 5 is essential for growth of lung cancer cells", Biochem J., (2012), pp. 235-241, vol. 446, No. 2.

Hsu, J.M., et al., "Crosstalk between Arg 1175 methylation and Tyr 1173 phosphorylation negatively modulates EGFR-mediated ERK activation", Nature Cell Biology, (2011), pp. 174-181, vol. 13, No. 2.

Hu, H., et al., "Small Molecule Inhibitors of Protein Arginine Methyltransferase", Expert Opinion on Investigational Drugs, (2016), pp. 335-358, vol. 25, No. 3.

Jansson, M., et al., "Arginine methylation regulates the p53 response", Nature Cell Biology, (2008), pp. 1431-1439, vol. 10, No. 12.

Karkhanis, V., et al., "Versatility of PRMT5-induced methylation in growth control and development", Trends in Biochemical Sciences, (2011), pp. 633-641, vol. 36, No. 12.

Kung, P.P., et al., "Design, synthesis, and biological evaluation of novel human 5'-deoxy-5'-methylthioadenosine phosphorylase (MTAP) substrates", Bioorganic & Medicinal Chemistry Letters, (2005), pp. 2829-2833, vol. 15.

Matsubara, S., et al., "[2+1] Cycloaddition reaction of bis(iodozincio)methane with 1,2-diketones: face-to-face complex of bis(iodozincio)methane and 1,2-diketones as a reaction intermediate", Tetrahedron, (2002), pp. 8255-8262, vol. 58.

Moukha-Chafiq, O., et al., "Synthesis and General Biological Activity of a Small Adenosine-5'-(Carboxamide and Sulfanilamide) Library", Nucleosides, Nucleotides and Nucleic Acids, (2014), pp. 709-729, vol. 33, No. 11.

Pal, S., et al., "Low levels of miR-92b/96 induce PRMT5 translation and H3R3 methylation in mantle cell lymphoma", The EMBO Journal, (2007), pp. 3558-3569, vol. 26, No. 15.

Penebre, E., et al., "Identification of a First-in-Class PRMT5 Inhibitor with Potent in Vitro and in Vivo Activity in Preclinical Models of Mantle Cell Lymphoma", Blood, (2014), see Abstract.

Prasad, R.N., et al., "Modification of the 5' Position of Purine Nucleosides. 2. Synthesis and Some Cardiovascular Properties of Adenosine-5'-(N-substituted)carboxamides[1,2]", J. Med. Chem., (1980), pp. 313-319, vol. 23, No. 3.

Schmidt, R.R., et al., "Synthese 5'-modifizierter Adenosinderivate", Chemische Berichte, (1968), pp. 590-594, vol. 101, No. 2.

Shendure, J., et al., "Next-generation DNA sequencing", Nature Biotechnolgoy, (2008), pp. 1135-1145, vol. 26, No. 10.

Shilo, K., et al., "Cellular localization of protein arginine methyltransferase-5 correlates with grade of lung tumors", Diagnostic Pathology, (2013), pp. 1-9, vol. 8, No. 201.

Stopa, N., et al., "The PRMT5 arginine methyltransferase: many roles in development, cancer and beyond", Cell. Mol. Life Sci., (2015), pp. 2041-2059, vol. 72, No. 11.

Vuilhorgne, M., et al., "New Synthetic S-Adenosyl-Homocysteine Analogues with Oncostatic and Antiviral Activity".

Wang, Q., et al., "Identification of a Novel Protein Arginine Methyltransferase 5 Inhibitor in Non-small Cell Lung Cancer by Structure-Based Virtual Screening", Frontiers in Pharmacology, (2018), pp. 1-10, vol. 9, article 173.

Wang, L., et al., "Protein Arginine Methyltransrerase 5 Suppresses the Transcription of the RB Family of Tumor Suppressors in Leukemia and Lymphoma Cells", Molecular and Cellular Biology, (2008), pp. 6262-6277, vol. 28, No. 20.

Wei, T.Y.W., et al., "Methylosome protein 50 promotes androgen- and estrogen-independent tumorigenesis", Cellular Signaling, (2014), pp. 2940-2950, vol. 26.

Wei, H., et al., "PRMT5 dimethylates R30 of the p65 subunit to activate NF-κB", Proc Natl Aced Sci USA, (2013), pp. 13516-13521, vol. 110, No. 33.

Zhao, Q., et al., "PRMT5-mediated methylation of histone H4R3 recruits DNMT3A, coupling histone and DNA methylation in gene silencing", Nat Struct Mol Biol, (2009), pp. 304-311, vol. 16, No. 3.

Deady, L.W., "Ring Nitrogen Oxidation of Amino Substituted Nitrogen Heterocycles with m-Chloroperbenzoic Acid", Synthetic Communications, (1977), pp. 509-514, vol. 7, No. 8.

March, J., "Advanced Organic Chemistry—Reactions, Mechanisms, and Structure", John Wiley & Sons, Inc., (2002), 4th Edition, A Wiley-Interscience Publication, see Table of Contents.

Stahl, P.H., et al., "Handbook of Pharmaceutical Salts: Properties, Selection, and Use", Journal of Medicinal Chemistry, Book Reviews, (2003), pp. 1277-1278, vol. 46, No. 7.

International Search Report PCT/EP2017/054324 dated May 2, 2017.

International Search Report PCT/EP2016/070097 dated Oct. 12, 2016.

International Search Report PCT/EP2017/074983 dated Nov. 16, 2017.

International Search Report PCT/EP2018/054644 dated May 3, 2018.

US 10,898,504 B2

SUBSTITUTED NUCLEOSIDE ANALOGUES FOR USE AS PRMT5 INHIBITORS

CROSS REFERENCE TO RELATED APPLICATIONS

This application is a national stage of PCT Application No. PCT/EP2017/054324, filed Feb. 24, 2017, which claims priority for U.S. Provisional Patent Application No. 62/306,222, filed Mar. 10, 2016 and EPO Patent Application No. 16162731.0, filed Mar. 30, 2016, all of which are hereby incorporated by reference in their entirety.

FIELD OF THE INVENTION

The present invention relates to novel substituted nucleoside analogues useful as PRMT5 inhibitors. The invention further relates to pharmaceutical compositions comprising said compounds as an active ingredient as well as the use of said compounds as a medicament.

BACKGROUND OF THE INVENTION

PRMT5, also described as Hsl7, Jbp1, Skb1, Capsuleen or Dart5, is one of the major methyltransferases responsible for mono- and symmetric dimethylation of arginines. Post-translational arginine methylation on histones and non-histone proteins seems to be crucial for a variety of biological processes, like genome organisation, transcription, differentiation, spliceosome function, signal transduction and regulation of cell-cycle progression, stem cells and T-cell fate [Stopa, N. et al., Cell Mol Life Sci, 2015.72(11): p. 2041-59] [Geoghegan, V. et al., Nat Commun, 2015. 6: p. 6758]. Metazoan PRMT5 forms a functional complex with the methylosome protein 50 (MEP50) also named as Wdr77, androgen receptor coactivator p44 and Valois. Both, elevated PRMT5-MEP50 protein level and cytoplasmic accumulation are implicated in cancer tumorigenesis and have recently been correlated with poor clinical outcome [Shilo, K. et al., Diagn Pathol, 2013. 8: p. 201]. Cellular rescue experiments that addressed both the catalytic and scaffold function of the PRMT5-MEP50 complex, beside comprehensive enzymological studies have substantiate the oncogenic link between protein level, localisation and enzymatic function [Gu, Z. et al., Biochem J, 2012.446(2): p. 235-41] [Di Lorenzo, A. et. al., FEBS Lett, 2011.585(13): p. 2024-31] [Chan-Penebre, E. et al., Nat Chem Biol, 2015. 11(6): p. 432-7]. This correlation turns PRMT5 into an essential small molecule drug target against cancer and other diseases [Stopa, N. et al., Cell Mol Life Sci, 2015. 72(11): p. 2041-59].

PRMT5 is a member of the type II PRMT subfamily that utilises S-adenosylmethionine (SAM) to generate symmetric dimethylated arginine on histones and non-histone protein substrates and S-adenosylhomocysteine (SAH). The crystal structure of the human hetereo-octameric complex (PRMT5)$_4$(MEP50)$_4$ co-crystalised with SAH and a histone H4 peptide substrate illustrated the mechanism of methylation and substrate recognition [Antonysamy, S. et al., Proc Natl Acad Sci USA, 2012. 109(44): p. 17960-5]. The regulation of PRMT5 activity occurs through a vast number of different binding partners, post-translational modification cross talk, miRNAs and subcellular localisation.

Methylation of histones H2A and H4 on Arg3 and histone H3 on Arg8 regulate chromatin organisation for specific repression of gene transcripts that are involved in differentiation, transformation, cell-cycle progression and tumour suppression [Karkhanis, V. et al., Trends Biochem Sci, 2011. 36(12): p. 633-41]. Furthermore, PRMT5-mediated methylation of histone H4 on Arg3 might recruit the DNA-methyltransferase DNMT3A to couple histone and DNA methylation for long-term gene silencing [Zhao, Q. et al., Nat Struct Mol Biol, 2009.16(3): p. 304-11].

Non-histone methylation can occur either in the cytoplasm or nucleus dependent on the cellular localisation of PRMT5. The methylation of the Sm proteins D1 and D3, which are required for the assembly of the nuclear splicesome, takes place in the cytoplasm as part of the PRMT5 containing "methylosome" [Friesen, W. J. et al., Mol Cell Biol, 2001. 21(24): p. 8289-300]. Further evidence for PRMT5 involved in splicing has been provided by the conditional PRMT5 knockout in mouse neural stem cells. Cells that lack PRMT5 showed a selective retention of introns and skipping of exons with weak 5' donor sites [Bezzi, M. et al., Genes Dev, 2013.27(17): p. 1903-16].

In addition to a role in splicing, PRMT5 influences key pathways involved in cell fate and homeostasis by direct methylation of key signalling nodules like p53 [Jansson, M. et al., Nat Cell Biol, 2008. 10(12): p. 1431-9], EGFR [Hsu, J. M. et al., Nat Cell Biol, 2011. 13(2): p. 174-81], CRAF [Andreu-Perez, P. et al., Sci Signal, 2011. 4(190): p. raS8], PI3K/AKT [Wei, T. Y. et al., Cell Signal, 2014. 26(12): p. 2940-50], NFκB [Wei, H. et al., Proc Natl Acad Sci USA, 2013.110(33): p. 13516-21].

Since PRMT5 is one of the major sym-Arg methyltransferases and involved in a multitude of cellular processes, an increased protein expression appears to be an important factor in its tumourigenicity. Interestingly, the translation of PRMT5 in mantle cell lymphoma (MCL) seems to be regulated by miRNAs. Although MCL cells show less mRNA and a slower transcription rate of PRMT5 than normal B lymphocytes, the PRMT5 level and the methylation of H3R8 and H4R3 are significantly increased [Pal, S. et al., EMBO J, 2007. 26(15): p. 3558-69]. Re-expression of miRNAs that binds the 3'UTR region of PRMT5 decreases PRMT5 protein level [Wang, L. et al., Mol Cell Biol, 2008.28(20): p. 6262-77]. Strikingly, a prmt5 antisense RNA has been found within the human prmt5 gene that supports the hypothesis of a specific translational regulation rather than high mRNA expression level [Stopa, N. et al., Cell Mol Life Sci, 2015. 72(11): p. 2041-59].

Although PRMT5 is considered as a clinical relevant target, very few selective PRMT5 inhibitors have been published, yet. Very recently, a novel sub-nanomolar potent PRMT5 inhibitor (EPZ015666) with anti-tumour activity in multiple MCL xenograft models has been described to be the first chemical probe suitable for further validation of PRMT5's biology and role in cancer [Chan-Penebre, E. et al., Nat Chem Biol, 2015. 11(6): p. 432-7].

Further development of specific small molecule inhibitors of PRMT5 may lead to novel chemotherapeutic approaches for cancer.

WO2014100695A1 discloses compounds useful for inhibiting PRMT5 activity; Methods of using the compounds for treating PRMT5-mediated disorders are also described.

WO2014100730A1 discloses PRMT5 inhibitors containing a dihydro- or tetrahydroisoquinoline and uses thereof.

Devkota, K. et al., ACS Med Chem Lett, 2014.5: p. 293-297, describes the synthesis of a series of analogues of the natural product sinefungin and the ability of these analogues to inhibit EHMT1 and EHMT2.

WO2003070739 discloses partial and full agonists of A1 adenosine receptors, their preparation, and their therapeutic use.

WO2012082436 discloses compounds and compositions as modulators of histone methyltransferases, and for treating diseases influenced by modulation of histone methyltransferase activity.

WO2012075500 discloses 7-deazapurine modulators of histone methyltransferase, and methods of use thereof.

WO2016135582 and US20160244475 describe substituted nucleoside derivatives useful as anticancer agents.

WO2014100719 discloses PRMT5 inhibitors and uses thereof.

WO03074083 discloses combination therapies that selectively kill methylthioadenosine phosphorylase deficient cells. Analogs of MTA are described herein as anti-toxicity agents.

Kung, P.-P. et al., Bioorg Med Chem Lett, 2005. 15: p. 2829-2833, describes the design, synthesis, and biological evaluation of novel human 5'-deoxy-5'-methylthioadenosine phosphorylase (MTAP) substrates.

There is thus a strong need for novel PRMT5 inhibitors thereby opening new avenues for the treatment or prevention of cancer, such as e.g. mantle cell lymphoma. It is accordingly an object of the present invention to provide such compounds.

SUMMARY OF THE INVENTION

It has been found that the compounds of the present invention are useful as PRMT5 inhibitors. The compounds according to the invention and compositions thereof, may be useful for the treatment or prevention, in particular for the treatment, of diseases such as a blood disorder, metabolic disorders, autoimmune disorders, cancer, inflammatory diseases, cardiovascular diseases, neurodegenerative diseases, pancreatitis, multiorgan failure, kidney diseases, platelet aggregation, sperm motility, transplantation rejection, graft rejection, lung injuries, and the like.

The present invention concerns novel compounds of Formula (I):

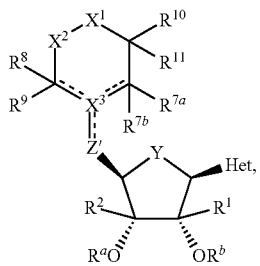

wherein
$R^1$ represents hydrogen or $CH_3$;
$R^2$ represents hydrogen;
$R^a$ represents hydrogen or $—C(=O)—C_{1-4}$alkyl;
$R^b$ represents hydrogen or $—C(=O)—C_{1-4}$alkyl;
Y represents $—O—$, $—CH_2—$ or $—CF_2—$;
$R^{7a}$ represents hydrogen;
$R^{7b}$ represents hydrogen, or $C_{1-4}$alkyl optionally substituted with one or more halo atoms;
$X^1$ represents a covalent bond or $—O—$;

$X^2$ represents a covalent bond, $—CH_2—$, $—CF_2—$, $—CH_2CH_2—$, $—CF_2CH_2—$, or $—CH_2CF_2—$; provided that $X^2$ represents a covalent bond, $—CH_2—$ or $—CF_2—$, when $X^1$ represents $—O—$;
$X^3$ represents N or CH; or in case one of the dotted lines represents an additional bond,
$X^3$ represents C;
$R^8$ and $R^{10}$ each independently are selected from the group consisting of hydrogen; halo; and $C_{1-6}$alkyl optionally substituted with one or more halo atoms;
$R^9$ and $R^{11}$ each independently are selected from the group consisting of hydrogen; halo; $—NH_2$; and $C_{1-6}$alkyl optionally substituted with one $—NR^{9a}R^{9b}$;
or $R^8$ and $R^9$ are linked together to form together with the common carbon atom to which they are attached a 4-, 5-, 6- or 7-membered saturated heterocyclyl, containing one or two N-atoms and optionally one oxygen atom; wherein said 4-, 5-, 6- or 7-membered saturated heterocyclyl is optionally substituted on one or more ring carbon atoms with one or more substituents each independently selected from the group consisting of halo, and $C_{1-6}$alkyl optionally substituted with one or more halo atoms; and wherein said 4-, 5-, 6- or 7-membered saturated heterocyclyl is optionally substituted on one or two ring N-atoms with a substituent selected from the group consisting of $C_{1-6}$alkyl; $Het^{1a}$; $C_{3-6}$cycloalkyl; $—C_{1-4}$alkyl-$C(=O)—NR^{5a}R^{5b}$; $C_{1-4}$alkyl substituted with one or more halo atoms; and $C_{1-4}$alkyl substituted with one substituent selected from the group consisting of $—OC_{1-4}$alkyl, cyano, $C_{3-6}$cycloalkyl, $Ar^{1a}$, $—O—Ar^{1a}$, $Het^{2}$ and $—O-Het^{2c}$;
or $R^{10}$ and $R^{11}$ are linked together to form together with the common carbon atom to which they are attached a 4-, 5-, 6- or 7-membered saturated heterocyclyl, containing one or two N-atoms and optionally one oxygen atom; wherein said 4-, 5-, 6- or 7-membered saturated heterocyclyl is optionally substituted on one or more ring carbon atoms with one or more substituents each independently selected from the group consisting of halo, and $C_{1-6}$alkyl optionally substituted with one or more halo atoms; and wherein said 4-, 5-, 6- or 7-membered saturated heterocyclyl is optionally substituted on one or two ring N-atoms with a substituent selected from the group consisting of $C_{1-6}$alkyl; $Het^{1b}$; $C_{3-6}$cycloalkyl; $—C_{1-4}$-alkyl-$C(=O)—NR^{6a}R^{6b}$; $C_{1-4}$alkyl substituted with one or more halo atoms; and $C_{1-4}$alkyl substituted with one substituent selected from the group consisting of $—OC_{1-4}$alkyl, cyano, $C_{3-6}$cycloalkyl, $Ar^{1b}$, $—O—Ar^{1b}$, $Het^{2b}$ and $—O-Het^{2d}$;
Z represents $—CH_2—$, $—C(=O)—$, or $—CH(C_{1-4}$alkyl)-;
and in case $X^3$ represents C, Z can also represent $=CH—$;
the dotted lines attached to $X^3$ are optional bonds that may be present when $X^3$ represents a carbon atom, provided that maximum one of the dotted lines represents an optional bond;
in case one of the dotted lines attached to $X^3$ represents an additional bond, $X^3$ represents C, and (i) $R^{7a}$ is absent or (ii) $R^8$ is absent or (iii) Z represents $=CH—$;
$R^{9a}$ and $R^{9b}$ each independently are selected from the group consisting of hydrogen and $C_{1-4}$alkyl; or $R^{9a}$ and $R^{9b}$ are linked together to form together with the common nitrogen atom to which they are attached a 4-, 5-, 6- or 7-membered saturated heterocyclyl which optionally contains one oxygen atom;
$R^{5a}$ and $R^{5b}$ each independently are selected from the group consisting of hydrogen and $C_{1-4}$alkyl;
$Het^{1a}$ and $Het^{1b}$ are attached to the remainder of the molecule of Formula (I) through any available ring carbon atom;

Het$^{1a}$ and Het$^{1b}$ each independently represent a 4-, 5-, 6- or 7-membered saturated heterocyclyl, containing one or two heteroatoms each independently selected from O, S, S(=O)$_p$ and N;

Ar$^{1a}$ and Ar$^{1b}$ each independently represent phenyl optionally substituted with one or more substituents each independently selected from the group consisting of halo; cyano; and C$_{1-4}$alkyl optionally substituted with one or more halo atoms;

Het$^{2a}$ and Het$^{2b}$ each independently represent a 4-, 5-, 6- or 7-membered monocyclic aromatic or non-aromatic heterocyclyl containing at least one heteroatom each independently selected from O, S, S(=O)$_p$ and N; or a fused 8-, 9-, 10- or 11-membered bicyclic aromatic or non-aromatic heterocyclyl containing at least one heteroatom each independently selected from O, S, S(=O)$_p$ and N; said monocyclic heterocyclyl or said fused bicyclic heterocyclyl optionally being substituted with one or more substituents each independently selected from the group consisting of halo, cyano, and C$_{1-4}$alkyl optionally substituted with one or more halo atoms;

Het$^{2c}$ and Het$^{2d}$ are attached to the remainder of the molecule of Formula (I) through any available ring carbon atom;

Het$^{2c}$ and Het$^{2d}$ each independently represent a 4-, 5-, 6- or 7-membered monocyclic aromatic or non-aromatic heterocyclyl containing at least one heteroatom each independently selected from O, S, S(=O)$_p$ and N; or a fused 8-, 9-, 10- or 11-membered bicyclic aromatic or non-aromatic heterocyclyl containing at least one heteroatom each independently selected from O, S, S(=O)$_p$ and N; said monocyclic heterocyclyl or said fused bicyclic heterocyclyl optionally being substituted with one or more substituents each independently selected from the group consisting of halo, cyano, and C$_{1-4}$alkyl optionally substituted with one or more halo atoms;

R$^{6a}$ and R$^{6b}$ each independently are selected from the group consisting of hydrogen and C$_{1-4}$alkyl;

p represents 1 or 2;

Het represents a bicyclic aromatic heterocyclic ring system selected from the group consisting of (a-1), (a-2), (a-3) and (a-4):

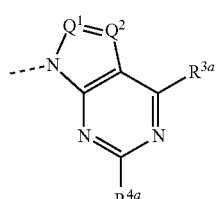
(a-1)

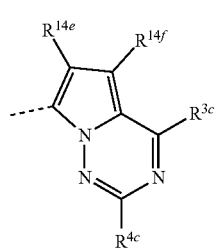
(a-2)

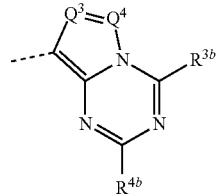
(a-3)

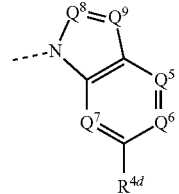
(a-4)

R$^{3a}$, R$^{3b}$, R$^{3c}$ and R$^{3d}$ each independently are selected from the group consisting of hydrogen, halo, —NR$^{12a}$R$^{12b}$, C$_{1-4}$alkyl, and —C$_{1-4}$alkyl;

R$^{12a}$ and R$^{12b}$ each independently are selected from the group consisting of hydrogen; C$_{3-6}$cycloalkyl; C$_{1-4}$alkyl; and C$_{1-4}$alkyl substituted with one phenyl which is optionally substituted with one or more substituents selected from the group consisting of halo, cyano, —OC$_{1-4}$alkyl, —OH, and C$_{1-4}$alkyl optionally substituted with one or more halo atoms;

R$^{4a}$, R$^{4b}$, R$^{4c}$, R$^{4d}$, R$^{4e}$ and R$^{4f}$ each independently are selected from the group consisting of hydrogen, halo, —NR$^{13a}$R$^{13b}$, and C$_{1-4}$alkyl;

R$^{13a}$ and R$^{13b}$ each independently are selected from the group consisting of hydrogen and C$_{1-4}$alkyl;

Q$^1$ represents N or CR$^{14a}$;
Q$^2$ represents N or CR$^{14b}$;
Q$^3$ represents N or CR$^{14c}$;
Q$^4$ represents N or CR$^{14d}$;
provided that maximum one of Q$^3$ and Q$^4$ represents N;
Q$^8$ represents N or CR$^{14g}$;
Q$^9$ represents N or CR$^{14h}$;
Q$^{10}$ represents N or CR$^{14i}$;
Q$^{11}$ represents N or CR$^{14j}$;
Q$^5$ represents CR$^{3d}$; Q$^6$ represents N; and Q$^7$ represents CR$^{4f}$; or
Q$^5$ represents CR$^{3d}$; Q$^6$ represents CR$^{4e}$; and Q$^7$ represents N; or
Q$^5$ represents N; Q$^6$ represents CR$^{4e}$; and Q$^7$ represents CR$^{4f}$; or
Q$^5$ represents N; Q$^6$ represents CR$^{4e}$; and Q$^7$ represents N; or
Q$^5$ represents N; Q$^6$ represents N; and Q$^7$ represents CR$^{4f}$; or
Q$^5$ represents N; Q$^6$ represents N; and Q$^7$ represents N;
R$^{14a}$, R$^{14b}$, R$^{14c}$, R$^{14d}$, R$^{14e}$, R$^{14f}$, R$^{14g}$, R$^{14h}$, R$^{14i}$, and R$^{14j}$ each independently are selected from the group consisting of hydrogen; halogen; C$_{1-4}$alkyl; NR$^{15a}$R$^{15b}$; and C$_{1-4}$alkyl substituted with one or more halo atoms;

R$^{15a}$ and R$^{15b}$ each independently are selected from the group consisting of hydrogen and C$_{1-4}$alkyl;

provided that R$^{10}$ and R$^{11}$ may not be linked together when R$^8$ and R$^9$ are linked together;

and wherein at least one of R$^8$, R$^9$, R$^{10}$ and R$^{11}$ contains a nitrogen atom;

and pharmaceutically acceptable addition salts, and solvates thereof.

The present invention also concerns methods for the preparation of compounds of the present invention and pharmaceutical compositions comprising them.

The compounds of the present invention were found to inhibit PRMT5 per se or can undergo metabolism to a (more) active form in vivo (prodrugs), and therefore may be useful in the treatment or prevention, in particular in the treatment, of diseases such as a blood disorder, metabolic disorders, autoimmune disorders, cancer, inflammatory diseases, cardiovascular diseases, neurodegenerative diseases, pancreatitis, multiorgan failure, kidney diseases, platelet aggregation, sperm motility, transplantation rejection, graft rejection, lung injuries, and the like.

In view of the aforementioned pharmacology of the compounds of Formula (I) and pharmaceutically acceptable addition salts, and solvates thereof, it follows that they may be suitable for use as a medicament.

In particular the compounds of Formula (I) and pharmaceutically acceptable addition salts, and solvates thereof, may be suitable in the treatment or prevention, in particular in the treatment, of any one of the diseases or conditions mentioned hereinbefore or hereinafter, in particular cancer.

The present invention also concerns the use of compounds of Formula (I) and pharmaceutically acceptable addition salts, and solvates thereof, for the manufacture of a medicament for the inhibition of PRMT5, for the treatment or prevention of any one of the diseases or conditions mentioned hereinbefore or hereinafter, in particular cancer.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

DETAILED DESCRIPTION

When describing the compounds of the invention, the terms used are to be construed in accordance with the following definitions, unless a context dictates otherwise.

When any variable occurs more than one time in any constituent or in any formula (e.g. Formula (I)), its definition in each occurrence is independent of its definition at every other occurrence.

Whenever the term "substituted" is used in the present invention, it is meant, unless otherwise is indicated or is clear from the context, to indicate that one or more hydrogens, in particular from 1 to 3 hydrogens, preferably 1 or 2 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

When two or more substituents are present on a moiety they may, unless otherwise is indicated or is clear from the context, replace hydrogens on the same atom or they may replace hydrogen atoms on different atoms in the moiety.

The expression "at least one" in particular means "one, two or three", more in particular "one or two", even more in particular "one".

$Het^{2a}$ and $Het^{2b}$ may be attached to the remainder of the molecule of formula (I) through any available ring carbon or heteroatom as appropriate, if not otherwise specified. Thus, for example, when the heterocyclyl is imidazolyl, it may be 1-imidazolyl, 2-imidazolyl, 4-imidazolyl and the like.

It will be clear for the skilled person that, unless otherwise is indicated or is clear from the context, a substituent on a 4-, 5-, 6- or 7-membered monocyclic aromatic or non-aromatic heterocyclyl containing at least one heteroatom each independently selected from O, S, $S(=O)_p$ and N (as in the definition of $Het^{2a}$, $Het^{2b}$, $Het^{2c}$ and $Het^{2d}$), may replace any hydrogen atom on a ring carbon atom or where possible on a ring nitrogen atom (in which case a hydrogen on a nitrogen atom may be replaced by a substituent).

The prefix "$C_{x-y}$" (where x and y are integers) as used herein refers to the number of carbon atoms in a given group. Thus, a $C_{1-4}$alkyl group contains from 1 to 4 carbon atoms, a $C_{1-3}$alkyl group contains from 1 to 3 carbon atoms and so on.

The term "halo" as a group or part of a group is generic for fluoro, chloro, bromo, iodo unless otherwise is indicated or is clear from the context.

The term "$C_{1-4}$alkyl" as a group or part of a group refers to a hydrocarbyl radical of Formula $C_nH_{2n+1}$ wherein n is a number ranging from 1 to 4. $C_{1-4}$alkyl groups comprise from 1 to 4 carbon atoms, preferably from 1 to 3 carbon atoms, more preferably 1 to 2 carbon atoms. $C_{1-4}$alkyl groups may be linear or branched and may be substituted as indicated herein. When a subscript is used herein following a carbon atom, the subscript refers to the number of carbon atoms that the named group may contain.

$C_{1-4}$alkyl includes all linear, or branched alkyl groups with between 1 and 4 carbon atoms, and thus includes methyl, ethyl, n-propyl, i-propyl, 2-methyl-ethyl, butyl and its isomers (e.g. n-butyl, isobutyl and tert-butyl), and the like.

Similar, the term '$C_{1-6}$alkyl' as used herein as a group or part of a group represents a straight or branched chain saturated hydrocarbon radical having from 1 to 6 carbon atoms such as the groups defined for $C_{1-4}$alkyl and n-pentyl, n-hexyl, 2-methylbutyl and the like.

In case Z is =CH—, it is intended that the double bond is attached to $X^3$ being C.

Whenever substituents are represented by chemical structure, "---" represents the bond of attachment to the remainder of the molecule of Formula (I). Lines drawn from substituents into ring systems indicate that the bond may be attached to any of the suitable ring atoms.

Non-limiting examples of $Het^{1a}$ and $Het^{1b}$ are carbon-linked oxetanyl (e.g. 3-oxetanyl), piperidinyl, tetrahydrofuranyl, pyrrolidinyl, thiolanyl, piperazinyl, tetrahydropyranyl and the like.

Non-limiting examples of $Het^{2c}$ and $Het^{2d}$ are carbon-linked oxetanyl (e.g. 3-oxetanyl), piperidinyl, tetrahydrofuranyl, pyrrolidinyl, thiolanyl, piperazinyl, tetrahydropyranyl, pyridinyl, furanyl, pyrizazinyl, thiazolyl, benzimidazolyl and the like; each of which may optionally be substituted, where possible, on carbon and/or nitrogen atoms according to any of the embodiments.

Non-limiting examples of $Het^{2a}$ and $Het^{2b}$ are carbon- or nitrogen-linked oxetanyl, piperidinyl, tetrahydrofuranyl, pyrrolidinyl, thiolanyl, piperazinyl, tetrahydropyranyl, pyridinyl, furanyl, pyrizazinyl, thiazolyl, benzimidazolyl and the like; each of which may optionally be substituted, where possible, on carbon and/or nitrogen atoms according to any of the embodiments.

Non-limiting examples of $R^8$ and $R^9$, or $R^{10}$ and $R^{11}$, taken together to form a 4-, 5-, 6- or 7-membered saturated heterocyclyl, are piperidinyl, azetidinyl, pyrrolidinyl, morpholinyl, hexahydro-1H-azepinyl; each of which may optionally be substituted, where possible, on carbon and/or nitrogen atoms according to any of the embodiments.

The term "subject" as used herein, refers to an animal, preferably a mammal (e.g. cat, dog, primate or human), more preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medicinal doctor or other clinician, which includes alleviation or reversal of the symptoms of the disease or disorder being treated.

The term "composition" is intended to encompass a product comprising the specified ingredients in the specified amounts, as well as any product which results, directly or indirectly, from combinations of the specified ingredients in the specified amounts.

The term "treatment", as used herein, is intended to refer to all processes wherein there may be a slowing, interrupting, arresting or stopping of the progression of a disease, but does not necessarily indicate a total elimination of all symptoms.

The term "compounds of the (present) invention" as used herein, is meant to include the compounds of Formula (I) and pharmaceutically acceptable addition salts, and solvates thereof.

Some of the compounds of Formula (I) may also exist in their tautomeric form. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerisations. Valence tautomers include interconversions by reorganisation of some of the bonding electrons.

Such forms in so far as they may exist, although not explicitly indicated in the above Formula (I), are intended to be included within the scope of the present invention.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers. Where the stereochemistry of any particular chiral atom is not specified in the structures shown herein, then all stereoisomers are contemplated and included as the compounds of the invention, either as a pure stereoisomer or as a mixture of two or more stereoisomers.

Hereinbefore and hereinafter, the term "compound of Formula (I)" is meant to include the stereoisomers thereof and the tautomeric forms thereof. However where stereochemistry, as mentioned in the previous paragraph, is specified by bonds which are shown as solid wedged or hashed wedged bonds, or are otherwise indicated as having a particular configuration (e.g. R, S), then that stereoisomer is so specified and defined. It will be clear this also applies to subgroups of Formula (I).

It follows that a single compound may, where possible, exist in both stereoisomeric and tautomeric form.

The terms "stereoisomers", "stereoisomeric forms" or "stereochemically isomeric forms" hereinbefore or hereinafter are used interchangeably.

Enantiomers are stereoisomers that are non-superimposable mirror images of each other. A 1:1 mixture of a pair of enantiomers is a racemate or racemic mixture.

Atropisomers (or atropoisomers) are stereoisomers which have a particular spatial configuration, resulting from a restricted rotation about a single bond, due to large steric hindrance. All atropisomeric forms of the compounds of Formula (I) are intended to be included within the scope of the present invention.

Diastereomers (or diastereoisomers) are stereoisomers that are not enantiomers, i.e. they are not related as mirror images.

Anomers are diastereoisomers of cyclic forms of sugars or similar molecules differing in the configuration at the anomeric carbon (C-1 atom of an aldose or the $C_{1-2}$ atom of a 2-ketose). The cyclic forms of carbohydrates can exist in two forms, α- and β-based on the position of the substituent at the anomeric center. Anomers are designated a if the configuration at the anomeric carbon is the same as that at the reference asymmetric carbon in a Fischer projection. If the configuration differs the anomer is designated β.

For example, α-D-glucopyranose and β-D-glucopyranose, the two cyclic forms of glucose, are anomers.

If a compound contains a double bond, the substituents may be in the E or the Z configuration. Substituents on bivalent cyclic (partially) saturated radicals may have either the cis- or trans-configuration; for example if a compound contains a disubstituted cycloalkyl group, the substituents may be in the cis or trans configuration.

Therefore, the invention includes enantiomers, atropisomers, diastereomers, racemates, E isomers, Z isomers, cis isomers, trans isomers and mixtures thereof, whenever chemically possible.

The meaning of all those terms, i.e. enantiomers, atropisomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of Formula (I) is for instance specified as (R), this means that the compound is substantially free of the (S) isomer, when a compound of Formula (I) is for instance specified as E, this means that the compound is substantially free of the Z isomer, when a compound of Formula (I) is for instance specified as cis, this means that the compound is substantially free of the trans isomer.

For therapeutic use, salts of the compounds of Formula (I) and solvates thereof, are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

Pharmaceutically-acceptable salts include acid addition salts and base addition salts. Such salts may be formed by conventional means, for example by reaction of a free acid or a free base form with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

The pharmaceutically acceptable addition salts as mentioned hereinabove or hereinafter are meant to comprise the therapeutically active non-toxic acid and base addition salt forms which the compounds of Formula (I) and solvates thereof, are able to form.

Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I) and solvates thereof containing an acidic proton may also be converted into their non-toxic metal or amine addition salt forms by treatment with appropriate organic and inorganic bases.

Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

For the purposes of this invention prodrugs are also included within the scope of the invention.

The term "prodrug" of a relevant compound of the invention includes any compound that, following oral or parenteral administration, in particular oral administration, is metabolised in vivo to a form that compound in an experimentally-detectable amount, and within a predetermined time (e.g. within a dosing interval of between 6 and 24 hours (i.e. once to four times daily)). For the avoidance of doubt, the term "parenteral" administration includes all forms of administration other than oral administration, in particular intravenous (IV), intramuscular (IM), and subcutaneous (SC) injection.

Prodrugs may be prepared by modifying functional groups present on the compound in such a way that the modifications are cleaved, in vivo when such prodrug is administered to a mammalian subject. The modifications typically are achieved by synthesising the parent compound with a prodrug substituent. In general, prodrugs include compounds of the invention wherein a hydroxyl, amino, sulfhydryl, carboxy or carbonyl group in a compound of the invention is bonded to any group that may be cleaved in vivo to regenerate the free hydroxyl, amino, sulfhydryl, carboxy or carbonyl group, respectively; in particular wherein a hydroxyl group in a compound of the invention is bonded to any group (e.g. —C(=O)—$C_{1-4}$alkyl) that may be cleaved in vivo to regenerate the free hydroxyl. Within the context of this invention, prodrugs in particular are compounds of Formula (I) or subgroups thereof wherein R and/or R represent —C(=O)—$C_{1-4}$alkyl.

Examples of prodrugs include, but are not limited to, esters and carbamates of hydroxy functional groups, esters groups of carboxyl functional groups, N-acyl derivatives and N-Mannich bases. General information on prodrugs may be found e.g. in Bundegaard, H. "Design of Prodrugs" p. 1-92, Elesevier, New York-Oxford (1985).

The term solvate comprises the hydrates and solvent addition forms which the compounds of Formula (I) are able to form, as well as pharmaceutically acceptable addition salts thereof. Examples of such forms are e.g. hydrates, alcoholates and the like.

The compounds of the invention as prepared in the processes described below may be synthesized in the form of mixtures of enantiomers, in particular racemic mixtures of enantiomers, that can be separated from one another following art-known resolution procedures. A manner of separating the enantiomeric forms of the compounds of Formula (I), and pharmaceutically acceptable addition salts, and solvates thereof, involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

The present invention also embraces isotopically-labeled compounds of the present invention which are identical to those recited herein, but for the fact that one or more atoms are replaced by an atom having an atomic mass or mass number different from the atomic mass or mass number usually found in nature (or the most abundant one found in nature).

All isotopes and isotopic mixtures of any particular atom or element as specified herein are contemplated within the scope of the compounds of the invention, either naturally occurring or synthetically produced, either with natural abundance or in an isotopically enriched form. Exemplary isotopes that can be incorporated into compounds of the invention include isotopes of hydrogen, carbon, nitrogen, oxygen, phosphorus, sulfur, fluorine, chlorine and iodine, such as $^2H$, $^3H$, $^{11}C$, $^{13}C$, $^{14}C$, $^{13}N$, $^{15}O$, $^{17}O$, $^{18}O$, $^{32}P$, $^{33}P$, $^{35}S$, $^{18}F$, $^{36}Cl$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^2H$, $^3H$, $^{11}C$ and $^{18}F$. More preferably, the radioactive isotope is $^2H$. In particular, deuterated compounds are intended to be included within the scope of the present invention.

Certain isotopically-labeled compounds of the present invention (e.g., those labeled with $^3H$ and $^{14}C$) are useful in compound and for substrate tissue distribution assays. Tritiated ($^3H$) and carbon-14 ($^{14}C$) isotopes are useful for their ease of preparation and detectability. Further, substitution with heavier isotopes such as deuterium (i.e., $^2H$ may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy.

In an embodiment, the present invention concerns novel compounds of Formula (I), wherein
$R^1$ represents hydrogen or $CH_3$;
$R^2$ represents hydrogen;
$R^{11}$ represents hydrogen or —C(=O)—$C_{1-4}$alkyl;
$R^1$ represents hydrogen or —C(=O)—$C_{1-4}$alkyl;
Y represents —O—, —$CH_2$— or —$CF_2$—;
$R^{7a}$ represents hydrogen;
$R^{7b}$ represents hydrogen, or $C_{1-4}$alkyl optionally substituted with one or more halo atoms;
$X^1$ represents a covalent bond or —O—;
$X^2$ represents a covalent bond, —$CH_2$—, —$CF_2$—, —$CH_2CH_2$—, —$CF_2CH_2$—, or —$CH_2CF_2$—;
provided that $X^2$ represents a covalent bond, —$CH_2$— or —$CF_2$—, when $X^1$ represents —O—;
$X^3$ represents N or CH; or in case one of the dotted lines represents an additional bond, $X^3$ represents C;
$R^8$ and $R^9$ each independently are selected from the group consisting of hydrogen; halo; and $C_{1-6}$alkyl optionally substituted with one or more halo atoms;
$R^9$ and $R^{11}$ each independently are selected from the group consisting of hydrogen; halo; —$NH_2$; and $C_{1-4}$alkyl optionally substituted with one —$NR^{9a}R^{9b}$;
or $R^8$ and $R^9$ are linked together to form together with the common carbon atom to which they are attached a 4-, 5-, 6- or 7-membered saturated heterocyclyl, containing one or two N-atoms and optionally one oxygen atom; wherein said 4-, 5-, 6- or 7-membered saturated heterocyclyl is optionally substituted on one or more ring carbon atoms with one or more substituents each independently selected from the group consisting of halo, and $C_{1-6}$alkyl optionally substituted with one or more halo atoms; and wherein said 4-, 5-, 6- or 7-membered saturated heterocyclyl is optionally substituted on one or two ring N-atoms with a substituent selected from the group consisting of $C_{1-6}$alkyl; $Het^{1a}$; $C_{3-6}$cycloalkyl; —$C_{1-4}$alkyl-C(=O)—$NR^{5a}R^{5b}$; $C_{1-4}$alkyl substituted with one or more halo atoms; and $C_{1-4}$alkyl substituted with one substituent selected from the group consisting of —$OC_{1-4}$alkyl, cyano, $C_{3-6}$cycloalkyl, $Ar^{1a}$, —O—$Ar^{1a}$, $Het^2$a and —O-$Het^{2c}$;
or $R^{10}$ and $R^{11}$ are linked together to form together with the common carbon atom to which they are attached a 4-, 5-, 6- or 7-membered saturated heterocyclyl, containing one or two N-atoms and optionally one oxygen atom; wherein said 4-, 5-, 6- or 7-membered saturated heterocyclyl is optionally substituted on one or more ring carbon atoms with one or more substituents each independently selected from the group consisting of halo, and $C_{1-6}$alkyl optionally substituted with one or more halo atoms; and wherein said 4-, 5-, 6- or 7-membered saturated heterocyclyl is optionally substituted on one or two ring N-atoms with a substituent selected from the group consisting of $C_{1-6}$alkyl; $Het^{1b}$; $C_{3-6}$cycloalkyl; —$C_{1-4}$alkyl-C(=O)—$NR^{6a}R^{6b}$; $C_{1-4}$alkyl substituted with one or more halo atoms; and $C_{1-4}$alkyl substituted with one substituent selected from the group consisting of —$OC_{1-4}$alkyl, cyano, $C_{3-6}$cycloalkyl, $Ar^{1b}$, —O—$Ar^1$b, $Het^{2b}$ and —O-$Het^{2d}$;
Z represents —$CH_2$—, —C(=O)—, or —CH($C_{1-4}$alkyl)-; and in case $X^3$ represents C, Z can also represent =CH—;
the dotted lines attached to $X^3$ are optional bonds that may be present when $X^3$ represents a carbon atom, provided that maximum one of the dotted lines represents an optional bond;
in case one of the dotted lines attached to $X^3$ represents an additional bond, $X^3$ represents C, and (i) $R^{7a}$ is absent or (ii) $R^8$ is absent or (iii) Z represents =CH—;
$R^{9a}$ and $R^{9b}$ each independently are selected from the group consisting of hydrogen and $C_{1-4}$alkyl; or $R^{9a}$ and $R^{9b}$ are linked together to form together with the common nitrogen atom to which they are attached a 4-, 5-, 6- or 7-membered saturated heterocyclyl which optionally contains one oxygen atom;
$R^{5a}$ and $R^{5b}$ each independently are selected from the group consisting of hydrogen and $C_{1-4}$alkyl;
$Het^{1a}$ and $Het^{1b}$ are attached to the remainder of the molecule of Formula (I) through any available ring carbon atom;
$Het^{1a}$ and $Het^{1b}$ each independently represent a 4-, 5-, 6- or 7-membered saturated heterocyclyl, containing one or two heteroatoms each independently selected from O, S, S(=O)$_p$ and N;
$Ar^{1a}$ and $Ar^{1b}$ each independently represent phenyl optionally substituted with one or more substituents each independently selected from the group consisting of halo; cyano; and $C_{1-4}$alkyl optionally substituted with one or more halo atoms;
$Het^{2a}$ and $Het^{2b}$ each independently represent a 4-, 5-, 6- or 7-membered monocyclic aromatic or non-aromatic heterocyclyl containing at least one heteroatom each independently selected from O, S, S(=O)$_p$ and N; or a fused 8-, 9-, 10- or 11-membered bicyclic aromatic or non-aromatic heterocyclyl containing at least one heteroatom each independently selected from O, S, S(=O)$_p$ and N; said monocyclic heterocyclyl or said fused bicyclic heterocyclyl optionally being substituted with one or more substituents each independently selected from the group consisting of halo, cyano, and $C_{1-4}$alkyl optionally substituted with one or more halo atoms;
$Het^{2c}$ and $Het^{2d}$ are attached to the remainder of the molecule of Formula (I) through any available ring carbon atom;
$Het^{2c}$ and $Het^{2d}$ each independently represent a 4-, 5-, 6- or 7-membered monocyclic aromatic or non-aromatic heterocyclyl containing at least one heteroatom each independently selected from O, S, S(=O)$_p$ and N; or a fused 8-, 9-, 10- or 11-membered bicyclic aromatic or non-aromatic heterocyclyl containing at least one heteroatom each independently selected from O, S, S(=O)$_p$ and N; said monocyclic heterocyclyl or said fused bicyclic heterocyclyl optionally being substituted with one or more substituents each independently selected from the group consisting of halo, cyano, and $C_{1-4}$alkyl optionally substituted with one or more halo atoms;
$R^{6a}$ and $R^{6b}$ each independently are selected from the group consisting of hydrogen and $C_{1-4}$alkyl;
p represents 1 or 2;
Het represents a bicyclic aromatic heterocyclic ring system selected from the group consisting of (a-1), (a-2) and (a-3);
$R^{3a}$, $R^{3b}$ and $R^{3c}$ each independently are selected from the group consisting of hydrogen, halo, —$NR^{12a}R^{12b}$, $C_{1-4}$alkyl, and —O—$C_{1-4}$alkyl;
$R^{12a}$ and $R^{12b}$ each independently are selected from the group consisting of hydrogen; $C_{3-6}$cycloalkyl; $C_{1-4}$alkyl; and $C_{1-4}$alkyl substituted with one phenyl which is optionally substituted with one or more substituents selected from the group consisting of halo, cyano, —$OC_{1-4}$alkyl, —OH, and $C_{1-4}$alkyl optionally substituted with one or more halo atoms;
$R^{4a}$, $R^{4b}$ and $R^{4c}$ each independently are selected from the group consisting of hydrogen, halo, —$NR^{13a}R^{13b}$, and $C_{1-4}$alkyl;

$R^{13a}$ and $R^{13b}$ each independently are selected from the group consisting of hydrogen and $C_{1-4}$alkyl;
$Q^1$ represents N or $CR^{14a}$;
$Q^2$ represents N or $CR^{14b}$;
$Q^3$ represents N or $CR^{14c}$;
$Q^4$ represents N or $CR^{14d}$;
provided that maximum one of $Q^3$ and $Q^4$ represents N;
$R^{14a}$, $R^{14b}$, $R^{14c}$, $R^{14d}$, $R^{14e}$ and $R^{14f}$ each independently are selected from the group consisting of hydrogen; halogen; $C_{1-4}$alkyl; $NR^{15a}R^{15b}$; and $C_{1-4}$alkyl substituted with one or more halo atoms;
$R^{15a}$ and $R^{15b}$ each independently are selected from the group consisting of hydrogen and $C_{1-4}$alkyl;
provided that $R^{10}$ and $R^{11}$ may not be linked together when $R^8$ and $R^9$ are linked together;
and wherein at least one of $R^8$, $R^9$, $R^{10}$ and $R^{11}$ contains a nitrogen atom;
and pharmaceutically acceptable addition salts, and solvates thereof.

In an embodiment, the present invention concerns novel compounds of Formula (I), wherein
$R^1$ represents hydrogen or $CH_3$;
$R^2$ represents hydrogen;
$R^a$ represents hydrogen;
$R^b$ represents hydrogen;
Y represents —O—, —$CH_2$— or —$CF_2$—;
$R^{7a}$ represents hydrogen;
$R^{7b}$ represents hydrogen, or $C_{1-4}$alkyl optionally substituted with one or more halo atoms;
$X^1$ represents a covalent bond or —O—;
$X^2$ represents a covalent bond, —$CH_2$—, —$CF_2$—, —$CH_2CH_2$—, —$CF_2CH_2$—, or —$CH_2CF_2$—;
provided that $X^2$ represents a covalent bond, —$CH_2$— or —$CF_2$—, when $X^1$ represents —O—;
$X^3$ represents N or CH; or in case one of the dotted lines represents an additional bond, $X^3$ represents C;
$R^8$ and $R^{10}$ each independently are selected from the group consisting of hydrogen; halo; and $C_{1-6}$alkyl optionally substituted with one or more halo atoms;
$R^9$ and $R^{11}$ each independently are selected from the group consisting of hydrogen; halo; —$NH_2$; and $C_{1-6}$alkyl optionally substituted with one —$NR^{9a}R^{9b}$;
or $R^8$ and $R^9$ are linked together to form together with the common carbon atom to which they are attached a 4-, 5-, 6- or 7-membered saturated heterocyclyl, containing one or two N-atoms and optionally one oxygen atom; wherein said 4-, 5-, 6- or 7-membered saturated heterocyclyl is optionally substituted on one or more ring carbon atoms with one or more substituents each independently selected from the group consisting of halo, and $C_{1-6}$alkyl optionally substituted with one or more halo atoms; and wherein said 4-, 5-, 6- or 7-membered saturated heterocyclyl is optionally substituted on one or two ring N-atoms with a substituent selected from the group consisting of $C_{1-6}$alkyl; $Het^{1a}$; $C_{3-6}$cycloalkyl; —$C_{1-4}$alkyl-C(=O)—$NR^{5a}R^{5b}$; $C_{1-4}$alkyl substituted with one or more halo atoms; and $C_{1-4}$alkyl substituted with one substituent selected from the group consisting of —$OC_{1-4}$alkyl, cyano, $C_{3-6}$cycloalkyl, $Ar^{1a}$, —O—$Ar^{1a}$, $Het^{2a}$ and —O-$Het^{2c}$;
or $R^{10}$ and $R^{11}$ are linked together to form together with the common carbon atom to which they are attached a 4-, 5-, 6- or 7-membered saturated heterocyclyl, containing one or two N-atoms and optionally one oxygen atom; wherein said 4-, 5-, 6- or 7-membered saturated heterocyclyl is optionally substituted on one or more ring carbon atoms with one or more substituents each independently selected from the group consisting of halo, and $C_{1-6}$alkyl optionally substituted with one or more halo atoms; and wherein said 4-, 5-, 6- or 7-membered saturated heterocyclyl is optionally substituted on one or two ring N-atoms with a substituent selected from the group consisting of $C_{1-6}$alkyl; $Het^{1b}$; $C_{3-6}$cycloalkyl; —$C_{1-4}$alkyl-C(=O)—$NR^{6a}R^{6b}$; $C_{1-4}$alkyl substituted with one or more halo atoms; and $C_{1-4}$alkyl substituted with one substituent selected from the group consisting of —$C_{1-4}$alkyl, cyano, $C_{3-6}$cycloalkyl, $Ar^{1b}$, —O—$Ar^{1b}$, $Het^{2b}$ and —O-$Het^{2d}$;
Z represents —$CH_2$—, —C(=O)—, or —$CH(C_{1-4}$alkyl)-;
and in case $X^3$ represents C, Z can also represent =CH—;
the dotted lines attached to $X^3$ are optional bonds that may be present when $X^3$ represents a carbon atom, provided that maximum one of the dotted lines represents an optional bond;
in case one of the dotted lines attached to $X^3$ represents an additional bond, $X^3$ represents C, and (i) $R^{7a}$ is absent or (ii) $R^8$ is absent or (iii) Z represents =CH—;
$R^{9a}$ and $R^{9b}$ each independently are selected from the group consisting of hydrogen and $C_{1-4}$alkyl; or $R^{9a}$ and $R^{9b}$ are linked together to form together with the common nitrogen atom to which they are attached a 4-, 5-, 6- or 7-membered saturated heterocyclyl which optionally contains one oxygen atom;
$R^{5a}$ and $R^{5b}$ each independently are selected from the group consisting of hydrogen and $C_{1-4}$alkyl;
$Het^{1a}$ and $Het^{1b}$ are attached to the remainder of the molecule of Formula (I) through any available ring carbon atom;
$Het^{1a}$ and $Het^{1b}$ each independently represent a 4-, 5-, 6- or 7-membered saturated heterocyclyl, containing one or two heteroatoms each independently selected from O, S, S(=O)$_p$ and N;
$Ar^{1a}$ and $Ar^{1b}$ each independently represent phenyl optionally substituted with one or more substituents each independently selected from the group consisting of halo; cyano; and $C_{1-4}$alkyl optionally substituted with one or more halo atoms;
$Het^{2a}$ and $Het^{2b}$ each independently represent a 4-, 5-, 6- or 7-membered monocyclic aromatic or non-aromatic heterocyclyl containing at least one heteroatom each independently selected from O, S, S(=O)$_p$ and N; or a fused 8-, 9-, 10- or 11-membered bicyclic aromatic or non-aromatic heterocyclyl containing at least one heteroatom each independently selected from O, S, S(=O)$_p$ and N; said monocyclic heterocyclyl or said fused bicyclic heterocyclyl optionally being substituted with one or more substituents each independently selected from the group consisting of halo, cyano, and $C_{1-4}$alkyl optionally substituted with one or more halo atoms;
$Het^{2c}$ and $Het^{2d}$ are attached to the remainder of the molecule of Formula (I) through any available ring carbon atom;
$Het^{2c}$ and $Het^{2d}$ each independently represent a 4-, 5-, 6- or 7-membered monocyclic aromatic or non-aromatic heterocyclyl containing at least one heteroatom each independently selected from O, S, S(=O)$_p$ and N; or a fused 8-, 9-, 10- or 11-membered bicyclic aromatic or non-aromatic heterocyclyl containing at least one heteroatom each independently selected from O, S, S(=O)$_p$ and N; said monocyclic heterocyclyl or said fused bicyclic heterocyclyl optionally being substituted with one or more substituents each independently selected from the group consisting of halo, cyano, and $C_{1-4}$alkyl optionally substituted with one or more halo atoms;
$R^{6a}$ and $R^{6b}$ each independently are selected from the group consisting of hydrogen and $C_{1-4}$alkyl;
p represents 1 or 2;

Het represents a bicyclic aromatic heterocyclic ring system selected from the group consisting of (a-1), (a-2) and (a-3);
$R^{3a}$, $R^{3b}$ and $R^{3c}$ each independently are selected from the group consisting of hydrogen, halo, —$NR^{12a}R^{12b}$, $C_{1-4}$alkyl, and —O—$C_{1-4}$alkyl;
$R^{12a}$ and $R^{12b}$ each independently are selected from the group consisting of hydrogen; $C_{3-6}$cycloalkyl; $C_{1-4}$alkyl; and $C_{1-4}$alkyl substituted with one phenyl which is optionally substituted with one or more substituents selected from the group consisting of halo, cyano, —$OC_{1-4}$alkyl, —OH, and $C_{1-4}$alkyl optionally substituted with one or more halo atoms;
$R^{4a}$, $R^{4b}$ and $R^{4c}$ each independently are selected from the group consisting of hydrogen, halo, —$NR^{13a}R^{13b}$, and $C_{1-4}$alkyl;
$R^{13a}$ and $R^{13b}$ each independently are selected from the group consisting of hydrogen and $C_{1-4}$alkyl;
$Q^1$ represents N or $CR^{14a}$;
$Q^2$ represents N or $CR^{14b}$;
$Q^3$ represents N or $CR^{14c}$;
$Q^4$ represents N or $CR^{14d}$;
provided that maximum one of $Q^3$ and $Q^4$ represents N;
$R^{14a}$, $R^{14b}$, $R^{14c}$, $R^{14d}$, $R^{14e}$ and $R^{14f}$ each independently are selected from the group consisting of hydrogen; halogen; $C_{1-4}$alkyl; $NR^{15a}R^{15b}$; and $C_{1-4}$alkyl substituted with one or more halo atoms;
$R^{15a}$ and $R^{15b}$ each independently are selected from the group consisting of hydrogen and $C_{1-4}$alkyl;
provided that $R^{10}$ and $R^{11}$ may not be linked together when $R^8$ and $R^9$ are linked together;
and wherein at least one of $R^8$, $R^9$, $R^{10}$ and $R^{11}$ contains a nitrogen atom;
and pharmaceutically acceptable addition salts, and solvates thereof.

In an embodiment, the present invention concerns novel compounds of Formula (I), wherein
$R^1$ represents hydrogen or $CH_3$;
$R^2$ represents hydrogen;
$R^a$ represents —C(=O)—$C_{1-4}$alkyl;
$R^b$ represents —C(=O)—$C_{1-4}$alkyl;
Y represents —O—, —$CH_2$— or —$CF_2$—;
$R^{7a}$ represents hydrogen;
$R^{7b}$ represents hydrogen, or $C_{1-4}$alkyl optionally substituted with one or more halo atoms;
$X^1$ represents a covalent bond or —O—;
$X^2$ represents a covalent bond, —$CH_2$—, —$CF_2$—, —$CH_2CH_2$—, —$CF_2CH_2$—, or —$CH_2CF_2$—; provided that $X^2$ represents a covalent bond, —$CH_2$— or —$CF_2$—, when $X^1$ represents —O—;
$X^3$ represents N or CH; or in case one of the dotted lines represents an additional bond,
$X^3$ represents C;
$R^8$ and $R^{10}$ each independently are selected from the group consisting of hydrogen; halo; and $C_{1-4}$alkyl optionally substituted with one or more halo atoms;
$R^9$ and $R^{11}$ each independently are selected from the group consisting of hydrogen; halo; —$NH_2$; and $C_{1-6}$alkyl optionally substituted with one —$NR^{9a}R^{9b}$;
or $R^8$ and $R^9$ are linked together to form together with the common carbon atom to which they are attached a 4-, 5-, 6- or 7-membered saturated heterocyclyl, containing one or two N-atoms and optionally one oxygen atom; wherein said 4-, 5-, 6- or 7-membered saturated heterocyclyl is optionally substituted on one or more ring carbon atoms with one or more substituents each independently selected from the group consisting of halo, and $C_{1-6}$alkyl optionally substituted with one or more halo atoms; and wherein said 4-, 5-, 6- or 7-membered saturated heterocyclyl is optionally substituted on one or two ring N-atoms with a substituent selected from the group consisting of $C_{1-4}$alkyl; $Het^{1a}$; $C_{3-6}$cycloalkyl; —$C_{1-4}$alkyl-C(O)—$NR^{5a}R^{5b}$; $C_{1-4}$alkyl substituted with one or more halo atoms; and $C_{1-4}$alkyl substituted with one substituent selected from the group consisting of —$OC_{1-4}$alkyl, cyano, $C_{3-6}$cycloalkyl, $Ar^{1a}$, —O—$Ar^{1a}$, $Het^{2a}$ and —O-$Het^{2c}$;
or $R^{10}$ and $R^{11}$ are linked together to form together with the common carbon atom to which they are attached a 4-, 5-, 6- or 7-membered saturated heterocyclyl, containing one or two N-atoms and optionally one oxygen atom; wherein said 4-, 5-, 6- or 7-membered saturated heterocyclyl is optionally substituted on one or more ring carbon atoms with one or more substituents each independently selected from the group consisting of halo, and $C_{1-6}$alkyl optionally substituted with one or more halo atoms; and wherein said 4-, 5-, 6- or 7-membered saturated heterocyclyl is optionally substituted on one or two ring N-atoms with a substituent selected from the group consisting of $C_{1-4}$alkyl; $Het^{1b}$; $C_{3-6}$cycloalkyl; —$C_{1-4}$alkyl-C(=O)—$NR^{6a}R^{6b}$; $C_{1-4}$alkyl substituted with one or more halo atoms; and $C_{1-4}$alkyl substituted with one substituent selected from the group consisting of —$OC_{1-4}$alkyl, cyano, $C_{3-6}$cycloalkyl, $Ar^{1b}$, —O—$Ar^{1b}$, $Het^{2b}$ and —O-$Het^{2d}$;
Z represents —$CH_2$—, —C(=O)—, or —CH($C_{1-4}$alkyl)-;
and in case $X^3$ represents C, Z can also represent =CH—;
the dotted lines attached to $X^3$ are optional bonds that may be present when $X^3$ represents a carbon atom, provided that maximum one of the dotted lines represents an optional bond;
in case one of the dotted lines attached to $X^3$ represents an additional bond, $X^3$ represents C, and (i) $R^{7a}$ is absent or (ii) $R^8$ is absent or (iii) Z represents =CH—;
$R^{9a}$ and $R^{9b}$ each independently are selected from the group consisting of hydrogen and $C_{1-4}$alkyl; or $R^{9a}$ and $R^{9b}$ are linked together to form together with the common nitrogen atom to which they are attached a 4-, 5-, 6- or 7-membered saturated heterocyclyl which optionally contains one oxygen atom;
$R^{5a}$ and $R^{5b}$ each independently are selected from the group consisting of hydrogen and $C_{1-4}$alkyl;
$Het^{1a}$ and $Het^{1b}$ are attached to the remainder of the molecule of Formula (I) through any available ring carbon atom;
$Het^{1a}$ and $Het^{1b}$ each independently represent a 4-, 5-, 6- or 7-membered saturated heterocyclyl, containing one or two heteroatoms each independently selected from O, S, S(=O)$_p$ and N;
$Ar^{1a}$ and $Ar^{1b}$ each independently represent phenyl optionally substituted with one or more substituents each independently selected from the group consisting of halo; cyano; and $C_{1-4}$alkyl optionally substituted with one or more halo atoms;
$Het^{2a}$ and $Het^{2b}$ each independently represent a 4-, 5-, 6- or 7-membered monocyclic aromatic or non-aromatic heterocyclyl containing at least one heteroatom each independently selected from O, S, S(=O)$_p$ and N; or a fused 8-, 9-, 10- or 1-membered bicyclic aromatic or non-aromatic heterocyclyl containing at least one heteroatom each independently selected from O, S, S(=O)$_p$ and N; said monocyclic heterocyclyl or said fused bicyclic heterocyclyl optionally being substituted with one or more substituents each independently selected from the group consisting of halo, cyano, and $C_{1-4}$alkyl optionally substituted with one or more halo atoms;
$Het^{2c}$ and $Het^{2d}$ are attached to the remainder of the molecule of Formula (I) through any available ring carbon atom;

Het$^{2c}$ and Het$^{2d}$ each independently represent a 4-, 5-, 6- or 7-membered monocyclic aromatic or non-aromatic heterocyclyl containing at least one heteroatom each independently selected from O, S, S(=O)$_p$ and N; or a fused 8-, 9-, 10- or 11-membered bicyclic aromatic or non-aromatic heterocyclyl containing at least one heteroatom each independently selected from O, S, S(=O)$_p$ and N; said monocyclic heterocyclyl or said fused bicyclic heterocyclyl optionally being substituted with one or more substituents each independently selected from the group consisting of halo, cyano, and C$_{1-4}$alkyl optionally substituted with one or more halo atoms;

R$^{6a}$ and R$^{6b}$ each independently are selected from the group consisting of hydrogen and C$_{1-4}$alkyl;

p represents 1 or 2;

Het represents a bicyclic aromatic heterocyclic ring system selected from the group consisting of (a-1), (a-2) and (a-3);

R$^{3a}$, R$^{3b}$ and R$^{3c}$ each independently are selected from the group consisting of hydrogen, halo, —NR$^{12a}$R$^{12b}$, C$_{1-4}$alkyl, and —O—C$_{1-4}$alkyl;

R$^{12a}$ and R$^{12b}$ each independently are selected from the group consisting of hydrogen; C$_{3-6}$cycloalkyl; C$_{1-4}$alkyl; and C$_{1-4}$alkyl substituted with one phenyl which is optionally substituted with one or more substituents selected from the group consisting of halo, cyano, —OC$_{1-4}$alkyl, —OH, and C$_{1-4}$alkyl optionally substituted with one or more halo atoms;

R$^{4a}$, R$^{4b}$ and R$^{4c}$ each independently are selected from the group consisting of hydrogen, halo, —NR$^{13a}$R$^{13b}$, and C$_{1-4}$alkyl;

R$^{13a}$ and R$^{13b}$ each independently are selected from the group consisting of hydrogen and C$_{1-4}$alkyl;

Q$^1$ represents N or CR$^{14a}$;

Q$^2$ represents N or CR$^{14b}$;

Q$^3$ represents N or CR$^{14c}$;

Q$^4$ represents N or CR$^{14d}$;

provided that maximum one of Q$^3$ and Q$^4$ represents N;

R$^{14a}$, R$^{14b}$, R$^{14c}$, R$^{14d}$, R$^{14e}$ and R$^{14f}$ each independently are selected from the group consisting of hydrogen; halogen; C$_{1-4}$alkyl; NR$^{15a}$R$^{15b}$; and C$_{1-4}$alkyl substituted with one or more halo atoms;

R$^{15a}$ and R$^{15b}$ each independently are selected from the group consisting of hydrogen and C$_{1-4}$alkyl;

provided that R$^{10}$ and R$^{11}$ may not be linked together when R$^8$ and R$^9$ are linked together;

and wherein at least one of R$^8$, R$^9$, R$^{10}$ and R$^{11}$ contains a nitrogen atom; and pharmaceutically acceptable addition salts, and solvates thereof.

In an embodiment, the present invention concerns novel compounds of Formula (I), wherein R$^1$ represents hydrogen or CH$_3$; in particular hydrogen;

R$^2$ represents hydrogen;

R$^a$ represents hydrogen or —C(=O)—C$_{1-4}$alkyl;

R$^b$ represents hydrogen or —C(=O)—C$_{1-4}$alkyl;

Y represents —O— or —CH$_2$—;

R$^{7a}$ represents hydrogen;

R$^{7b}$ represents hydrogen, or C$_{1-4}$alkyl optionally substituted with one or more halo atoms;

X$^1$ represents a covalent bond or —O—;

X$^2$ represents a covalent bond, —CH$_2$—, —CF$_2$CH$_2$—, or —CH$_2$CF$_2$—;

provided that X$^2$ represents a covalent bond or —CH$_2$—, when X$^1$ represents —O—;

X$^3$ represents N; or in case one of the dotted lines represents an additional bond, X$^3$ represents C;

R$^8$ and R$^{10}$ each independently are selected from the group consisting of hydrogen; halo; and C$_{1-6}$alkyl optionally substituted with one or more halo atoms;

R$^9$ and R$^{11}$ each independently are selected from the group consisting of hydrogen; halo; —NH$_2$; and C$_{1-6}$alkyl optionally substituted with one —NR$^{9a}$R$^{9b}$;

or R$^8$ and R$^9$ are linked together to form together with the common carbon atom to which they are attached a 4-, 5-, 6- or 7-membered saturated heterocyclyl, containing one or two N-atoms; wherein said 4-, 5-, 6- or 7-membered saturated heterocyclyl is optionally substituted on one or two ring N-atoms with a substituent selected from the group consisting of C$_{1-6}$alkyl; Het$^{1a}$; C$_{3-6}$cycloalkyl; —C$_{1-4}$alkyl-C(=O)—NR$^{5a}$R$^{5b}$; C$_{1-4}$alkyl substituted with one or more halo atoms; and C$_{1-4}$alkyl substituted with one substituent selected from the group consisting of —OC$_{1-4}$alkyl, cyano, C$_{3-6}$cycloalkyl, Ar$^{1a}$, —O—Ar$^{1a}$, and Het$^{2a}$;

or R$^{10}$ and R$^{11}$ are linked together to form together with the common carbon atom to which they are attached a 4-, 5-, 6- or 7-membered saturated heterocyclyl, containing one or two N-atoms and optionally one oxygen atom; wherein said 4-, 5-, 6- or 7-membered saturated heterocyclyl is optionally substituted on one or more ring carbon atoms with one or more halo substituents; and wherein said 4-, 5-, 6- or 7-membered saturated heterocyclyl is optionally substituted on one or two ring N-atoms with a substituent selected from the group consisting of C$_{1-6}$alkyl; and C$_{1-4}$alkyl substituted with one Ar$^{1b}$;

Z represents —CH$_2$— or —C(=O)—; and in case X$^3$ represents C, Z can also represent =CH—; the dotted lines attached to X$^3$ are optional bonds that may be present when X$^3$ represents a carbon atom, provided that maximum one of the dotted lines represents an optional bond;

in case one of the dotted lines attached to X$^3$ represents an additional bond, X$^3$ represents C, and (i) R$^{7a}$ is absent or (ii) R$^8$ s absent or (iii) Z represents =CH—;

R$^{9a}$ and R$^{9b}$ each independently are selected from the group consisting of hydrogen and C$_{1-4}$alkyl; or R$^{9a}$ and R$^{9b}$ are linked together to form together with the common nitrogen atom to which they are attached a 4-, 5-, 6- or 7-membered saturated heterocyclyl which optionally contains one oxygen atom;

R$^{5a}$ and R$^{5b}$ each independently are selected from the group consisting of hydrogen and C$_{1-4}$alkyl;

Het$^{1a}$ is attached to the remainder of the molecule of Formula (I) through any available ring carbon atom;

Het$^{1a}$ represents a 4-, 5-, 6- or 7-membered saturated heterocyclyl, containing one or two heteroatoms each independently selected from 0;

Ar$^{1a}$ and Ar$^{1b}$ each independently represent phenyl optionally substituted with one or more halo substituents;

Het$^{2a}$ represents a 4-, 5-, 6- or 7-membered monocyclic aromatic or non-aromatic heterocyclyl containing at least one heteroatom each independently selected from O, S, S(=O)$_p$ and N; or a fused 8-, 9-, 10- or 11-membered bicyclic aromatic or non-aromatic heterocyclyl containing at least one heteroatom each independently selected from O, S, S(=O)$_p$ and N; said monocyclic heterocyclyl or said fused bicyclic heterocyclyl optionally being substituted with one or more C$_{1-4}$alkyl substituents;

p represents 1 or 2;

Het represents a bicyclic aromatic heterocyclic ring system selected from the group consisting of (a-1), (a-2) and (a-3);

R$^{3a}$, R$^{3b}$ and R$^{3c}$ each independently are selected from the group consisting of hydrogen, halo, and —NR$^{12a}$R$^{12b}$;

$R^{12a}$ and $R^{12b}$ each independently are selected from the group consisting of hydrogen; $C_{3-6}$cycloalkyl; $C_{1-4}$alkyl; and $C_{1-4}$alkyl substituted with one phenyl which is optionally substituted with one or more halo substituents;

$R^{4a}$, $R^{4b}$ and $R^{4c}$ each independently are selected from the group consisting of hydrogen and $C_{1-4}$alkyl;

$Q^1$ represents $CR^{14a}$;

$Q^2$ represents N or $CR^{14b}$;

$Q^3$ represents $CR^{14c}$;

$Q^4$ represents N;

$R^{14a}$, $R^{14b}$, $R^{14c}$, $R^{14e}$ and $R^{14f}$ each independently are selected from the group consisting of hydrogen and halogen; provided that $R^{10}$ and $R^{11}$ may not be linked together when $R^8$ and $R^9$ are linked together;

and wherein at least one of $R^8$, $R^9$, $R^{10}$ and $R^{11}$ contains a nitrogen atom;

and pharmaceutically acceptable addition salts, and solvates thereof.

In an embodiment, the present invention concerns novel compounds of Formula (I), wherein $R^1$ represents hydrogen or $CH_3$; in particular hydrogen;

$R^2$ represents hydrogen;

$R^a$ represents hydrogen or —C(=O)—$C_{1-4}$alkyl;

$R^b$ represents hydrogen or —C(=O)—$C_{1-4}$alkyl;

Y represents —O— or —$CH_2$—;

$R^{7a}$ represents hydrogen;

$R^{7b}$ represents hydrogen, or $C_{1-4}$alkyl optionally substituted with one or more halo atoms;

$X^1$ represents a covalent bond or —O—;

$X^2$ represents a covalent bond, —$CH_2$—, —$CF_2CH_2$—, or —$CH_2CF_2$—;

provided that $X^2$ represents a covalent bond or —$CH_2$—, when $X^1$ represents —O—;

$X^3$ represents N; or in case one of the dotted lines represents an additional bond, $X^3$ represents C;

$R^8$ and $R^{10}$ each independently are selected from the group consisting of hydrogen; halo; and $C_{1-4}$alkyl optionally substituted with one or more halo atoms;

$R^9$ and $R^{11}$ each independently are selected from the group consisting of hydrogen; halo; —$NH_2$; and $C_{1-6}$alkyl optionally substituted with one —$NR^{9a}R^{9b}$;

or $R^8$ and $R^9$ are linked together to form together with the common carbon atom to which they are attached a 4-, 5-, 6- or 7-membered saturated heterocyclyl, containing one or two N-atoms; wherein said 4-, 5-, 6- or 7-membered saturated heterocyclyl is optionally substituted on one or two ring N-atoms with a substituent selected from the group consisting of $C_{1-6}$alkyl; Het$^{1a}$; $C_{3-6}$cycloalkyl; —$C_{1-4}$alkyl-C(=O)—$NR^{5a}R^{5b}$; $C_{1-4}$alkyl substituted with one or more halo atoms; and $C_{1-4}$alkyl substituted with one substituent selected from the group consisting of —$C_{1-4}$alkyl, cyano, $C_{3-6}$cycloalkyl, Ar$^{1a}$, —O—Ar$^{1a}$, and Het$^{2a}$;

or $R^{10}$ and $R^{11}$ are linked together to form together with the common carbon atom to which they are attached a 4-, 5-, 6- or 7-membered saturated heterocyclyl, containing one or two N-atoms and optionally one oxygen atom; wherein said 4-, 5-, 6- or 7-membered saturated heterocyclyl is optionally substituted on one or more ring carbon atoms with one or more halo substituents; and wherein said 4-, 5-, 6- or 7-membered saturated heterocyclyl is optionally substituted on one or two ring N-atoms with a substituent selected from the group consisting of $C_{1-6}$alkyl; and $C_{1-4}$alkyl substituted with one Ar$^{1b}$;

Z represents —$CH_2$— or —C(=O)—; and in case $X^3$ represents C, Z can also represent =CH—; the dotted lines attached to $X^3$ are optional bonds that may be present when $X^3$ represents a carbon atom, provided that maximum one of the dotted lines represents an optional bond;

in case one of the dotted lines attached to $X^3$ represents an additional bond, $X^3$ represents C, and (i) $R^{7a}$ is absent or (ii) $R^8$ is absent or (iii) Z represents =CH—;

$R^{9a}$ and $R^{9b}$ each independently are selected from the group consisting of hydrogen and $C_{1-4}$alkyl; or $R^{9a}$ and $R^{9b}$ are linked together to form together with the common nitrogen atom to which they are attached a 4-, 5-, 6- or 7-membered saturated heterocyclyl which optionally contains one oxygen atom;

$R^{5a}$ and $R^{5b}$ each independently are selected from the group consisting of hydrogen and $C_{1-4}$alkyl;

Het$^{1a}$ is attached to the remainder of the molecule of Formula (I) through any available ring carbon atom;

Het$^{1a}$ represents a 4-, 5-, 6- or 7-membered saturated heterocyclyl, containing one or two heteroatoms each independently selected from 0;

Ar$^{1a}$ and Ar$^{1b}$ each independently represent phenyl optionally substituted with one or more halo substituents;

Het$^2$a represents a 4-, 5-, 6- or 7-membered monocyclic aromatic or non-aromatic heterocyclyl containing at least one heteroatom each independently selected from O, S, S(=O)$_p$ and N; or a fused 8-, 9-, 10- or 1-membered bicyclic aromatic or non-aromatic heterocyclyl containing at least one heteroatom each independently selected from O, S, S(=O)$_p$ and N; said monocyclic heterocyclyl or said fused bicyclic heterocyclyl optionally being substituted with one or more $C_{1-4}$alkyl substituents;

p represents 1 or 2;

Het represents a bicyclic aromatic heterocyclic ring system selected from the group consisting of (a-1), (a-2), (a-3) and (a-4);

$R^{3a}$, $R^{3b}$, $R^{3c}$ and $R^{3d}$ each independently are selected from the group consisting of hydrogen, halo, and —$NR^{12a}R^{12b}$;

$R^{12a}$ and $R^{12b}$ each independently are selected from the group consisting of hydrogen; $C_{3-6}$cycloalkyl; $C_{1-4}$alkyl; and $C_{1-4}$alkyl substituted with one phenyl which is optionally substituted with one or more halo substituents;

$R^{4a}$, $R^{4b}$, $R^{4c}$ and $R^{4d}$ each independently are selected from the group consisting of hydrogen and $C_{1-4}$alkyl;

$R^{4f}$ represent hydrogen;

$Q^1$ represents $CR^{14a}$;

$Q^2$ represents N or $CR^{14b}$;

$Q^3$ represents $CR^{14c}$;

$Q^4$ represents N;

$Q^8$ represents $CR^{14g}$;

$Q^9$ represents $CR^{14h}$;

$Q^5$ represents $CR^{3d}$; $Q^6$ represents N; and $Q^7$ represents $CR^{4f}$;

$R^{14a}$, $R^{14b}$, $R^{14c}$, $R^{14e}$ and $R^{14f}$ each independently are selected from the group consisting of hydrogen and halogen;

$R^{14g}$ and $R^{14h}$ represent hydrogen;

provided that $R^{10}$ and $R^{11}$ may not be linked together when $R^8$ and $R^9$ are linked together;

and wherein at least one of $R^8$, $R^9$, $R^{10}$ and $R^{11}$ contains a nitrogen atom;

and pharmaceutically acceptable addition salts, and solvates thereof.

Another embodiment of the present invention relates to those compounds of Formula (I), and pharmaceutically acceptable addition salts, and solvates thereof, or any subgroup thereof as mentioned in any of the other embodiments, wherein one or more of the following restrictions apply:

(i) $R^1$ represents hydrogen;

(ii) Y represents —O— or —$CH_2$—;

(iii) $X^2$ represents a covalent bond, —$CH_2$—, —$CF_2CH_2$—, or —$CH_2CF_2$—; provided that $X^2$ represents a covalent bond or —$CH_2$—, when $X^1$ represents —O—;
(iv) $X^3$ represents N; or in case one of the dotted lines represents an additional bond, $X^3$ represents C;
(v) $R^8$ and $R^{10}$ each independently are selected from the group consisting of hydrogen; halo; and $C_{1-6}$alkyl optionally substituted with one or more halo atoms;
$R^9$ and $R^{11}$ each independently are selected from the group consisting of hydrogen; halo; —$NH_2$; and $C_{1-6}$alkyl optionally substituted with one —$NR^{9a}R^{9b}$;
or $R^8$ and $R^9$ are linked together to form together with the common carbon atom to which they are attached a 4-, 5-, 6- or 7-membered saturated heterocyclyl, containing one or two N-atoms; wherein said 4-, 5-, 6- or 7-membered saturated heterocyclyl is optionally substituted on one or two ring N-atoms with a substituent selected from the group consisting of $C_{1-6}$alkyl; $Het^{1a}$; $C_{3-6}$cycloalkyl; —$C_{1-4}$alkyl-C(=O)—$NR^{5a}R^{5b}$; $C_{1-4}$alkyl substituted with one or more halo atoms; and $C_{1-4}$alkyl substituted with one substituent selected from the group consisting of —$OC_{1-4}$alkyl, cyano, $C_{3-6}$cycloalkyl, $Ar^{1a}$, —O—$Ar^{1a}$, and $Het^{2a}$;
or $R^{10}$ and $R^{11}$ are linked together to form together with the common carbon atom to which they are attached a 4-, 5-, 6- or 7-membered saturated heterocyclyl, containing one or two N-atoms and optionally one oxygen atom; wherein said 4-, 5-, 6- or 7-membered saturated heterocyclyl is optionally substituted on one or more ring carbon atoms with one or more halo substituents; and wherein said 4-, 5-, 6- or 7-membered saturated heterocyclyl is optionally substituted on one or two ring N-atoms with a substituent selected from the group consisting of $C_{1-6}$alkyl; and $C_{1-4}$alkyl substituted with one $Ar^{1b}$;
(vi) Z represents —$CH_2$— or —C(=O)—; and in case $X^3$ represents C, Z can also represent =CH—;
the dotted lines attached to $X^3$ are optional bonds that may be present when $X^3$ represents a carbon atom, provided that maximum one of the dotted lines represents an optional bond;
in case one of the dotted lines attached to $X^3$ represents an additional bond, $X^3$ represents C, and (i) $R^{7a}$ is absent or (ii) $R^8$ is absent or (iii) Z represents =CH—;
(vii) $Het^{1a}$ is attached to the remainder of the molecule of Formula (I) through any available ring carbon atom;
$Het^{1a}$ represents a 4-, 5-, 6- or 7-membered saturated heterocyclyl, containing one or two heteroatoms each independently selected from 0;
(viii) $Ar^{1a}$ and $Ar^{1b}$ each independently represent phenyl optionally substituted with one or more halo substituents;
(ix) $Het^{2a}$ represents a 4-, 5-, 6- or 7-membered monocyclic aromatic or non-aromatic heterocyclyl containing at least one heteroatom each independently selected from O, S, S(=O)$_p$ and N; or a fused 8-, 9-, 10- or 11-membered bicyclic aromatic or non-aromatic heterocyclyl containing at least one heteroatom each independently selected from O, S, S(=O)$^p$ and N; said monocyclic heterocyclyl or said fused bicyclic heterocyclyl optionally being substituted with one or more $C_{1-4}$alkyl substituents;
(x) $R^{3a}$, $R^{3b}$ and $R^{3c}$ each independently are selected from the group consisting of hydrogen, halo, and —$NR^{12a}R^{12b}$;
(xi) $R^{12a}$ and $R^{12b}$ each independently are selected from the group consisting of hydrogen; $C_{3-6}$cycloalkyl; $C_{1-4}$alkyl; and $C_{1-4}$alkyl substituted with one phenyl which is optionally substituted with one or more halo substituents;
(xii) $R^{4a}$, $R^{4b}$ and $R^{4c}$ each independently are selected from the group consisting of hydrogen and $C_{1-4}$alkyl;
(xiii) $Q^1$ represents $CR^{14a}$;
(xiv) $Q^2$ represents N or $CR^{14b}$;
(xv) $Q^3$ represents $CR^{14c}$;
(xvi) $Q^4$ represents N;
(xvii) $R^{14a}$, $R^{14b}$, $R^{14c}$, $R^{14e}$ and $R^{14f}$ each independently are selected from the group consisting of hydrogen and halogen.

In an embodiment, the present invention concerns novel compounds of Formula (I), wherein
$R^1$ represents hydrogen; $R^2$ represents hydrogen;
$R^a$ represents hydrogen or —C(=O)—$C_{1-4}$alkyl;
$R^b$ represents hydrogen or —C(=O)—$C_{1-4}$alkyl;
Y represents —O— or —$CH_2$—;
$R^{7a}$ represents hydrogen;
$R^{7b}$ represents hydrogen;
$X^1$ represents a covalent bond or —O—;
$X^2$ represents a covalent bond or —$CH_2$—;
$X^3$ represents N; or in case one of the dotted lines represents an additional bond, $X^3$ represents C;
$R^8$ and $R^{10}$ each independently are selected from the group consisting of hydrogen and halo;
$R^9$ and $R^{11}$ each independently are selected from the group consisting of hydrogen and halo;
or $R^8$ and $R^9$ are linked together to form together with the common carbon atom to which they are attached a 4-, 5-, 6- or 7-membered saturated heterocyclyl, containing one N-atom; wherein said 4-, 5-, 6- or 7-membered saturated heterocyclyl is optionally substituted on one ring N-atom with $C_{1-6}$alkyl;
or $R^{10}$ and $R^{11}$ are linked together to form together with the common carbon atom to which they are attached a 4-, 5-, 6- or 7-membered saturated heterocyclyl, containing one N-atom; wherein said 4-, 5-, 6- or 7-membered saturated heterocyclyl is optionally substituted on one ring N-atom with $C_{1-6}$alkyl;
provided that $R^{10}$ and $R^{11}$, or $R^8$ and $R^9$ are linked together;
Z represents —$CH_2$—; and in case $X^3$ represents C, Z can also represent =CH—;
the dotted lines attached to $X^3$ are optional bonds that may be present when $X^3$ represents a carbon atom, provided that maximum one of the dotted lines represents an optional bond;
in case one of the dotted lines attached to $X^3$ represents an additional bond, $X^3$ represents C, and (i) $R^{7a}$ is absent or (ii) $R^8$ is absent or (iii) Z represents =CH—;
Het represents a bicyclic aromatic heterocyclic ring system selected from the group consisting of (a-1) and (a-2);
$R^{3a}$ and $R^{3c}$ represent $NH_2$;
$R^{4a}$ and $R^{4c}$ represent hydrogen;
$Q^1$ represents $CR^{14a}$;
$Q^2$ represents $CR^{14b}$;
$R^{14a}$, $R^{14b}$, $R^{14e}$ and $R^{14f}$ each independently are selected from the group consisting of hydrogen and halogen;
and pharmaceutically acceptable addition salts, and solvates thereof.

In an embodiment, the present invention relates to those compounds of Formula (I) and pharmaceutically acceptable addition salts, and solvates thereof, or any subgroup thereof as mentioned in any of the other embodiments, wherein the compounds of Formula (I) are restricted to the compounds of Formula (I-1):

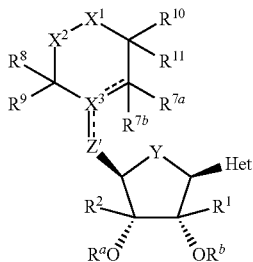

(I-1)

wherein all variables are defined as for compounds of Formula (I) or any subgroup thereof as mentioned in any of the other embodiments.

In an embodiment, the present invention concerns novel compounds of Formula (I-1)

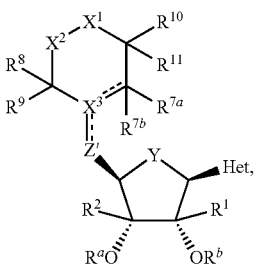

(I-1)

wherein
$R^1$ represents hydrogen; $R^2$ represents hydrogen;
$R^a$ represents hydrogen or —C(=O)—$C_{1-4}$alkyl;
$R^b$ represents hydrogen or —C(=O)—$C_{1-4}$alkyl;
Y represents —O— or —$CH_2$—;
$R^{7a}$ represents hydrogen;
$R^{1b}$ represents hydrogen;
$X^1$ represents a covalent bond or —O—;
$X^2$ represents a covalent bond or —$CH_2$—;
$X^3$ represents N; or in case one of the dotted lines represents an additional bond, $X^3$ represents C;
$R^{10}$ represents hydrogen or halo;
$R^{11}$ represents hydrogen or halo;
$R^8$ and $R^9$ are linked together to form together with the common carbon atom to which they are attached a 4-, 5-, 6- or 7-membered saturated heterocyclyl, containing one N-atom; wherein said 4-, 5-, 6- or 7-membered saturated heterocyclyl is optionally substituted on one ring N-atom with $C_{1-6}$alkyl;
Z represents —$CH_2$—; and in case $X^3$ represents C, Z can also represent =CH—; the dotted lines attached to $X^3$ are optional bonds that may be present when $X^3$ represents a carbon atom, provided that maximum one of the dotted lines represents an optional bond;
in case one of the dotted lines attached to $X^3$ represents an additional bond, $X^3$ represents C, and (i) $R^{7a}$ is absent or (iii) Z represents =CH—;
Het represents a bicyclic aromatic heterocyclic ring system selected from the group consisting of (a-1);
$R^{3a}$ represents $NH_2$; $R^{4a}$ represents hydrogen;
$Q^1$ represents $CR^{14a}$; $Q^2$ represents $CR^{14b}$;
$R^{14a}$ and $R^{14b}$ each independently are selected from the group consisting of hydrogen and halogen; in particular $R^{14a}$ represents hydrogen;

and pharmaceutically acceptable addition salts, and solvates thereof.

Another embodiment of the present invention relates to those compounds of Formula (I), and pharmaceutically acceptable addition salts, and solvates thereof, or any subgroup thereof as mentioned in any of the other embodiments, wherein one or more of the following restrictions apply:
(i) $R^1$ represents hydrogen;
(ii) Y represents —O— or —$CH_2$—;
(iii) $R^{7b}$ represents hydrogen;
(iv) $X^2$ represents a covalent bond or —$CH_2$—;
(v) $X^3$ represents N; or in case one of the dotted lines represents an additional bond, $X^3$ represents C;
(vi) $R^8$ and $R^{10}$ each independently are selected from the group consisting of hydrogen and halo;
$R^9$ and $R^{11}$ each independently are selected from the group consisting of hydrogen and halo;
or $R^8$ and $R^9$ are linked together to form together with the common carbon atom to which they are attached a 4-, 5-, 6- or 7-membered saturated heterocyclyl, containing one N-atom; wherein said 4-, 5-, 6- or 7-membered saturated heterocyclyl is optionally substituted on one ring N-atom with $C_{1-6}$alkyl;
or $R^{10}$ and $R^{11}$ are linked together to form together with the common carbon atom to which they are attached a 4-, 5-, 6- or 7-membered saturated heterocyclyl, containing one N-atom; wherein said 4-, 5-, 6- or 7-membered saturated heterocyclyl is optionally substituted on one ring N-atom with $C_{1-6}$alkyl;
(vii) Z represents —$CH_2$—; and in case $X^3$ represents C, Z can also represent =CH—; the dotted lines attached to $X^3$ are optional bonds that may be present when $X^3$ represents a carbon atom, provided that maximum one of the dotted lines represents an optional bond;
in case one of the dotted lines attached to $X^3$ represents an additional bond, $X^3$ represents C, and (i) $R^{7a}$ is absent or (ii) $R^8$ is absent or (iii) Z represents =CH—;
(viii) Het represents a bicyclic aromatic heterocyclic ring system selected from the group consisting of (a-1) and (a-2);
(ix) $R^{3a}$ and $R^{3c}$ represent $NH_2$;
(x) $R^{4a}$ and $R^{4c}$ represent hydrogen;
(xi) $Q^1$ represents $CR^{4a}$;
(xii) $Q^2$ represents $CR^{14}b$;
(xiii) $R^{14a}$, $R^{14b}$, $R^{14e}$ and $R^{14f}$ each independently are selected from the group consisting of hydrogen and halogen.

In an embodiment, the present invention relates to those compounds of Formula (I) and pharmaceutically acceptable addition salts, and solvates thereof, or any subgroup thereof as mentioned in any of the other embodiments, wherein $R^a$ and $R^b$ represent hydrogen.

In an embodiment, the present invention relates to those compounds of Formula (I) and pharmaceutically acceptable addition salts, and solvates thereof, or any subgroup thereof as mentioned in any of the other embodiments, wherein $R^a$ represents-C(=O)—$C_{1-4}$alkyl; $R^b$ represents-C(=O)—$C_{1-4}$alkyl.

In an embodiment, the present invention relates to those compounds of Formula (I) and pharmaceutically acceptable addition salts, and solvates thereof, or any subgroup thereof as mentioned in any of the other embodiments, wherein the compounds of Formula (I) are restricted to the compounds of Formula (I-1)

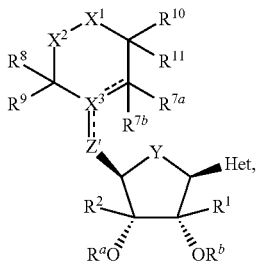

(I-1)

wherein $R^8$ and $R^9$ are always linked together.

In an embodiment, the present invention relates to those compounds of Formula (I) and pharmaceutically acceptable addition salts, and solvates thereof, or any subgroup thereof as mentioned in any of the other embodiments, wherein the compounds of Formula (I) are restricted to the compounds of Formula (I-1), wherein Het represents a bicyclic aromatic heterocyclic ring system selected from the group consisting of (a-1), and wherein $R^8$ and $R^9$ are always linked together.

In an embodiment, the present invention relates to those compounds of Formula (I) and pharmaceutically acceptable addition salts, and solvates thereof, or any subgroup thereof as mentioned in any of the other embodiments, wherein the compounds of Formula (I) are restricted to the compounds of Formula (I-2):

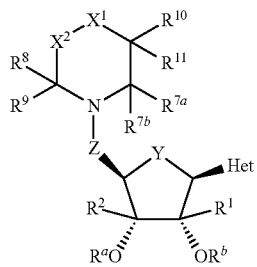

(I-2)

wherein all variables are defined as for compounds of Formula (I) or any subgroup thereof as mentioned in any of the other embodiments.

In an embodiment, the present invention relates to those compounds of Formula (I) and pharmaceutically acceptable addition salts, and solvates thereof, or any subgroup thereof as mentioned in any of the other embodiments, wherein the compounds of Formula (I) are restricted to the compounds of Formula (I-2)

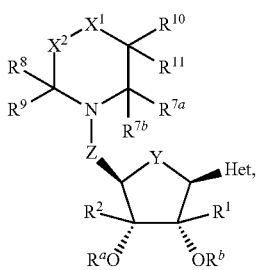

(I-2)

wherein $R^8$ and $R^9$ are always linked together.

In an embodiment, the present invention relates to those compounds of Formula (I) and pharmaceutically acceptable addition salts, and solvates thereof, or any subgroup thereof as mentioned in any of the other embodiments, wherein $R^8$ and $R^9$ are always linked together.

In an embodiment, the present invention relates to those compounds of Formula (I) and pharmaceutically acceptable addition salts, and solvates thereof, or any subgroup thereof as mentioned in any of the other embodiments, wherein the compounds of Formula (I) are restricted to the compounds of Formula (I-3)

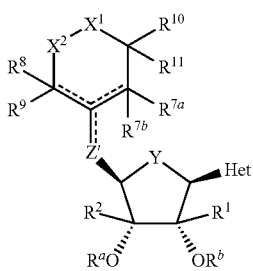

(I-3)

wherein all variables are defined as for compounds of Formula (I) or any subgroup thereof as mentioned in any of the other embodiments.

In an embodiment, the present invention relates to those compounds of Formula (I) and pharmaceutically acceptable addition salts, and solvates thereof, or any subgroup thereof as mentioned in any of the other embodiments, wherein the compounds of Formula (I) are restricted to the compounds of Formula (I-3a)

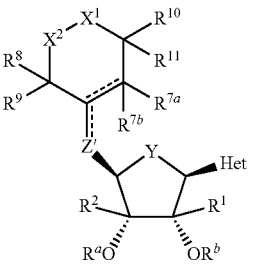

(I-3a)

wherein all variables are defined as for compounds of Formula (I) or any subgroup thereof as mentioned in any of the other embodiments.

In an embodiment, the present invention relates to those compounds of Formula (I) and pharmaceutically acceptable addition salts, and solvates thereof, or any subgroup thereof as mentioned in any of the other embodiments, wherein the compounds of Formula (I) are restricted to the compounds of Formula (I-3a)

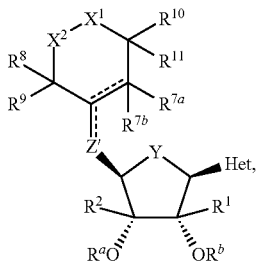

(I-3a)

wherein $R^8$ and $R^9$ are always linked together.

In an embodiment, the present invention relates to those compounds of Formula (I) and pharmaceutically acceptable addition salts, and solvates thereof, or any subgroup thereof as mentioned in any of the other embodiments, wherein the compounds of Formula (I) are restricted to the compounds of Formula (I-3)

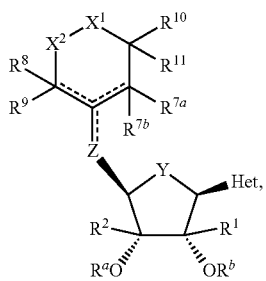

(I-3)

and wherein at least one of the dotted lines represents an additional bond.

In an embodiment, the present invention relates to those compounds of Formula (I) and pharmaceutically acceptable addition salts, and solvates thereof, or any subgroup thereof as mentioned in any of the other embodiments, wherein the compounds of Formula (I) are restricted to the compounds of Formula (I-3a)

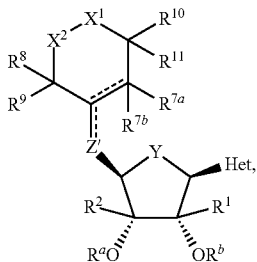

(I-3a)

wherein $R^8$ and $R^9$ are always linked together, and wherein at least one of the dotted lines represents an additional bond.

All variables in the structures of Formula (I-1), (I-2), (I-3) or (I-3a), may be defined as defined for the compounds of Formula (I) or any subgroup thereof as mentioned in any of the other embodiments.

In an embodiment, the present invention relates to those compounds of Formula (I) and pharmaceutically acceptable addition salts, and solvates thereof, or any subgroup thereof as mentioned in any of the other embodiments, wherein at least one of the dotted lines, where possible, represent an additional bond.

In an embodiment, the present invention relates to those compounds of Formula (I) and pharmaceutically acceptable addition salts, and solvates thereof, or any subgroup thereof as mentioned in any of the other embodiments, wherein $X^3$ represents N.

In an embodiment, the present invention relates to those compounds of Formula (I) and pharmaceutically acceptable addition salts, and solvates thereof, or any subgroup thereof as mentioned in any of the other embodiments, wherein $X^3$ represents C or CH.

In an embodiment, the present invention relates to those compounds of Formula (I) and pharmaceutically acceptable addition salts, and solvates thereof, or any subgroup thereof as mentioned in any of the other embodiments, wherein $R^{10}$ and $R^{11}$, or $R^8$ and $R^9$ are linked together.

In an embodiment, the present invention relates to those compounds of Formula (I) and pharmaceutically acceptable addition salts, and solvates thereof, or any subgroup thereof as mentioned in any of the other embodiments, wherein Het represents a bicyclic aromatic heterocyclic ring system selected from the group consisting of (a-1), and wherein $R^8$ and $R^9$ are always linked together.

In an embodiment, the present invention relates to those compounds of Formula (I) and pharmaceutically acceptable addition salts, and solvates thereof, or any subgroup thereof as mentioned in any of the other embodiments, wherein Het represents a bicyclic aromatic heterocyclic ring system selected from the group consisting of (a-1), and wherein $R^{10}$ and $R^{11}$, or $R^8$ and $R^9$ are linked together.

In an embodiment, the present invention relates to those compounds of Formula (I) and pharmaceutically acceptable addition salts, and solvates thereof, or any subgroup thereof as mentioned in any of the other embodiments, wherein $R^8$ and $R^{10}$ each independently are selected from the group consisting of hydrogen; halo; and $C_{1-6}$alkyl optionally substituted with one or more halo atoms;

$R^9$ and $R^{11}$ each independently are selected from the group consisting of hydrogen; halo; $-NH_2$; and $C_{1-6}$alkyl optionally substituted with one $-NR^{9a}R^{9b}$;

or $R^8$ and $R^9$ are linked together to form together with the common carbon atom to which they are attached a 5-, 6- or 7-membered saturated heterocyclyl, containing one or two N-atoms and optionally one oxygen atom; wherein said 5-, 6- or 7-membered saturated heterocyclyl is optionally substituted on one or more ring carbon atoms with one or more substituents each independently selected from the group consisting of halo, and $C_{1-6}$alkyl optionally substituted with one or more halo atoms; and wherein said 5-, 6- or 7-membered saturated heterocyclyl is optionally substituted on one or two ring N-atoms with a substituent selected from the group consisting of $C_{1-6}$alkyl; $Het^{1a}$; $C_{3-6}$cycloalkyl; $-C_{1-4}$alkyl-C(=O)-$NR^{5a}R^{5b}$; $C_{1-4}$alkyl substituted with one or more halo atoms; and $C_{1-4}$alkyl substituted with one substituent selected from the group consisting of $-OC_{1-4}$alkyl, cyano, $C_{3-6}$cycloalkyl, $Ar^{1a}$, $-O-Ar^{1a}$, $Het^{2a}$ and $-O-Het^{2c}$;

or $R^{10}$ and $R^{11}$ are linked together to form together with the common carbon atom to which they are attached a 5-, 6- or 7-membered saturated heterocyclyl, containing one or two N-atoms and optionally one oxygen atom; wherein said 5-, 6- or 7-membered saturated heterocyclyl is optionally substituted on one or more ring carbon atoms with one or more substituents each independently selected from the group consisting of halo, and $C_{1-6}$alkyl optionally substituted with one or more halo atoms; and wherein said 5-, 6- or 7-membered saturated heterocyclyl is optionally substituted on one or two ring N-atoms with a substituent selected from the group consisting of $C_{1-6}$alkyl; $Het^{1b}$; $C_{3-6}$cycloalkyl; —$C_{1-4}$alkyl-C(=O)—$NR^{6a}R^{6b}$; $C_{1-4}$alkyl substituted with one or more halo atoms; and $C_{1-4}$alkyl substituted with one substituent selected from the group consisting of —$OC_{1-4}$alkyl, cyano, $C_{3-6}$cycloalkyl, $Ar^{1b}$, —O—$Ar^{1b}$, $Het^{2b}$ and —O-$Het^{2d}$.

In an embodiment, the present invention relates to those compounds of Formula (I) and pharmaceutically acceptable addition salts, and solvates thereof, or any subgroup thereof as mentioned in any of the other embodiments, wherein
$X^2$ is other than a covalent bond;
$R^8$ and $R^{10}$ each independently are selected from the group consisting of hydrogen; halo; and $C_{1-6}$alkyl optionally substituted with one or more halo atoms;
$R^9$ and $R^{11}$ each independently are selected from the group consisting of hydrogen; halo; —$NH_2$; and $C_{1-6}$alkyl optionally substituted with one-$NR^{9a}R^{9b}$;
or $R^8$ and $R^9$ are linked together to form together with the common carbon atom to which they are attached a 5-, 6- or 7-membered saturated heterocyclyl, containing one or two N-atoms and optionally one oxygen atom; wherein said 5-, 6- or 7-membered saturated heterocyclyl is optionally substituted on one or more ring carbon atoms with one or more substituents each independently selected from the group consisting of halo, and $C_{1-6}$alkyl optionally substituted with one or more halo atoms; and wherein said 5-, 6- or 7-membered saturated heterocyclyl is optionally substituted on one or two ring N-atoms with a substituent selected from the group consisting of $C_{1-4}$alkyl; $Het^{1a}$; $C_{3-6}$cycloalkyl; —$C_{1-6}$alkyl-C(=O)—$NR^{5a}R^{5b}$; $C_{1-4}$alkyl substituted with one or more halo atoms; and $C_{1-6}$alkyl substituted with one substituent selected from the group consisting of —$OC_{1-4}$alkyl, cyano, $C_{3-6}$cycloalkyl, $Ar^{1a}$, —O—$Ar^{1a}$, $Het^{2a}$ and —O-$Het^{2c}$;
or $R^{10}$ and $R^{11}$ are linked together to form together with the common carbon atom to which they are attached a 5-, 6- or 7-membered saturated heterocyclyl, containing one or two N-atoms and optionally one oxygen atom; wherein said 5-, 6- or 7-membered saturated heterocyclyl is optionally substituted on one or more ring carbon atoms with one or more substituents each independently selected from the group consisting of halo, and $C_{1-6}$alkyl optionally substituted with one or more halo atoms; and wherein said 5-, 6- or 7-membered saturated heterocyclyl is optionally substituted on one or two ring N-atoms with a substituent selected from the group consisting of $C_{1-6}$alkyl; $Het^{1b}$; $C_{3-6}$cycloalkyl; —$C_{1-4}$alkyl-C(=O)—$NR^{6a}R^{6b}$; $C_{1-4}$alkyl substituted with one or more halo atoms; and $C_{1-4}$alkyl substituted with one substituent selected from the group consisting of —$OC_{1-4}$alkyl, cyano, $C_{3-6}$cycloalkyl, $Ar^{1b}$, —O—$Ar^{1b}$, $Het^2b$ and —O-$Het^{2d}$.

In an embodiment, the present invention relates to those compounds of Formula (I) and pharmaceutically acceptable addition salts, and solvates thereof, or any subgroup thereof as mentioned in any of the other embodiments, wherein
$X^1$ is a covalent bond;
$X^2$ is other than a covalent bond;
$R^8$ and $R^{10}$ each independently are selected from the group consisting of hydrogen; halo; and $C_{1-6}$alkyl optionally substituted with one or more halo atoms;
$R^9$ and $R^{11}$ each independently are selected from the group consisting of hydrogen; halo; —$NH_2$; and $C_{1-6}$alkyl optionally substituted with one —$NR^{9a}R^{9b}$;

or $R^8$ and $R^9$ are linked together to form together with the common carbon atom to which they are attached a 5-, 6- or 7-membered saturated heterocyclyl, containing one or two N-atoms and optionally one oxygen atom; wherein said 5-, 6- or 7-membered saturated heterocyclyl is optionally substituted on one or more ring carbon atoms with one or more substituents each independently selected from the group consisting of halo, and $C_{1-6}$alkyl optionally substituted with one or more halo atoms; and wherein said 5-, 6- or 7-membered saturated heterocyclyl is optionally substituted on one or two ring N-atoms with a substituent selected from the group consisting of $C_{1-6}$alkyl; $Het^{1a}$; $C_{3-6}$cycloalkyl; —$C_{1-4}$alkyl-C(=O)—$NR^{5a}R^{5b}$; $C_{1-4}$alkyl substituted with one or more halo atoms; and $C_{1-6}$alkyl substituted with one substituent selected from the group consisting of —$OC_{1-4}$alkyl, cyano, $C_{3-6}$cycloalkyl, $Ar^{1a}$, —O—$Ar^{1a}$, $Het^{2a}$ and —O-$Het^{2c}$;
or $R^{10}$ and $R^{11}$ are linked together to form together with the common carbon atom to which they are attached a 5-, 6- or 7-membered saturated heterocyclyl, containing one or two N-atoms and optionally one oxygen atom; wherein said 5-, 6- or 7-membered saturated heterocyclyl is optionally substituted on one or more ring carbon atoms with one or more substituents each independently selected from the group consisting of halo, and $C_{1-6}$alkyl optionally substituted with one or more halo atoms; and wherein said 5-, 6- or 7-membered saturated heterocyclyl is optionally substituted on one or two ring N-atoms with a substituent selected from the group consisting of $C_{1-6}$alkyl; $Het^{1b}$; $C_{3-6}$cycloalkyl; —$C_{1-4}$alkyl-C(=O)—$NR^{6a}R^{6b}$; $C_{1-4}$alkyl substituted with one or more halo atoms; and $C_{1-4}$alkyl substituted with one substituent selected from the group consisting of —$OC_{1-4}$alkyl, cyano, $C_{3-6}$cycloalkyl, $Ar^{1b}$, —O—$Ar^{1b}$, $Het^{2b}$ and —O-$Het^{2d}$.

In an embodiment, the present invention relates to those compounds of Formula (I) and pharmaceutically acceptable addition salts, and solvates thereof, or any subgroup thereof as mentioned in any of the other embodiments, wherein
$X^1$ is a covalent bond;
$X^2$ is other than a covalent bond;
$R^8$ and $R^{10}$ each independently are selected from the group consisting of hydrogen;
halo; and $C_{1-6}$alkyl optionally substituted with one or more halo atoms;
$R^9$ and $R^{11}$ each independently are selected from the group consisting of hydrogen;
halo; —$NH_2$; and $C_{1-6}$alkyl optionally substituted with one —$NR^{9a}R^{9b}$;
or $R^8$ and $R^9$ are linked together to form together with the common carbon atom to which they are attached a 5-, 6- or 7-membered saturated heterocyclyl, containing one or two N-atoms and optionally one oxygen atom; wherein said 5-, 6- or 7-membered saturated heterocyclyl is optionally substituted on one or more ring carbon atoms with one or more substituents each independently selected from the group consisting of halo, and $C_{1-6}$alkyl optionally substituted with one or more halo atoms; and wherein said 5-, 6- or 7-membered saturated heterocyclyl is optionally substituted on one or two ring N-atoms with a substituent selected from the group consisting of $C_{1-6}$alkyl; $Het^{1a}$; $C_{3-6}$cycloalkyl; —$C_{1-4}$alkyl-C(=O)—$NR^{5a}R^{5b}$; $C_{1-4}$alkyl substituted with one or more halo atoms; and $C_{1-4}$alkyl substituted with one substituent selected from the group consisting of —$OC_{1-4}$alkyl, cyano, $C_{3-6}$cycloalkyl, $Ar^{1a}$, —O—$Ar^{1a}$, $Het^{2a}$ and —O-$Het^{2c}$;
or $R^{10}$ and $R^{11}$ are linked together to form together with the common carbon atom to which they are attached a 5-, 6- or 7-membered saturated heterocyclyl, containing one or two N-atoms and optionally one oxygen atom; wherein said 5-, 6- or 7-membered saturated heterocyclyl is optionally substituted on one or more ring carbon atoms with one or more substituents each independently selected from the group consisting of halo, and $C_{1-4}$alkyl optionally substituted with one or more halo atoms; and wherein said 5-, 6- or 7-membered saturated heterocyclyl is optionally substituted on one or two ring N-atoms with a substituent selected from the group consisting of $C_{1-6}$alkyl; Het$^{1b}$; $C_{3-6}$cycloalkyl; —$C_{1-4}$alkyl-C(=O)—NR$^{6a}$R$^{6b}$; $C_{1-4}$alkyl substituted with one or more halo atoms; and $C_{1-4}$alkyl substituted with one substituent selected from the group consisting of —O$C_{1-4}$alkyl, cyano, $C_{3-6}$cycloalkyl, Ar$^{1b}$, —O—Ar$^{1b}$, Het$^{2b}$ and —O-Het$^{2d}$; Het represents (a-1).

In an embodiment, the present invention relates to those compounds of Formula (I) and pharmaceutically acceptable addition salts, and solvates thereof, or any subgroup thereof as mentioned in any of the other embodiments, wherein
$X^1$ is a covalent bond;
$X^2$ is other than a covalent bond;
$R^8$ and $R^9$ are linked together to form together with the common carbon atom to which they are attached a 5-, 6- or 7-membered saturated heterocyclyl, containing one or two N-atoms and optionally one oxygen atom; wherein said 5-, 6- or 7-membered saturated heterocyclyl is optionally substituted on one or more ring carbon atoms with one or more substituents each independently selected from the group consisting of halo, and $C_{1-6}$alkyl optionally substituted with one or more halo atoms; and wherein said 5-, 6- or 7-membered saturated heterocyclyl is optionally substituted on one or two ring N-atoms with a substituent selected from the group consisting of $C_{1-6}$alkyl; Het$^{1a}$; $C_{3-6}$cycloalkyl; —$C_{1-4}$alkyl-C(=O)—NR$^{5a}$R$^{5b}$; $C_{1-4}$alkyl substituted with one or more halo atoms; and $C_{1-4}$alkyl substituted with one substituent selected from the group consisting of —O$C_{1-4}$alkyl, cyano, $C_{3-6}$cycloalkyl, Ar$^{1a}$, —O—Ar$^{1a}$, Het$^{2a}$ and —O-Het$^{2c}$;
$R^{10}$ is selected from the group consisting of hydrogen; halo; and $C_{1-6}$alkyl optionally substituted with one or more halo atoms;
$R^{11}$ is selected from the group consisting of hydrogen; halo; —NH$_2$; and $C_{1-6}$alkyl optionally substituted with one —NR$^{9a}$R$^{9b}$;
Het represents (a-1).

In an embodiment, the present invention relates to those compounds of Formula (I) and pharmaceutically acceptable addition salts, and solvates thereof, or any subgroup thereof as mentioned in any of the other embodiments, wherein $X^1$ represents a covalent bond.

In an embodiment, the present invention relates to those compounds of Formula (I) and pharmaceutically acceptable addition salts, and solvates thereof, or any subgroup thereof as mentioned in any of the other embodiments, wherein all 4-, 5-, 6- or 7-membered saturated heterocyclyls are restricted to 5-, 6- or 7-membered saturated heterocyclyls, each of which may be optionally substituted according to any of the other embodiments; $X^1$ represents a covalent bond; and Het represents (a-1).

In an embodiment, the present invention relates to those compounds of Formula (I) and pharmaceutically acceptable addition salts, and solvates thereof, or any subgroup thereof as mentioned in any of the other embodiments, wherein Y represents —CH$_2$— or —CF$_2$—; in particular wherein Y represents —CH$_2$—.

In an embodiment, the present invention relates to those compounds of Formula (I) and pharmaceutically acceptable addition salts, and solvates thereof, or any subgroup thereof as mentioned in any of the other embodiments, wherein maximum one of $Q^1$ and $Q^2$ represents N.

In an embodiment, the present invention relates to those compounds of Formula (I) and pharmaceutically acceptable addition salts, and solvates thereof, or any subgroup thereof as mentioned in any of the other embodiments, wherein $Q^1$ represents CR$^{14a}$; and $Q^2$ represents CR$^{14a}$; in particular wherein $Q^1$ represents CH; and $Q^2$ represents CH.

In an embodiment, the present invention relates to those compounds of Formula (I) and pharmaceutically acceptable addition salts, and solvates thereof, or any subgroup thereof as mentioned in any of the other embodiments, wherein Het represents (a-1); $Q^1$ represents CR$^{14a}$; and $Q^2$ represents CR$^{14b}$; in particular wherein $Q^1$ represents CH; and $Q^2$ represents CH.

In an embodiment, the present invention relates to those compounds of Formula (I) and pharmaceutically acceptable addition salts, and solvates thereof, or any subgroup thereof as mentioned in any of the other embodiments, wherein $R^1$ and $R^2$ represent hydrogen; and Y represents —O—.

In an embodiment, the present invention relates to those compounds of Formula (I) and pharmaceutically acceptable addition salts, and solvates thereof, or any subgroup thereof as mentioned in any of the other embodiments, wherein $R^a$ and $R^b$ represent hydrogen; and Y represents —O—.

In an embodiment, the present invention relates to those compounds of Formula (I) and pharmaceutically acceptable addition salts, and solvates thereof, or any subgroup thereof as mentioned in any of the other embodiments, wherein $R^a$ and $R^b$ represent hydrogen; $R^1$ and $R^2$ represent hydrogen; and Y represents —O—.

In an embodiment, the present invention relates to those compounds of Formula (I) and pharmaceutically acceptable addition salts, and solvates thereof, or any subgroup thereof as mentioned in any of the other embodiments, wherein Het represents a bicyclic aromatic heterocyclic ring system selected from the group consisting of (a-1) and (a-2).

In an embodiment, the present invention relates to those compounds of Formula (I) and pharmaceutically acceptable addition salts, and solvates thereof, or any subgroup thereof as mentioned in any of the other embodiments, wherein Het represents a bicyclic aromatic heterocyclic ring system of Formula (a-1).

In an embodiment, the present invention relates to any one of the compounds of Formula (I-1), (I-2), (I-3) or (I-3a), wherein Het represents a bicyclic aromatic heterocyclic ring system selected from the group consisting of (a-1) and (a-2), in particular wherein Het represents a bicyclic aromatic heterocyclic ring system of Formula (a-1).

In an embodiment, the present invention relates to those compounds of Formula (I) and pharmaceutically acceptable addition salts, and solvates thereof, or any subgroup thereof as mentioned in any of the other embodiments, wherein
Het represents a bicyclic aromatic heterocyclic ring system selected from the group consisting of (a-1), (a-2), (a-3) and (a-4);
$R^{3a}$, $R^{3b}$, $R^{3c}$ and $R^{3d}$ each independently are selected from the group consisting of hydrogen, halo, and —NR$^{12a}$R$^{12b}$;
$R^{12a}$ and $R^{12b}$ each independently are selected from the group consisting of hydrogen; $C_{3-6}$cycloalkyl; $C_{1-4}$alkyl; and $C_{1-4}$alkyl substituted with one phenyl which is optionally substituted with one or more halo substituents;
$R^{4a}$, $R^{4b}$, $R^{4c}$ and $R^{4d}$ each independently are selected from the group consisting of hydrogen and $C_{1-4}$alkyl;
$R^{4f}$ represent hydrogen;
$Q^1$ represents CR$^{14a}$;

$Q^2$ represents N or $CR^{14b}$;
$Q^3$ represents $CR^{14c}$;
$Q^4$ represents N;
$Q^8$ represents $CR^{14g}$;
$Q^9$ represents $CR^{14h}$;
$Q^5$ represents $CR^{3d}$; $Q^6$ represents N; and $Q^7$ represents $CR^{4f}$;
$R^{14a}$, $R^{14b}$, $R^{14c}$, $R^{14e}$ and $R^{14f}$ each independently are selected from the group consisting of hydrogen and halogen; $R^{14g}$ and $R^{14h}$ represent hydrogen.

In an embodiment, the present invention relates to those compounds of Formula (I) and pharmaceutically acceptable addition salts, and solvates thereof, or any subgroup thereof as mentioned in any of the other embodiments, wherein $R^1$ and $R^2$ represent hydrogen.

In an embodiment, the present invention relates to those compounds of Formula (I) and pharmaceutically acceptable addition salts, and solvates thereof, or any subgroup thereof as mentioned in any of the other embodiments, wherein $R^1$ and $R^2$ represent hydrogen; Y represents —O—; and Het represents a bicyclic aromatic heterocyclic ring system of Formula (a-1).

In an embodiment, the present invention relates to those compounds of Formula (I) and pharmaceutically acceptable addition salts, and solvates thereof, or any subgroup thereof as mentioned in any of the other embodiments, wherein $R^a$ and $R^b$ represent hydrogen; Y represents —O—; and Het represents a bicyclic aromatic heterocyclic ring system of Formula (a-1).

In an embodiment, the present invention relates to those compounds of Formula (I) and pharmaceutically acceptable addition salts, and solvates thereof, or any subgroup thereof as mentioned in any of the other embodiments, wherein $R^a$ and $R^b$ represent hydrogen; $R^1$ and $R^2$ represent hydrogen; Y represents —O—; and Het represents a bicyclic aromatic heterocyclic ring system of Formula (a-1).

In an embodiment, the present invention relates to those compounds of Formula (I) and pharmaceutically acceptable addition salts, and solvates thereof, or any subgroup thereof as mentioned in any of the other embodiments, wherein $R^{3a}$, $R^{3c}$, $R^{3b}$ represent hydrogen; and $R^{4a}$, $R^{4c}$, $R^{4b}$ represent hydrogen, halo, or $C_{1-6}$alkyl; in particular $R^{4a}$, $R^{4c}$, $R^{4b}$ represent halo, or $C_{1-4}$alkyl.

In an embodiment, the present invention relates to those compounds of Formula (I) and pharmaceutically acceptable addition salts, and solvates thereof, or any subgroup thereof as mentioned in any of the other embodiments, wherein $R^{3a}$, $R^{3C}$, $R^{3b}$ represent hydrogen, halo, $-NR^{12a}R^{12b}$, or $-O-C_{1-4}$alkyl; in particular $R^{3a}$, $R^{3c}$, $R^{3b}$ represent halo, $-NR^{12a}R^{12b}$, or $-O-C_{1-4}$alkyl; $R^{4a}$, $R^{4c}$, $R^{4b}$ represent hydrogen.

In an embodiment, the present invention relates to those compounds of Formula (I) and pharmaceutically acceptable addition salts, and solvates thereof, or any subgroup thereof as mentioned in any of the other embodiments, wherein $R^{3a}$, $R^{3c}$, $R^{3b}$ represent hydrogen, when $R^{4a}$, $R^{4c}$, $R^{4b}$ are different from hydrogen.

In an embodiment, the present invention relates to those compounds of Formula (I) and pharmaceutically acceptable addition salts, and solvates thereof, or any subgroup thereof as mentioned in any of the other embodiments, wherein $R^{4a}$, $R^{4c}$, $R^{4b}$ represent hydrogen, when $R^{3a}$, $R^{3c}$, $R^{3b}$ are different from hydrogen.

In an embodiment, the present invention relates to those compounds of Formula (I) and pharmaceutically acceptable addition salts, and solvates thereof, or any subgroup thereof as mentioned in any of the other embodiments, wherein $=R^{7a}$ and $R^{7b}$ represent hydrogen.

In an embodiment, the present invention relates to those compounds of Formula (I) and pharmaceutically acceptable addition salts, and solvates thereof, or any subgroup thereof as mentioned in any of the other embodiments, wherein Het represents (a-1); $R^{3a}$ represents $-NR^{12a}R^{12b}$; and $R^{12a}$ and $R^{12b}$ represent hydrogen.

In an embodiment, the present invention relates to those compounds of Formula (I) and pharmaceutically acceptable addition salts, and solvates thereof, or any subgroup thereof as mentioned in any of the other embodiments, wherein $R^{3a}$, $R^{3b}$ and $R^{3c}$ represent other than halo.

In an embodiment, the present invention relates to those compounds of Formula (I) and pharmaceutically acceptable addition salts, and solvates thereof, or any subgroup thereof as mentioned in any of the other embodiments, wherein $R^{3a}$, $R^{3b}$ and $R^{3c}$ represent $-NH_2$.

In an embodiment, the present invention relates to those compounds of Formula (I) and pharmaceutically acceptable addition salts, and solvates thereof, or any subgroup thereof as mentioned in any of the other embodiments, wherein $Het^{2a}$, $Het^{2b}$, $Het^{2c}$ and $Het^{2d}$ are aromatic.

In an embodiment, the present invention relates to a subgroup of Formula (I) as defined in the general reaction schemes.

In an embodiment the compound of Formula (I) is selected from the group consisting of compounds 19, 29, 74, 94, 95a, 95b, 101, 107, 108, 166, 167, 178, 179, 181, 206 and 207.

In an embodiment the compound of Formula (I) is selected from the group consisting of compounds 19, 29, 74, 94, 95a, 95b, 101, 107, 108, 166, 167, 178, 179, 181, 206 and 207, and pharmaceutically acceptable addition salts, the free bases, and solvates thereof.

In an embodiment the compound of Formula (I) is selected from the group consisting of any of the exemplified compounds, and the free bases, the pharmaceutically acceptable addition salts, and the solvates thereof.

All possible combinations of the above-indicated embodiments are considered to be embraced within the scope of this invention.

Methods for the Preparation

In this section, as in all other sections unless the context indicates otherwise, references to formula (I) also include all other sub-groups and examples thereof as defined herein.

The general preparation of some typical examples of the compounds of Formula (I) is described hereunder and in the specific examples, and are generally prepared from starting materials which are either commercially available or prepared by standard synthetic processes commonly used by those skilled in the art. The following schemes are only meant to represent examples of the invention and are in no way meant to be a limit of the invention.

Alternatively, compounds of the present invention may also be prepared by analogous reaction protocols as described in the general schemes below, combined with standard synthetic processes commonly used by those skilled in the art of organic chemistry.

The skilled person will realize that in the reactions described in the Schemes, it may be necessary to protect reactive functional groups, for example hydroxy, amino, or carboxy groups, where these are desired in the final product, to avoid their unwanted participation in the reactions. Conventional protecting groups can be used in accordance with standard practice. This is illustrated in the specific examples.

The skilled person will realize that in the reactions described in the Schemes, it may be advisable or necessary to perform the reaction under an inert atmosphere, such as for example under N₂-gas atmosphere, for example when NaH is used in the reaction.

It will be apparent for the skilled person that it may be necessary to cool the reaction mixture before reaction work-up (refers to the series of manipulations required to isolate and purify the product(s) of a chemical reaction such as for example quenching, column chromatography, extraction).

The skilled person will realize that heating the reaction mixture under stirring may enhance the reaction outcome. In some reactions microwave heating may be used instead of conventional heating to shorten the overall reaction time.

The skilled person will realize that another sequence of the chemical reactions shown in the Schemes below, may also result in the desired compound of formula (I).

The skilled person will realize that intermediates and final compounds shown in the schemes below may be further functionalized according to methods well-known by the person skilled in the art. For example, a primary or secondary amine group may be reductively alkylated by reaction with an aldehyde or a keton in the presence of a suitable reducing reagent such as for example sodium triacetoxyborohydride (NaBH(AcO)₃) together with a suitable solvent such as for example DCM at a suitable temperature such as for example room temperature; or alternatively in the presence of NaBH₃CN together with a suitable solvent such as for example MeOH at a suitable temperature such as for example between room temperature and 50° C.

The skilled person will understand that analogous chemistry as described in Schemes 1 to 6, may also be applied to make compounds of Formula (I) wherein Het represents a bicyclic aromatic heterocyclic ring system (a-4). Some typical examples are illustrated in the specific examples. In addition, this information may be combined with standard synthetic processes commonly used by those skilled in the art of organic chemistry to obtain more compounds of Formula (I) wherein Het represents (a-4).

The skilled person will realize that more Compounds of formula (I) can be prepared by using similar synthetic protocols as described in the Schemes below.

In case one of the starting materials is available as a salt form, the skilled person will realize that it may be necessary to first treat the salt with a base, such as for example N,N-diisopropylethylamine (DIPEA).

All variables are defined as mentioned hereabove unless otherwise is indicated or is clear from the context.

In general, compounds of formula (I) wherein X³ represents N, wherein R and RP are hydrogen, and wherein Het is as shown in the scheme below, can be prepared according to Scheme 1:

Scheme 1:

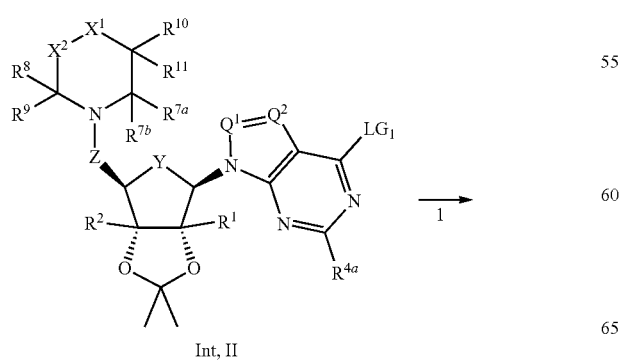

Int, II

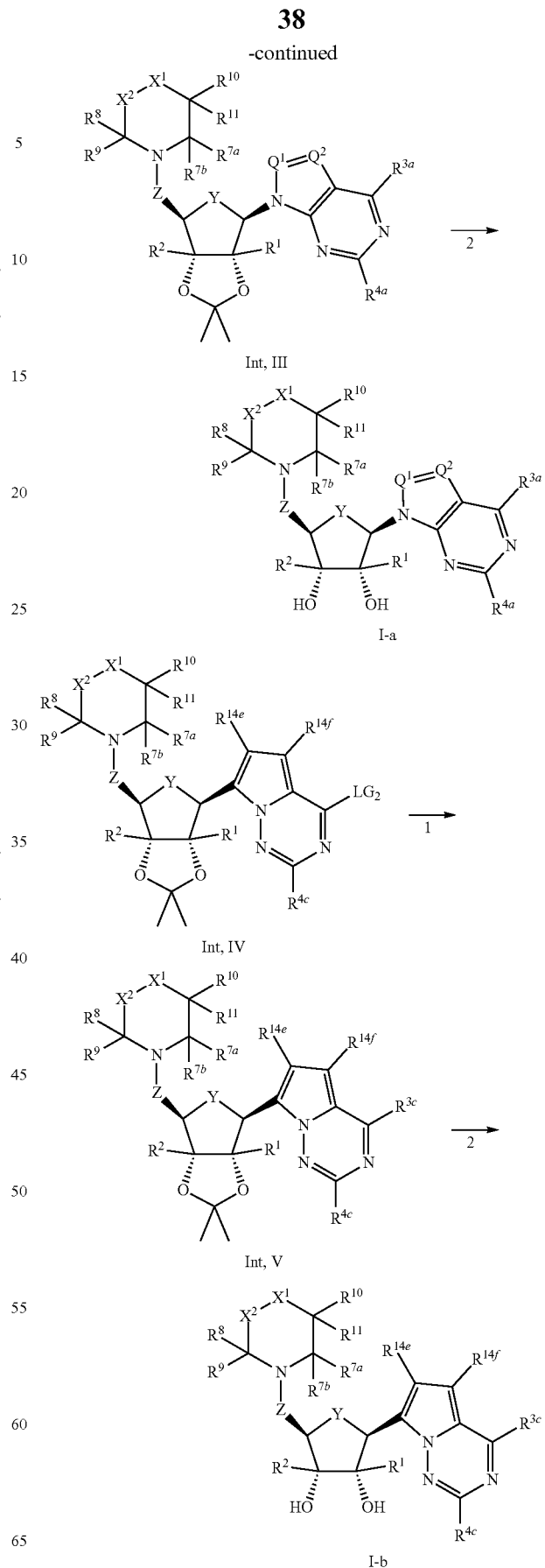

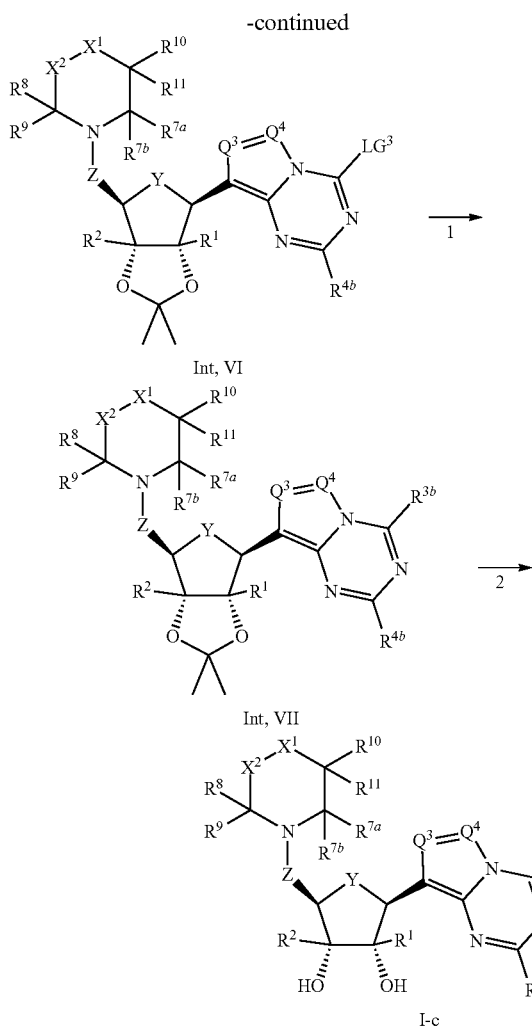

Int, VI

Int, VII

I-c

In scheme 1, 'LG$_1$' is defined as a leaving group such as halogen; 'LG$_2$' is defined as leaving group such as halogen or —SCH$_3$; 'LG$_3$' is defined as leaving group such as halogen or —SCH$_3$. All other variables in Scheme 1 are defined according to the scope of the present invention.

In scheme 1, the following reaction conditions typically apply:
1: Different sets of reaction conditions dependent on the definition of R$^{3a}$, R$^{3b}$ or R$^{3c}$:
1a: When R$^{3a}$, R$^{3b}$ or R$^{3c}$ is halogen, step 1 can be skipped.
1b: When R$^{3a}$, R$^{3b}$ or R$^{3c}$ is NR$^{12a}$R$^{12b}$, in the presence of a suitable amine of formula HNR$^{12a}$R$^{12b}$, with a suitable solvent such as for example, H$_2$O, methanol (MeOH), or ethanol (EtOH), at a suitable temperature such as for example between 100-130° C. typically under microwave conditions or using an autoclave vessel for heating.
1c: When R$^{3a}$, R$^{3b}$ or R$^{3c}$ is —O—C$_{1-4}$alkyl, in the presence of a suitable HO—C$_{1-6}$alkyl, with a suitable base such as for example NaH, potassium tert-butoxide (tBuOK) in a suitable solvent such as for example tetrahydrofuran (THF) at a suitable temperature. Alternatively in the presence of the suitable HO—C$_{1-4}$alkyl as solvent with a suitable acid such as for example HCl.
1d: When R$^{3a}$, R$^{3b}$ or R$^{3c}$ is hydrogen, under hydrogenation conditions: H$_2$-gas atmosphere in the presence of a catalyst such as for example Raney Ni, Pd/C (for example wt % or 10 wt %) or Pt/C (for example 5 wt %) in a suitable solvent such as for example methanol (MeOH), ethanol (EtOH) or THF.
1e: When R$^{3a}$, R$^{3b}$ or R$^{3c}$ is C$_{1-4}$alkyl, in the presence of a suitable boronic acid or ester such as for example methylboronic acid, with a suitable catalyst such as for example 1,1'-bis(diphenylphosphino)ferrocene, and with a suitable base such as for example K$_3$PO$_4$ in a in a suitable solvent or solvent mixture such as for example dioxane/H$_2$O typically in a 5 to 1 ratio at a suitable temperature such as for example between 80-100° C.
2: in the presence of a suitable acid, such as for example 4M HCl in dioxane or 4M HCl in MeOH, with a suitable solvent such as for example MeOH at a suitable temperature such as for example room temperature; or alternatively in the presence of a suitable acid such as for example trifluoroacetic acid (TFA) in dichloromethane (DCM) at a suitable temperature, or acetic acid in THF and water at a suitable temperature such as for example room temperature.

The starting materials in scheme 1 are commercially available or can be prepared by standard means obvious to those skilled in the art or as described in following general schemes.

In general, intermediates of Formula II, IV and VI wherein Z represents —CH$_2$— can be prepared according to Scheme 2a. All other variables in Scheme 2a are defined according to the scope of the present invention.

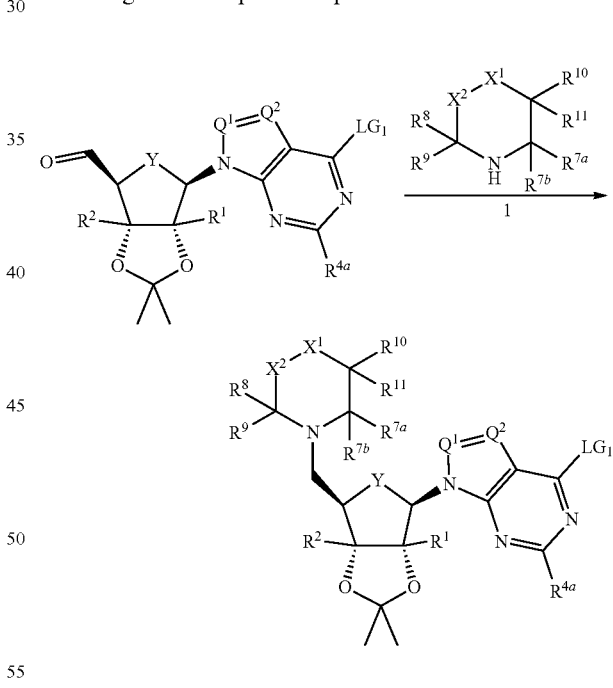

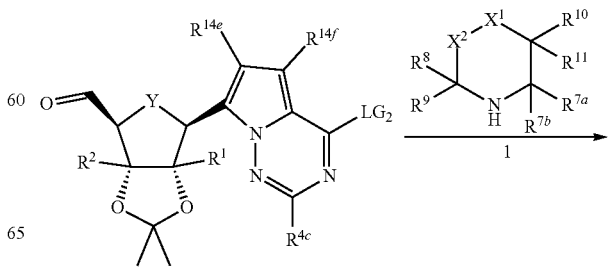

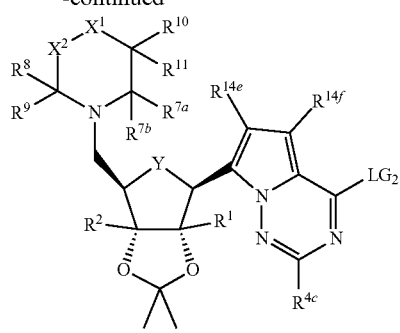

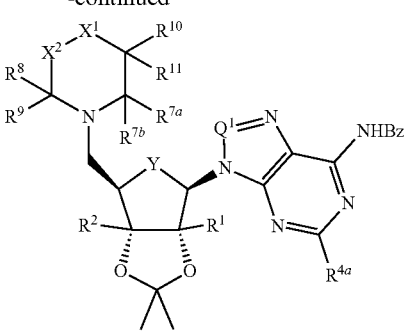

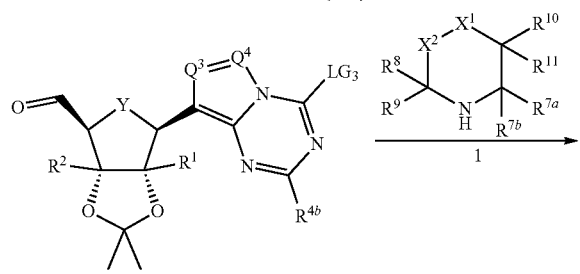

In scheme 2b, the following reaction conditions apply:

1: in the presence of a suitable reduction reagent such as for example sodium triacetoxyborohydride (NaBH(AcO)$_3$) together with a suitable solvent such as for example DCM at a suitable temperature such as for example room temperature; or alternatively, NaBH$_3$CN together with a suitable solvent such as for example MeOH at a suitable temperature such as for example between room temperature and 50° C.

In general, intermediates of Formula II, IV and VI wherein Z represents —C(=O)— can be prepared according to scheme 3. All other variables in Scheme 3 are defined as before or according to the scope of the present invention.

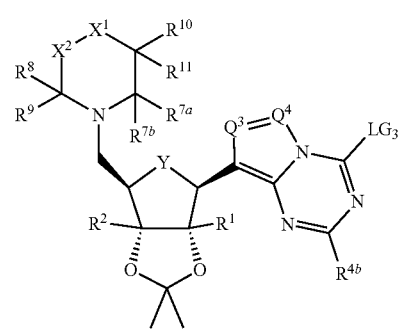

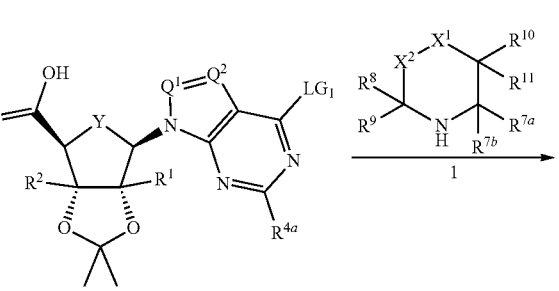

In scheme 2a, the following reaction conditions apply:

1: in the presence of a suitable reduction reagent such as for example sodium triacetoxyborohydride (NaBH(AcO)$_3$) together with a suitable solvent such as for example DCM at a suitable temperature such as for example room temperature; or alternatively NaBH$_3$CN together with a suitable solvent such as for example MeOH at a suitable temperature such as for example between room temperature and 50° C.

Alternatively, intermediate of Formula II wherein Z represents —CH$_2$—, R$^{3a}$ represents NHBz (Bz is benzoyl) and Het is as shown in the scheme below, can be prepared according to scheme 2b. All other variables in Scheme 2b are defined according to the scope of the present invention.

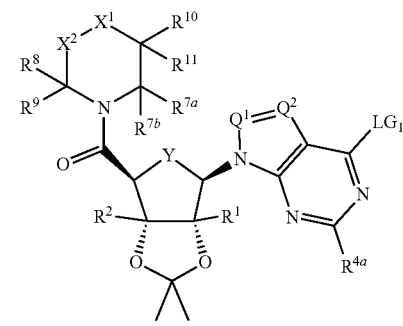

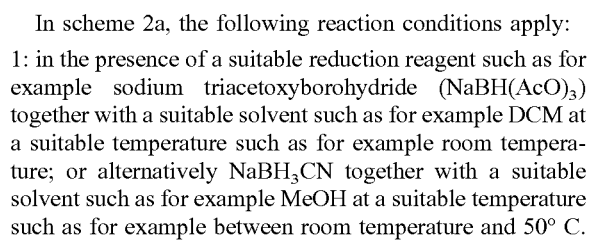

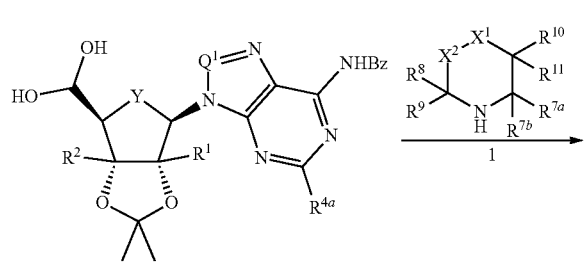

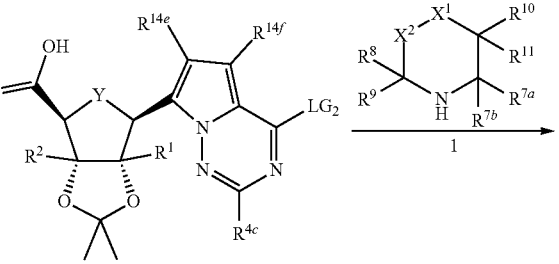

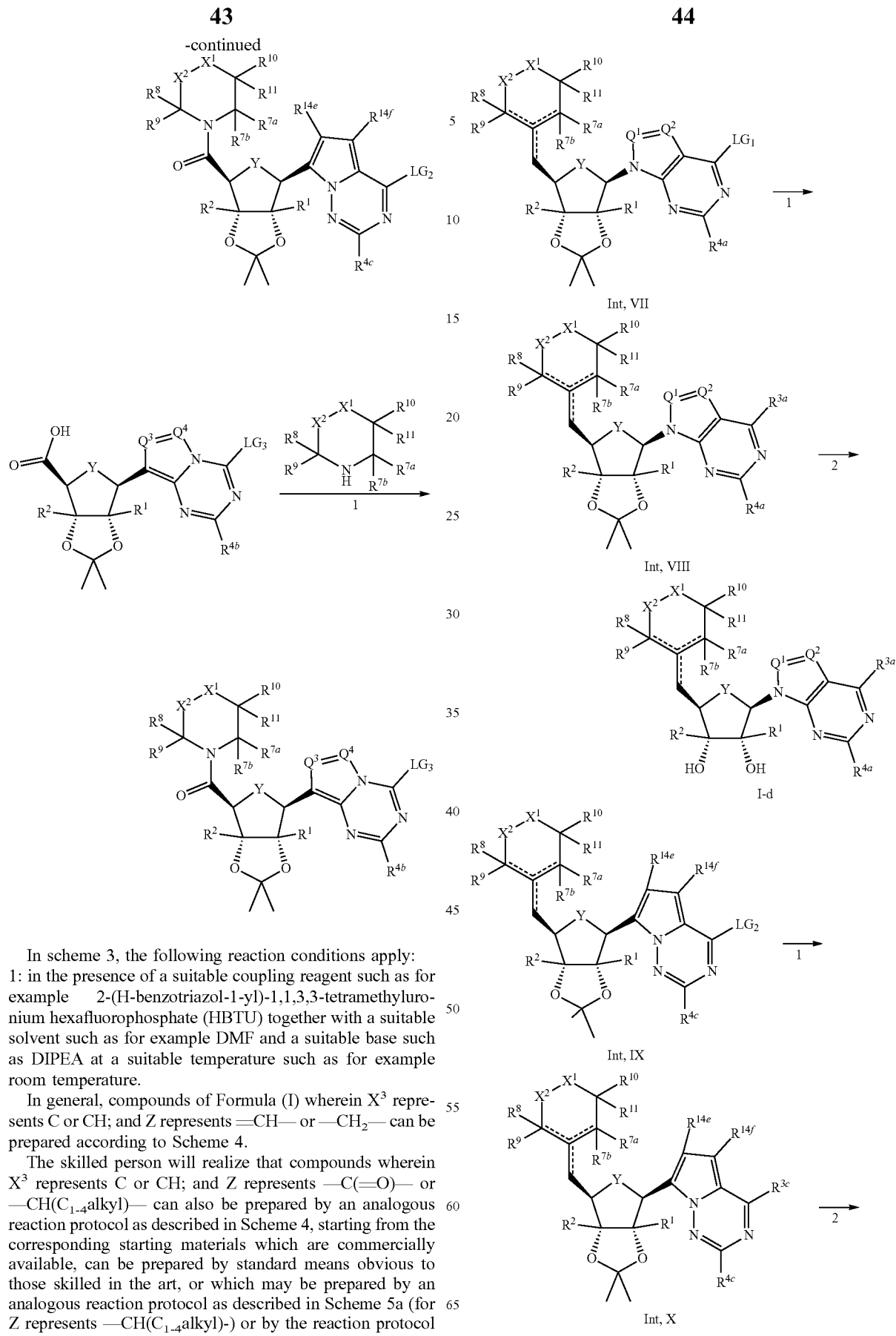

In scheme 3, the following reaction conditions apply:
1: in the presence of a suitable coupling reagent such as for example 2-(H-benzotriazol-1-yl)-1,1,3,3-tetramethyluronium hexafluorophosphate (HBTU) together with a suitable solvent such as for example DMF and a suitable base such as DIPEA at a suitable temperature such as for example room temperature.

In general, compounds of Formula (I) wherein $X^3$ represents C or CH; and Z represents =CH— or —CH$_2$— can be prepared according to Scheme 4.

The skilled person will realize that compounds wherein $X^3$ represents C or CH; and Z represents —C(=O)— or —CH(C$_{1-4}$alkyl)— can also be prepared by an analogous reaction protocol as described in Scheme 4, starting from the corresponding starting materials which are commercially available, can be prepared by standard means obvious to those skilled in the art, or which may be prepared by an analogous reaction protocol as described in Scheme 5a (for Z represents —CH(C$_{1-4}$alkyl)-) or by the reaction protocol as described in Scheme 5b (for Z represents —C(=O)—).

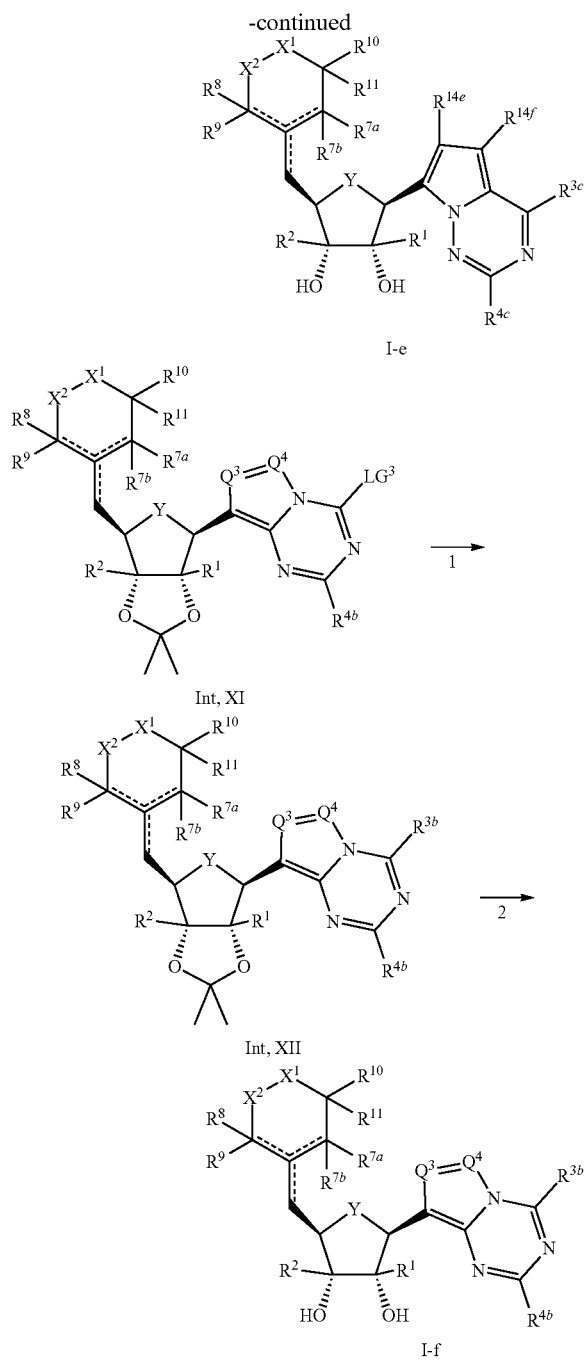

example between 100-130° C. typically under microwave conditions or using an autoclave vessel for heating.

1c: When $R^{3a}$, $R^{3b}$ or $R^{3c}$ is —O—$C_{1-4}$alkyl, in the presence of a suitable HO—$C_{1-6}$alkyl, with a suitable base such as for example NaH, potassium tert-butoxide (tBuOK) in a suitable solvent such as for example tetrahydrofuran (THF) at a suitable temperature. Alternatively in the presence of the suitable HO—$C_{1-4}$alkyl as solvent with a suitable acid such as for example HCl.

1d: When $R^{3a}$, $R^{3b}$ or $R^{3c}$ is hydrogen, under hydrogenation conditions: $H_2$-gas atmosphere in the presence of a catalyst such as for example Raney Ni, Pd/C (for example wt % or 10 wt %) or Pt/C (for example 5 wt %) in a suitable solvent such as for example methanol (MeOH), ethanol (EtOH) or THF.

1e: When $R^{3a}$, $R^{3b}$ or $R^{3c}$ is $C_{1-4}$alkyl, in the presence of a suitable boronic acid or ester such as for example methylboronic acid, with a suitable catalyst such as for example 1,1'-bis(diphenylphosphino)ferrocene, and with a suitable base such as for example $K_3PO_4$ in a in a suitable solvent or solvent mixture such as for example dioxane/$H_2O$ typically in a 5 to 1 ratio at a suitable temperature such as for example between 80-100° C.

2: in the presence of a suitable acid, such as for example 4M HCl in dioxane or 4M HCl in MeOH, with a suitable solvent such as for example MeOH at a suitable temperature such as for example room temperature; or alternatively in the presence of a suitable acid such as for example trifluoroacetic acid (TFA) in dichloromethane (DCM) at a suitable temperature, or acetic acid in THF and water at a suitable temperature such as for example room temperature.

The starting materials in scheme 4 are commercially available or can be prepared by standard means obvious to those skilled in the art or as described in following general scheme 5a. The skilled person will realize that an analogous reaction protocol can be used to prepare the corresponding intermediates wherein Z represents —CH($C_{1-4}$alkyl)-.

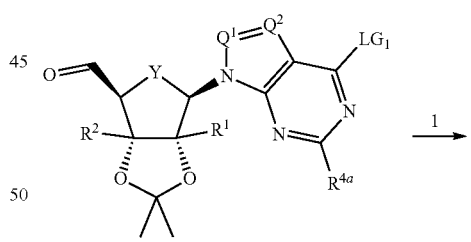

In scheme 4, '$LG_1$' is defined as a leaving group such as halogen; '$LG_2$' is defined as leaving group such as halogen or —$SCH_3$; '$LG_3$' is defined as leaving group such as halogen or —$SCH_3$. All other variables in Scheme 4 are defined according to the scope of the present invention.

In scheme 4, the following reaction conditions typically apply:
1: Different sets of reaction conditions dependent on the definition of $R^{3a}$, $R^{3b}$ or $R^{3c}$:
1a: When $R^{3a}$, $R^{3b}$ or $R^{3c}$ is halogen, step 4 can be skipped.
1b: When $R^{3a}$, $R^{3b}$ or $R^{3c}$ is $NR^{12a}R^{12b}$, in the presence of a suitable amine of formula $HNR^{12a}R^{12b}$, with a suitable solvent such as for example, $H_2O$, methanol (MeOH), or ethanol (EtOH), at a suitable temperature such as for

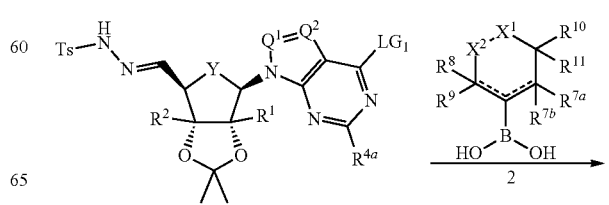

-continued

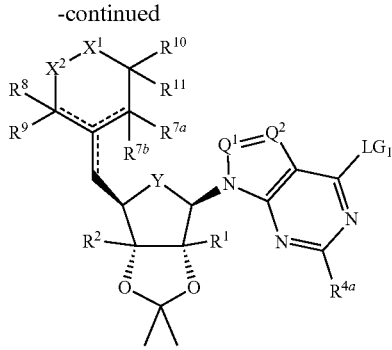

Int, VII

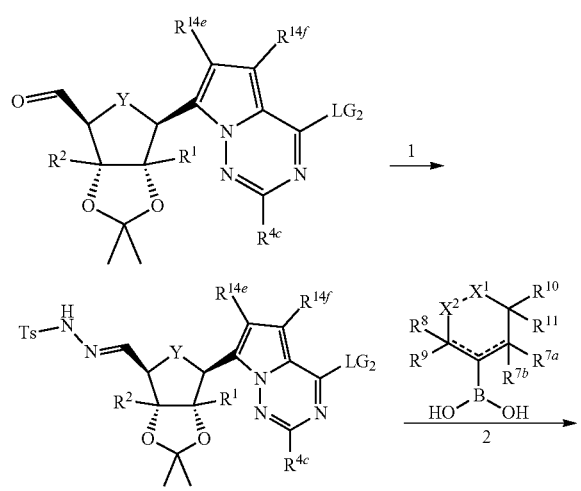

Int, IX

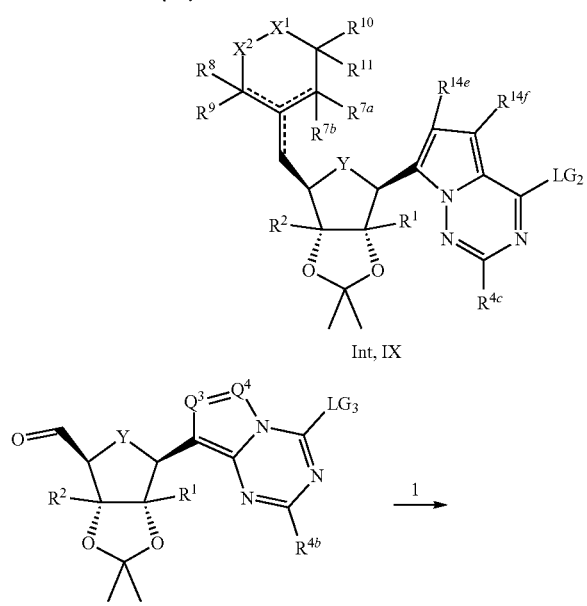

-continued

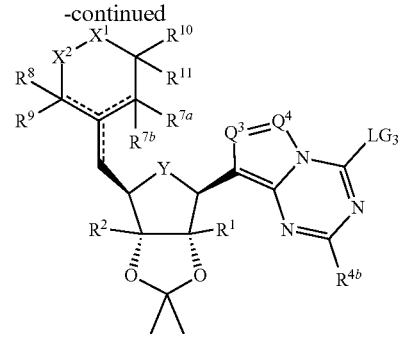

Int, XI

In scheme 5a the following reaction conditions apply:
1: in the presence of p-toluenesulfone hydrazide together with a suitable solvent such as MeOH at a suitable temperature such as for example room temperature.
2: in the presence of a suitable boronic acid together with a suitable solvent such as 1,4 dioxane and a suitable base such as $K_2CO_3$ at a suitable temperature such as for example 110° C.

In general, intermediates of Formula VII-a, IX-a and XI-a, wherein $X^3$ represents C or CH; and Z represents —C(=O)— can be prepared according to Scheme 5b wherein the other variables are defined as before or according to the scope. The skilled person will realize that the intermediates of Formula VII-a, IX-a and XI-a can be further reacted in an analogous reaction protocol as described in Scheme 4 to obtain the corresponding final compounds.

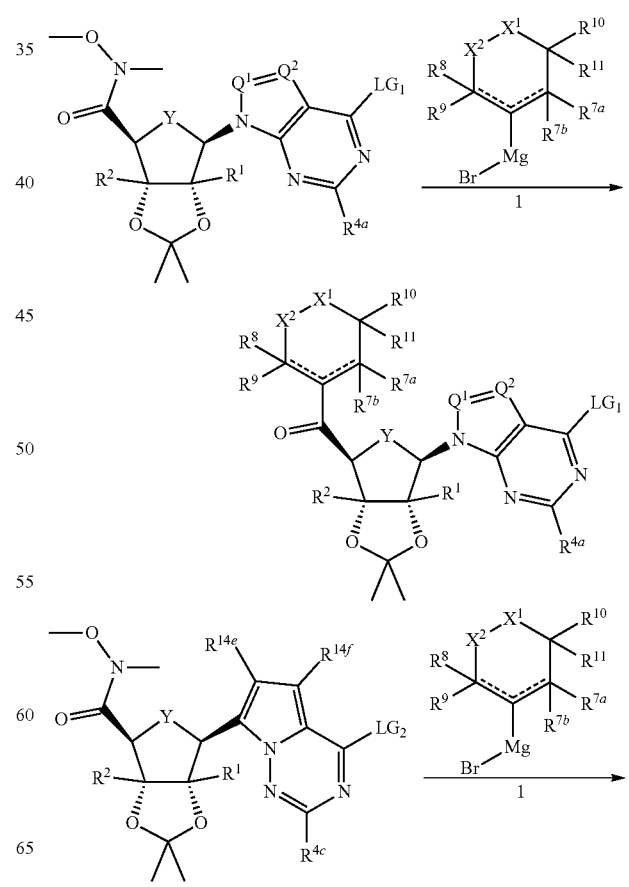

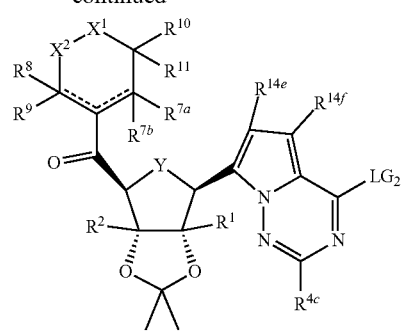
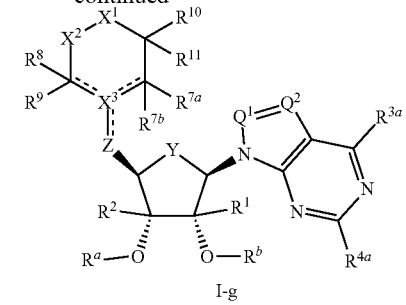
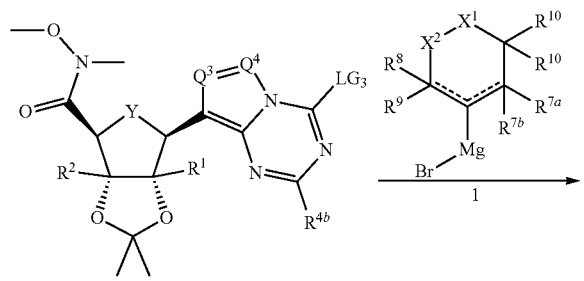
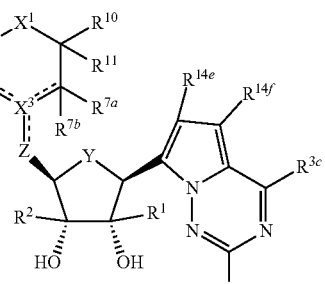
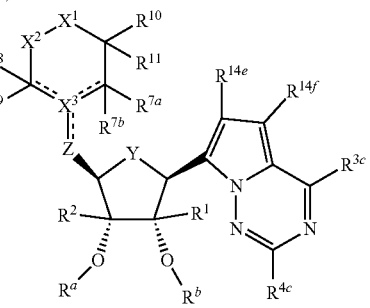
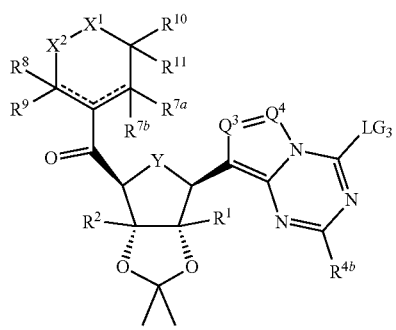
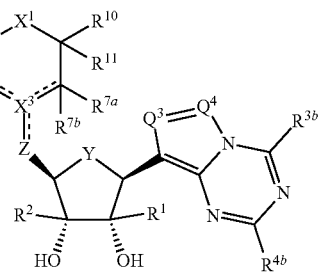

In scheme 5b, the following reaction conditions apply:

1: in the presence of a suitable solvent such as for example THF and a suitable temperature such as for example −40° C.

In general, compounds of formula (I) wherein $R^a$ and/or $R^b$ represents —C(=O)—$C_{1-4}$alkyl and $R^{3a}$, $R^{3b}$ and $R^{3c}$ each independently represent hydrogen, halo $NR^{12a}R^{12b}$, $C_{1-4}$alkyl, or —O—$C_{1-4}$alkyl can be prepared according to Scheme 6. All other variables in Scheme 6 are defined according to the scope of the present invention.

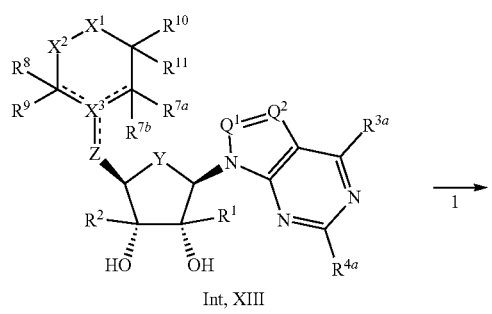
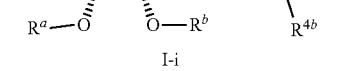

In scheme 6, following reaction conditions apply

1a. When $R^{3a}$, $R^{3b}$ or $R^{3c}$ represents hydrogen, halo, $C_{1-4}$alkyl, —O—$C_{1-4}$alkyl, or $NR^{12a}R^{12b}$ with $R^{12a}$ and $R^{12b}$ both being $C_{3-6}$cycloalkyl or optionally substituted $C_{1-4}$alkyl: in the presence of a suitable anhydride such as isobutyric anhydride or acetic anhydride in a suitable solvent such as pyridine at a suitable temperature such as for example 50° C. 1b. When $R^{3a}$, $R^{3b}$ or $R^{3c}$ represents $NR^{12a}R^{12b}$ with $R^{12a}$ or $R^{12b}$ is hydrogen: in the presence of a suitable anhydride such as isobutyric anhydride or acetic anhydride in a suitable solvent such as pyridine at a suitable temperature such as for example 50° C. and in a next step in the presence of a suitable solvent such as MeOH at a suitable temperature such as 130° C.

In all these preparations, the reaction products may be isolated from the reaction medium and, if necessary, further purified according to methodologies generally known in the art such as, for example, extraction, crystallization, trituration and chromatography.

The chirally pure forms of the compounds of Formula (I) form a preferred group of compounds. It is therefore that the chirally pure forms of the intermediates and their salt forms are particularly useful in the preparation of chirally pure compounds of Formula (I). Also enantiomeric mixtures of the intermediates are useful in the preparation of compounds of Formula (I) with the corresponding configuration.

Pharmacology

It has been found that the compounds of the present invention inhibit PRMT5 activity.

It is therefore anticipated that the compounds according to the present invention or pharmaceutical compositions thereof may be useful for treating or preventing, in particular treating, of diseases such as a blood disorder, metabolic disorders, autoimmune disorders, cancer, inflammatory diseases, cardiovascular diseases, neurodegenerative diseases, pancreatitis, multiorgan failure, kidney diseases, platelet aggregation, sperm motility, transplantation rejection, graft rejection, lung injuries and the like.

In particular the compounds according to the present invention or pharmaceutical compositions thereof may be useful for treating or preventing, in particular treating, of diseases such as allergy, asthma, hematopoietic cancer, lung cancer, prostate cancer, melanoma, metabolic disorder, diabetes, obesity, blood disorder, sickle cell anemia, and the like.

The compounds according to the present invention or pharmaceutical compositions thereof may be useful for treating or preventing, in particular treating, of diseases such as a proliferative disorder, such as an autoimmune disease, cancer, a benign neoplasm, or an inflammatory disease.

The compounds according to the present invention or pharmaceutical compositions thereof may be useful for treating or preventing, in particular treating, of diseases such as a metabolic disorder comprising diabetes, obesity; a proliferative disorder comprising cancer, hematopoietic cancer, lung cancer, prostate cancer, melanoma, or pancreatic cancer; blood disorder; hemoglobinopathy; sickle cell anemia; β-thalessemia, an inflammatory disease, and autoimmune disease e.g. rheumatoid arthritis, systemic lupus erythematosus, Sjogren's syndrome, diarrhea, gastroesophageal reflux disease, and the like.

In some embodiments, the inhibition of PRMT5 by a provided compound may be useful in treating or preventing, in particular treating, the following non-limiting list of cancers: breast cancer, lung cancer, esophageal cancer, bladder cancer, hematopoietic cancer, lymphoma, medulloblastoma, rectum adenocarcinoma, colon adenocarcinoma, gastric cancer, pancreatic cancer, liver cancer, adenoid cystic carcinoma, lung adenocarcinoma, head and neck squamous cell carcinoma, brain tumors, hepatocellular carcinoma, renal cell carcinoma, melanoma, oligodendroglioma, ovarian clear cell carcinoma, and ovarian serous cystadenoma.

Examples of metabolic disorders which may be treated or prevented, in particular treated, include, but are not limited to, diabetes or obesity.

Examples of blood disorders which may be treated or prevented, in particular treated, include, but are not limited to, hemoglobinopathy, such as sickle cell disease or p-thalassemia.

Examples of cancers which may be treated or prevented, in particular treated, include, but are not limited to, acoustic neuroma, adenocarcinoma, adrenal gland cancer, anal cancer, angiosarcoma (e.g., lymphangio sarcoma, lymphangioendothelio sarcoma, hemangio sarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), chordoma, choriocarcinoma, craniopharyngioma, colorectal cancer (e.g., colon cancer, rectal cancer, colorectal adenocarcinoma), epithelial carcinoma, ependymoma, endothelio sarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., pharyngeal cancer, laryngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL)(e.g., B-cell CLL, T-cell CLL); lymphoma such as Hodgkin lymphoma (HL) (e.g., B-cell HL, T-cell HL) and non-Hodgkin lymphoma (NHL)(e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenstrom's macro globulinemia"), immunoblastic large cell lymphoma, hairy cell leukemia (HCL), precursor B-lymphoblastic lymphoma and primary central nervous system (CNS) lymphoma; and T-cell NHL such as precursor T-lymphoblastic lymphoma/leukemia, peripheral T-cell lymphoma (PTCL)(e.g., cutaneous T-cell lymphoma (CTCL)(e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, non-small cell lung cancer (NSCLC), squamous lung cancer (SLC), adenocarcinoma of the lung, Lewis lung carcinoma, lung neuroendocrine tumors: typical carcinoid, atypical carcinoid, small cell lung cancer (SCLC), and large cell neuroendocrine carcinoma), leiomyosarcoma (LMS), mastocytosis (e.g., systemic mastocytosis), myelodysplastic syndromes (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer, and vulvar cancer (e.g., Paget's disease of the vulva).

Examples of neurodegenerative diseases which may be treated or prevented, in particular treated, include, but are not limited to, motor neurone disease, progressive supranuclear palsy, corticobasal degeneration, Pick's disease, Alzheimer's disease, AIDS-related dementia, Parkinson's disease, amyotropic lateral sclerosis, retinitis pigmentosa, spinal muscular atropy, and cerebellar degeneration.

Examples of cardiovascular diseases which may be treated or prevented, in particular treated, include, but are not limited to, cardiac hypertrophy, restenosis, atherosclerosis, and glomerulonephritis.

Examples of inflammatory diseases which may be treated or prevented, in particular treated, include, but are not limited to, inflammation associated with acne, anemia (e.g., aplastic anemia, haemolytic autoimmune anaemia), rhinitis, asthma, arteritis (e.g., polyarteritis, temporal arteritis, periarteritis nodosa, Takayasu's arteritis), arthritis (e.g., crystalline arthritis, osteoarthritis, psoriatic arthritis, gouty arthritis, reactive arthritis, rheumatoid arthritis and Reiter's arthritis), upper respiratory tract disease, ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, chronic obstructive pulmonary disease, diverticulitis, cermatomyositis, diabetes (e.g., type I diabetes mellitus, type 2 diabetes mellitus), a skin condition (e.g., psoriasis, eczema, eczema hypersensitivity reactions, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, morphea, myeasthenia gravis, myocardial ischemia, multiple sclerosis, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, reperfusion injury, regional enteritis, rheumatic fever, systemic lupus erythematosus, schlerodema, scierodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegeners granulomatosis.

In particular the inflammatory disease is an acute inflammatory disease (e.g., for example, inflammation resulting from infection). In particular the inflammatory disease is a chronic inflammatory disease (e.g., conditions resulting from asthma, arthritis and inflammatory bowel disease). The compounds may also be useful in treating inflammation associated with trauma and non-inflammatory myalgia. The compounds may also be useful in treating inflammation associated with cancer.

Examples of autoimmune diseases which may be treated or prevented, in particular treated, include, but are not limited to, arthritis (including rheumatoid arthritis, spondyloarthopathies, gouty arthritis, degenerative joint diseases such as osteoarthritis, systemic lupus erythematosus, Sjogren's syndrome, ankylosing spondylitis, undifferentiated spondylitis, Behcet's disease, haemolytic autoimmune anaemias, amyotrophic lateral sclerosis, amylosis, multiple sclerosis, acute painful shoulder, psoriatic, and juvenile arthritis), asthma, atherosclerosis, osteoporosis, bronchitis, tendonitis, bursitis, skin condition (e.g., psoriasis, eczema, eczema hypersensitivity reactions, burns, dermatitis, pruritus (itch)), enuresis, eosinophilic disease, gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), and disorders ameliorated by a gastroprokinetic agent (e.g., ileus, postoperative ileus and ileus during sepsis; gastroesophageal reflux disease (GORD, or its syrnonym GERD); eosinophilic esophagitis, gastroparesis such as diabetic gastroparesis; food intolerances and food allergies and other functional bowel disorders, such as non-ulcerative dyspepsia (NUD) and non-cardiac chest pain (NCCP, including costo-chondritis)).

In a particular embodiment, a provided compound may be useful in somatic cell reprogramming, such as reprogramming somatic cells into stem cells. In a particular embodiment, a provided compound may be useful in germ cell development, and are thus envisioned useful in the areas of reproductive technology and regenerative medicine.

Other diseases which may be treated or prevented, in particular treated, include, but are not limited to, ischemic injury associated myocardial infarctions, immunological diseases, stroke, arrhythmia, toxin-induced or alcohol related liver diseases, aspirin-sensitive rhinosinusitis, cystic fibrosis, cancer pain, and haematological diseases, for example chronic anemia and aplastic anemia.

The compounds of the present invention may also have therapeutic applications in sensitising tumour cells for radiotherapy and chemotherapy.

Hence the compounds of the present invention may be used as "radiosensitizer" and/or "chemosensitizer" or can be given in combination with another "radiosensitizer" and/or "chemosensitizer".

The term "radiosensitizer", as used herein, is defined as a molecule, preferably a low molecular weight molecule, administered to animals in therapeutically effective amounts to increase the sensitivity of the cells to ionizing radiation and/or to promote the treatment of diseases which are treatable with ionizing radiation.

The term "chemosensitizer", as used herein, is defined as a molecule, preferably a low molecular weight molecule, administered to animals in therapeutically effective amounts to increase the sensitivity of cells to chemotherapy and/or promote the treatment of diseases which are treatable with chemotherapeutics.

Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogues of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

The compounds of the present invention might also reduce the risk of cancer recurrence.

The invention relates to compounds of Formula (I) and pharmaceutically acceptable addition salts, and solvates thereof, for use as a medicament.

The invention relates to compounds of Formula (I) and pharmaceutically acceptable addition salts, and solvates thereof, for use in the inhibition of PRMT5 activity.

The compounds of the present invention can be "anti-cancer agents", which term also encompasses "anti-tumor cell growth agents" and "anti-neoplastic agents".

The invention relates to compounds of Formula (I) and pharmaceutically acceptable addition salts, and solvates thereof, for use in the treatment of diseases mentioned above.

The invention relates to compounds of Formula (I) and pharmaceutically acceptable addition salts, and solvates thereof, for the treatment or prevention, in particular for the treatment, of said diseases.

The invention relates to compounds of Formula (I) and pharmaceutically acceptable addition salts, and solvates thereof, for the treatment or prevention, in particular in the treatment, of PRMT5 mediated diseases or conditions.

The invention relates to compounds of Formula (I) and pharmaceutically acceptable addition salts, and solvates thereof, for the manufacture of a medicament.

The invention relates to compounds of Formula (I) and pharmaceutically acceptable addition salts, and solvates thereof, for the manufacture of a medicament for the inhibition of PRMT5.

The invention relates to compounds of Formula (I) and pharmaceutically acceptable addition salts, and solvates thereof, for the manufacture of a medicament for the treatment or prevention, in particular for the treatment, of any one of the disease conditions mentioned hereinbefore.

The invention relates to compounds of Formula (I) and pharmaceutically acceptable addition salts, and solvates thereof, for the manufacture of a medicament for the treatment of any one of the disease conditions mentioned hereinbefore.

The invention relates to compounds of Formula (I) and pharmaceutically acceptable addition salts, and solvates thereof, can be administered to mammals, preferably humans, for the treatment or prevention of any one of the diseases mentioned hereinbefore.

In view of the utility of the compounds of Formula (I) and pharmaceutically acceptable addition salts, and solvates thereof, there is provided a method of treating warm-blooded animals, including humans, suffering from or a method of preventing warm-blooded animals, including humans, to suffer from any one of the diseases mentioned hereinbefore.

Said methods comprise the administration, i.e. the systemic or topical administration, preferably oral administration, of an effective amount of a compound of Formula (I) or a pharmaceutically acceptable addition salt, or a solvate thereof, to warm-blooded animals, including humans.

Those of skill in the treatment of such diseases could determine the effective therapeutic daily amount from the test results presented hereinafter. An effective therapeutic daily amount would be from about 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. A particular effective therapeutic daily amount might be from about 0.01 to 1.00 g twice a day (BID), more in particular 0.30 to 0.85 g BID; even more in particular 0.40 g BID. The amount of a compound according to the present invention, also referred to here as the active ingredient, which is required to achieve a therapeutically effect will of course, vary on case-by-case basis, for example with the particular compound, the route of administration, the age and condition of the recipient, and the particular disorder or disease being treated.

A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The compounds of the present invention, that can be suitable to treat or prevent cancer or cancer-related conditions, may be administered alone or in combination with one or more additional therapeutic agents. Combination therapy includes administration of a single pharmaceutical dosage formulation which contains a compound of Formula (I), a pharmaceutically acceptable addition salt, or a solvate thereof, and one or more additional therapeutic agents, as well as administration of the compound of Formula (I), a pharmaceutically acceptable addition salt, or a solvate thereof, and each additional therapeutic agents in its own separate pharmaceutical dosage formulation. For example, a compound of Formula (I), a pharmaceutically acceptable addition salt, or a solvate thereof, and a therapeutic agent may be administered to the patient together in a single oral dosage composition such as a tablet or capsule, or each agent may be administered in separate oral dosage formulations.

While it is possible for the active ingredient to be administered alone, it is preferable to present it as a pharmaceutical composition.

Accordingly, the present invention further provides a pharmaceutical composition and, as active ingredient, a therapeutically effective amount of a compound of Formula (I), a pharmaceutically acceptable addition salt, or a solvate thereof.

Accordingly, the present invention further provides a pharmaceutical composition comprising a pharmaceutically acceptable carrier and, as active ingredient, a therapeutically effective amount of a compound of Formula (I), a pharmaceutically acceptable addition salt, or a solvate thereof.

The carrier or diluent must be "acceptable" in the sense of being compatible with the other ingredients of the composition and not deleterious to the recipients thereof.

For ease of administration, the subject compounds may be formulated into various pharmaceutical forms for administration purposes. The compounds according to the invention, in particular the compounds of Formula (I) and pharmaceutically acceptable addition salts, and solvates thereof, or any subgroup or combination thereof may be formulated into various pharmaceutical forms for administration purposes. As appropriate compositions there may be cited all compositions usually employed for systemically administering drugs.

To prepare the pharmaceutical compositions of this invention, an effective amount of the particular compound as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions containing a compound of Formula (I), a pharmaceutically acceptable addition salt, or a solvate thereof, may be formulated in an oil for prolonged action. Appropriate oils for this purpose are, for example, peanut oil, sesame oil, cottonseed oil, corn oil, soybean oil, synthetic glycerol esters of long chain fatty acids and mixtures of these and other oils.

Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid or base addition salts of compounds of Formula (I) due to their increased water solubility over the corresponding base or acid form, are more suitable in the preparation of aqueous compositions.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

In order to enhance the solubility and/or the stability of the compounds of Formula (I) and pharmaceutically acceptable addition salts, and solvates thereof, in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

Depending on the mode of administration, the pharmaceutical composition will preferably comprise from 0.05 to 99% by weight, more preferably from 0.1 to 70% by weight, even more preferably from 0.1 to 50% by weight of the compound of Formula (I), a pharmaceutically acceptable addition salt, or a solvate thereof, and from 1 to 99.95% by weight, more preferably from 30 to 99.9% by weight, even more preferably from 50 to 99.9% by weight of a pharmaceutically acceptable carrier, all percentages being based on the total weight of the composition.

As another aspect of the present invention, a combination of a compound of the present invention with another anti-cancer agent is envisaged, especially for use as a medicine, more specifically for use in the treatment of cancer or related diseases.

For the treatment of the above conditions, the compounds of the invention may be advantageously employed in combination with antibody based immune cell redirection, for example T-cell/neutrophil redirection. This can be achieved for example by the use of bispecific monoclonal antibodies or artificial T-cell receptors.

For the treatment of the above conditions, the compounds of the invention may be advantageously employed in combination with one or more other medicinal agents, more particularly, with other anti-cancer agents or adjuvants in cancer therapy.

Examples of anti-cancer agents or adjuvants (supporting agents in the therapy) include but are not limited to:
  platinum coordination compounds for example cisplatin optionally combined with amifostine, carboplatin or oxaliplatin;
  taxane compounds for example paclitaxel, paclitaxel protein bound particles (Abraxane™) or docetaxel;
  topoisomerase I inhibitors such as camptothecin compounds for example irinotecan, SN-38, topotecan, topotecan hcl;
  topoisomerase II inhibitors such as anti-tumour epipodophyllotoxins or podophyllotoxin derivatives for example etoposide, etoposide phosphate or teniposide;
  anti-tumour vinca alkaloids for example vinblastine, vincristine or vinorelbine;
  anti-tumour nucleoside derivatives for example 5-fluorouracil, leucovorin, gemcitabine, gemcitabine hcl, capecitabine, cladribine, fludarabine, nelarabine;
  alkylating agents such as nitrogen mustard or nitrosourea for example cyclophosphamide, chlorambucil, carmustine, thiotepa, mephalan (mephalan), lomustine, altretamine, busulfan, dacarbazine, estramustine, ifosfamide optionally in combination with mesna, pipobroman, procarbazine, streptozocin, temozolomide, uracil;
  anti-tumour anthracycline derivatives for example daunorubicin, doxorubicin optionally in combination with dexrazoxane, doxil, idarubicin, mitoxantrone, epirubicin, epirubicin hcl, valrubicin;
  molecules that target the IGF-1 receptor for example picropodophilin;
  tetracarcin derivatives for example tetrocarcin A;
  glucocorticods for example prednisone;
  antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;
  estrogen receptor antagonists or selective estrogen receptor modulators or inhibitors of estrogen synthesis for example tamoxifen, fulvestrant, toremifene, droloxifene, faslodex, raloxifene or letrozole;
  aromatase inhibitors such as exemestane, anastrozole, letrazole, testolactone and vorozole;
  differentiating agents such as retinoids, vitamin D or retinoic acid and retinoic acid metabolism blocking agents (RAMBA) for example accutane;
  DNA methyl transferase inhibitors for example azacytidine or decitabine;
  antifolates for example premetrexed disodium;
  antibiotics for example antinomycin D, bleomycin, mitomycin C, dactinomycin, carminomycin, daunomycin, levamisole, plicamycin, mithramycin;
  antimetabolites for example clofarabine, aminopterin, cytosine arabinoside or methotrexate, azacitidine, cytarabine, floxuridine, pentostatin, thioguanine;
  apoptosis inducing agents and antiangiogenic agents such as Bcl-2 inhibitors for example YC 137, BH 312, ABT 737, gossypol, HA 14-1, TW 37 or decanoic acid;
  tubuline-binding agents for example combrestatin, colchicines or nocodazole;
  kinase inhibitors (e.g. EGFR (epithelial growth factor receptor) inhibitors, MTKI (multi target kinase inhibitors), mTOR inhibitors) for example flavoperidol, imatinib mesylate, erlotinib, gefitinib, dasatinib, lapatinib, lapatinib ditosylate, sorafenib, sunitinib, sunitinib maleate, temsirolimus;
  farnesyltransferase inhibitors for example tipifarnib;
  histone deacetylase (HDAC) inhibitors for example sodium butyrate, suberoylanilide hydroxamic acid (SAHA), depsipeptide (FR 901228), NVP-LAQ824, R306465, JNJ-26481585, trichostatin A, vorinostat;
  Inhibitors of the ubiquitin-proteasome pathway for example PS-341, MLN 0.41 or bortezomib;
  Yondelis;
  Telomerase inhibitors for example telomestatin;
  Matrix metalloproteinase inhibitors for example batimastat, marimastat, prinostat or metastat.
  Recombinant interleukins for example aldesleukin, denileukin diftitox, interferon alfa 2a, interferon alfa 2b, peginterferon alfa 2b
  MAPK inhibitors
  Retinoids for example alitretinoin, bexarotene, tretinoin
  Arsenic trioxide
  Asparaginase
  Steroids for example dromostanolone propionate, megestrol acetate, nandrolone (decanoate, phenpropionate), dexamethasone Gonadotropin releasing hormone agonists or antagonists for example abarelix, goserelin acetate, histrelin acetate, leuprolide acetate Thalidomide, lenalidomide Mercaptopurine, mitotane, pamidronate, pegademase, pegaspargase, rasburicase BH3 mimetics for example ABT-737

MEK inhibitors for example PD98059, AZD6244, CI-1040 colony-stimulating factor analogs for example filgrastim, pegfilgrastim, sargramostim; erythropoietin or analogues thereof (e.g. darbepoetin alfa); interleukin 11; oprelvekin; zoledronate, zoledronic acid; fentanyl; bisphosphonate; palifermin a steroidal cytochrome P450 17alpha-hydroxylase-17,20-lyase inhibitor (CYP17), e.g. abiraterone, abiraterone acetate Glycolysis inhibitors, such as 2-deoxyglucose mTOR inhibitors such as rapamycins and rapalogs, and mTOR kinase inhibitors PI3K inhibitors and dual mTOR/PI3K inhibitors autophagy inhibitors, such as chloroquine and hydroxychloroquine antibodies that re-activate the immune response to tumors, for example nivolumab (anti-PD-1), lambrolizumab (anti-PD-1), ipilimumab (anti-CTLA4), and MPDL3280A (anti-PD-L1).

The present invention further relates to a product containing as first active ingredient a compound according to the invention and as further active ingredient one or more anticancer agents, as a combined preparation for simultaneous, separate or sequential use in the treatment of patients suffering from cancer.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art.

Furthermore, it is evident that the effective daily amount may be lowered or increased depending on the response of the treated subject and/or depending on the evaluation of the physician prescribing the compounds of the instant invention. A particular weight ratio for the present compound of Formula (I) and another anticancer agent may range from 1/10 to 10/1, more in particular from 1/5 to 5/1, even more in particular from 1/3 to 3/1.

The platinum coordination compound is advantageously administered in a dosage of 1 to 500 mg per square meter ($mg/m^2$) of body surface area, for example 50 to 400 $mg/m^2$, particularly for cisplatin in a dosage of about 75 $mg/m^2$ and for carboplatin in about 300 $mg/m^2$ per course of treatment.

The taxane compound is advantageously administered in a dosage of 50 to 400 mg per square meter ($mg/m^2$) of body surface area, for example 75 to 250 $mg/m^2$, particularly for paclitaxel in a dosage of about 175 to 250 $mg/m^2$ and for docetaxel in about 75 to 150 $mg/m^2$ per course of treatment.

The camptothecin compound is advantageously administered in a dosage of 0.1 to 400 mg per square meter ($mg/m^2$) of body surface area, for example 1 to 300 $mg/m^2$, particularly for irinotecan in a dosage of about 100 to 350 $mg/m^2$ and for topotecan in about 1 to 2 $mg/m^2$ per course of treatment.

The anti-tumour podophyllotoxin derivative is advantageously administered in a dosage of 30 to 300 mg per square meter ($mg/m^2$) of body surface area, for example 50 to 250 $mg/m^2$, particularly for etoposide in a dosage of about 35 to 100 $mg/m^2$ and for teniposide in about 50 to 250 $mg/m^2$ per course of treatment.

The anti-tumour vinca alkaloid is advantageously administered in a dosage of 2 to 30 mg per square meter ($mg/m^2$) of body surface area, particularly for vinblastine in a dosage of about 3 to 12 $mg/m^2$, for vincristine in a dosage of about 1 to 2 $mg/m^2$, and for vinorelbine in dosage of about 10 to 30 $mg/m^2$ per course of treatment.

The anti-tumour nucleoside derivative is advantageously administered in a dosage of 200 to 2500 mg per square meter ($mg/m^2$) of body surface area, for example 700 to 1500 $mg/m^2$, particularly for 5-FU in a dosage of 200 to 500 $mg/m^2$, for gemcitabine in a dosage of about 800 to 1200 $mg/m^2$ and for capecitabine in about 1000 to 2500 $mg/m^2$ per course of treatment.

The alkylating agents such as nitrogen mustard or nitrosourea is advantageously administered in a dosage of 100 to 500 mg per square meter ($mg/m^2$) of body surface area, for example 120 to 200 $mg/m^2$, particularly for cyclophosphamide in a dosage of about 100 to 500 $mg/m^2$, for chlorambucil in a dosage of about 0.1 to 0.2 mg/kg, for carmustine in a dosage of about 150 to 200 $mg/m^2$, and for lomustine in a dosage of about 100 to 150 $mg/m^2$ per course of treatment.

The anti-tumour anthracycline derivative is advantageously administered in a dosage of 10 to 75 mg per square meter ($mg/m^2$) of body surface area, for example 15 to 60 $mg/m^2$, particularly for doxorubicin in a dosage of about 40 to 75 $mg/m^2$, for daunorubicin in a dosage of about 25 to 45 $mg/m^2$, and for idarubicin in a dosage of about 10 to 15 $mg/m^2$ per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m$^2$) of body surface area, or as known in the art, if different. Trastuzumab is advantageously administered in a dosage of 1 to 5 mg per square meter (mg/m$^2$) of body surface area, particularly 2 to 4 mg/m$^2$ per course of treatment.

These dosages may be administered for example once, twice or more per course of treatment, which may be repeated for example every 7, 14, 21 or 28 days.

The following examples illustrate the present invention. Stereocenters for which no specific stereochemistry is indicated were obtained as mixtures of R and S.

The skilled person will realize that typically after a column purification, the desired fractions were collected and the solvent was evaporated to obtain the desired compound or intermediate.

EXAMPLES

Hereinafter, the term "rt" or "r.t." means room temperature; "Me" means methyl; "MeOH" means MeOH; "Et" means ethyl; "EtOH" means ethanol; "HMPA" means hexamethylphosphorous triamide; "TosOH" means 4-methyl-benzenesulfonic acid; "NaBH(AcO)$_3$" or "NaBH(OAc)$_3$" means sodium triacetoxyborohydride; "EtOAc" means ethyl acetate; "Et$_3$N" means triethylamine; "DCM" means dichloromethane; "q.s." means quantum sufficit; "Int." Means intermediate; "ACN" means acetonitrile; "DMF" means N,N-dimethyl formamide; "THF" means tetrahydrofuran; 'iPrOH" means 2-propanol; "LC" means liquid chromatography; "LCMS" means Liquid Chromatography/Mass spectrometry; "(prep) HPLC" means (preparative) high-performance liquid chromatography; "TFA" means trifluoroacetic acid; "m.p." means melting point; "RP" means reversed phase; "min" means minute(s); "h" means hour(s); "PE" means petroleum ether; "CV" means column volume(s); "Celite®" means diatomaceous earth; "DMSO" means dimethyl sulfoxide; "SFC" means Supercritical Fluid Chromatography; "DIPEA" means N,N-diisopropylethylamine; "PPh$_3$" means triphenylphosphine; "Et$_2$O" means diethyl ether; "Pd/C" means palladium on carbon; "Pt/C" means platina on carbon; "TBAF" means tetrabutylammonium fluoride; "psi" means pound-force per square inch; "eq." means equivalent(s); "AcOH" means acetic acid; "Dess-Martin periodinane" means 1,1,1-Triacetoxy-1,1-dihydro-1,2-benziodoxol-3(1H)-one; "Ph$_3$PCH$_3$Br" means methyltriphenylphosphonium bromide; "Bn" means benzyl; "Bz" means benzoyl; "p-TSA" means 4-methylbenzenesulfonic acid; "BF$_3$.Et$_2$O" means Boron Trifluoride-Ethyl Ether Complex; "MTBE" means Methyl tert-butyl ether, "Ac$_2$O" means acetic anhydride; "Co." means final compound; "Rf" means retention factor; "NH$_4$Ac" means ammonium acetate; "PPTS" means pyridinium p-toluenesulfonate; "LiHMDS" means lithium hexamethyldisilazane; "HOAc" means acetic acid; "MeCN" means methyl cyanide; "Boc" or "BOC" means tert-butoxycarbonyl; "atm" means atmosphere; "DIPE" means diisopropyl ether, "HBTU" means 1-[bis(dimethylamino)methylene]-1H-benzotriazol-1-ium 3-oxide hexafluorophosphate; "TMSCI" means trimethylsilyl chloride; "BINAP" means [1,1'-binaphthalene]-2,2'-diylbis[diphenylphosphine] (racemic); "Pd$_2$(dba)$_3$" means tris(dibenzylideneacetone)dipalladium; "t-BuONa" means sodium tert-butoxide; "KOAc" means potassium acetate; "TEMPO" means 2,2,6,6-tetramethyl-1-piperidinyloxy; "TsOH.H$_2$O" means p-toluenesulfonic acid monohydrate; "Ts" or "Tos" means tosyl (p-toluenesulfonyl); "Tf" means trifluoromethanesulfonyl (triflyl); and "TLC" means thin layer chromatography.

The typical concentration of ammonia in MeOH used in the reactions below, is 7 N.

A. Preparation of Intermediates

Example A1

Preparation of Intermediate 1

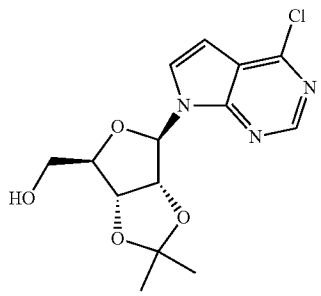 [SMILES: CC1(C)O[C@@H]2[C@H](O1)[C@@H](CO)O[C@H]2n1ccc2c(Cl)ncnc21]

To a mixture of 6-chloro-7-deazapurinebeta-d-riboside (25.0 g, 87.5 mmol) in acetone (330 mL) was added 2,2-dimethoxypropane (18.2 g, 175 mmol) and TosOH (1.51 g, 8.75 mmol) in one portion at 25° C. under N$_2$. The mixture was stirred at 60° C. for 2 hours. The mixture was cooled to 25° C. The reaction was quenched by adding saturated NaHCO$_3$ (100 mL) slowly and then extracted with ethyl acetate (5 times 125 mL). The combined organic phases were washed with saturated brine (120 mL), dried with anhydrous MgSO$_4$, filtered and concentrated in vacuum. The residue was purified by silica gel chromatography (gradient elution: DCM/Ethyl acetate from 1:0 to 2:1) to afford crude Intermediate 1 (38.0 g) as light yellow gum.

Below intermediates were prepared by an analogous reaction protocol as was used for the preparation of Intermediate 1 using the appropriate starting materials:

intermediate 4, starting from 6-chloro-9-(2-C-methyl-β-D-ribofuranosyl)-9H-Purine,

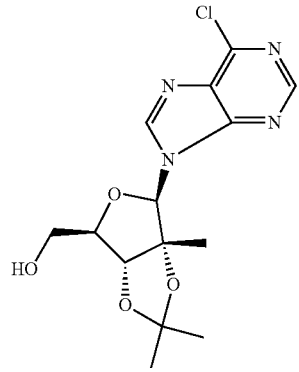 [SMILES: CC1(C)O[C@@H]2[C@@H](CO)O[C@@H](n3cnc4c(Cl)ncnc43)[C@]2(C)O1]

Intermediate 4

Example A2

Preparation of Intermediate 3

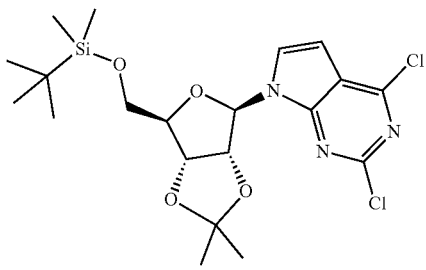 [SMILES: CC1(C)O[C@@H]2[C@H](O1)[C@@H](CO[Si](C)(C)C(C)(C)C)O[C@H]2n1ccc2c(Cl)nc(Cl)nc21]

To a solution of 5-O-tert-butyldimethylsilyl-2,3-o-isopropylidene-D-ribofuranose (=intermediate 2=commercial) (79.8 mmol) in $CCl_4$ (12.8 mL, 133 mmol) and toluene (200 ml) was added dropwise HMPA (16.32 g, 100 mmol) at −50° C. over 30 minutes. After the mixture was stirred at −50° C. for 2 hours, the reaction mixture was quickly washed with ice cold brine (30 mL), dried over anhydrous $Na_2SO_4$ and added immediately to a heavily stirred mixture of powdered KOH (6.5 g, 117 mmol), 2,4-dichloro-7H-pyrrolopyrimidine (10.0 g, 53 mmol), tris(3,6-dioxaheptyl)amine (8.27 mL, 26.6 mmol) and toluene (200 ml). The mixture was stirred at r.t. for 48 hours. Then the solvent was concentrated. The residue was treated with 250 ml $NH_4Cl$ solution and extracted with ethyl acetate (two times 300 ml). The organic layers were combined and dried with $Na_2SO_4$, filtered and the filtrate was concentrated in vacuum. The residue was purified by column chromatography over silica gel (gradient elution: petroleum ether/ethyl acetate from 25:1 to 15:1). The product fractions were collected and the solvent was evaporated to give the desired intermediate 3 (6.50 g, 21% yield).

Below intermediates were prepared by ananalogous reaction protocol as was used for the preparation of intermediate 3 using the appropriate starting materials (Table 1).

TABLE 1

| Int. | Structure | Starting materials |
|---|---|---|
| 5 | 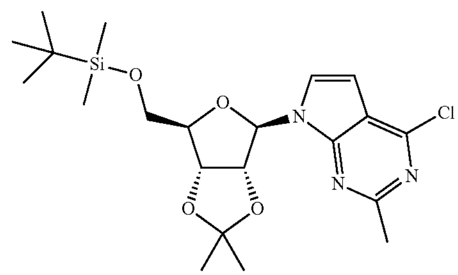 [SMILES: Cc1nc(Cl)c2ccn([C@@H]3O[C@H](CO[Si](C)(C)C(C)(C)C)[C@H]4OC(C)(C)O[C@H]43)c2n1] | Intermediate 2 and 4-chloro-2-methyl-7H-pyrrolo[2,3-d]pyrimidine |
| 6 | 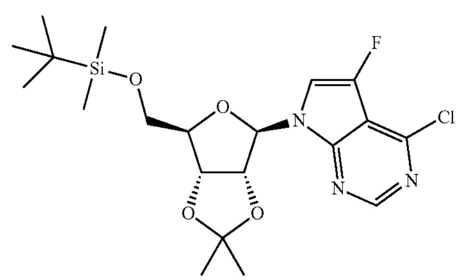 [SMILES: CC1(C)O[C@@H]2[C@H](O1)[C@@H](CO[Si](C)(C)C(C)(C)C)O[C@H]2n1cc(F)c2c(Cl)ncnc21] | Intermediate 2 and 4-Chloro-5-fluoro-7H-pyrrolo[2,3-d]-pyrimidine |
| 7 | 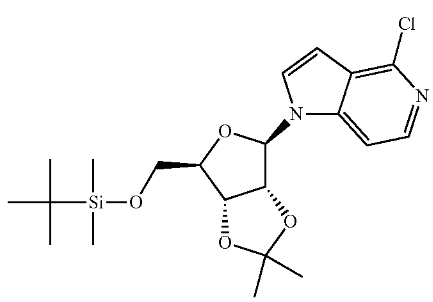 [SMILES: CC1(C)O[C@@H]2[C@H](O1)[C@@H](CO[Si](C)(C)C(C)(C)C)O[C@H]2n1ccc2c(Cl)nccc21] | Intermediate 2 and 4-chloro-1H-pyrrolo[3,2-c]pyridine |

TABLE 1-continued

| Int. | Structure | Starting materials |
|---|---|---|
| 8 | 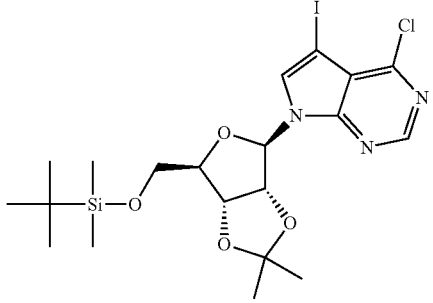 [SMILES: CC1(C)O[C@@H]2[C@H](O1)[C@@H](CO[Si](C)(C)C(C)(C)C)O[C@H]2n1cc(I)c2c(Cl)ncnc21] | Intermediate 2 and 4-chloro-5-iodo-7H-pyrrolo[2,3-d]-pyrimidine |

Example A3

Preparation of Intermediate 9

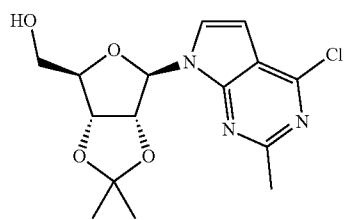 [SMILES: Cc1nc(Cl)c2ccn([C@@H]3O[C@H](CO)[C@H]4OC(C)(C)O[C@H]43)c2n1]

To a solution of intermediate 5 (9.50 g, 20.9 mmol) in THF (82 mL) was added 1M TBAF solution in THF (41.8 mL, 41.8 mmol) at room temperature. The reaction mixture was stirred at room temperature for 3 hours. The mixture was evaporated to dryness. The residue was taken up into water and extracted with DCM (two times 150 ml). The organic layers were dried (Na$_2$SO$_4$), filtered and the filtrate was concentrated. The residue was purified by column chromatography over silica gel (gradient elution: petroleum ether/ethyl acetate from 10/1 to 4/1) to give the desired intermediate 9 (3.68 g, 51% yield).

Below intermediate was prepared by an analogous reaction protocol as was used for the preparation of intermediate 9 using the appropriate starting materials (Table 2).

TABLE 2

| Int. | Structure | Starting material |
|---|---|---|
| 10 | 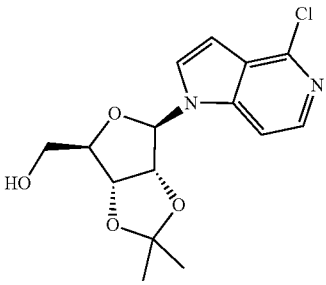 | Intermediate 6 |
| 11 | 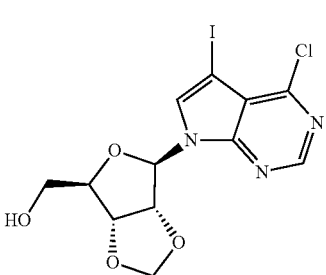 | Intermediate 7 |
| 12 | 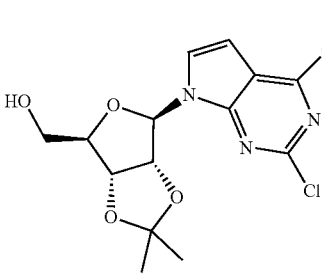 | Intermediate 8 |
| 15 | 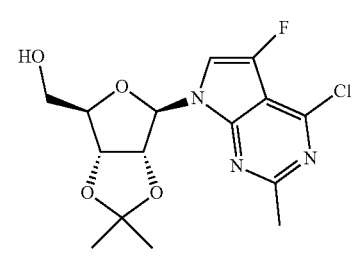 [SMILES: Cc1nc(Cl)c2c(F)cn([C@@H]3O[C@H](CO)[C@H]4OC(C)(C)O[C@H]43)c2n1] | intermediate 3 |

Example A4

Preparation of Intermediate 13

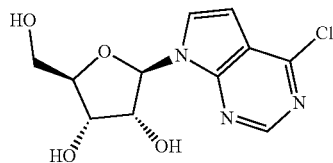 [SMILES: OC[C@H]1O[C@@H](n2ccc3c(Cl)ncnc32)[C@H](O)[C@@H]1O]

To a mixture of 4,6-dichloro-5-(2,2-diethoxyethyl)pyrimidine (14.0 g, 52.8 mmol) and (1R,2S,3R,5R)-3-amino-5-(hydroxymethyl)cyclopentane-1,2-diol hydrochloride (10.7 g, 58.1 mmol) in propan-2-ol/H$_2$O (208 mL, 7:1), was added Et$_3$N (13.4 g, 132 mmol) in one portion at 25° C. under N$_2$. The mixture was stirred at 90° C. for 23 hours. The mixture was cooled to 50° C. and 4M HCl (24 mL, 106 mmol) was added slowly. The reaction mixture was then stirred at 50° C. for 2 hours. The reaction mixture was cooled to 25° C. and NaHCO$_3$ (14 g, 100 mmol) was added slowly. Ethyl acetate (230 mL) was added, followed by the addition of a half-saturated NaHCO$_3$ solution. The organic phase was isolated and the aqueous phase was extracted with ethyl acetate (two times 230 mL). The combined organic phase was dried with anhydrous MgSO$_4$, filtered and concentrated to afford intermediate 13 as yellow solid (17.40 g, quantitative yield in 2 steps). The crude product was directly used as such in the next reaction step without further purification.

Preparation of Intermediate 14

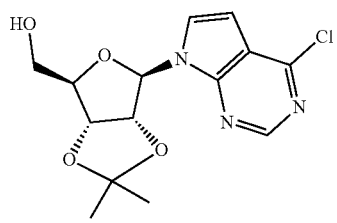 [SMILES: CC1(C)O[C@@H]2[C@H](O1)[C@@H](CO)O[C@H]2n1ccc2c(Cl)ncnc21]

To a mixture of intermediate 13 (17.4 g, 52.7 mmol) in acetone (250 mL) was added 2,2-dimethoxypropane (11.0 g, 105 mmol) and TsOH.H$_2$O (908 mg, 5.27 mmol) in one portion at 25° C. under N$_2$. The mixture was stirred at 60° C. for 2 hours. The mixture was cooled to 25° C. and the solution was concentrated, quenched by saturated NaHCO$_3$ (100 mL) slowly and then extracted with ethyl acetate (three times 100 mL). The combined organic phase was washed with saturated brine (100 mL), dried with anhydrous MgSO$_4$, filtered and concentrated in vacuum. The residue was purified by flash chromatography on silica gel (gradient elution: DCM/Ethyl acetate from 1/0 to 2/1) to afford intermediate 14 as light yellow gum (15.50 g, 89% yield).

Example A5

Preparation of Intermediate 18

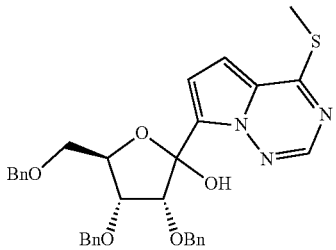

Two batches of the reaction described below were carried out in parallel.

An oven-dried flask was charged with 7-bromo-4-(methylthio)pyrrolo[2,1-f][1,2,4]triazine (45.0 g, 184.3 mmol) and dry THF (1.20 L) under N$_2$. The yellow solution was cooled to −78° C. and a yellow suspension was formed. n-BuLi (2.5 M, 79.63 mL, 1.1 eq) was added drop wise to the reaction mixture over period of 25 minutes at −78° C. The reaction mixture was stirred at −78° C. for 1 hour and a yellow-brown solution was formed. A pre-cooled solution of D-Lyxonic acid, 2,3,5-tris-O-(phenylmethyl)-, γ-lactone (84.0 g, 201 mmol (=intermediate 17=commercial) 1.09 eq) in dry THF (800 mL) in another flask (−78° C.) was added to the solution under N$_2$.

The resulting red-brown solution was stirred at −78° C. for 1.5 h. The reaction was quenched by addition of a saturated NH$_4$Cl aqueous solution (300 mL) at −78° C., and subsequently the mixture was warmed to 10° C. The mixture was extracted with ethyl acetate (3 times 500 mL). The combined organic layers were washed with brine, dried over MgSO$_4$, filtered and concentrated under reduced pressure. The combined residues of the two reactions were load on silica gel then purified by column chromatography (SiO$_2$, gradient elution: Petroleum ether/Ethyl acetate from 10/1 to 3:1) to afford intermediate 18 (148.50 g, 242 mmol, 65.6% yield) as an orange gum.

Preparation of Intermediate 19

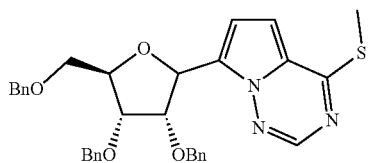

Two batches of the reaction described below were carried out in parallel.

To a stirred solution of intermediate 18 (74.0 g, 126.8 mmol, 1.0 eq) and triethylsilane (59.9 g, 514.7 mmol, 4.1 eq) in DCM (1.80 L) was added BF$_3$.Et$_2$O (90.9 g, 640.2 mmol, 5.1 eq) dropwise between −30 and −20° C. The resulting orange solution was stirred between −30 and −20° C. for 4.5 hours. The reaction mixture was carefully poured into a saturated NaHCO$_3$ aqueous solution (2.5 L) with vigorous stirring (gas evolution). The mixture was stirred for 2 hours. The organic layer was separated and the aqueous phase was extracted with DCM (200 mL×3). The combined organic layers were washed with brine (500 mL×2), dried over MgSO$_4$, filtered and concentrated under reduced pressure.

The combined residues of the two reactions were purified by column chromatography (silica gel, petroleum ether/ethyl acetate=12:1 to 8:1), affording intermediate 19 as a light yellow gum (125.7 g, 83% yield)(mixture of anomers α/β).

Preparation of Intermediate 20

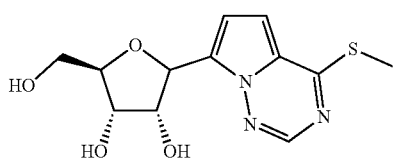 [SMILES: CSc1ncnn2c(C3O[C@H](CO)[C@@H](O)[C@H]3O)ccc12]

1M BCl$_3$ in CH$_2$Cl$_2$ (860 mL, 860 mmol) was added dropwise at −78° C. to a stirred solution of intermediate 19 (75.0 g, 132.1 mmol) in DCM (1.20 L) dropwise over period of 2.5 hours under N$_2$. The mixture was stirred at −78° C. for 1 hour. The reaction mixture was slowly warmed to −40° C. The reaction mixture was poured into MeOH (2.5 L, 20° C.) with stirring. The resulting red solution was stirred for 3 hours. Water (250 mL) was added into the mixture and left at 20° C. for 16 hours. The solution was portion wise poured onto solid NaHCO$_3$ (500 g) carefully with vigorous stirring (gas evolution, the color of mixture was turned from orange-red to yellow). The resulting suspension was filtered and the filtrate was concentrated under reduced pressure. The residue was dispensed in iPrOH/CH$_2$Cl$_2$ (1:3, 1 L) then filtered (to remove some inorganic salt) and the filtrate was concentrated under reduced pressure. The residue was triturated with petroleum ether (500 mL×3) to afford crude intermediate 20 (40.2 g, crude) (mixture of anomers α/β) as an orange solid, which used in the next reaction step without further purification.

Preparation of Intermediate 21

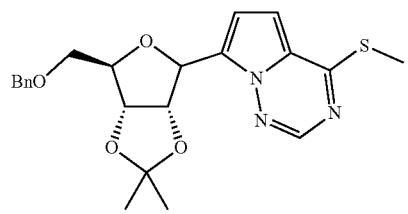 [SMILES: CSc1ncnn2c(C3O[C@H](COCc4ccccc4)[C@H]4OC(C)(C)O[C@@H]34)ccc12]

To a suspension of intermediate 20 (40.2 g, crude) and 2,2-dimethoxypropane (34 mL, 277.2 mmol) in acetone (600 mL) was added TsOH.H$_2$O (5.92 g, 31.1 mmol, 0.23 eq) at 25° C. (pH=2). The resulting mixture was heated at 60° C. for 2 hours. After being cooled to 25° C., the reaction mixture was concentrated under reduced pressure. The residue was partitioned between ethyl acetate (500 mL) and saturated aqueous NaHCO$_3$ solution (500 mL). The layers were separated and the aqueous phase was extracted with ethyl acetate (three times 200 mL). The combined organic layers were washed with brine (100 mL), dried over MgSO$_4$, filtered and concentrated under reduced pressure. The residue was purified by column chromatography (silica gel, CH$_2$Cl$_2$/Ethyl acetate=10/1 to 6/1). The fractions containing intermediate 21 were combined and concentrated under reduced pressure. The residue (28 g, about 80% purity) was purified again by column chromatography (silica gel, Petroleum ether/Ethyl acetate=20/1 to 4/1). The desired fractions were combined and concentrated under reduced pressure. The residue was diluted with CH$_2$Cl$_2$ (15 mL) then petroleum ether/ethyl acetate (4:1, 200 mL) was added. The mixture was concentrated to about 150 mL and solids were precipitated. The slurry was diluted with petroleum ether to about 400 mL and stirred for 16 hours at 20° C. The mixture was filtered and the solid was rinsed with petroleum ether/ethyl acetate (20/1, 100 mL). The solids were collected and dried under high vacuum to afford pure intermediate 21 as white solid (18.6 g, yield: 41.7% for 2 steps) (pure β anomer).

Example A6

Preparation of Intermediate 22

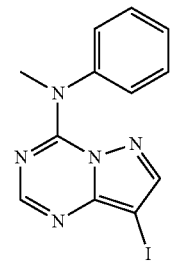 [SMILES: CN(c1ccccc1)c1ncnc2c(I)cnn12]

A solution of compound 8-iodo-3H-pyrazolo [1,5-a] [1,3,5] triazin-4-one (2000 mg, 7.6 mmol), phosphorus oxychloride (15 mL, 160.3 mmol) and N, N-dimethylaminopyridine (2798 mg, 22.9 mmol) was heated at reflux for 2 hours. The volatile compounds were removed by evaporation. Then the mixture was dried under reduced pressure for 1 hour. The residue was dissolved in dry CH$_2$C$_{1-2}$ and cooled in an ice bath before the dropwise addition of N-methylaniline (3315 µL, 30.5 mmol, followed by trimethylamine (6.4 mL, 45.8 mmol). The solution was stirred at room temperature for 1 hour. Water was added and the aqueous layer was extracted with CH$_2$Cl$_2$. The organic layers were combined and washed with brine, dried over magnesium sulfate and evaporated Example A7

Preparation of Intermediate 23

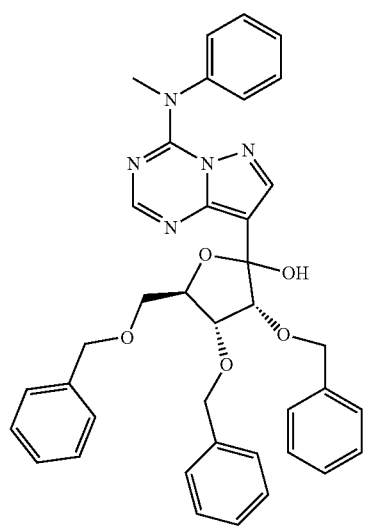 [SMILES: CN(c1ccccc1)c1ncnc2c(C3(O)O[C@H](COCc4ccccc4)[C@@H](OCc4ccccc4)[C@H]3OCc3ccccc3)cnn12]

Intermediate 22 (1400 mg, 4 mmol) was dissolved in 50 mL dry THF (dried on sodium) and cooled to −78° C. under N₂. Isopropyl magnesium chloride (3.4 mL, 4.4 mmol, 13M) was added drop wise to the reaction flask and the mixture was stirred for 30 min. D-Lyxonic acid, 2,3,5-tris-O-(phenylmethyl)-, γ-lactone (=intermediate 17=commercial) was dissolved in 20 mL of dry THF and dropwise added to the reaction mixture and the reaction mixture was further stirred at −78° C. After two hours the reaction mixture was allowed to warm to room temperature and was stirred for another 2 hours. The reaction mixture was quenched with saturated aqueous NH₄Cl and the mixture was diluted with EtOAc. The layers were separated and the aqueous phase was extracted with EtOAc. The combined organic layers were washed with water and brine, dried (MgSO₄) and concentrated under reduced pressure. The crude product was purified by column chromatography (heptane/EtOAc: 8/2 to 1/1) to give intermediate 23 (170 mg, 0.26 mmol, 6.6% yield)

Preparation of Intermediate 24

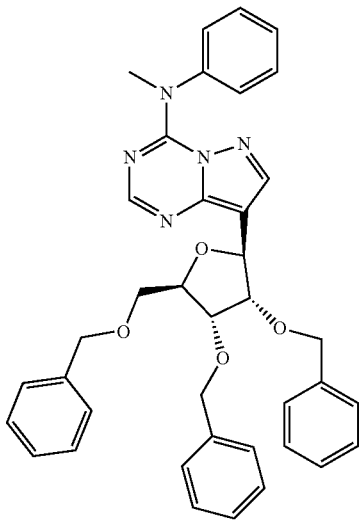 [SMILES: CN(c1ccccc1)c1ncnc2c([C@@H]3O[C@H](COCc4ccccc4)[C@@H](OCc4ccccc4)[C@H]3OCc3ccccc3)cnn12]

Et₃SiH (2262.8 μL, 14.17 mmol) was added in one portion to a stirred solution of intermediate 23 (2280 mg, 3.54 mmol) in dry CH₂Cl₂ (34 mL) on an ice bath (0° C.) under an atmosphere of nitrogen. After 5 min, boron trifluoride etherate (2234 μL, 17.7 mmol) was added over 1 min by syringe. The resulting mixture was stirred overnight. The reaction mixture was poured into saturated Na₂CO₃ and extracted with CH₂Cl₂. The organic layer was dried with MgSO₄, and concentrated under vacuum. The crude product was purified by column chromatography (heptane/EtOAc: 8/2 to 1/1 to give intermediate 24 (1810 mg, 2.88 mmol, 81.4% yield).

Preparation of Intermediate 25

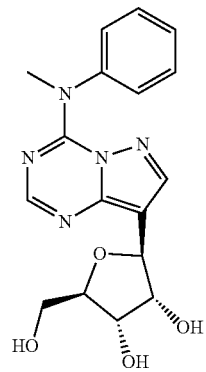 [SMILES: CN(c1ccccc1)c1ncnc2c([C@@H]3O[C@H](CO)[C@@H](O)[C@H]3O)cnn12]

HCl Salt

BCl₃ (1M in DCM, 20.4 mL, 20.4 mmol) was added to a solution of intermediate 24 (1600 mg, 2.55 mmol) and pentamethylbenzene (1889 mg, 12.7 mmol) in DCM at −78° C. The reaction mixture was stirred for 2 hours after which the reaction was quenched with MeOH and subsequently concentrated in vacuo. The solid was triturated with heptane 3 times and dried in vacuo to give intermediate 25 (1100 mg, 2.79 mmol) as the HCl salt, which was used as such without further purification.

Preparation of Intermediate 26

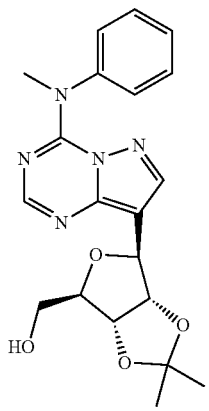 [SMILES: CN(c1ccccc1)c1ncnc2c([C@@H]3O[C@H](CO)[C@H]4OC(C)(C)O[C@H]43)cnn12]

Dimethoxypropane (1417 µL, 11.4 mmol) was added to a mixture of intermediate 25 (900 mg, 2.28 mmol) and p-TSA (434.7 mg, 2.28 mmol) in acetone, the reaction mixture was stirred at room temperature for 4 hours. Sat. NaHCO$_3$ was added and the mixture was extracted with EtOAc. The combined organic layers were washed with water and brine, dried with MgSO$_4$ and concentrated. The residue was purified by silicagel column chromatography (heptane/ethyl acetate: 20/80 to 50/50) to give Intermediate 26 (648 mg, 1.63 mmol, 71.3% yield).

Example A8

Preparation of Intermediate 27

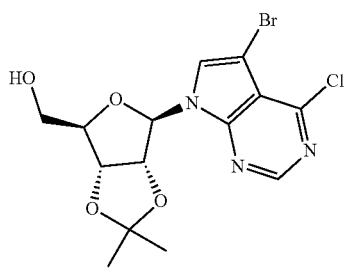 [SMILES: CC1(C)O[C@@H]2[C@H](O1)[C@@H](CO)O[C@H]2n1cc(Br)c2c(Cl)ncnc21]

To a stirred solution of intermediate 1 (5.39 g, 16.55 mmol) in DMF (25 mL) at room temperature was added portion wise N-bromo succinimide (2.95 g, 16.55 mmol). The mixture was stirred at room temperature for 1 hour. The reaction mixture was poured into water and extracted with ethyl acetate. The combined organic phases were washed with water, dried, filtered and concentrated under reduced pressure. The residue was purified by flash chromatography on silica gel (DCM/MeOH: 99/1) to afford intermediate 27 (1.8 g, 4.45 mmol, 26.8% yield)

Example A9

Preparation of Intermediate 28

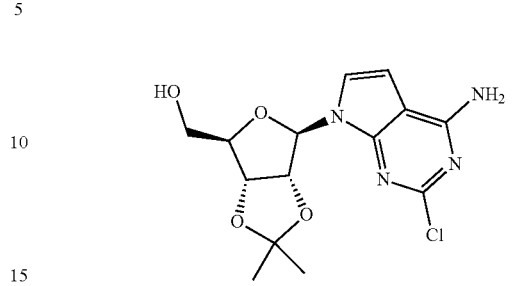

To a solution of Intermediate 15 (1.8 g, 5 mmol) in 1,4-dioxane (30 mL) was added NH$_3$.H$_2$O (30 mL). The reaction mixture was heated to 80° C. for 12 hours in a sealed tube. The mixture was cooled to room temperature and the solvent was evaporated in vacuum affording intermediate 28 (1.8 g, 98% yield) as yellow oil.

Example A10

Preparation of Intermediate 29

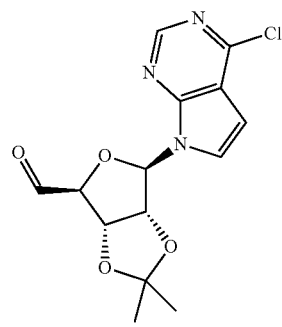 [SMILES: CC1(C)O[C@@H]2[C@H](O1)[C@@H](C=O)O[C@H]2n1ccc2c(Cl)ncnc21]

To a mixture of Intermediate 1 (2.00 g, 6.18 mmol) in DCM (40 mL) was added Dess-Martin periodinane (5.24 g, 12.36 mmol) in one portion at 0'C under N$_2$. The mixture was stirred at 0° C. for 3 hours. To the mixture was added Na$_2$S$_2$O$_3$ (4 g) in saturated NaHCO$_3$ (20 mL) and the mixture was stirred for 10 min. The aqueous phase was extracted with DCM (three times 20 mL). The combined organic phases were washed with saturated brine (two times 20 mL), dried with anhydrous MgSO$_4$, filtered and concentrated in vacuum to afford Intermediate 29 (1.80 g, crude) as light yellow gum. The crude product was directly used for the next reaction step without further purification.

Below intermediates were prepared by an analogous reaction protocol as was used for the preparation of intermediate 29 using the appropriate starting materials (Table 3).

TABLE 3
| Intermediate structure | | Starting material |
|---|---|---|
| 30 | 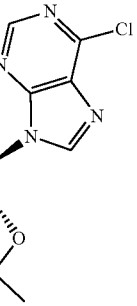 | 6-chloro-9-beta-d-(2,3-isopropylidene)ribofuranosylpurine |
| 31 | 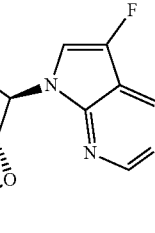 | intermediate 10 |
| 32 | 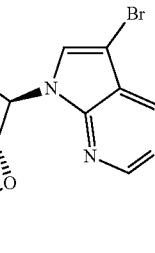 | intermediate 27 |
| 33 | 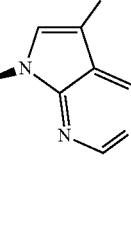 | Intermediate 12 |
| 34 | 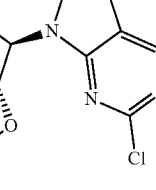 | intermediate 15 |
| 35 | 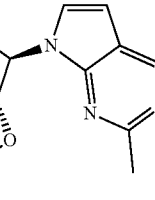 | intermediate 9 |

TABLE 3-continued
| Intermediate structure | | Starting material |
|---|---|---|
| 36 | 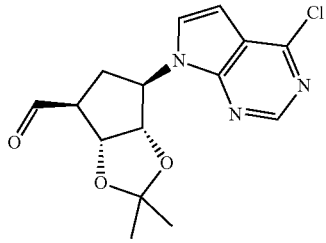 [SMILES: CC1(C)O[C@@H]2[C@H](O1)[C@@H](C=O)C[C@H]2n1ccc2c(Cl)ncnc21] | intermediate 14 |
| 37 | 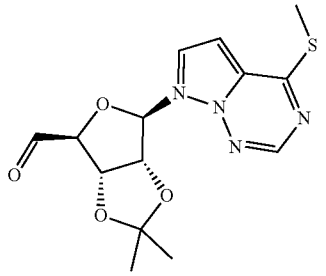 | intermediate 21 |
| 38 | 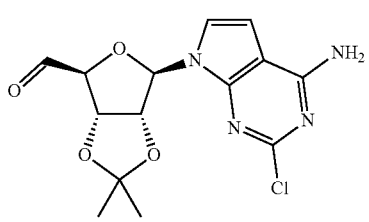 [SMILES: CC1(C)O[C@@H]2[C@H](O1)[C@@H](C=O)O[C@H]2n1ccc2c(N)nc(Cl)nc21] | Intermediate 28 |
| 39 | 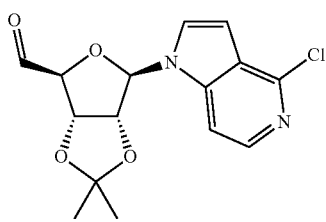 [SMILES: CC1(C)O[C@@H]2[C@H](O1)[C@@H](C=O)O[C@H]2n1ccc2c(Cl)nccc21] | Intermediate 7 |
| 40 | 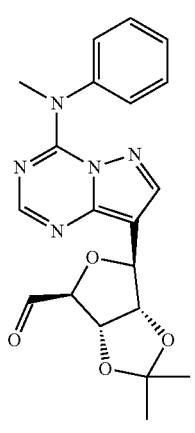 [SMILES: CN(c1ccccc1)c1ncnc2c([C@@H]3O[C@H](C=O)[C@H]4OC(C)(C)O[C@H]43)cnn12] | Intermediate 26 |

TABLE 3-continued

| Intermediate structure | Starting material |
|---|---|
| 41 | Intermediate 4 |

Example A11

Preparation of Intermediate 42

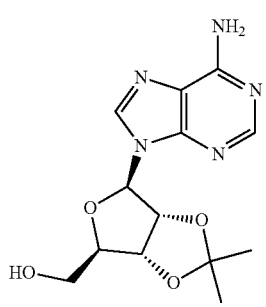 [SMILES: CC1(C)O[C@@H]2[C@H](O1)[C@@H](CO)O[C@H]2n1cnc2c(N)ncnc21]

A solution of adenosine (20 g, 74.8 mmol) and p-toluenesulfonic acid monohydrate (14.8 g, 77.9 mmol) in acetone (786 mL) was stirred for 30 min at r.t. and then triethyl orthoformate anhydrous (57 mL, 342.8 mmol) was added. After 2 days volatiles were evaporated and the residue was partitioned in NaHCO$_3$ aq. and CH$_2$Cl$_2$. The solid was filtered and was washed with water and ether to give 20.2 g of intermediate 42. The filtrate was evaporated and the residue was partitioned in NaHCO$_3$ ac and CH$_2$Cl$_2$. The separated organic layer was washed with brine, dried over MgSO$_4$ and evaporated. The yellow solid was washed with ether to give another 1.89 g of Intermediate 42 In total 22.1 g of Intermediate 42 (22.1 g, 69.7 mmol, 93% yield)) is formed and isolated.

Preparation of Intermediate 43

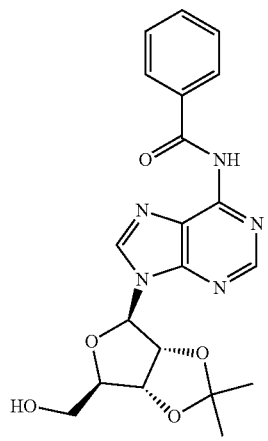 [SMILES: CC1(C)O[C@@H]2[C@H](O1)[C@@H](CO)O[C@H]2n1cnc2c(NC(=O)c3ccccc3)ncnc21]

A solution of Intermediate 42 (26 g, 84.6 mmol) in pyridine (436 mL) was cooled on an ice bath under nitrogen atmosphere and chlorotrimethylsilane (54.1 mL, 423 mmol) was added over 10 min. The reaction mixture was stirred at room temperature for 2 hours. Then the solution was cooled again on an ice bath and benzoyl chloride (12.8 mL, 110 mmol) was added slowly. The reaction mixture was stirred at room temperature overnight. An extra amount of Benzoyl chloride (7 mL) was added and the mixture was stirred at room temperature overnight. The mixture was cooled to 0° C. and diluted with water (100 mL). After 10 min, a NH$_3$-solution in water (50 ml) was added and the mixture was stirred overnight at room temperature. An additional amount of ammonia (10 mL) was added and the reaction mixture was stirred overnight. The solvents were evaporated. The residue was dissolved in CH$_2$Cl$_2$ (100 mL), washed in successively with IM HCl (2 times 100 mL), saturated NaHCO$_3$ (100 mL), H$_2$O (100 mL) and brine (100 mL), dried over MgSO$_4$ and evaporated yielding a yellow solid. The solid was purified by column chromatography (silica; DCM/MeOH from 100:0 to 0:100). The desired fractions were collected and concentrated in vacuo to give Intermediate 43 (25.91 g, 62.3 mmol 74% yield).

Preparation of Intermediate 44

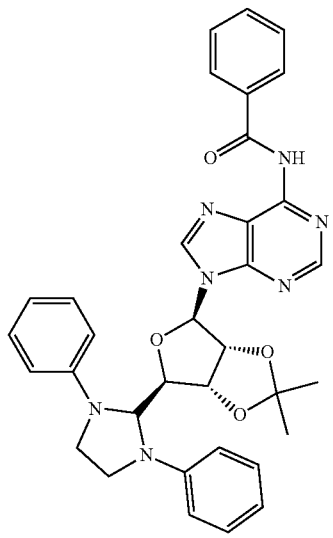 [SMILES: CC1(C)O[C@@H]2[C@H](O1)[C@@H](C1N(c3ccccc3)CCN1c1ccccc1)O[C@H]2n1cnc2c(NC(=O)c3ccccc3)ncnc21]

A solution of intermediate 43 (48.53 g, 0.12 mol) and N,N'-dicyclohexylarbodiimide (72.8 g, 0.35 mol) in DMSO anhydrous (266 mL) was stirred with ice cooling while dichloroacetic acid (4.87 mL, 0.06 mol) was added dropwise. The mixture was stirred at r.t. for 90 min until the reaction was completed. A solution of oxalic acid (21.2 g, 0.24 mol) in MeOH (117.7 mL) was slowly added, and after 30 min at r.t. the mixture was filtered and the crystalline residue of dicyclohexylureum was washed with cold MeOH. N,N'-diphenylethylenediamine (28.8 g, 0.14 mol) was added to the combined filtrate and washings and the resulting solution was stored at room temperature for 1 hour. Water was then added to slight turbidity and the solid was filtered. The filtrate was partitioned between water and chloroform and the organic phase was washed twice with water, dried over MgSO₄ and evaporated. The solid and the residue of organic phase were recrystallized in ethanol to give intermediate 44 (34.79 g, 47.8 mmol, 40% yield).

Preparation of Intermediate 45

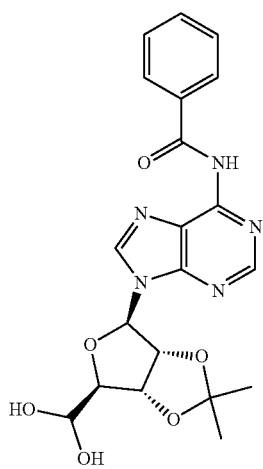 [SMILES: CC1(C)O[C@@H]2[C@H](O1)[C@@H](C(O)O)O[C@H]2n1cnc2c(NC(=O)c3ccccc3)ncnc21]

Dowex 50WX4 (CAS: 69011-20-7) (26 g) was added to a solution of intermediate 44 (13.05 g, 21.6 mmol) in THF (520 mL) and water (520 mL). The suspension was stirred at room temperature for 5 hours. The resin was removed by filtration and washed with THF (4 times 36 mL). The combined filtrates were evaporated to half its volume and the resulting white solid was filtered, washed with water and dried in vacuo giving intermediate 45 (5.90 g, 12.7 mmol, 64% yield)

Example A12

Preparation of Intermediate 46

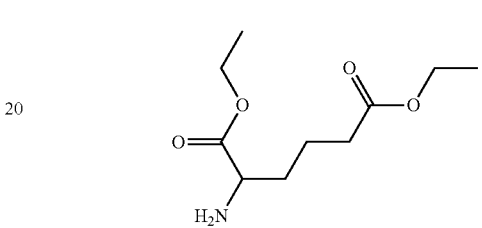

SOCl₂ (11.25 mL, 1.64 g/mL, 155 mmol) was added dropwise to a stirred suspension of dl-2-aminoadipic acid (10 g, 62.1 mmol) in EtOH (200 mL) at 0° C. After addition the reaction mixture was stirred at room temperature for 2 days. The solvents were evaporated to give intermediate 46 (17.1 g 78.7 mmol), which was used as such without further purification.

Below intermediates were prepared by an analogous reaction protocol as was used for the preparation of intermediate 46 using the appropriate starting materials (Table 4).

TABLE 4

| Intermediate | Structure | Starting materials |
| --- | --- | --- |
| 47 | 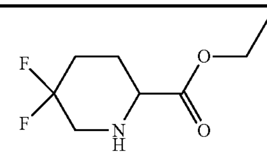 | 5,5-difluoro-2-piperidinecarboxyclic acid |

Example A13

Preparation of Intermediate 48

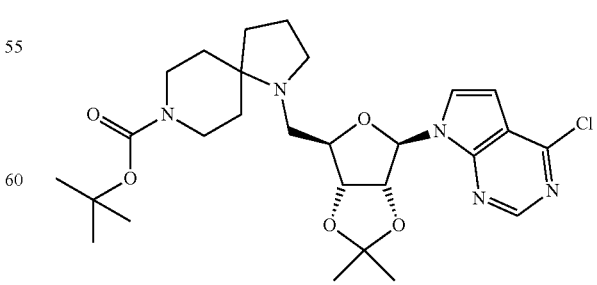

Sodium triacetoxyborohydride (163.8 g, 772.7 mmol) was added to a stirred solution of 1,8-diazospiro[4.5]decane-8- carboxylic acid tert-butyl ester (65 g, 270.4 mmol) and acetic acid (15.5 mL, 270.4 mmol) in DCM (3000 mL). Then a solution of intermediate 29 (125.1 g, 386.3 mmol) in DCM (2500 mL) was added dropwise to the reaction mixture at room temperature. After addition the reaction mixture was stirred at room temperature for 18 hours. The reaction mixture was filtered over a pad of Celite. The pad was washed with DCM (3×). The solvents of the filtrate were evaporated. The residue was dissolved in DCM, washed two times with a saturated aqueous NaHCO₃ solution, washed with brine, dried with MgSO₄, filtered and the solvents of the filtrate evaporated yielding intermediate 48 (188.1 g, 236.8 mmol, 61% yield).

Alternatively also sodium cyanoborohydride in MeOH instead of triacetoxyborohydride in DCM can be used to perform the reaction.

Below intermediates were prepared by an analogous reaction protocol as was used for the preparation of intermediate 48 using the appropriate starting materials (Table 5).

TABLE 5

| Intermediate | Structure | Starting materials and conditions |
|---|---|---|
| 49 | 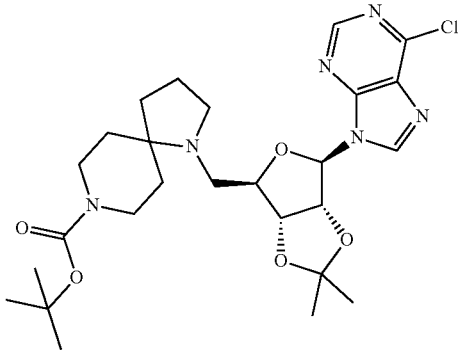 [SMILES: CC(C)(C)OC(=O)N1CCC2(CCCN2C[C@H]2O[C@@H](n3cnc4c(Cl)ncnc43)[C@@H]3OC(C)(C)O[C@@H]32)CC1] | a) Intermediate 30<br>b) NaBH(OAc)₃ in DCM<br>c) 1,8-diazospiro[4.5]decane-8-carboxylic acid tert-butyl ester |
| 50 | 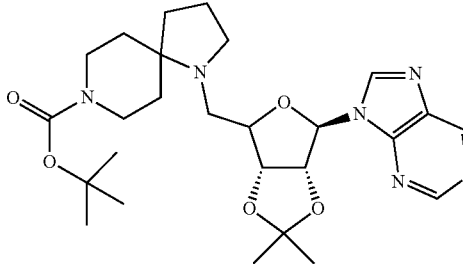 | a) Intermediate 30<br>b) NaBH(OAc)₃ in DCM<br>c) 1,8-diazospiro[4.5]decane-8-carboxylic acid tert-butyl ester |
| 52 | 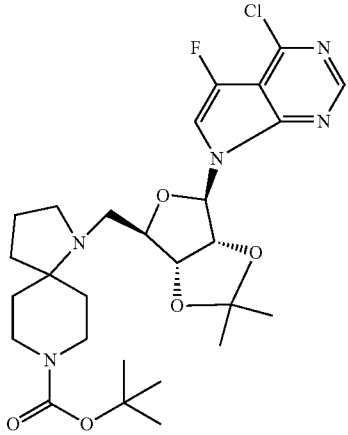 [SMILES: CC(C)(C)OC(=O)N1CCC2(CCCN2C[C@H]2O[C@@H](n3cc(F)c4c(Cl)ncnc43)[C@@H]3OC(C)(C)O[C@@H]32)CC1] | a) Intermediate 31<br>b) NaBH₃CN in MeOH<br>c) 1,8-diazospiro[4.5]decane-8-carboxylic acid tert-butyl ester |

TABLE 5-continued

| Intermediate | Structure | Starting materials and conditions |
|---|---|---|
| 53 | 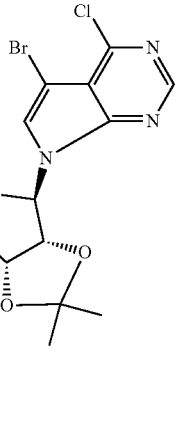 | a) Intermediate 32<br>b) NaBH$_3$CN in MeOH<br>c) 1,8-diazospiro [4.5]decane-8-carboxylic acid tert-butyl ester |
| 54 | 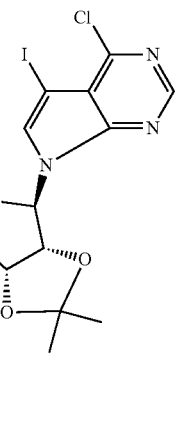 | a) Intermediate 33<br>b) NaBH$_3$CN in MeOH<br>c) 1,8-diazospiro [4.5]decane-8-carboxylic acid tert-butyl ester |
| 55 | 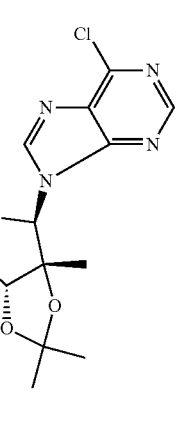 | a) Intermediate 41<br>b) NaBH$_3$CN in MeOH<br>c) 1,8-diazospiro [4.5]decane-8-carboxylic acid tert-butyl ester |
| 56 | 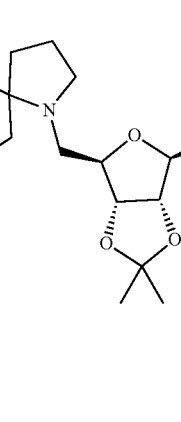 | a) Intermediate 39<br>b) NaBH$_3$CN in MeOH<br>c) 1,8-diazospiro [4.5]decane-8-carboxylic acid tert-butyl ester |

TABLE 5-continued

| Intermediate | Structure | Starting materials and conditions |
|---|---|---|
| 57 | 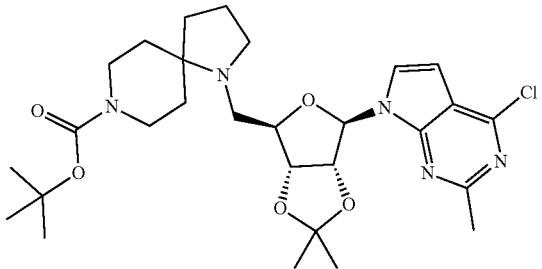 [SMILES: Cc1nc(Cl)c2ccn([C@@H]3O[C@H](CN4CCCC45CCN(C(=O)OC(C)(C)C)CC5)[C@H]4OC(C)(C)O[C@H]43)c2n1] | a) Intermediate 35<br>b) NaBH₃CN in MeOH<br>c) 1,8-diazospiro [4.5]decane-8-carboxylic acid tert-butyl ester |
| 58 | 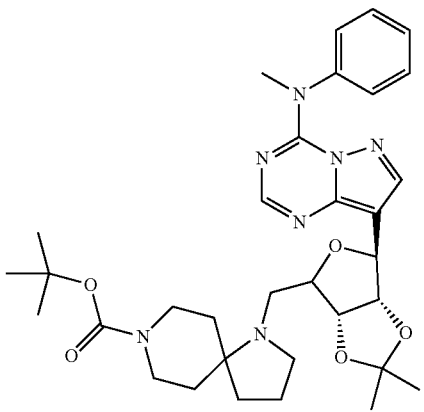 [SMILES: CN(c1ccccc1)c1ncnc2c([C@@H]3OC(CN4CCCC45CCN(C(=O)OC(C)(C)C)CC5)[C@H]4OC(C)(C)O[C@H]43)cnn12] | a) Intermediate 40<br>b) NaBH(OAc)₃ in DCM<br>c) 1,8-diazospiro [4.5]decane-8-carboxylic acid tert-butyl ester |
| 59 | 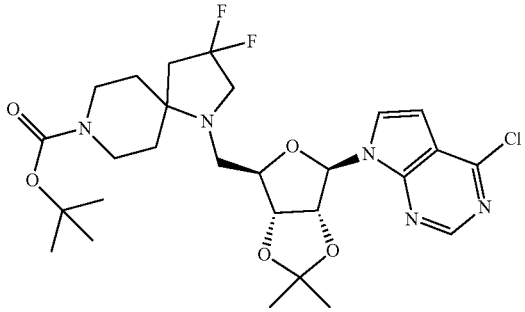 [SMILES: CC(C)(C)OC(=O)N1CCC2(CC1)CC(F)(F)CN2C[C@H]1O[C@@H](n2ccc3c(Cl)ncnc32)[C@@H]2OC(C)(C)O[C@@H]21] | a) Intermediate 29<br>b) NaBH(OAc)₃ in DCM<br>c) 3,3-difluoro-1,8-diaza spiro[4.5]decane-8-carboxylic acid tert-butyl ester |
| 60 | 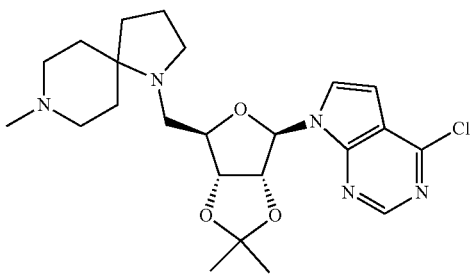 [SMILES: CN1CCC2(CCCN2C[C@H]2O[C@@H](n3ccc4c(Cl)ncnc43)[C@@H]3OC(C)(C)O[C@@H]32)CC1] | a) Intermediate 29<br>b) NaBH(OAc)₃ in DCM<br>c) 8-methyl-1,8-diazospiro[4.5]decane |
| 61 | 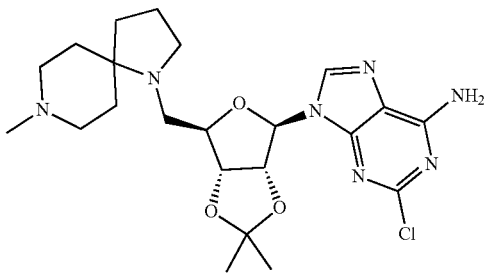 [SMILES: CN1CCC2(CCCN2C[C@H]2O[C@@H](n3cnc4c(N)nc(Cl)nc43)[C@@H]3OC(C)(C)O[C@@H]32)CC1] | a) Intermediate 38<br>b) NaBH₃CN in MeOH<br>c) 8-methyl-1,8-diazospiro[4.5]decane |

TABLE 5-continued

| Intermediate | Structure | Starting materials and conditions |
|---|---|---|
| 62 | 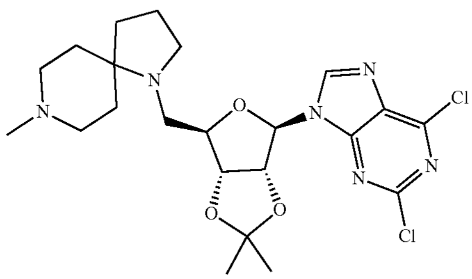 [SMILES: CN1CCC2(CCCN2C[C@H]2O[C@@H](n3cnc4c(Cl)nc(Cl)nc43)[C@@H]3OC(C)(C)O[C@@H]32)CC1] | a) Intermediate 34<br>b) NaBH₃CN in MeOH<br>c) 8-methyl-1,8-diazaspiro[4.5]decane |
| 63 | 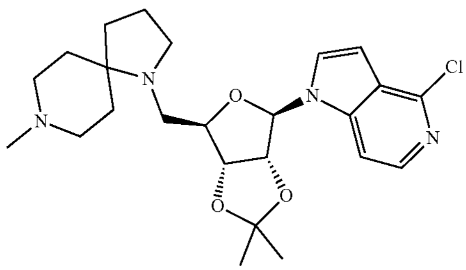 [SMILES: CN1CCC2(CCCN2C[C@H]2O[C@@H](n3ccc4c(Cl)nccc43)[C@@H]3OC(C)(C)O[C@@H]32)CC1] | a) Intermediate 39<br>b) NaBH₃CN in MeOH<br>c) 8-methyl-1,8-diazaspiro[4.5]decane |
| 64 | 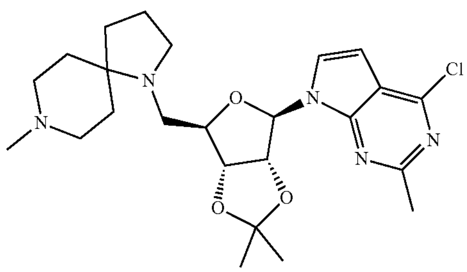 [SMILES: Cc1nc(Cl)c2ccn([C@@H]3O[C@H](CN4CCCC45CCN(C)CC5)[C@H]4OC(C)(C)O[C@H]43)c2n1] | a) Intermediate 35<br>b) NaBH₃CN in MeOH<br>c) 8-methyl-1,8-diazaspiro[4.5]decane |
| 65 | 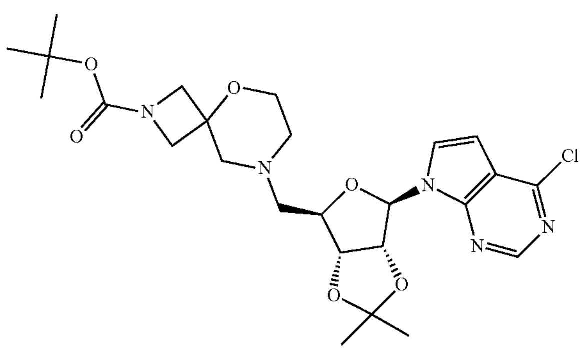 [SMILES: CC(C)(C)OC(=O)N1CC2(CN(C[C@H]3O[C@@H](n4ccc5c(Cl)ncnc54)[C@@H]4OC(C)(C)O[C@@H]43)CCO2)C1] | a) Intermediate 29<br>b) NaBH(OAc)₃ in DCM<br>c) tert-butyl 5oxa-2,8-diazaspiro[3.5]nonane-2-carboxylate |
| 66 | 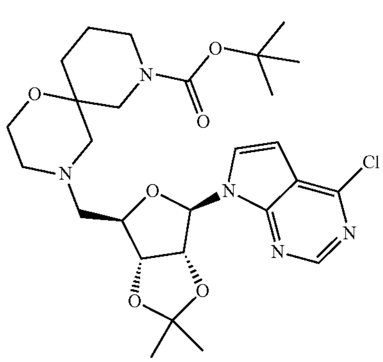 [SMILES: CC(C)(C)OC(=O)N1CCCC2(CN(C[C@H]3O[C@@H](n4ccc5c(Cl)ncnc54)[C@@H]4OC(C)(C)O[C@@H]43)CCO2)C1] | a) Intermediate 29<br>b) NaBH₃CN in MeOH<br>c) tert-butyl 1-oxa-4,8-diazaspiro[5.5]undecane-8-carboxylate |

TABLE 5-continued

| Intermediate | Structure | Starting materials and conditions |
|---|---|---|
| 67 | 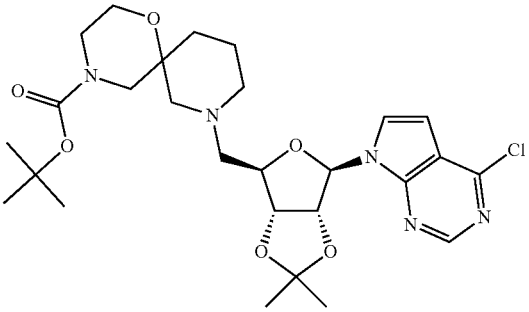 [SMILES: CC(C)(C)OC(=O)N1CCOC2(CCCN(C[C@H]3O[C@@H](n4ccc5c(Cl)ncnc54)[C@@H]4OC(C)(C)O[C@@H]43)C2)C1] | a) Intermediate 29<br>b) NaBH(OAc)₃ in DCM<br>c) tert-butyl 1-oxa-4,8-diazaspiro[5.5]undecane-4-carboxylate |
| 68 | 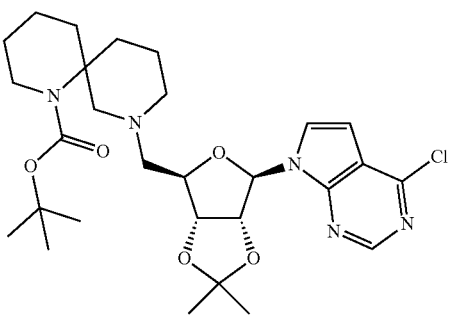 [SMILES: CC(C)(C)OC(=O)N1CCCCC12CCCN(C[C@H]1O[C@@H](n3ccc4c(Cl)ncnc43)[C@@H]3OC(C)(C)O[C@@H]31)C2] | a) Intermediate 29<br>b) NaBH(OAc)₃ in DCM<br>c) tert-butyl 1,8-diazospiro[5.5]undecane-1-carboxylate |
| 69 | 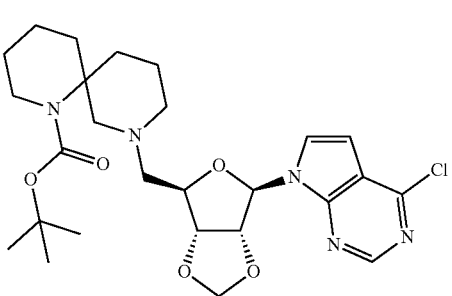 | a) Intermediate 29<br>b) NaBH(OAc)₃ in DCM<br>c) tert-butyl 4-oxa-1,8-diazospiro[5.5]undecane-1-carboxylate |
| 70 | 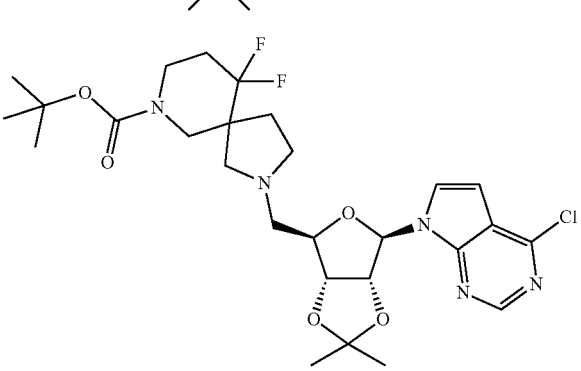 | a) Intermediate 29<br>b) NaBH₃CN in MeOH<br>c) tert-butyl 10,10-difluoro-2,7-diazospiro[4.5]decane-7-carboxylate |
| 71 | 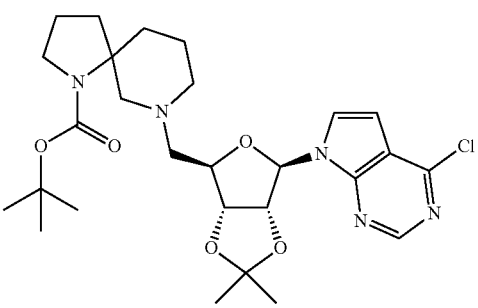 [SMILES: CC(C)(C)OC(=O)N1CCCC12CCCN(C[C@H]1O[C@@H](n3ccc4c(Cl)ncnc43)[C@@H]3OC(C)(C)O[C@@H]31)C2] | a) Intermediate 29<br>b) NaBH(OAc)₃ in DCM<br>c) tert-butyl 1,7-diazospiro[4.5]decane-1-carboxylate |

TABLE 5-continued

| Intermediate | Structure | Starting materials and conditions |
|---|---|---|
| 72 | 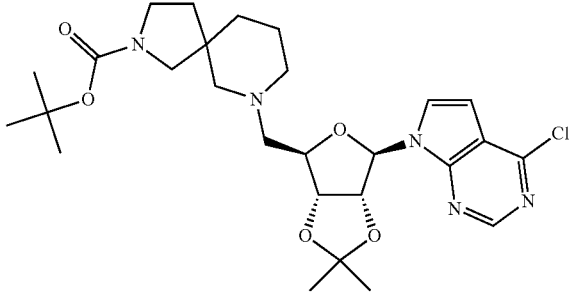 [SMILES: CC(C)(C)OC(=O)N1CCC2(CCCN(C[C@H]3O[C@@H](n4ccc5c(Cl)ncnc54)[C@@H]4OC(C)(C)O[C@@H]43)C2)C1] | a) Intermediate 29<br>b) NaBH(OAc)₃ in DCM<br>c) tert-butyl 2,7-diazaspiro[4.5]decane-2-carboxylate |
| 73 | 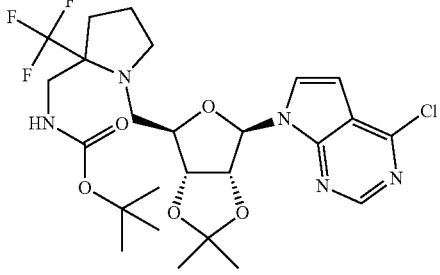 | a) Intermediate 29<br>b) NaBH₃CN in MeOH<br>c) tert-butyl {[2-(trifluoromethyl)pyrrolidin-2-yl]methy}carbamate |
| 74 | 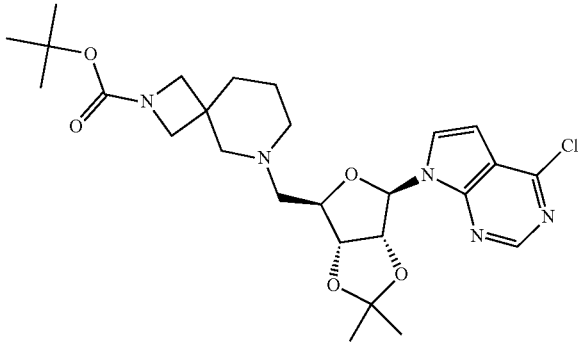 [SMILES: CC(C)(C)OC(=O)N1CC2(CCCN(C[C@H]3O[C@@H](n4ccc5c(Cl)ncnc54)[C@@H]4OC(C)(C)O[C@@H]43)C2)C1] | a) Intermediate 29<br>b) NaBH(OAc)₃ in DCM<br>c) tert-butyl 2,6-diazaspiro[3.5]nonane-2-carboxylate |
| 75 | 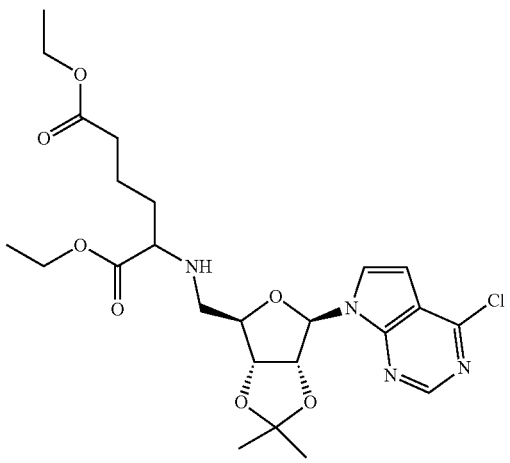 [SMILES: CCOC(=O)CCCC(NC[C@H]1O[C@@H](n2ccc3c(Cl)ncnc32)[C@@H]2OC(C)(C)O[C@@H]21)C(=O)OCC] | a) Intermediate 29<br>b) NaBH(OAc)₃ in DCM<br>c) Intermediate 46 |

TABLE 5-continued

| Intermediate | Structure | Starting materials and conditions |
|---|---|---|
| 76 | 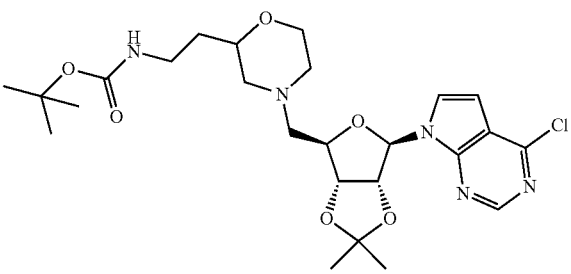 [SMILES: CC(C)(C)OC(=O)NCCC1CN(C[C@H]2O[C@@H](n3ccc4c(Cl)ncnc43)[C@@H]3OC(C)(C)O[C@@H]32)CCO1] | a) Intermediate 29<br>b) NaBH(OAc)$_3$ in DCM<br>c) tert-butyl (2-morpholin-2-ylethyl)carbamate |
| 77 | 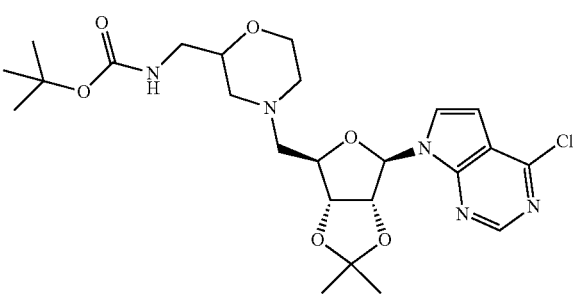 [SMILES: CC(C)(C)OC(=O)NCC1CN(C[C@H]2O[C@@H](n3ccc4c(Cl)ncnc43)[C@@H]3OC(C)(C)O[C@@H]32)CCO1] | a) Intermediate 29<br>b) NaBH(OAc)$_3$ in DCM<br>c) tert-butyl morpholin-2-ylmethylcarbamate |
| 78 | 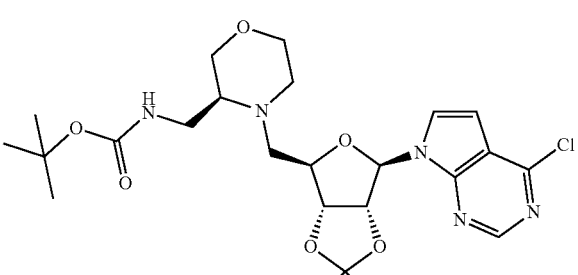 | a) Intermediate 29<br>b) NaBH(OAc)$_3$ in DCM<br>c) (S)-tert-butyl (morpholin-3-ylmethyl)carbamate |
| 79 | 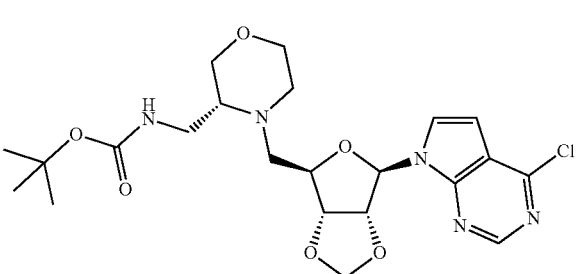 | a) Intermediate 29<br>b) NaBH(OAc)$_3$ in DCM<br>c) (R)-tert-butyl (morpholin-3-ylmethyl)carbamate |
| 80 | 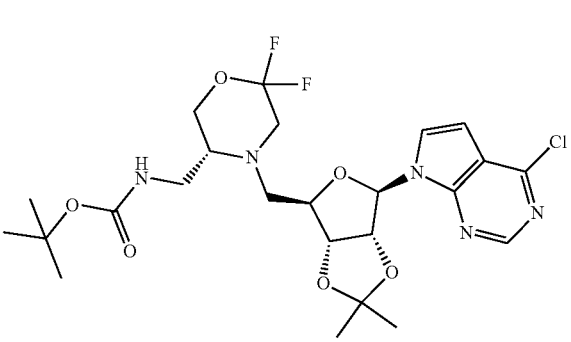 [SMILES: CC(C)(C)OC(=O)NC[C@@H]1COC(F)(F)CN1C[C@H]1O[C@@H](n2ccc3c(Cl)ncnc32)[C@@H]2OC(C)(C)O[C@@H]21] | a) Intermediate 29<br>b) NaBH(OAc)$_3$ in DCM<br>c) Intermediate 47 |

TABLE 5-continued

| Intermediate | Structure | Starting materials and conditions |
|---|---|---|
| 81 | 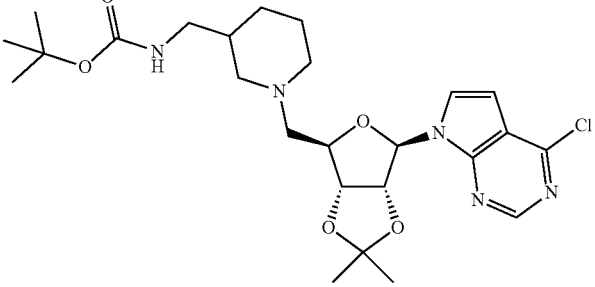 | a) intermediate 29<br>b) NaBH(OAc)$_3$ in DCM<br>c) 3-N-boc-aminomethyl piperidine |
| 82 | 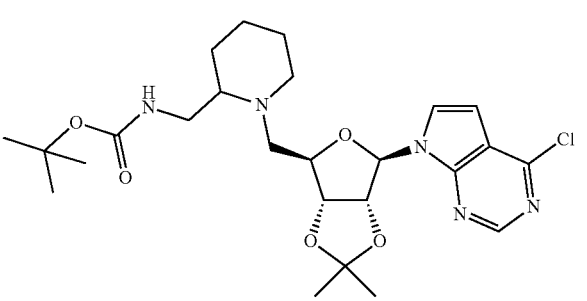 [SMILES: CC(C)(C)OC(=O)NCC1CCCCN1C[C@H]1O[C@@H](n2ccc3c(Cl)ncnc32)[C@@H]2OC(C)(C)O[C@@H]21] | a) Intermediate 29<br>b) NaBH(OAc)$_3$ in DCM<br>c) 2-(boc-aminomethyl)-piperidine |
| 83 | 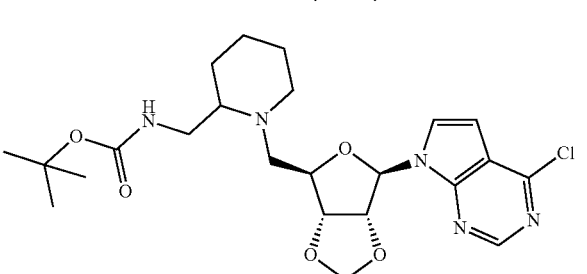 | a) Intermediate 29<br>b) NaBH(OAc)$_3$ in DCM<br>c) 3-boc-aminopiperidine |
| 84 | 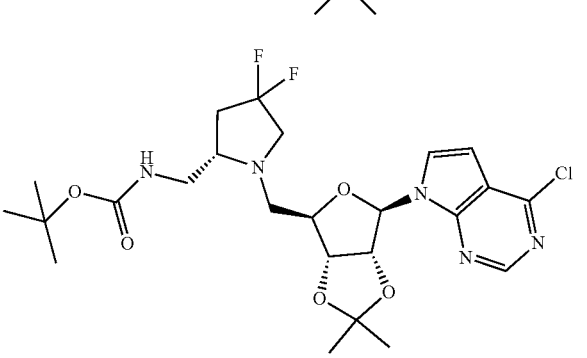 | a) Intermediate 29<br>b) NaBH(OAc)$_3$ in DCM<br>(S)-2-(boc-aminomethyl)-4,4-difluoropyrrolidine |
| 85 | 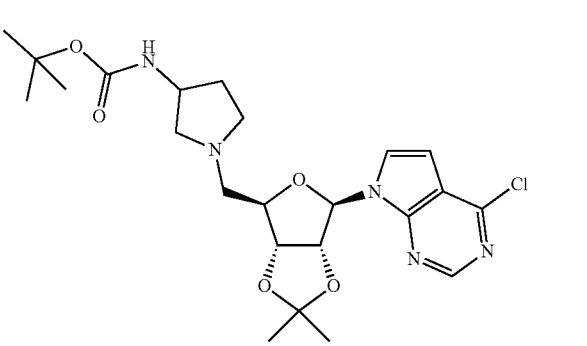 [SMILES: CC(C)(C)OC(=O)NC1CCN(C[C@H]2O[C@@H](n3ccc4c(Cl)ncnc43)[C@@H]3OC(C)(C)O[C@@H]32)C1] | a) Intermediate 29<br>b) NaBH(OAc)$_3$ in DCM<br>c) 3-(tert-butoxycarbonylamino)pyrrolidine |

TABLE 5-continued

| Intermediate | Structure | Starting materials and conditions |
|---|---|---|
| 86 | 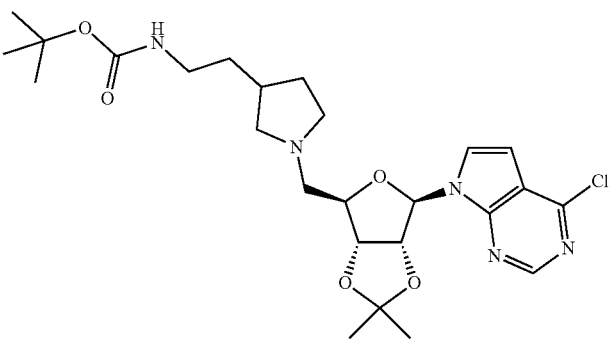 [SMILES: CC(C)(C)OC(=O)NCCC1CCN(C[C@H]2O[C@@H](n3ccc4c(Cl)ncnc43)[C@@H]3OC(C)(C)O[C@@H]32)C1] | a) Intermediate 29<br>b) NaBH(OAc)₃ in DCM<br>c) tert-butyl 2-(pyrrolidine-3-yl)ethylcarbamate |
| 87 | 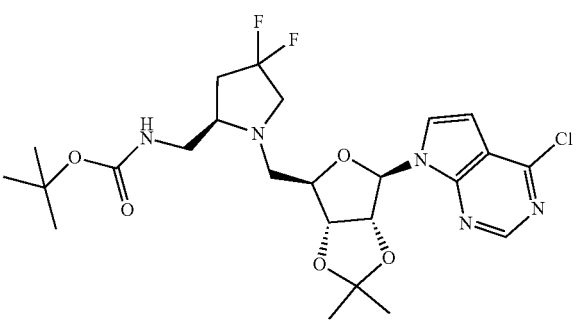 [SMILES: CC(C)(C)OC(=O)NC[C@H]1CC(F)(F)CN1C[C@H]1O[C@@H](n2ccc3c(Cl)ncnc32)[C@@H]2OC(C)(C)O[C@@H]21] | a) Intermediate 29<br>b) NaBH(OAc)₃ in DCM<br>c) (R)-2-(boc-aminomethyl)-4,4-difluoropyrrolidine |
| 88 | 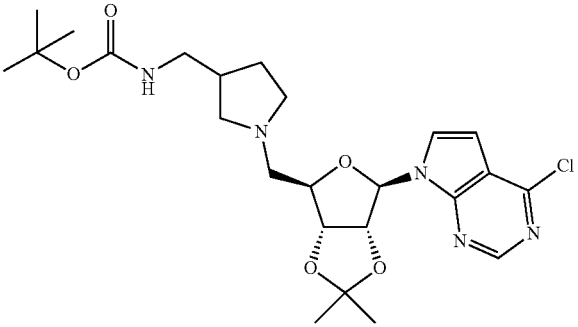 [SMILES: CC(C)(C)OC(=O)NCC1CCN(C[C@H]2O[C@@H](n3ccc4c(Cl)ncnc43)[C@@H]3OC(C)(C)O[C@@H]32)C1] | a) Intermediate 29<br>b) NaBH(OAc)₃ in DCM<br>c) 3-boc-aminomethyl pyrrolidine |
| 89 | 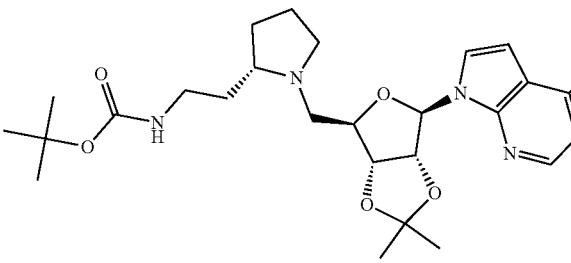 | a) Intermediate 29<br>b) NaBH(OAc)₃ in DCM<br>c) tert-butyl {2-[(2S)-pyrrolidin-2-yl]ethyl}carbamate |
| 90a | 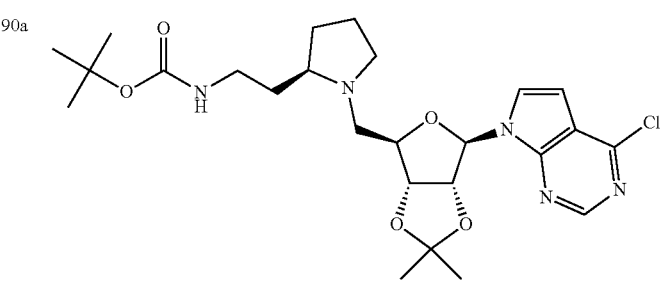 | a) Intermediate 30<br>b) NaBH(OAc)₃ in DCM<br>c) tert-butyl {2-[(2R)-pyrrolidin-2-yl]ethyl}carbamate |

TABLE 5-continued

| Intermediate | Structure | Starting materials and conditions |
|---|---|---|
| 90b | 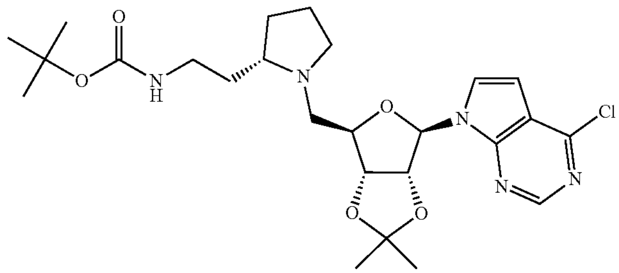 [SMILES: CC(C)(C)OC(=O)NCC[C@@H]1CCCN1C[C@H]1O[C@@H](n2ccc3c(Cl)ncnc32)[C@@H]2OC(C)(C)O[C@@H]21] | d) Intermediate 30<br>e) NaBH(OAc)₃ in DCM<br>f) tert-butyl {2-[(2S)-pyrrolidin-2-yl]ethyl}carbamate |
| 91 | 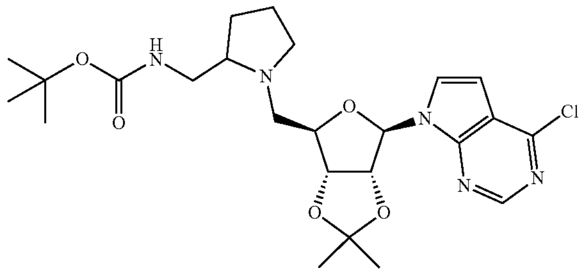 [SMILES: CC(C)(C)OC(=O)NCC1CCCN1C[C@H]1O[C@@H](n2ccc3c(Cl)ncnc32)[C@@H]2OC(C)(C)O[C@@H]21] | a) Intermediate 29<br>b) NaBH(OAc)₃ in DCM<br>c) 2-boc amino methylpyrrolidine |

Example A 14

Preparation of Intermediate 92

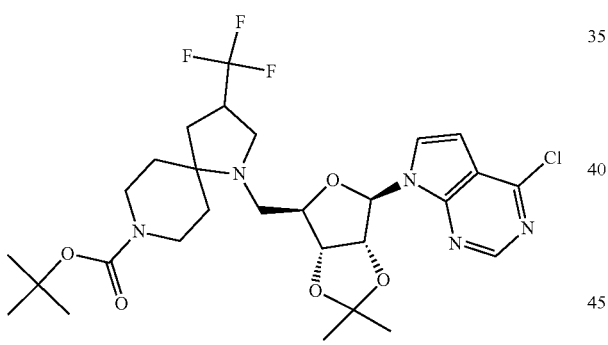

TFA (0.56 mL, 7.3 mmol) was added to a stirred solution of N,N'-di-t-boc-3-(trifluoromethyl)-1,8-diazaspiro[4.5]decane (0.5 g, 1.2 mmol) in DCM (20 mL) at room temperature. The reaction mixture was stirred at room temperature for 18 hours. 50 mL DIPE was added to the reaction mixture. The resulting suspension was stirred for 18 hours at room temperature. The precipitate was filtered off and dried on the air. The residue was stirred in DCM (15 mL) and then AcOH (0.07 mL, 1.2 mmol) and NaBH(OAc)₃ (0.519 g, 2.45 mmol) were added. The reaction mixture was stirred for 10 minutes and then a solution of intermediate 29 (0.55 g, 1.7 mmol) in DCM (8 mL) was added dropwise. After addition the reaction mixture was stirred at room temperature for 18 hours. The reaction mixture was filtered over a pad of Celite. The pad was washed three times with DCM. The solvents of the filtrate were evaporated. The residue was dissolved in DCM, washed two times with a saturated aqueous NaHCO₃ solution, washed with brine, dried with MgSO₄, filtered and the solvents of the filtrate evaporated. The residue was dissolved in DCM and purified over a SiO₂ column, type Grace Reveleris SRC, 12 g, Si 40, on a Armen Spot II Ultimate purification system using DCM and MeOH as eluens in a gradient starting from 100/DCM and ending with 20% MeOH and 80% DCM. The fractions containing product were combined and the solvents were evaporated to give intermediate 92 (218 mg, 8.7% yield).

Example A15

Preparation of Intermediate 93

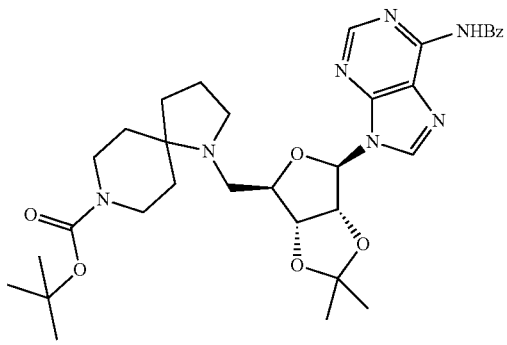

Intermediate 45 (0.48 g, 0.95 mmol) tert-butyl 1,8-diazospiro[4.5]decane-8-caroboxylate (0.3 g, 1.051 mmol) and sodium acetate (0.0391 g, 0.477 mmol) were dissolved in dichloroethane (9 mL) and stirred for 30 min. Then sodium triacetoxyborohydride (0.304 g, 1.433 mmol) was added and the solution was stirred overnight at room temperature. The mixture was diluted with DCM (50 mL) and washed with Na₂CO₃(IM, 50 mL). The organic layer was dried (MgSO₄) and filtered. The solvents were evaporated to dryness to give crude intermediate 93 (0.824 g, 1 mmol, yield: 103%). No further purification was done.

Below intermediates were prepared by an analogous reaction protocol as was used for the preparation of intermediate 93 using the appropriate starting materials (Table 6).

TABLE 6

| Intermediate | Structure | Starting materials and conditions |
|---|---|---|
| 94 | 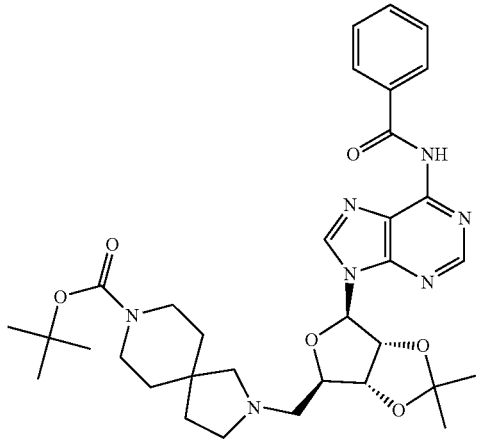 [SMILES: CC(C)(C)OC(=O)N1CCC2(CCN(C[C@H]3O[C@@H](n4cnc5c(NC(=O)c6ccccc6)ncnc54)[C@@H]4OC(C)(C)O[C@@H]43)C2)CC1] | a) intermediate 45<br>b) tert-Butyl 2,8-diazaspiro[4.5]decane-8-carboxylate<br>c) NaBH(OAc)₃ in DCM |
| 95 | 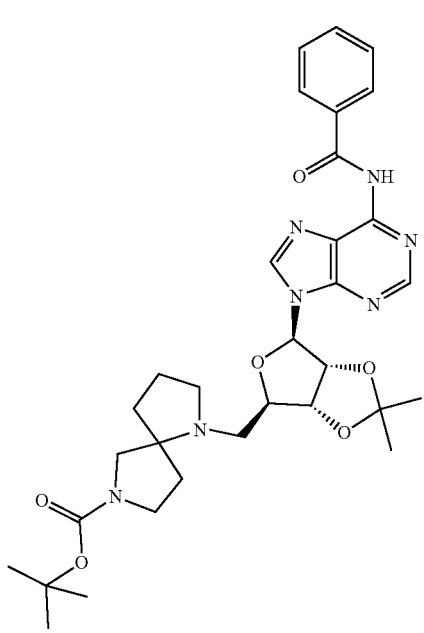 [SMILES: CC(C)(C)OC(=O)N1CCC2(CCCN2C[C@H]2O[C@@H](n3cnc4c(NC(=O)c5ccccc5)ncnc43)[C@@H]3OC(C)(C)O[C@@H]32)C1] | a) intermediate 45<br>b) tert-Butyl 1,7-diazaspiro[4.4]nonane-7-carboxylate<br>c) NaBH(OAc)₃ in DCM |

TABLE 6-continued

| Intermediate | Structure | Starting materials and conditions |
|---|---|---|
| 96 | 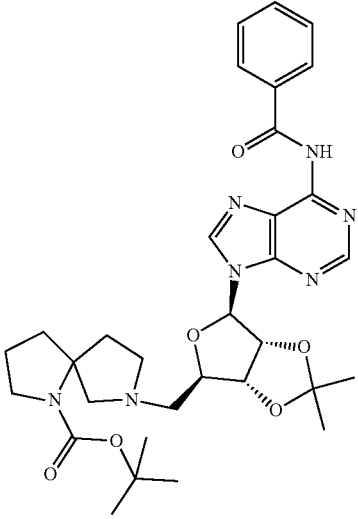 [SMILES: CC(C)(C)OC(=O)N1CCCC12CCN(C[C@H]1O[C@@H](n3cnc4c(NC(=O)c5ccccc5)ncnc43)[C@@H]3OC(C)(C)O[C@@H]31)C2] | a) intermediate 45<br>b) tert-Butyl 1,7-diazaspiro[4,4]nonane-1-carboxylate<br>c) NaBH(OAc)₃ in dichloroethane |
| 97 | 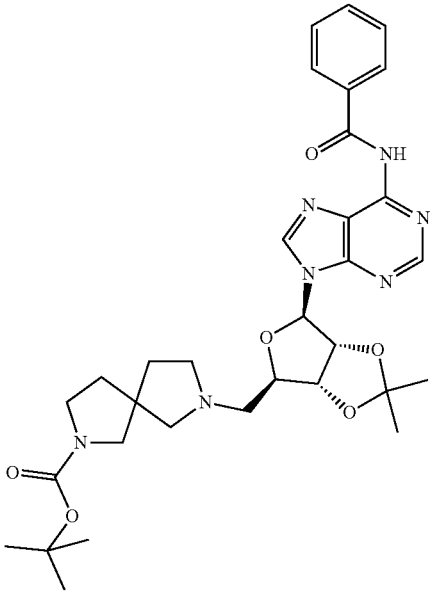 [SMILES: CC(C)(C)OC(=O)N1CCC2(CCN(C[C@H]3O[C@@H](n4cnc5c(NC(=O)c6ccccc6)ncnc54)[C@@H]4OC(C)(C)O[C@@H]43)C2)C1] | a) intermediate 45<br>b) Tert-Butyl 2,7-Diaza-Spiro[4.4]Nonane-2-Carboxylate<br>c) NaBH(OAc)₃ in DCM |
| 98 | 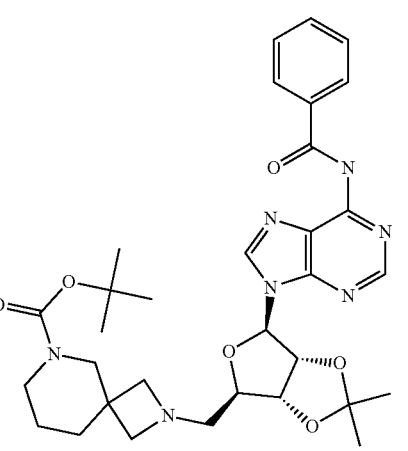 | a) intermediate 45<br>b) tert-Butyl-2,6-diazaspiro[3.5]nonane-6-carboxylate-oxalate<br>c) NaBH(OAc)₃ in dichloroethane |

TABLE 6-continued

| Intermediate | Structure | Starting materials and conditions |
|---|---|---|
| 99 | 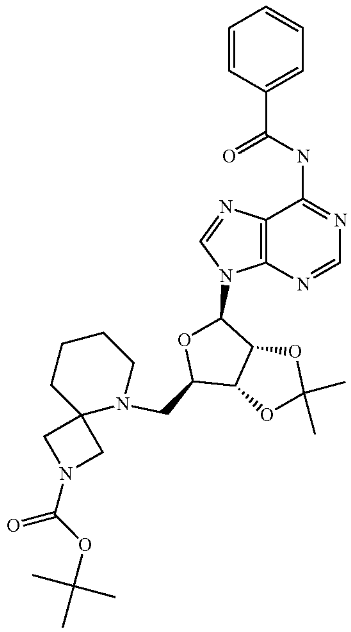 [SMILES: CC(C)(C)OC(=O)N1CC2(CCCCN2C[C@H]2O[C@@H](n3cnc4c(NC(=O)c5ccccc5)ncnc43)[C@@H]3OC(C)(C)O[C@@H]32)C1] | a) intermediate 45<br>b) tert-Butyl 2,5-diazaspiro[3.5]nonane-2-carboxylate<br>c) NaBH(OAc)$_3$ in dichloroethane |
| 100 | 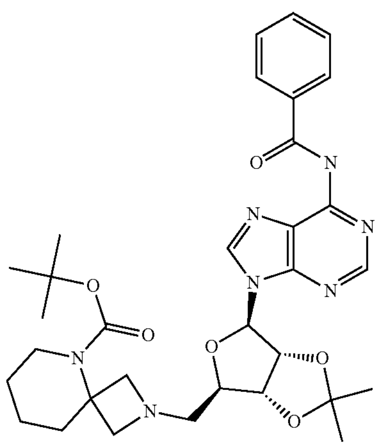 [SMILES: CC(C)(C)OC(=O)N1CCCCC12CN(C[C@H]1O[C@@H](n3cnc4c(NC(=O)c5ccccc5)ncnc43)[C@@H]3OC(C)(C)O[C@@H]31)C2] | a) intermediate 45<br>b) tert-Butyl 2,5-diazaspiro[3.5]nonane-5-carboxylate<br>c) NaBH(OAc)$_3$ in dichloroethane |
| 101 | 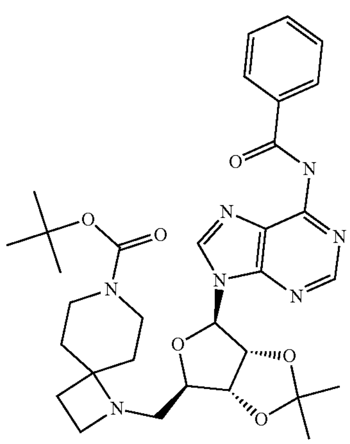 [SMILES: CC(C)(C)OC(=O)N1CCC2(CC1)CCN2C[C@H]1O[C@@H](n2cnc3c(NC(=O)c4ccccc4)ncnc32)[C@@H]2OC(C)(C)O[C@@H]21] | a) intermediate 45<br>b) tert-Butyl 1,7-diazaspiro[3.5]nonane-7-carboxylate<br>c) NaBH(OAc)$_3$ in dichloroethane |

TABLE 6-continued

| Intermediate | Structure | Starting materials and conditions |
| --- | --- | --- |
| 102 | 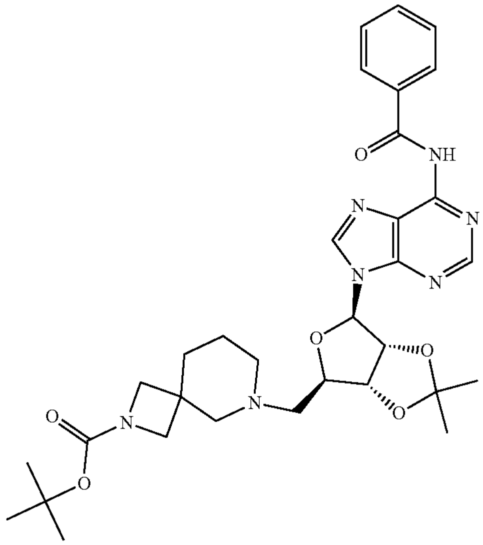 [SMILES: CC(C)(C)OC(=O)N1CC2(CCCN(C[C@H]3O[C@@H](n4cnc5c(NC(=O)c6ccccc6)ncnc54)[C@@H]4OC(C)(C)O[C@@H]43)C2)C1] | a) intermediate 45<br>b) tert-Butyl 2,6-diazaspiro[3.5]nonane-2-carboxylate oxalate<br>c) NaBH(OAc)₃ in dichloroethane |
| 103 | 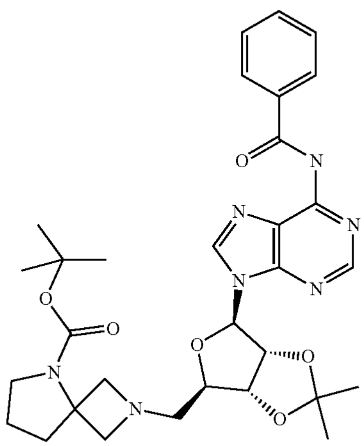 [SMILES: CC(C)(C)OC(=O)N1CCCC12CN(C[C@H]1O[C@@H](n3cnc4c(NC(=O)c5ccccc5)ncnc43)[C@@H]3OC(C)(C)O[C@@H]31)C2] | a) intermediate 45<br>b) tert-Butyl 2,5-diazaspiro[3.4]octane-5-carboxylate<br>c) NaBH(OAc)₃ in dichloroethane |
| 104 | 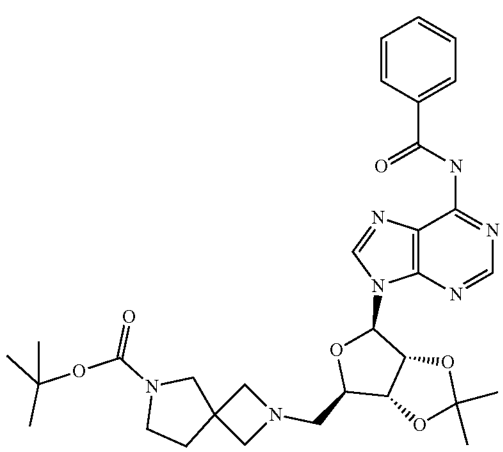 [SMILES: CC(C)(C)OC(=O)N1CCC2(CN(C[C@H]3O[C@@H](n4cnc5c(NC(=O)c6ccccc6)ncnc54)[C@@H]4OC(C)(C)O[C@@H]43)C2)C1] | a) intermediate 45<br>b) tert-Butyl 2,6-diazaspiro[3.4]octane-6-carboxylate<br>c) NaBH(OAc)₃ in dichloroethane |

TABLE 6-continued
| Intermediate | Structure | Starting materials and conditions |
|---|---|---|
| 105 | 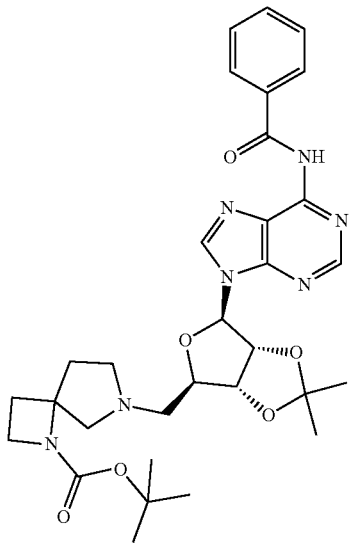 [SMILES: CC(C)(C)OC(=O)N1CCC12CCN(C[C@H]1O[C@@H](n3cnc4c(NC(=O)c5ccccc5)ncnc43)[C@@H]3OC(C)(C)O[C@@H]31)C2] | a) intermediate 45<br>b) tert-Butyl 1,6-diazaspiro[3.4]octane-1-carboxylate<br>c) NaBH(OAc)$_3$ in dichloroethane |
| 106 | 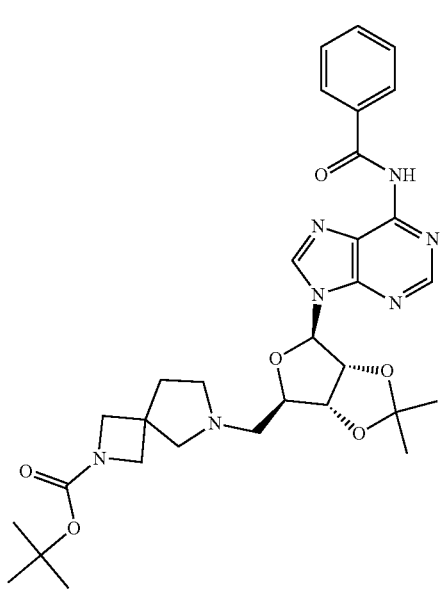 [SMILES: CC(C)(C)OC(=O)N1CC2(CCN(C[C@H]3O[C@@H](n4cnc5c(NC(=O)c6ccccc6)ncnc54)[C@@H]4OC(C)(C)O[C@@H]43)C2)C1] | a) intermediate 45<br>b) tert-Butyl 2,6-diazaspiro[3.4]octane-2-carboxylate<br>c) NaBH(OAc)$_3$ in dichloroethane |

TABLE 6-continued
| Intermediate | Structure | Starting materials and conditions |
|---|---|---|
| 107 | 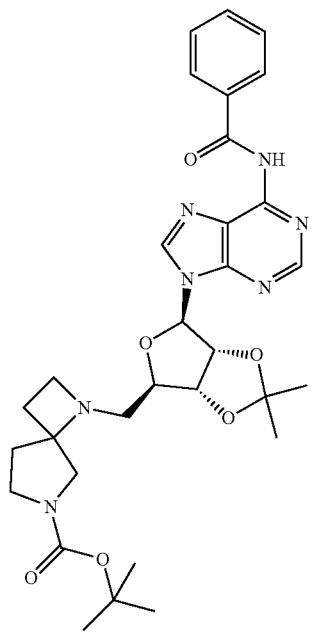 [SMILES: CC(C)(C)OC(=O)N1CCC2(CCN2C[C@H]2O[C@@H](n3cnc4c(NC(=O)c5ccccc5)ncnc43)[C@@H]3OC(C)(C)O[C@@H]32)C1] | a) intermediate 45<br>b) tert-Butyl 1,6-diazaspiro[3.4]octane-6-carboxylate<br>c) NaBH(OAc)$_3$ in dichloroethane |
| 108 | 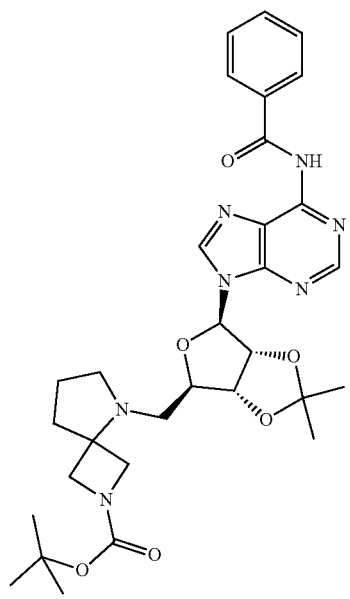 [SMILES: CC(C)(C)OC(=O)N1CC2(CCCN2C[C@H]2O[C@@H](n3cnc4c(NC(=O)c5ccccc5)ncnc43)[C@@H]3OC(C)(C)O[C@@H]32)C1] | a) intermediate 45<br>b) tert-butyl 2,5-diazaspiro[3.4]octane-2-carboxylate<br>c) NaBH(OAc)$_3$ in dichloroethane |

TABLE 6-continued
| Intermediate | Structure | Starting materials and conditions |
|---|---|---|
| 109 | 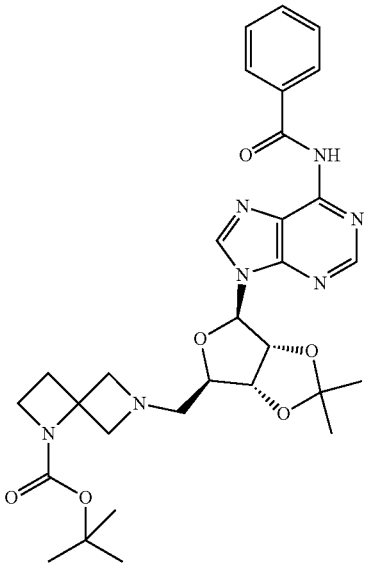 [SMILES: CC(C)(C)OC(=O)N1CCC12CN(C[C@H]1O[C@@H](n3cnc4c(NC(=O)c5ccccc5)ncnc43)[C@@H]3OC(C)(C)O[C@@H]31)C2] | a) intermediate 45<br>b) tert-Butyl 1,6-diazaspiro[3.3]heptane-1-carboxylate<br>c) NaBH(OAc)$_3$ in dichloroethane |
| 110 | 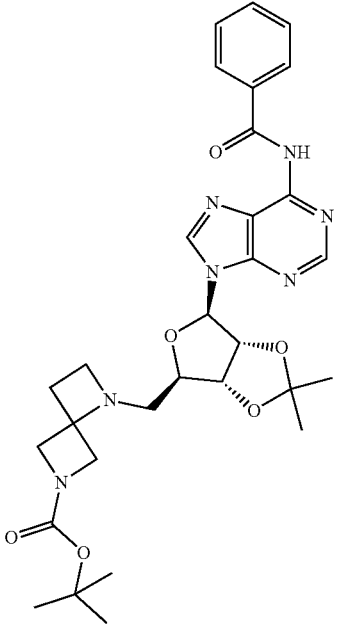 [SMILES: CC(C)(C)OC(=O)N1CC2(CCN2C[C@H]2O[C@@H](n3cnc4c(NC(=O)c5ccccc5)ncnc43)[C@@H]3OC(C)(C)O[C@@H]32)C1] | a) intermediate 45<br>b) tert-Butyl 1,6-diazaspiro[3.3]heptane-6-carboxylate<br>NaBH(OAc)$_3$ in dichloroethane |

Example A17

Preparation of Intermediate 113 and Intermediate 114

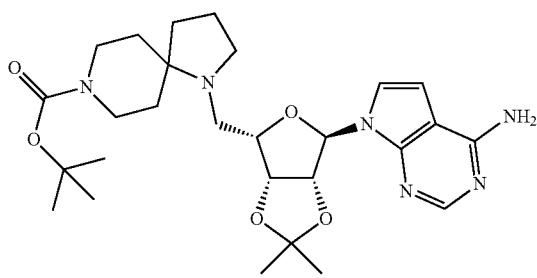 [SMILES: CC(C)(C)OC(=O)N1CCC2(CCCN2C[C@@H]2O[C@@H](n3ccc4c(N)ncnc43)[C@@H]3OC(C)(C)O[C@@H]32)CC1]

Intermediate 113

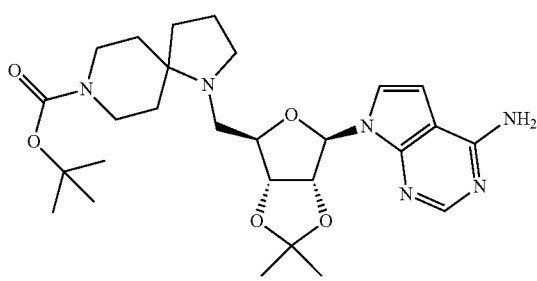 [SMILES: CC(C)(C)OC(=O)N1CCC2(CCCN2C[C@H]2O[C@@H](n3ccc4c(N)ncnc43)[C@@H]3OC(C)(C)O[C@@H]32)CC1]

Intermediate 114

A solution of crude Intermediate 50 (1.3 g, 2.37 mmol) in NH₃ (0.34 mL, 2.4 mmol, 7M in MeOH) was stirred at 130° C. for 4 hours in a Biotage microwave reactor. The solvent was removed and a purification was performed via Prep HPLC (Stationary phase: RP XBridge Prep C18 OBD-10 µm, 30×150 mm, Mobile phase: 0.1% TFA solution in water+5% CH₃CN, CH₃CN) to give intermediate 113 (90 mg, 0.17 mmol) and intermediate 114 (300 mg, 0.567 mmol, 24% yield).

Example A18

Preparation of Intermediate 114

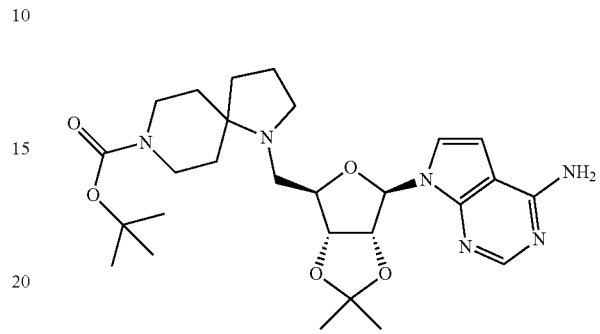

A solution of Intermediate 48 (52.3 g, 62 mmol) in NH₃ (500 mL, 3500 mmol, 7M in MeOH) was stirred and heated at 130° C. for 4 hours in a stainless steel autoclave. The solvents were evaporated. The residue was dissolved in DCM and purified over a SiO₂ column, type Grace Reveleris SRC, 330 g, Si 40, on a Armen Spot II Ultimate purification system using DCM and MeOH as eluens in a gradient starting from 100% DCM and ending with 5% MeOH and 95% DCM. The fractions containing product were combined and the solvents were evaporated yielding the crude Intermediate 114. A purification was performed via Prep HPLC (Stationary phase: Uptisphere C18 ODB—10 µm, 200 g, 5 cm, Mobile phase: 0.25% NH₄HCO₃ solution in water, CH₃CN) yielding pure Intermediate 114 (18.28 g, yield: 55.7%).

Below intermediates were prepared by an analogous reaction protocol as was used for the preparation of Intermediate 114 using the appropriate starting materials (Table 7).

TABLE 7

| Intermediate | Structure | Starting materials and conditions |
|---|---|---|
| 115 | | a) intermediate 49<br>b) NH₃ (7M) in MeOH |
| 115 | | a) Intermediate 50<br>b) NH₃ (7M) in MeOH |

TABLE 7-continued
| Intermediate | Structure | Starting materials and conditions |
|---|---|---|
| 117 | 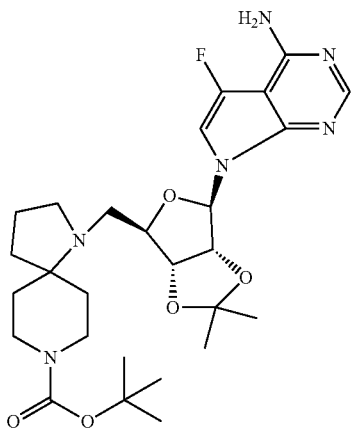 [SMILES: CC(C)(C)OC(=O)N1CCC2(CCCN2C[C@H]2O[C@@H](n3cc(F)c4c(N)ncnc43)[C@@H]3OC(C)(C)O[C@@H]32)CC1] | a) Intermediate 52<br>b) NH$_3$ 28% in H$_2$O |
| 118 | 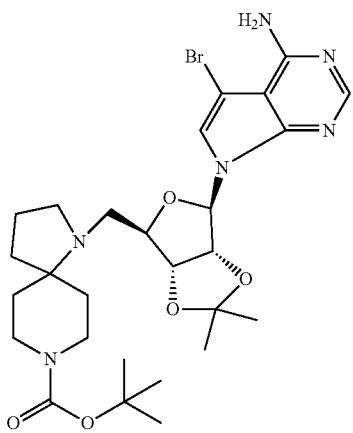 [SMILES: CC(C)(C)OC(=O)N1CCC2(CCCN2C[C@H]2O[C@@H](n3cc(Br)c4c(N)ncnc43)[C@@H]3OC(C)(C)O[C@@H]32)CC1] | a) Intermediate 53<br>b) NH$_3$ 28% in H$_2$O |
| 119 | 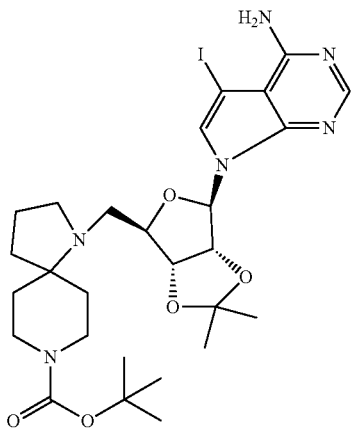 [SMILES: CC(C)(C)OC(=O)N1CCC2(CCCN2C[C@H]2O[C@@H](n3cc(I)c4c(N)ncnc43)[C@@H]3OC(C)(C)O[C@@H]32)CC1] | a) Intermediate 54<br>b) NH$_3$ 28% in H$_2$O |

TABLE 7-continued

| Intermediate | Structure | Starting materials and conditions |
|---|---|---|
| 120 | 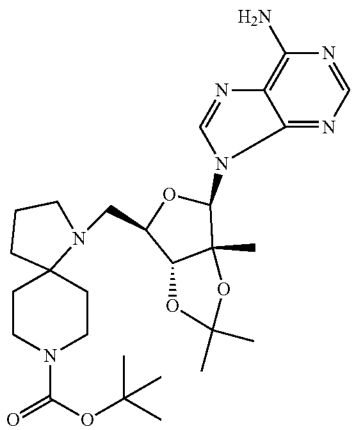 [SMILES: CC(C)(C)OC(=O)N1CCC2(CCCN2C[C@H]2O[C@@H](n3cnc4c(N)ncnc43)[C@]3(C)OC(C)(C)O[C@H]23)CC1] | a) Intermediate 55<br>b) NH₄OH in THF |
| 121 | 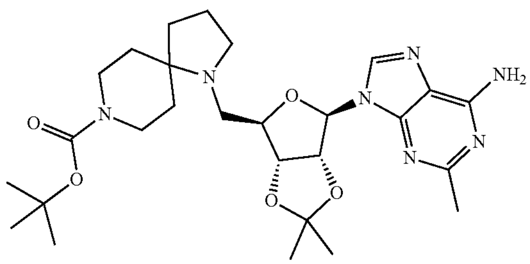 [SMILES: Cc1nc(N)c2ncn([C@@H]3O[C@H](CN4CCCC45CCN(C(=O)OC(C)(C)C)CC5)[C@H]4OC(C)(C)O[C@H]43)c2n1] | a) Intermediate 57<br>b) NH₃·H₂O in 1,4 dioxane |
| 122 | 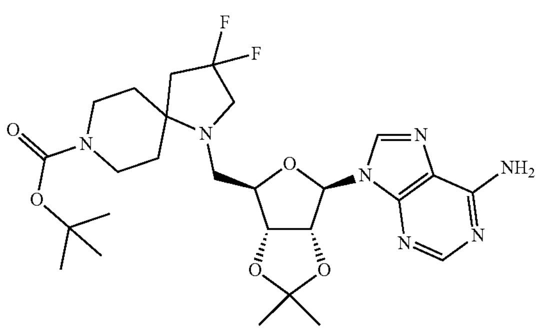 [SMILES: CC(C)(C)OC(=O)N1CCC2(CC1)CC(F)(F)CN2C[C@H]1O[C@@H](n2cnc3c(N)ncnc32)[C@@H]2OC(C)(C)O[C@@H]21] | a) Intermediate 59<br>b) NH₃ in MeOH |
| 123 | 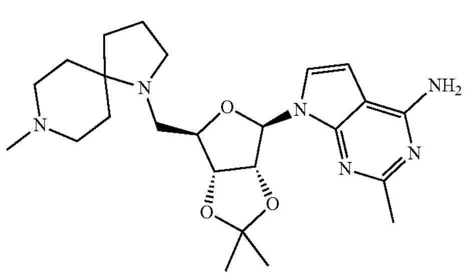 [SMILES: Cc1nc(N)c2ccn([C@@H]3O[C@H](CN4CCCC45CCN(C)CC5)[C@H]4OC(C)(C)O[C@H]43)c2n1] | a) Intermediate 64<br>b) NH₃·H₂O in 1,4 dioxane |

TABLE 7-continued

| Intermediate | Structure | Starting materials and conditions |
|---|---|---|
| 124 | 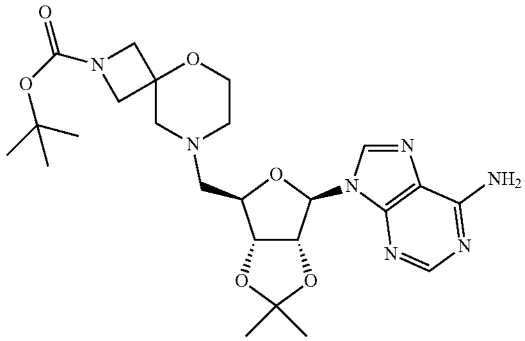 [SMILES: CC(C)(C)OC(=O)N1CC2(CN(C[C@H]3O[C@@H](n4cnc5c(N)ncnc54)[C@@H]4OC(C)(C)O[C@@H]43)CCO2)C1] | a) Intermediate 65<br>b) NH₃ in MeOH |
| 125 | 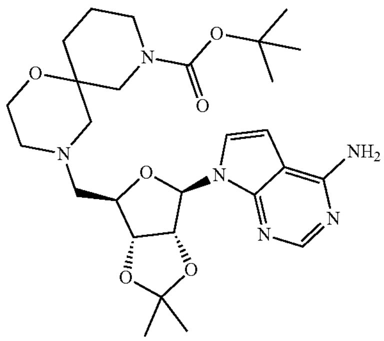 [SMILES: CC(C)(C)OC(=O)N1CCCC2(CN(C[C@H]3O[C@@H](n4ccc5c(N)ncnc54)[C@@H]4OC(C)(C)O[C@@H]43)CCO2)C1] | a) Intermediate 66<br>b) NH₄OH in dioxane |
| 126 | 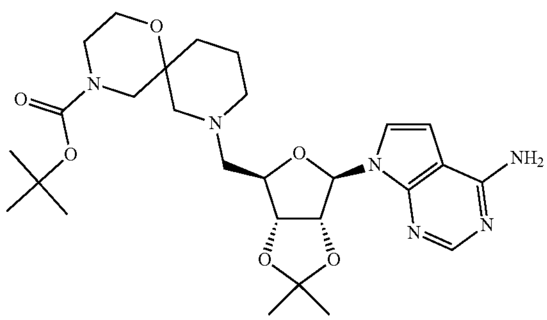 [SMILES: CC(C)(C)OC(=O)N1CCOC2(CCCN(C[C@H]3O[C@@H](n4ccc5c(N)ncnc54)[C@@H]4OC(C)(C)O[C@@H]43)C2)C1] | a) Intermediate 67<br>b) NH₃ (7M) in MeOH |
| 127 | (R or S) | a) Intermediate 68<br>b) NH₃ (7M) in MeOH |

TABLE 7-continued
| Intermediate | Structure | Starting materials and conditions |
|---|---|---|
| 128 | 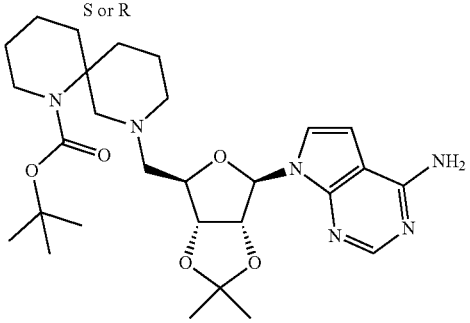 [SMILES: CC(C)(C)OC(=O)N1CCCCC12CCCN(C[C@H]1O[C@@H](n3ccc4c(N)ncnc43)[C@@H]3OC(C)(C)O[C@@H]31)C2] | a) Intermediate 68<br>b) NH₃ (7M) in MeOH |
| 129 | 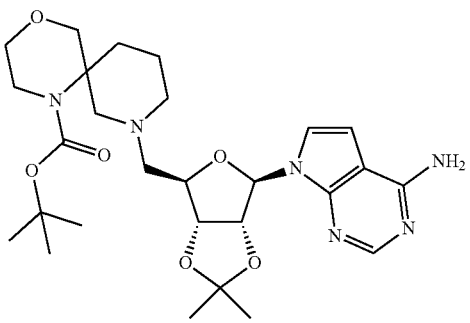 [SMILES: CC(C)(C)OC(=O)N1CCOCC12CCCN(C[C@H]1O[C@@H](n3ccc4c(N)ncnc43)[C@@H]3OC(C)(C)O[C@@H]31)C2] | a) Intermediate 69<br>b) NH₃ (7M) in MeOH |
| 130 | 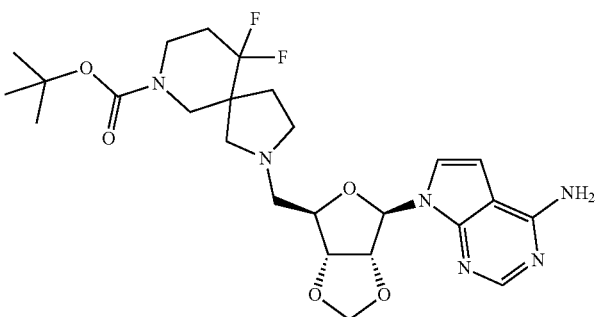 | a) Intermediate 70<br>b) NH₄OH in dioxane |
| 131 | 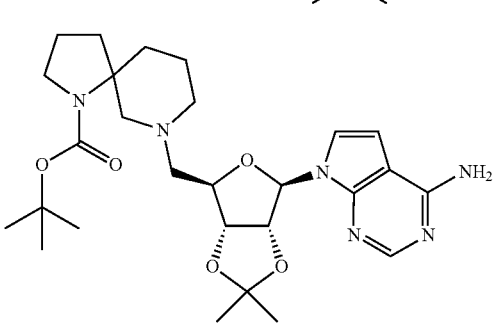 | a) Intermediate 71<br>b) NH₃ in MeOH |
| 132 | 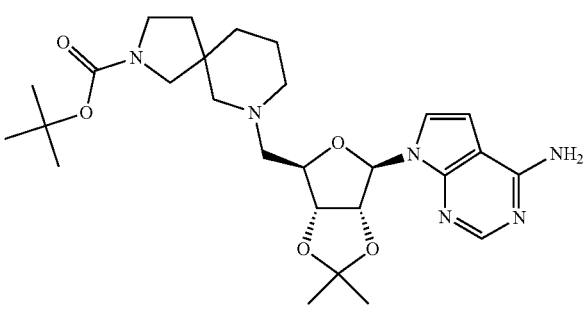 [SMILES: CC(C)(C)OC(=O)N1CCC2(CCCN(C[C@H]3O[C@@H](n4ccc5c(N)ncnc54)[C@@H]4OC(C)(C)O[C@@H]43)C2)C1] | a) Intermediate 72<br>b) NH₃ in MeOH |

TABLE 7-continued

| Intermediate | Structure | Starting materials and conditions |
|---|---|---|
| 133 | 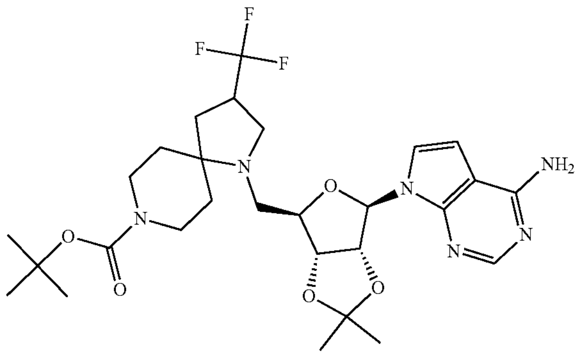 [SMILES: CC(C)(C)OC(=O)N1CCC2(CC1)CC(C(F)(F)F)CN2C[C@H]1O[C@@H](n2ccc3c(N)ncnc32)[C@@H]2OC(C)(C)O[C@@H]21] | a) Intermediate 92<br>b) NH₃ in MeOH |
| 134 | 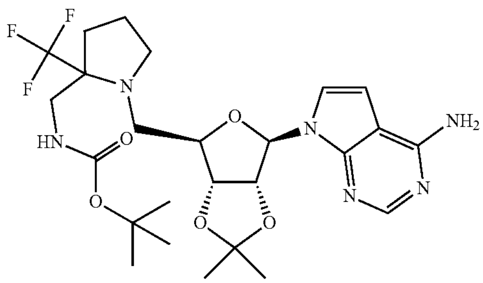 [SMILES: CC(C)(C)OC(=O)NCC1(C(F)(F)F)CCCN1C[C@H]1O[C@@H](n2ccc3c(N)ncnc32)[C@@H]2OC(C)(C)O[C@@H]21] | a) Intermediate 73<br>b) NH₄OH in dioxane |
| 135 | 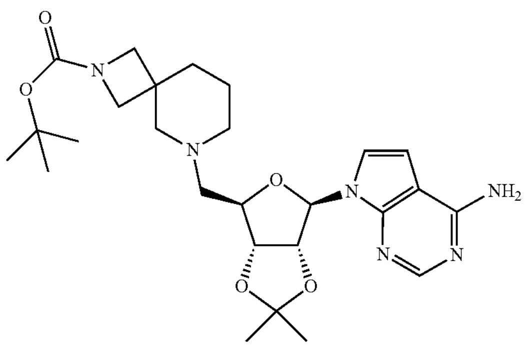 [SMILES: CC(C)(C)OC(=O)N1CC2(CCCN(C[C@H]3O[C@@H](n4ccc5c(N)ncnc54)[C@@H]4OC(C)(C)O[C@@H]43)C2)C1] | a) Intermediate 74<br>b) NH₃ in MeOH |
| 138 | 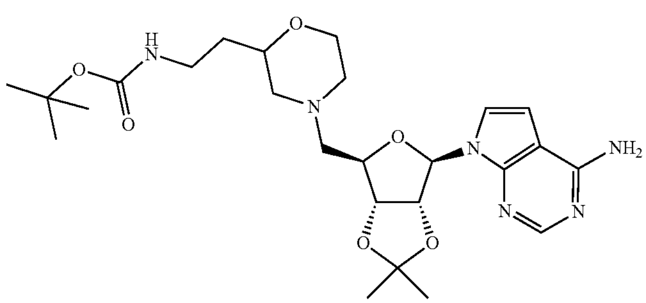 [SMILES: CC(C)(C)OC(=O)NCCC1CN(C[C@H]2O[C@@H](n3ccc4c(N)ncnc43)[C@@H]3OC(C)(C)O[C@@H]32)CCO1] | a) Intermediate 76<br>b) NH₃ in MeOH |
| 139 | 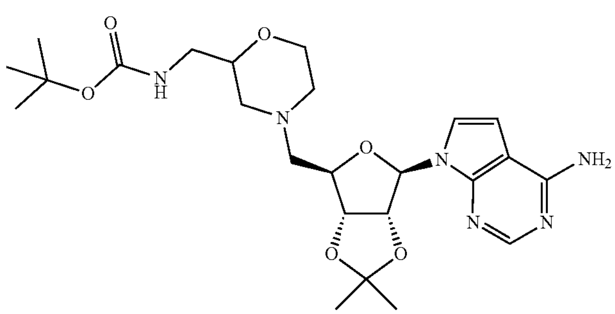 [SMILES: CC(C)(C)OC(=O)NCC1CN(C[C@H]2O[C@@H](n3ccc4c(N)ncnc43)[C@@H]3OC(C)(C)O[C@@H]32)CCO1] | a) Intermediate 77<br>b) NH₃ in MeOH |

TABLE 7-continued

| Intermediate | Structure | Starting materials and conditions |
|---|---|---|
| 140 | 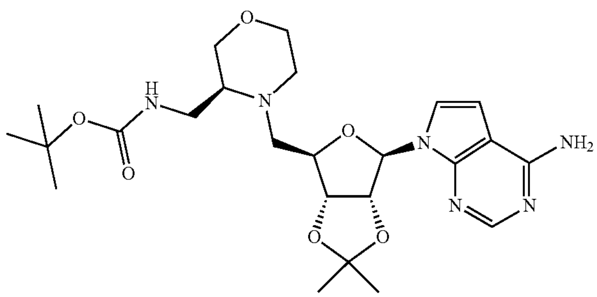 [SMILES: CC(C)(C)OC(=O)NC[C@H]1COCCN1C[C@H]1O[C@@H](n2ccc3c(N)ncnc32)[C@@H]2OC(C)(C)O[C@@H]21] | a) Intermediate 78<br>b) NH₃ in MeOH |
| 141 | 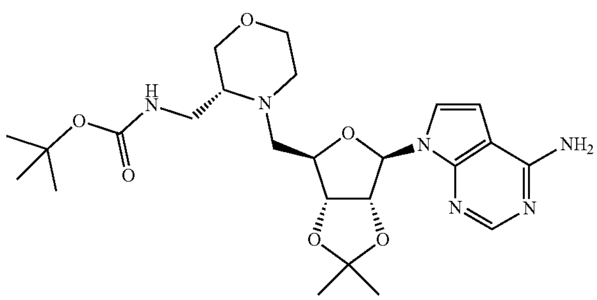 [SMILES: CC(C)(C)OC(=O)NC[C@@H]1COCCN1C[C@H]1O[C@@H](n2ccc3c(N)ncnc32)[C@@H]2OC(C)(C)O[C@@H]21] | a) Intermediate 79<br>b) NH₃ in MeOH |
| 142 | 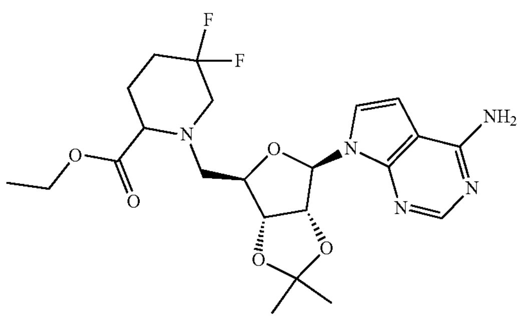 [SMILES: CCOC(=O)C1CCC(F)(F)CN1C[C@H]1O[C@@H](n2ccc3c(N)ncnc32)[C@@H]2OC(C)(C)O[C@@H]21] | a) Intermediate 80<br>b) NH₃ in MeOH |
| 143 | 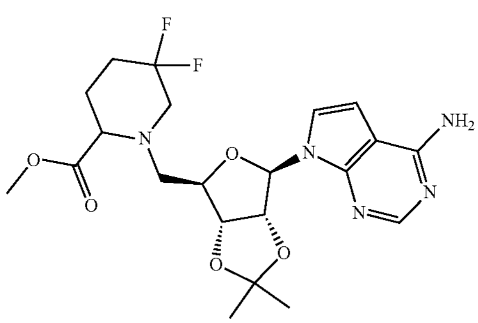 [SMILES: COC(=O)C1CCC(F)(F)CN1C[C@H]1O[C@@H](n2ccc3c(N)ncnc32)[C@@H]2OC(C)(C)O[C@@H]21] | a) Intermediate 80<br>b) NH₃ in MeOH |
| 144 | 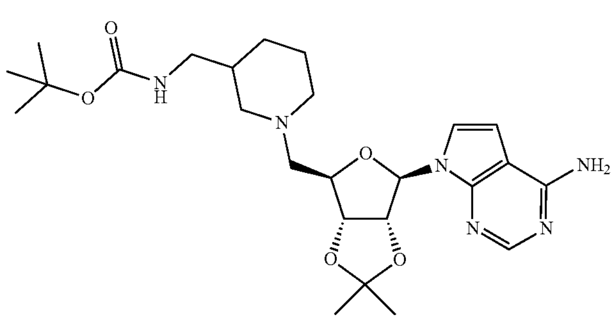 [SMILES: CC(C)(C)OC(=O)NCC1CCCN(C[C@H]2O[C@@H](n3ccc4c(N)ncnc43)[C@@H]3OC(C)(C)O[C@@H]32)C1] | a) Intermediate 81<br>b) NH₃ in MeOH |

TABLE 7-continued

| Intermediate | Structure | Starting materials and conditions |
|---|---|---|
| 145 | 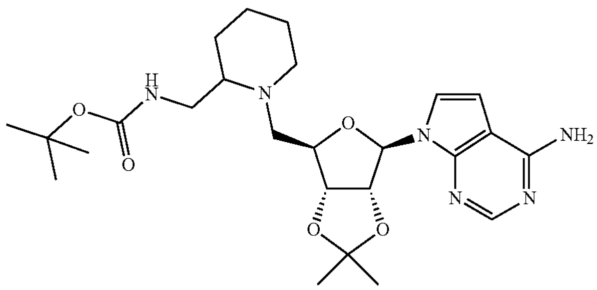 [SMILES: CC(C)(C)OC(=O)NCC1CCCCN1C[C@H]1O[C@@H](n2ccc3c(N)ncnc32)[C@@H]2OC(C)(C)O[C@@H]21] | a) Intermediate 82<br>b) NH₃ in MeOH |
| 146 | 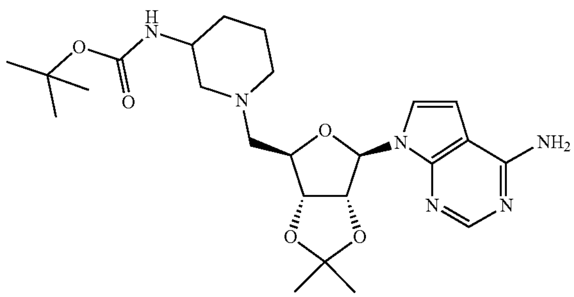 [SMILES: CC(C)(C)OC(=O)NC1CCCN(C[C@H]2O[C@@H](n3ccc4c(N)ncnc43)[C@@H]3OC(C)(C)O[C@@H]32)C1] | a) Intermediate 83<br>b) NH₃ in MeOH |
| 147 | 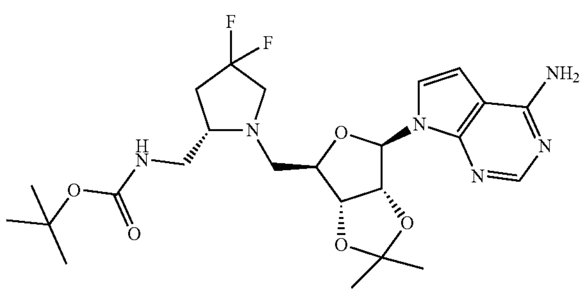 [SMILES: CC(C)(C)OC(=O)NC[C@@H]1CC(F)(F)CN1C[C@H]1O[C@@H](n2ccc3c(N)ncnc32)[C@@H]2OC(C)(C)O[C@@H]21] | a) Intermediate 84<br>b) NH₃ in MeOH |
| 148 | 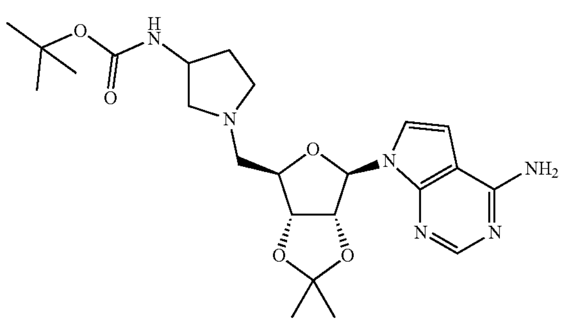 [SMILES: CC(C)(C)OC(=O)NC1CCN(C[C@H]2O[C@@H](n3ccc4c(N)ncnc43)[C@@H]3OC(C)(C)O[C@@H]32)C1] | a) Intermediate 85<br>b) NH₃ in MeOH |
| 149 | 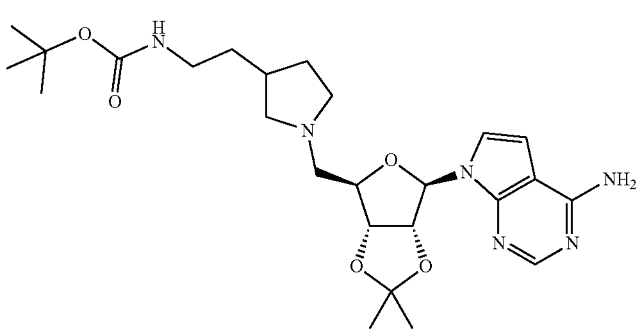 [SMILES: CC(C)(C)OC(=O)NCCC1CCN(C[C@H]2O[C@@H](n3ccc4c(N)ncnc43)[C@@H]3OC(C)(C)O[C@@H]32)C1] | a) Intermediate 86<br>b) NH₃ in MeOH |

TABLE 7-continued

| Intermediate | Structure | Starting materials and conditions |
| --- | --- | --- |
| 150 | 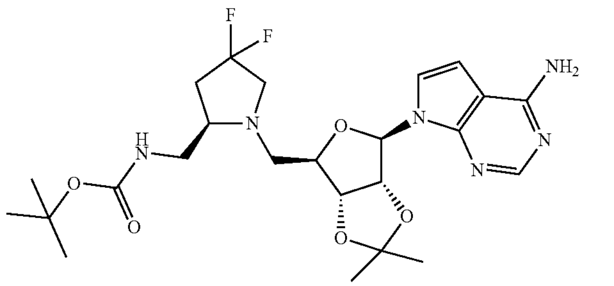 [SMILES: CC(C)(C)OC(=O)NC[C@H]1CC(F)(F)CN1C[C@H]1O[C@@H](n2ccc3c(N)ncnc32)[C@@H]2OC(C)(C)O[C@@H]21] | a) Intermediate 87<br>b) NH$_3$ in MeOH |
| 151 | 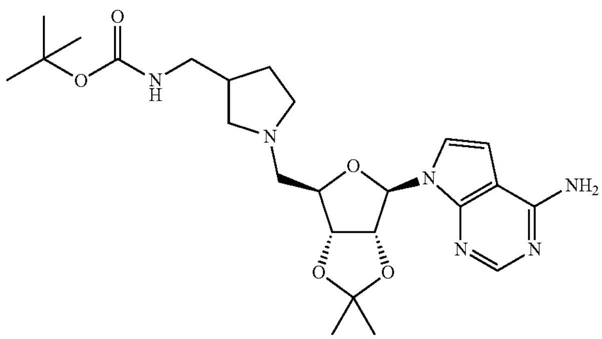 [SMILES: CC(C)(C)OC(=O)NCC1CCN(C[C@H]2O[C@@H](n3ccc4c(N)ncnc43)[C@@H]3OC(C)(C)O[C@@H]32)C1] | a) Intermediate 88<br>b) NH$_3$ in MeOH |
| 152 | 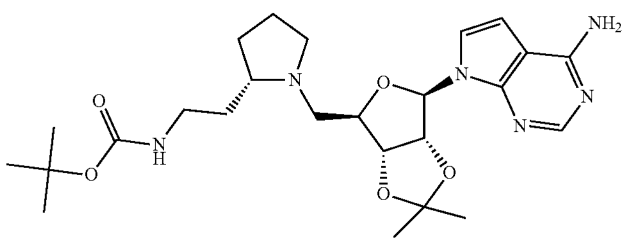 [SMILES: CC(C)(C)OC(=O)NCC[C@@H]1CCCN1C[C@H]1O[C@@H](n2ccc3c(N)ncnc32)[C@@H]2OC(C)(C)O[C@@H]21] | a) Intermediate 89<br>b) NH$_3$ in MeOH |
| 153a | 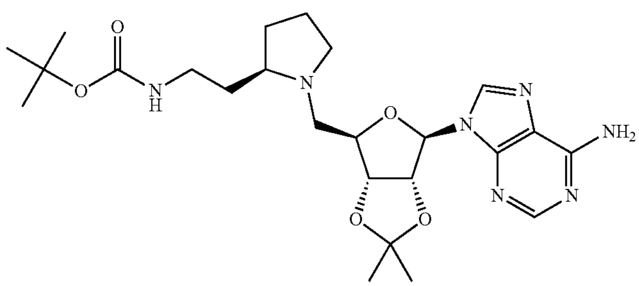 [SMILES: CC(C)(C)OC(=O)NCC[C@H]1CCCN1C[C@H]1O[C@@H](n2cnc3c(N)ncnc32)[C@@H]2OC(C)(C)O[C@@H]21] | a) Intermediate 90a<br>b) NH$_3$ in MeOH |
| 153b | 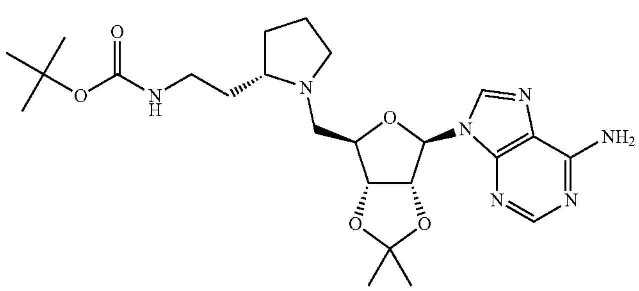 [SMILES: CC(C)(C)OC(=O)NCC[C@@H]1CCCN1C[C@H]1O[C@@H](n2cnc3c(N)ncnc32)[C@@H]2OC(C)(C)O[C@@H]21] | c) Intermediate 90b<br>d) NH$_3$ in MeOH |

TABLE 7-continued

| Intermediate | Structure | Starting materials and conditions |
|---|---|---|
| 154 | 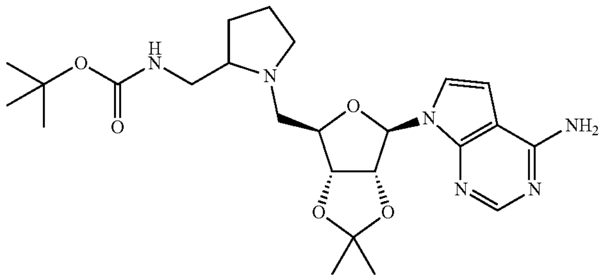 [SMILES: CC(C)(C)OC(=O)NCC1CCCN1C[C@H]1O[C@@H](n2ccc3c(N)ncnc32)[C@@H]2OC(C)(C)O[C@@H]21] | a) Intermediate 91<br>b) $NH_3$ in MeOH |

Example A19

Preparation of Intermediate 155

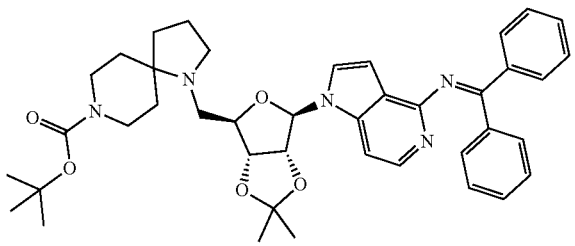 [SMILES: CC(C)(C)OC(=O)N1CCC2(CCCN2C[C@H]2O[C@@H](n3ccc4c(N=C(c5ccccc5)c5ccccc5)nccc43)[C@@H]3OC(C)(C)O[C@@H]32)CC1]

Intermediate 56 (290 mg, 0.53 mmol), benzophenone imine (144 mg. 0.8 mmol), $Pd_2(dba)_3$ (48.5 mg, 0.05 mmol), BINAP (33.0 mg, 0.05 mmol) and t-BuONa (101.9 mg, 1.06 mmol) were dissolved in toluene (20 mL). The mixture was stirred at 110° C. for 2 hours under $N_2$, after which it was filtered and the solvent was evaporated. The crude product was purified by preparative HPLC (gradient elution: 0.05% $NH_3 \cdot H_2O$ in $CH_3CN$/0.05% $NH_3 \cdot H_2O$ in $H_2O$). The combined fractions were evaporated to give the desired intermediate 155 (160 mg, 40% yield).

Below intermediates were prepared by an analogous reaction protocol as was used for the preparation of Intermediate 155 using the appropriate starting materials (Table 8).

Example A20

Preparation of Intermediate 157

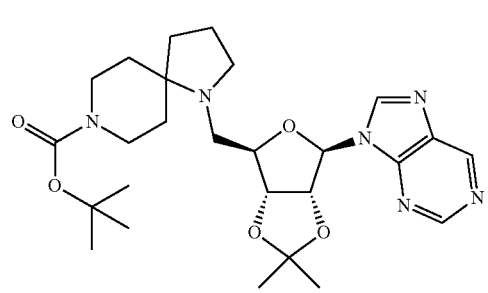 [SMILES: CC(C)(C)OC(=O)N1CCC2(CCCN2C[C@H]2O[C@@H](n3cnc4cncnc43)[C@@H]3OC(C)(C)O[C@@H]32)CC1]

MeOH (50 mL) was gently added to Pd/C 10% (87.7 mg) under nitrogen atmosphere. Thiophene 4% solution in DIPE (0.5 mL) and KOAc (222 mg, 2.26 mmol) were added to the solution. Then Intermediate 49 (620 mg, 1.13 mmol) was added and then the reaction mixture was hydrogenated at room temperature under 1 atm of hydrogen gas until 1 equivalent of hydrogen was absorbed. The catalyst was filtered off over a pad of dicalite and the residue was washed with MeOH. The filtrate was diluted with EtOAc (100 mL) after which $NaHCO_3$ (50 mL) was added. The organic layer was extracted and washed with water (50 mL), dried over $MgSO_4$ and concentrated under vacuo to give intermediate 157 (480 mg, 0.6 mmol, yield: 56%)

TABLE 8

| Intermediate | Structure | Starting materials and conditions |
|---|---|---|
| 156 | 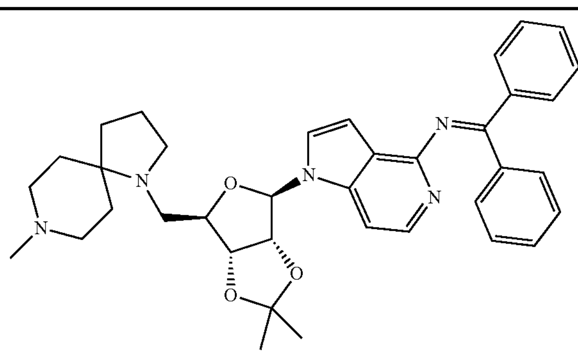 | a) Intermediate 63<br>b) Benzophenone imine |

Example A21

Preparation of Intermediate 158

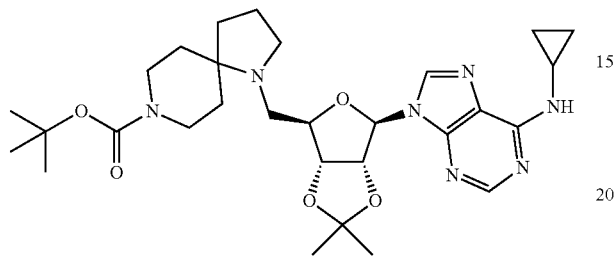

To a solution of intermediate 49 (100 mg, 0.13 mmol) in EtOH (5 mL) was added cyclopropylamine (87.1 µL, 1.26 mmol). Then the vial was sealed and heated for 30 minutes in a microwave at 150° C. The reaction mixture was concentrated under vacuo yielding crude intermediate 158 (67 mg). No further purification was done.

Example A22

Preparation of Intermediate 159

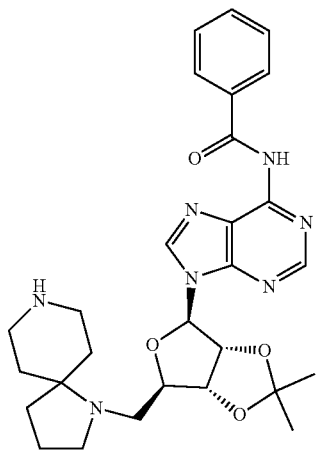 [SMILES: CC1(C)O[C@@H]2[C@H](O1)[C@@H](CN1CCCC13CCNCC3)O[C@H]2n1cnc2c(NC(=O)c3ccccc3)ncnc21]

Intermediate 93 (824 mg, 0.99 mmol) was dissolved in DCM (10 mL) and cooled to 0° C. The suspension was treated with trifluoroacetic acid (5.8 mL) dropwise. The mixture was stirred at room temperature overnight. The mixture was evaporated to dryness yielding crude intermediate 159 (640 mg, 100% yield) which was used as such without further purification.

Below intermediates were prepared by an analogous reaction protocol as was used for the preparation of intermediate 159 using the appropriate starting materials (Table 9). Table 9

TABLE 9

| Intermediate | Structure | Starting materials and conditions |
| --- | --- | --- |
| 160 | 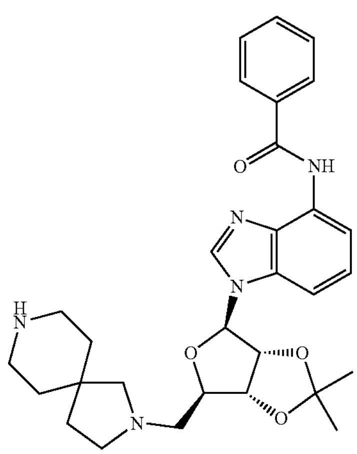 [SMILES: CC1(C)O[C@@H]2[C@H](O1)[C@@H](CN1CCC3(CCNCC3)C1)O[C@H]2n1cnc2c(NC(=O)c3ccccc3)cccc21] | a) Intermediate 94<br>b) TFA in DCM |

TABLE 9-continued
| Intermediate | Structure | Starting materials and conditions |
|---|---|---|
| 161 | 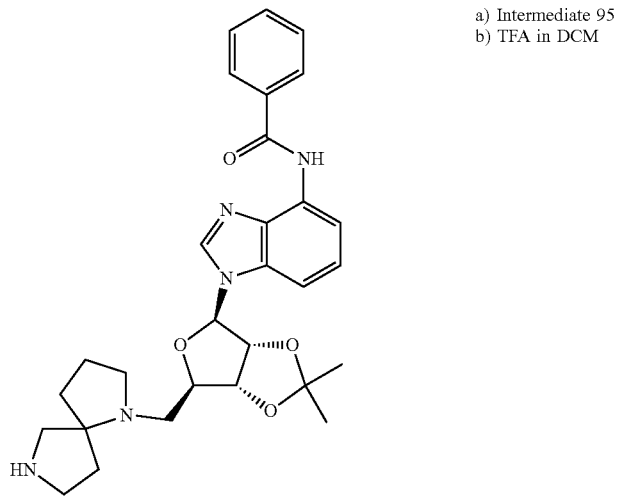 | a) Intermediate 95<br>b) TFA in DCM |
| 162 | 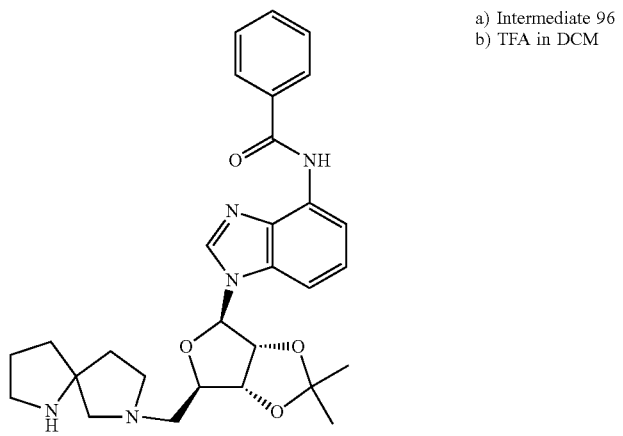 | a) Intermediate 96<br>b) TFA in DCM |
| 163 | 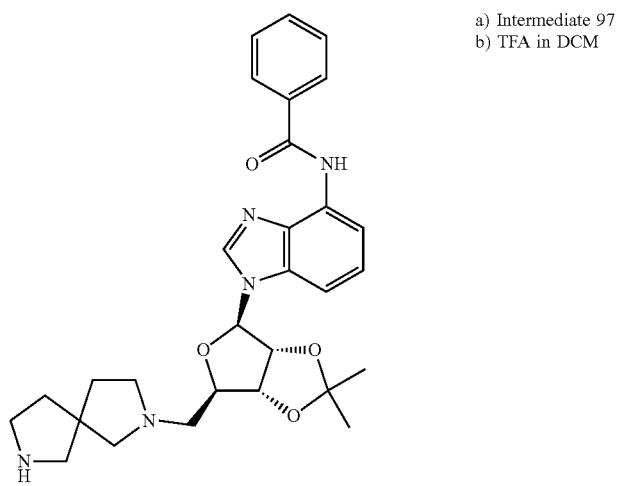 | a) Intermediate 97<br>b) TFA in DCM |

TABLE 9-continued
| Intermediate | Structure | Starting materials and conditions |
|---|---|---|
| 164 | 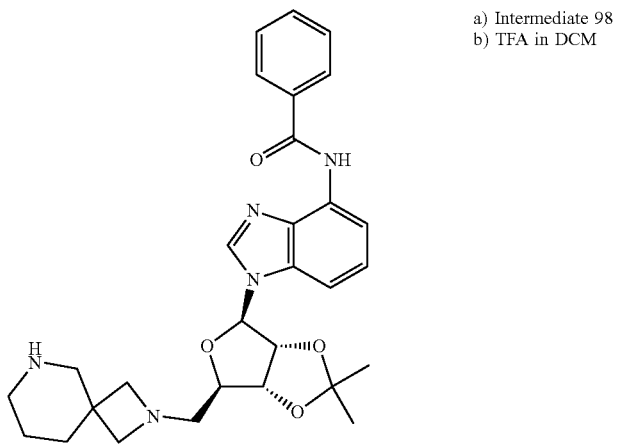 | a) Intermediate 98<br>b) TFA in DCM |
| 165 | 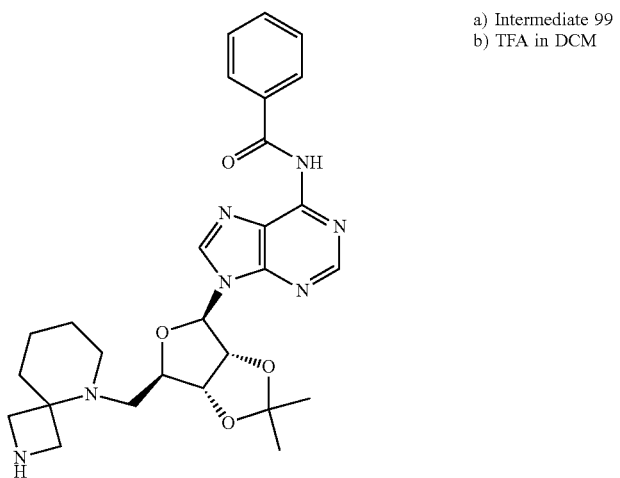 | a) Intermediate 99<br>b) TFA in DCM |
| 166 | 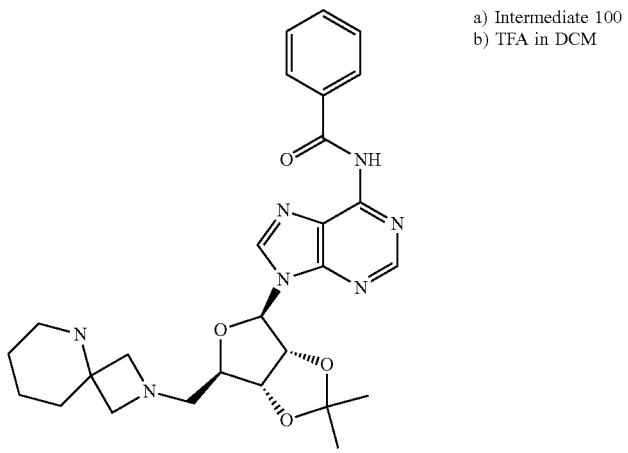 | a) Intermediate 100<br>b) TFA in DCM |

TABLE 9-continued
| Intermediate | Structure | Starting materials and conditions |
|---|---|---|
| 167 | 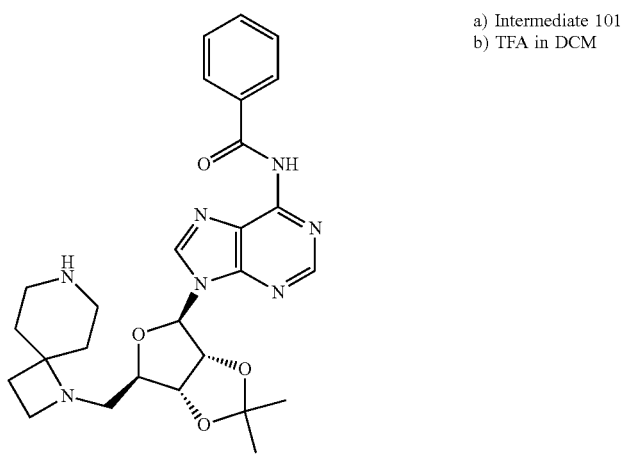 | a) Intermediate 101<br>b) TFA in DCM |
| 168 | 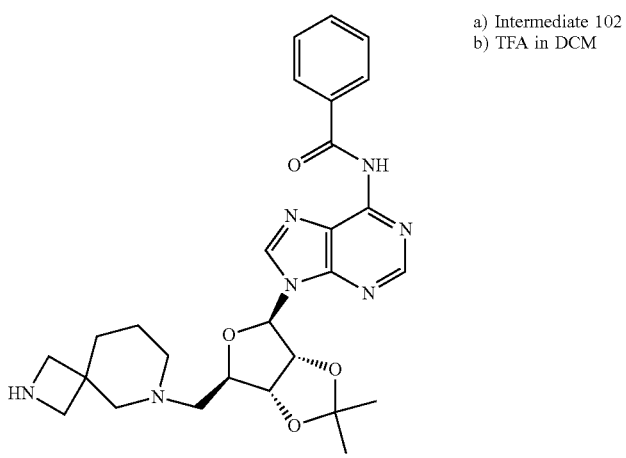 | a) Intermediate 102<br>b) TFA in DCM |
| 169 | 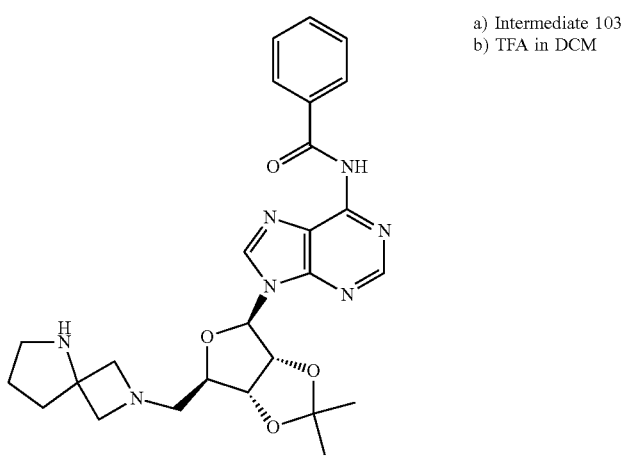 | a) Intermediate 103<br>b) TFA in DCM |

147                                                                                               148
TABLE 9-continued
| Intermediate | Structure | Starting materials and conditions |
| --- | --- | --- |
| 170 | 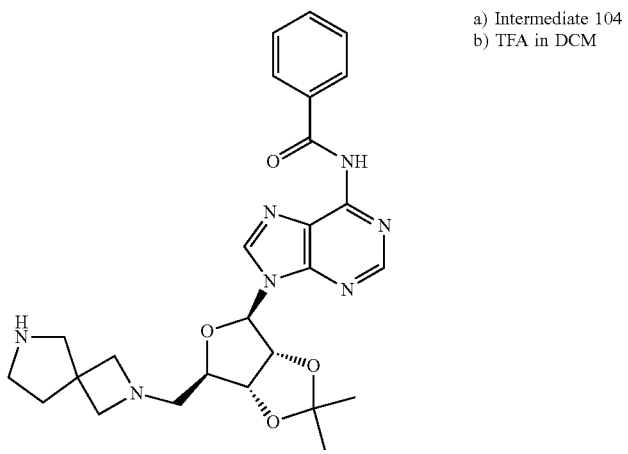 | a) Intermediate 104<br>b) TFA in DCM |
| 171 | 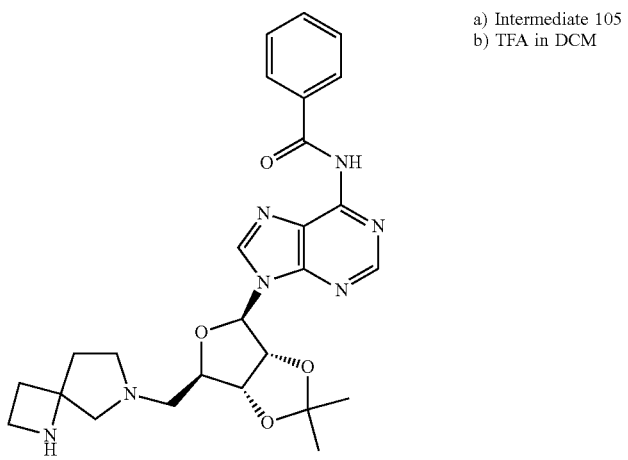 | a) Intermediate 105<br>b) TFA in DCM |
| 172 | 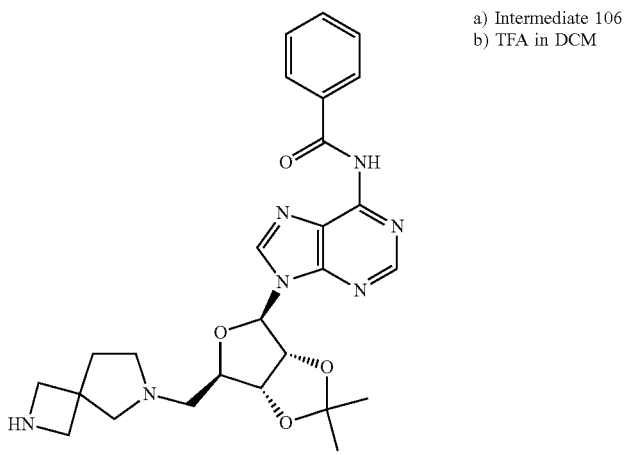 | a) Intermediate 106<br>b) TFA in DCM |

TABLE 9-continued
| Intermediate | Structure | Starting materials and conditions |
|---|---|---|
| 173 | 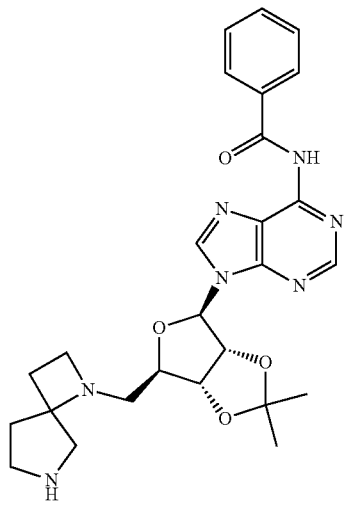 [SMILES: CC1(C)O[C@@H]2[C@H](O1)[C@@H](CN1CCC13CCNC3)O[C@H]2n1cnc2c(NC(=O)c3ccccc3)ncnc21] | a) Intermediate 107<br>b) TFA in DCM |
| 174 | 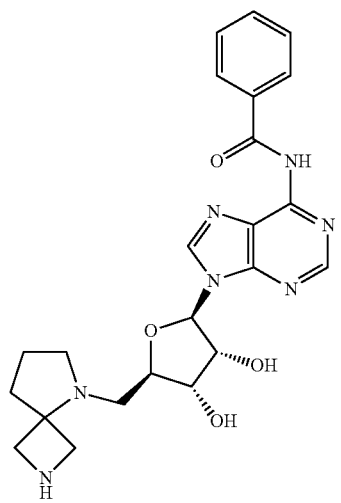 [SMILES: O=C(Nc1ncnc2c1ncn2[C@@H]1O[C@H](CN2CCCC23CNC3)[C@@H](O)[C@H]1O)c1ccccc1] | a) Intermediate 108<br>b) TFA in DCM/H$_2$O |
| 175 | 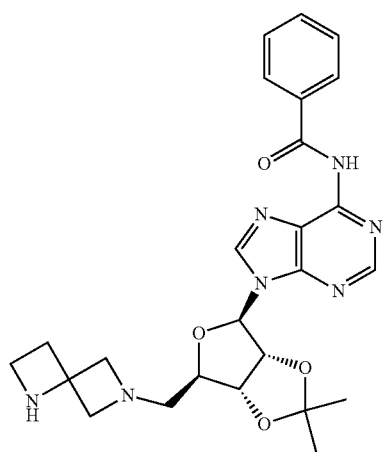 [SMILES: CC1(C)O[C@@H]2[C@H](O1)[C@@H](CN1CC3(CCN3)C1)O[C@H]2n1cnc2c(NC(=O)c3ccccc3)ncnc21] | a) Intermediate 109<br>b) TFA in DCM |

TABLE 9-continued

| Intermediate | Structure | Starting materials and conditions |
|---|---|---|
| 176 | 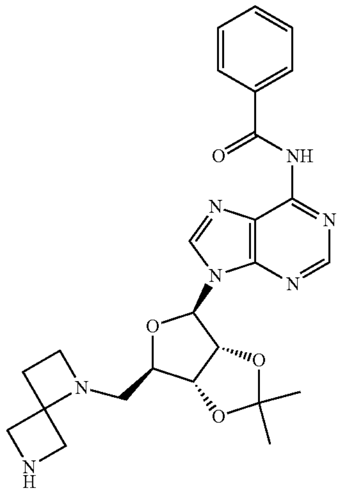 [SMILES: CC1(C)O[C@@H]2[C@H](O1)[C@@H](CN1CCC13CNC3)O[C@H]2n1cnc2c(NC(=O)c3ccccc3)ncnc21] | a) Intermediate 110<br>b) TFA in DCM |
| 177 | 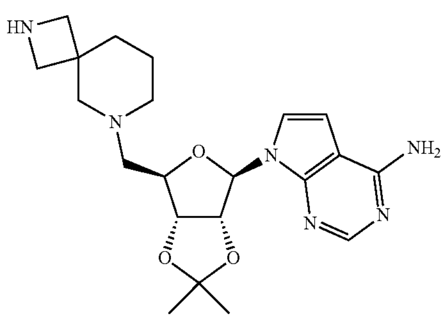 [SMILES: CC1(C)O[C@@H]2[C@H](O1)[C@@H](CN1CCCC3(CNC3)C1)O[C@H]2n1ccc2c(N)ncnc21] | a) Intermediate 135<br>b) TFA in DCM |
| 178 | 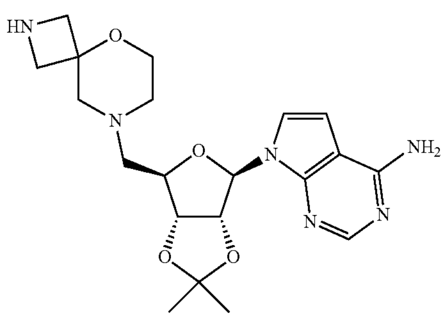 [SMILES: CC1(C)O[C@@H]2[C@H](O1)[C@@H](CN1CCOC3(CNC3)C1)O[C@H]2n1ccc2c(N)ncnc21] | a) Intermediate 124<br>b) TFA in DCM |
| 179 | 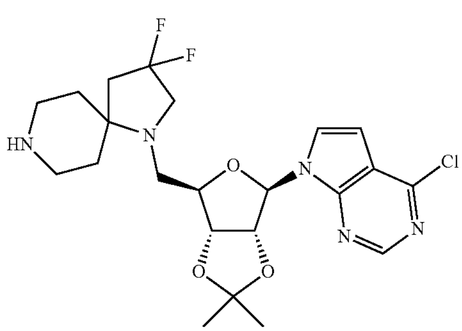 [SMILES: CC1(C)O[C@@H]2[C@H](O1)[C@@H](CN1CC(F)(F)CC13CCNCC3)O[C@H]2n1ccc2c(Cl)ncnc21] | a) Intermediate 59<br>b) TFA in DCM |

Example A23

Preparation of Intermediate 180

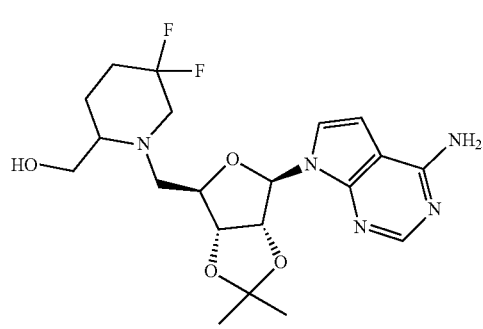 [SMILES: CC1(C)O[C@@H]2[C@H](O1)[C@@H](CN1CC(F)(F)CCC1CO)O[C@H]2n1ccc2c(N)ncnc21]

Preparation of Intermediate 181

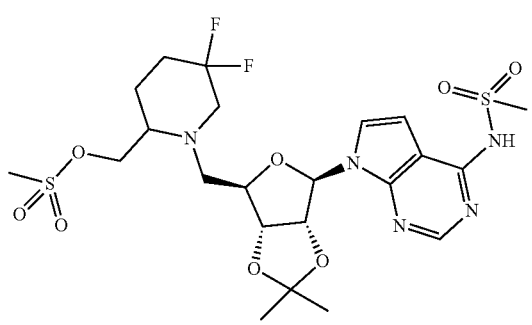

Lithium aluminum hydride (0.765 mL, 0.765 mmol, 1M in THF) was added dropwise to a stirred solution of intermediate 143 (104 mg, 0.19 mmol) in THF (4 mL, anhydrous) at 0° C. and under nitrogen atmosphere. After addition the reaction mixture was stirred at 0° C. for 10 minutes. The reaction was cooled to 0° C. and then quenched with water. MeOH was added and the resulting suspension was filtered. The residue was washed with MeOH. The combined solvents of the filtrate were evaporated. A purification was performed via Prep HPLC (Stationary phase: RP XBridge Prep C18 OBD-10 μm, 30×150 mm, Mobile phase: 0.25% $NH_4HCO_3$ solution in water and $CH_3CN$ to give intermediate 180 (48 mg, 57% yield)

Below intermediates were prepared by an analogous reaction protocol as was used for the preparation of intermediate 180 using the appropriate starting materials (Table 10).

Methanesulfonyl chloride (0.078 mL, 1.0 mmol) was added dropwise to a stirred solution of intermediate 180 (173 mg, 0.39 mmol) and $Et_3N$ (0.14 mL, 1.0 mmol) in DCM (5 mL) at 0° C. After addition the reaction mixture was stirred at room temperature for 1 hour. The reaction mixture was cooled to 0° C. and then an additional amount of $Et_3N$ (0.28 mL, 2.0 mmol) was added followed by the addition of methanesulfonyl chloride (0.16 mL, 2.0 mmol). The reaction mixture was stirred at 0° C. for 1 hour. The reaction was diluted with 5 mL DCM and then quenched with 3 mL water. The organic layer was separated, dried with $MgSO_4$, filtered and the solvents of the filtrate evaporated to give crude intermediate 181 (346 mg, 63.6% yield), directly used as such in the next reaction step.

TABLE 10

| Intermediate | Structure | Starting materials and conditions |
|---|---|---|
| 180 | 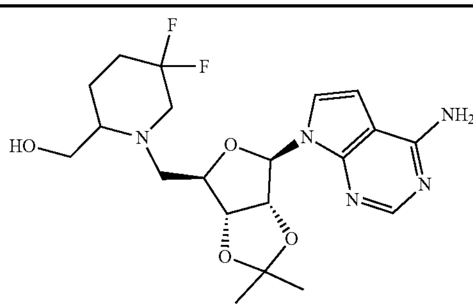 | a) Intermediate 142<br>b) Lithium aluminium hydride 1M in THF |

Preparation of Intermediate 182

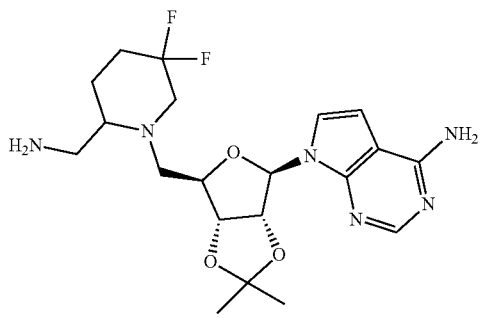 [SMILES: CC1(C)O[C@@H]2[C@H](O1)[C@@H](CN1CC(F)(F)CCC1CN)O[C@H]2n1ccc2c(N)ncnc21]

Intermediate 181 (346 mg, 0.215 mmol) was dissolved in NH$_3$ (5 mL, 35 mmol, 7 M in MeOH) in a microwave vial and then stirred and heated at 100° C. using microwave irradiation for 2 hour. The solvents were evaporated and the residue was purified with Prep HPLC (Stationary phase: RP XBridge Prep C18 OBD-10 µm, 30×150 mm, Mobile phase: 0.25% NH$_4$HCO$_3$ solution in water, MeOH) to give intermediate 182 (39.6 mg, 30% yield).

Example A24

Preparation of Intermediate 186

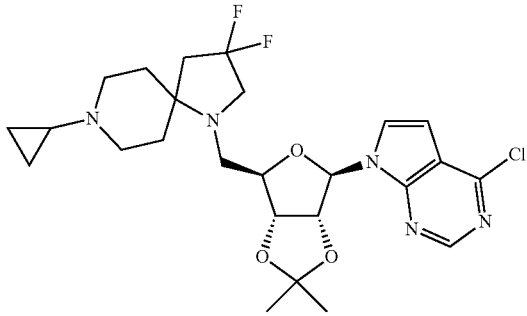 [SMILES: CC1(C)O[C@@H]2[C@H](O1)[C@@H](CN1CC(F)(F)CC13CCN(C1CC1)CC3)O[C@H]2n1ccc2c(Cl)ncnc21]

To a solution of intermediate 179 in MeOH (4 mL) was added (1-ethoxycyclopropoxy)trimethylsilane (227 mg, 1.3 mmol) and AcOH (0.025 mL, 0.4 mmol) at room temperature. Then NaBH$_3$CN (95.4 mg, 1.5 mmol) was added into the reaction mixture. The resulting mixture was stirred at 60° C. for 15 hours. The reaction mixture was diluted with MeOH (20 mL) and was filtered through celite. The filtrate was concentrated to dryness after which the residue was purified via silica column chromatography (gradient: DCM/MeOH from 100:0 to 95:5). The desired fractions were collected and concentrated to be dry to give Intermediate 186 (50 mg, 44% yield)

Example A25

Preparation of Intermediate 187

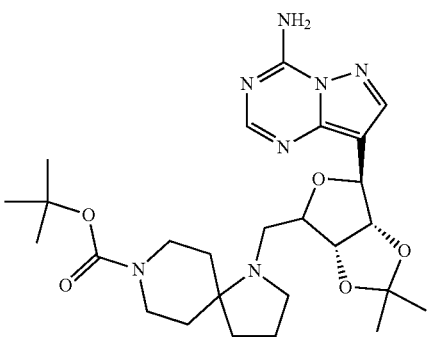 [SMILES: CC(C)(C)OC(=O)N1CCC2(CCCN2CC2O[C@@H](c3cnn4c(N)ncnc34)[C@@H]3OC(C)(C)O[C@H]23)CC1]

A solution of intermediate 58 (328 mg, 0.53 mmol) and NH$_3$ 7 M in MeOH (3.78 mL, 26.462 mmol) was stirred in EtOH at 110° C. for 13 hours after which the reaction mixture was stirred at room temperature overnight. The reaction mixture was evaporated under the reduced pressure and the residue was purified by silica gel column chromatography (DCM/MeOH 100/0 to 96/4, collection at 275 nm) to give intermediate 187 (200 mg, 71% yield).

Example A26

Preparation of Intermediate 188

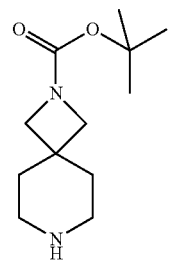 [SMILES: CC(C)(C)OC(=O)N1CC2(CCNCC2)C1]

Pd/C 10% (0.67 g, 0.63 mmol) was added to a solution of tert-Butyl 7-benzyl-2,7-diazaspiro[3.5]nonane-2-carboxylate (2 g, 6.26 mmol) in MeOH (50 mL) under nitrogen atmosphere at 0° C. The reaction was hydrogenated at room temperature under 1 atm hydrogen gas for 4 days. An extra amount of Pd/C 10% (0.67 g, 0.63 mmol) was added and the mixture was stirred overnight The crude was filtered over celite and concentrated in vacuo to give crude intermediate 188 (1.25 g, 87% yield). No further purification was done.

Preparation of Intermediate 189

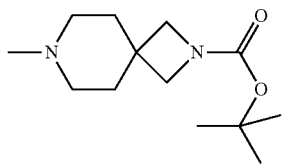 [SMILES: CN1CCC2(CC1)CN(C(=O)OC(C)(C)C)C2]

Intermediate 188 (250 mg, 1.1 mmol) and formaldehyde solution 37 wt. % in H$_2$O (0.09 mL, 1.21 mmol) were dissolved in THF (5 mL) and the mixture was stirred 30 min. Then sodium triacetoxyborohydride (351.2 mg, 1.66 mmol) was added and the solution was stirred at room temperature overnight. The mixture was diluted with DCM (50 mL) and washed with saturated Na$_2$CO$_3$ 1M (50 mL). The organic layer was dried over MgSO$_4$ and filtered. The solvents were evaporated to dryness to give crude intermediate 189 (0.245 g, 90% yield), which was used as such without further purification.

Preparation of Intermediate 190

Intermediate 189 was dissolved in DCM (15 mL) and cooled to 0° C. The suspension was treated with TFA (3.1 mL) dropwise. The mixture was stirred at room temperature for 3 hours The solvents were evaporated to dryness and the product was triturated with ether to give crude intermediate 190 (0.273 g, 100% yield), which was used a such without further purification.

Example A27

Preparation of Intermediate 324

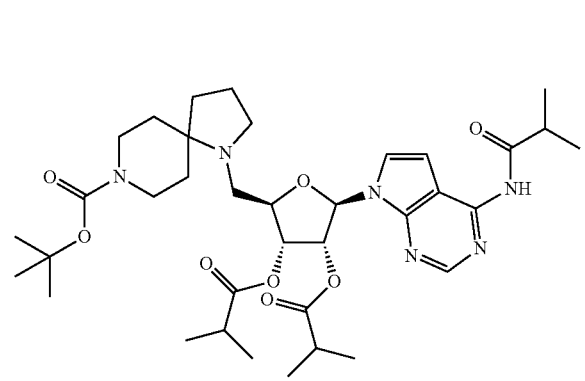 [SMILES: CC(C)C(=O)Nc1ncnc2c1ccn2[C@@H]1O[C@H](CN2CCCC23CCN(C(=O)OC(C)(C)C)CC3)[C@@H](OC(=O)C(C)C)[C@H]1OC(=O)C(C)C]

Isobutyric anhydride (6.82 mL, 40.9 mmol) was added to a stirred solution of Intermediate 210 (2 g, 4.1 mmol) in pyridine (80 mL) at room temperature. After addition the reaction mixture was stirred at 50° C. for 18 hours. The mixture was cooled to room temperature and then diluted with ethylacetate. This mixture was washed three times with water and the organic layer was dried with MgSO$_4$, filtered and the solvents of the filtrate evaporated. The residue was co-evaporated with toluene to give crude intermediate 324 (4.11 g, yield: 127%).

Preparation of Intermediate 325

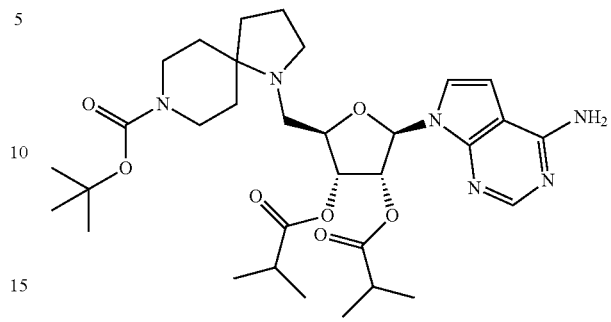

A solution of intermediate 324 (2.05 g, 2.6 mmol) in MeOH (20 mL) was stirred and heated at 130° C. using microwave irradiation for 6 hours. The solvents were evaporated after which a purification was performed via Prep HPLC (Stationary phase: RP XBridge Prep C18 OBD-10 µm, 50×150 mm, Mobile phase: 0.5% NH$_4$Ac solution in water+10% CH$_3$CN, CH$_3$CN). The organic solvents were evaporated. The product was extracted from the remaining water layer three times with DCM. The combined organic layer was washed with water, washed with brine, dried with MgSO$_4$, filtered and the solvents of the filtrate evaporated to give Intermediate 325 (0.89 g, yield: 27.0%)

Example A28

Preparation of Intermediate 327

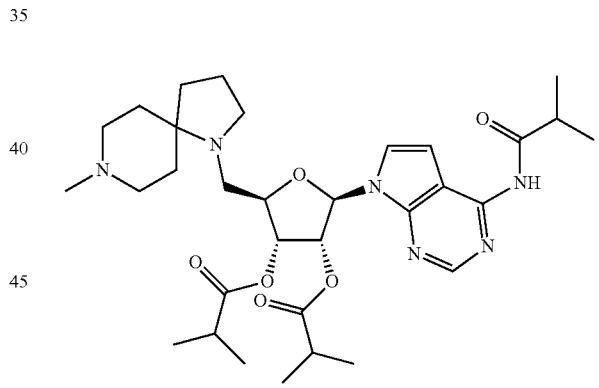

Isobutyric anhydride (66.3 mL, 398 mmol) was added to a stirred solution of compound 168 (18 g, 39.8 mmol) in pyridine (500 mL) at room temperature. After addition the reaction mixture was stirred at 50° C. for 6 hours. The solvents were evaporated. The residue was co-evaporated with toluene. The remaining liquid was diluted with ethylacetate. The resulting suspension was filtered over Dicalite. The pad of Dicalite was washed twice with ethyl acetate. The combined filtrates were washed three times with water, once with brine, dried with MgSO$_4$, filtered and the solvents of the filtrate evaporated. The residue was purified over a SiO$_2$ column, type Grace Reveleris SRC, 80 g, Si 40, on a Grace Reveleris X$^2$ purification system using dichlormethane and MeOH as eluens in a gradient starting from 100% DCM to 25% MeOH and 75% DCM.

The fractions containing product were combined and the solvents were evaporated yielding 10.5 g crude intermediate 327. The combined water layers were extracted again three times with DCM with some MeOH. The combined organic layer was dried (MgSO₄), filtered and the solvents of the filtrate evaporated yielding 6.62 g crude intermediate 327. The water layer was evaporated yielding 12.3 g crude intermediate 327. The three crude fractions were combined and purified over a SiO₂ column, type Grace Reveleris SRC, 120 g, Si 40, on a Grace Reveleris X² purification system with a solid sample loader using DCM and MeOH as eluens in a gradient starting from 100% DCM to 25% MeOH and 75% DCM. The fractions containing product were combined and the solvents were evaporated yielding 18.1 g of pure intermediate 327 (yield: 72.7%).

Example A29

Preparation of Intermediate 329

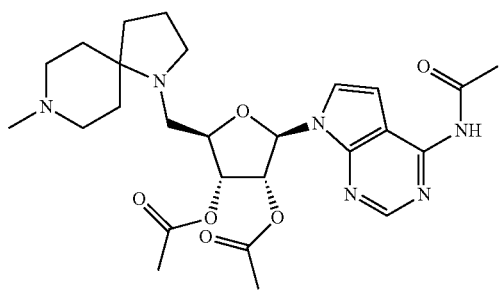 [SMILES: CC(=O)Nc1ncnc2c1ccn2[C@@H]1O[C@H](CN2CCCC23CCN(C)CC3)[C@@H](OC(C)=O)[C@H]1OC(C)=O]

Ac₂O (54.8 mL, 579 mmol) was added to a stirred solution of compound 168 (26.2 g, 57.9 mmol) in pyridine (700 mL) at room temperature. After addition the reaction mixture was stirred at 50° C. for 18 hours. The solvents were evaporated. The residue was co-evaporated with toluene and was purified over a SiO₂ column, type Grace Reveleris SRC, 330 g, Si 40, which was neutralized by flushing for 5 column volumes with a solution of 2% Et₃N in DCM and then for 5 column volumes with DCM, on a Grace Reveleris X² purification system using DCM and MeOH as eluens in a gradient starting from 100% DCM to 100% MeOH. The fractions containing product were combined and the solvents were evaporated. The residue was repurified over a SiO₂ column, type Grace Reveleris SRC, 330 g, Si 40, which was neutralized by flushing for 5 column volumes with a solution of 2% Et₃N in DCM and then for 5 column volumes with DCM, on a Grace Reveleris X² purification system using DCM and MeOH as eluens in a gradient starting from 100% DCM to 100% MeOH. The fractions containing product were combined and the solvents were evaporated to give Intermediate 329 (29.5 g, yield: 93.5%).

Example A30

Preparation of Intermediate 332

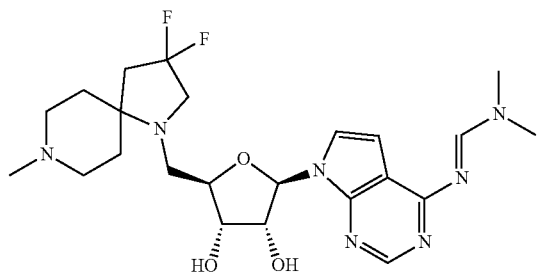

A suspension of compound 181 (1.14 g, 2.3 mmol) in N,N-dimethylformamide dimethyl acetal (3.8 mL) and DCM (200 mL) and DMF (50 mL) was stirred at room temperature for 18 hours. The reaction mixture was stirred and heated at 50° C. allowing the DCM to be evaporated from the reaction mixture under a flow of nitrogen gas. The remaining solution in DMF was stirred and heated at 50° C. for 3 hours and then at room temperature for 18 hours. The solvents were evaporated. The residue was co-evaporated with toluene yielding intermediate 332 (1.83 g).

Preparation of Intermediate 333

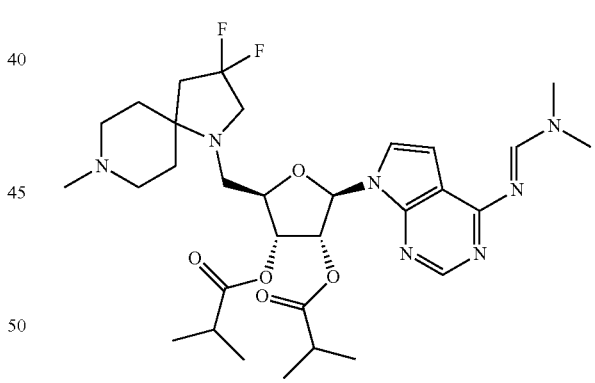

Isobutyric anhydride (1.07 mL, 6.45 mmol) was added to a stirred solution of intermediate 332 (1.83 g, 2.15 mmol) in pyridine (50 mL) at room temperature. After addition the reaction mixture was stirred at 65° C. for 3 days. The solvents were evaporated. The residue was co-evaporated with toluene. The residue was dissolved in EtOAc and washed twice with a saturated aqueous NaHCO₃ solution, washed with water, dried with MgSO₄, filtered and the solvents of the filtrate evaporated to give intermediate 333 (1.10 g)

Example A31

Preparation of Intermediate 335

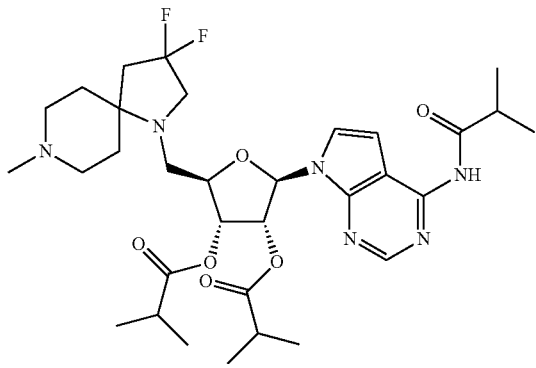 [SMILES: CC(C)C(=O)Nc1ncnc2c1ccn2[C@@H]1O[C@H](CN2CC(F)(F)CC23CCN(C)CC3)[C@@H](OC(=O)C(C)C)[C@H]1OC(=O)C(C)C]

Isobutyric anhydride (2.4 mL, 14.4 mmol) was added to a stirred solution of compound 181 (0.68 g, 1.44 mmol) in pyridine (30 mL) at room temperature. After addition the reaction mixture was stirred at room temperature for 18 hours. The solvents were evaporated. The residue was co-evaporated with toluene. The residue was dissolved in DCM and washed twice with water, once with brine, dried with MgSO$_4$, filtered and the solvents of the filtrate evaporated yielding intermediate 335 (0.71 g).

Example A32

Preparation of Intermediate 335

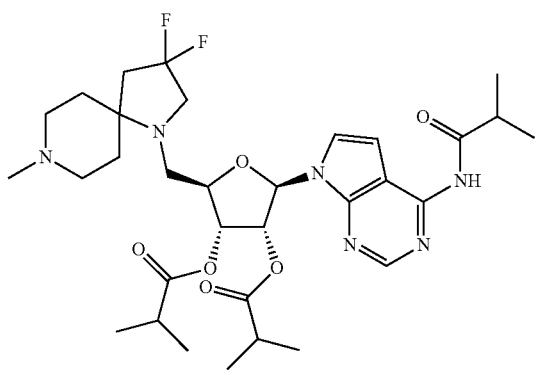 [SMILES: CC(C)C(=O)Nc1ncnc2c1ccn2[C@@H]1O[C@H](CN2CC(F)(F)CC23CCN(C)CC3)[C@@H](OC(=O)C(C)C)[C@H]1OC(=O)C(C)C]

Isobutyric anhydride (86.4 mL, 518.7 mmol) was added to a stirred solution of compound 181 (29.7 g, 51.9 mmol) in pyridine (1 L) at room temperature. After addition the reaction mixture was stirred at 50° C. for 18 hours. The solvents were evaporated. The residue was co-evaporated with toluene. The residue was dissolved in DCM and purified over a SiO$_2$ column, type Grace Reveleris SRC, 330 g, Si 40, on a Armen Spot II Ultimate purification system using DCM and MeOH as eluens in a gradient starting from 100% DCM and ending with 40% MeOH and 60% DCM. The fractions containing product were combined and the solvents were evaporated to give crude intermediate 335 (18.1 g, yield: 40.2%).

Example A33

Preparation of Intermediate 349

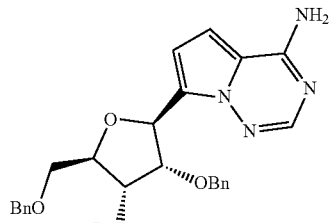

A mixture of intermediate 19 (10.5 g, 18.5 mmol) in THF (50 mL), iPrOH (50 mL) and NH$_4$OH (100 mL) were taken into an autoclave. The mixture was stirred at 70° C. for 72 h. The reaction was concentrated to dryness. The crude was purified by chromatography on silica gel (0%-70% PE: EtOAc) to give intermediate 349 (4.30 g, 8.0 mmol, 43.3% yield) as yellow oil.

Preparation of Intermediate 341

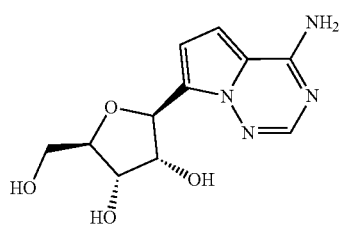 [SMILES: Nc1ncnn2c([C@@H]3O[C@H](CO)[C@@H](O)[C@H]3O)ccc12]

To a solution of intermediate 340 (2.00 g, 3.7 mmol) in acetic acid (100 mL) was added Pd/C (2.0 g, 18.9 mmol). The suspension was stirred under an atmosphere of H2 (15 psi) at 20° C. for 15 h. The reaction was filtered and concentrated to dryness. The crude was added HCl/MeOH (10 mL) and concentrated to dryness. Intermediate 341 (900 mg, 2.53 mmol, 67.7% yield) was obtained as a yellow solid.

Preparation of Intermediate 342

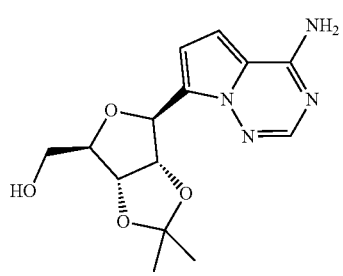 [SMILES: CC1(C)O[C@@H]2[C@H](O1)[C@@H](CO)O[C@H]2c1ccc2c(N)ncnn12]

To a solution of intermediate 341 (900 mg, 2.97 mmol) in DMF (10 mL) and acetone (10 mL) were added 2,2-dimethoxypropane (3.1 g, 29.7 mmol) and TsOH.H$_2$O (622 mg, 3.27 mmol). The mixture was stirred at 60° C. for 15 h. NaHCO$_3$ was added to the mixture and the mixture was extracted with EtOAc (three times 50 mL). The organic layer was washed with brine and dried over MgSO₄. The crude was purified by column (DCM:MeOH 20:1) to obtain Intermediate 342 (400 mg, 1.18 mmol, 39.7% yield).

Preparation of Intermediate 343

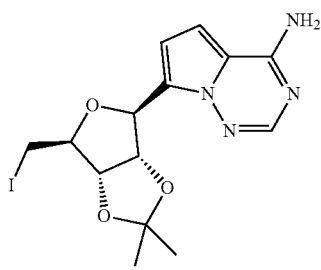 [SMILES: CC1(C)O[C@@H]2[C@H](O1)[C@@H](CI)O[C@H]2c1ccc2c(N)ncnn12]

To a solution of intermediate 342 (1.40 g, 4.57 mmol) in THF (30 mL) were added imidazole (622 mg, 9.14 mmol), I2 (1.51 g, 5.94 mmol) and PPh₃ (1.56 g, 5.94 mmol). The mixture was stirred at 40° C. for 15 h. 10% Na₂S₂O₃ was added. The mixture was diluted with EtOAc. The organic layer was washed with brine, dried over MgSO₄ and concentrated to obtain a crude which was purified by column chromatography (DCM: EtOH 20:1 to obtain Intermediate 343 (800 mg, 1.92 mmol, 42.0% yield).

Preparation of Intermediate 344

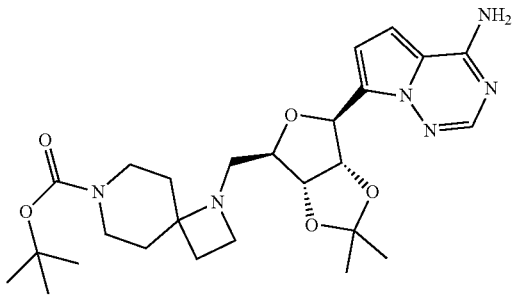 [SMILES: CC(C)(C)OC(=O)N1CCC2(CC1)CCN2C[C@H]1O[C@@H](c2ccc3c(N)ncnn23)[C@@H]2OC(C)(C)O[C@@H]21]

To a solution of Intermediate 343 (100 mg, 240.2 μmol, 1 eq) in CH₃CN (5 mL) were added tert-butyl 1, 7-diazaspiro[3.5]nonane-7-carboxylate (109 mg, 480.5 μmol, 2 eq) and K₂CO₃ (199 mg, 1.44 mmol, 6 eq). The mixture was stirred at 70° C. for 15 h. The mixture was extracted with EtOAc and the organic-layer was concentrated to dryness. The crude was purified by TLC (EtOAc), to give intermediate 344 (40 mg, 54.4 μmol, 22.6% yield).

Example A34

Preparation of Intermediate 345

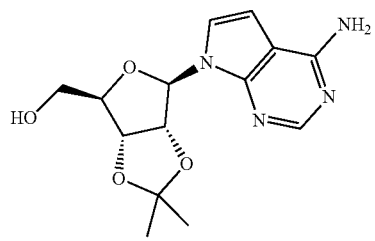 [SMILES: CC1(C)O[C@@H]2[C@H](O1)[C@@H](CO)O[C@H]2n1ccc2c(N)ncnc21]

To a mixture of intermediate 14 (500 mg, 1.54 mmol, 1 eq) in THF (1.0 mL) and propan-2-ol (3.0 mL) was added NH₄OH (4.55 g, 129.8 mmol, 84.3 eq) in one portion at 25° C. The mixture was stirred at 85° C. for 5 days in sealed tube. The mixture was concentrated in vacuum. The residue was purified by silica gel chromatography (ISCO®; 12 g SepaFlash® Silica Flash Column, Eluent of 0-100% Ethyl acetate/DCM, 0-5% 7N NH₃ in MeOH/DCM gradient @ 30 mL/min). Intermediate 345 (490 mg, 1.53 mmol, 99.3% yield) was obtained as a white solid.

Preparation of Intermediate 346

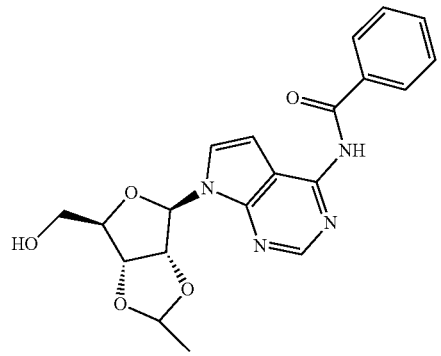

To a mixture of intermediate 345 (490 mg, 1.61 mmol, 1 eq) in pyridine (10 mL) was added TMSCl (875 mg, 8.0 mmol, 5 eq) in one portion at 25° C. The mixture was stirred at 25° C. for 30 min. Then benzoylchloride (294 mg, 2.1 mmol, 1.3 eq) was added at 25° C. for 4 h. The mixture was cooled to 0° C. and diluted with water (0.33 mL) and after 10 min, NH₄OH (2.97 g, 84.85 mmol, 52.7 eq) was added. The mixture was allowed to 25° C. for 30 min. The mixture was concentrated in vacuum. The residue was purified by silica gel chromatography (ISCO®; 12 g SepaFlash® Silica Flash Column, Eluent of 0-50% Ethyl acetate/DCM gradient @ 30 mL/min). Intermediate 346 (520 mg, 1.23 mmol, 76.7% yield) was obtained as a white solid.

165

Preparation of Intermediate 347

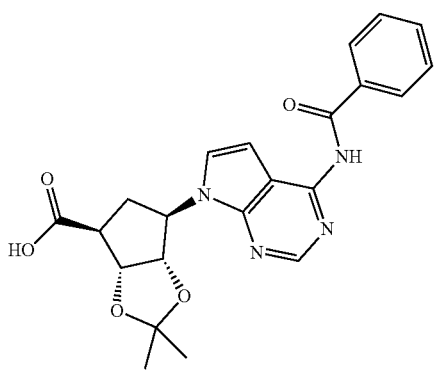 [SMILES: CC1(C)O[C@@H]2[C@H](O1)[C@@H](C(=O)O)C[C@H]2n1ccc2c(NC(=O)c3ccccc3)ncnc21]

To a mixture of intermediate 346 (400 mg, 979 µmol, 1 eq) in CH$_3$CN/H$_2$O (1:1)(2.0 mL) was added TEMPO (30.8 mg, 196 µmol, 0.2 eq) and [acetoxy(phenyl)-iodanyl]acetate (694 mg, 2.15 mmol, 2.2 eq) in one portion at 25° C. The mixture was stirred at 25° C. for 4 h. The mixture was washed by iPr$_2$O (5 mL). The crude product was used into the next step without further purification. Intermediate 347 (420 mg, crude) was obtained as a light yellow solid.

Example A35

Preparation of Intermediate 348

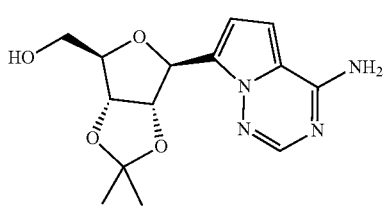 [SMILES: CC1(C)O[C@@H]2[C@H](O1)[C@@H](CO)O[C@H]2c1ccc2c(N)ncnn12]

A solution of intermediate 21 (500 mg, 1.48 mmol, 1 eq) in THF (4.0 mL) and iPrOH (4.0 mL) was taken up into a sealed tube. NH$_4$OH (7.28 g, 51.9 mmol, 35 eq) was added to the mixture and the resulting suspension was heated at 80° C. for 2.5 days. The reaction mixture was concentrated under reduced pressure. The residue was purified by flash silica gel chromatography (ISCO®; 12 g SepaFlash® Silica Flash Column, Eluent of 0-3% MeOH/DCM gradient @ 18 mL/min) to afford intermediate 348 (442 mg, 1.37 mmol, 92.6% yield) as a white foam solid.

Preparation of Intermediate 349

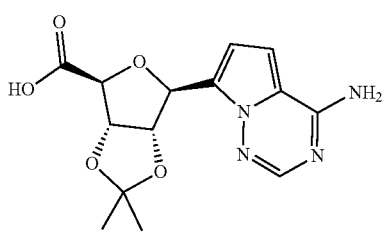 [SMILES: CC1(C)O[C@@H]2[C@H](O1)[C@@H](C(=O)O)O[C@H]2c1ccc2c(N)ncnn12]

166

To a solution of intermediate 348 (227 mg, 741 µmol, 1 eq) in CH$_3$CN (800 uL) and Water (800 uL) was added TEMPO (25 mg, 159 µmol, 0.21 eq) followed by [acetoxy(phenyl)-iodanyl] acetate (478 mg, 1.48 mmol, 2 eq) at 25° C. The mixture was stirred at 25° C. for 16 hours. MTBE (3 mL) was added into the reaction mixture and stirred for 16 hours. The resulting suspension was filtered and the solid was collected and triturated with MTBE, dried under high vacuum to afford desired Intermediate 349 (138 mg, 383 µmol, 51.7% yield) as white solid, which was used as such in the next reaction step without further purification.

Example A36

Preparation of Intermediate 350

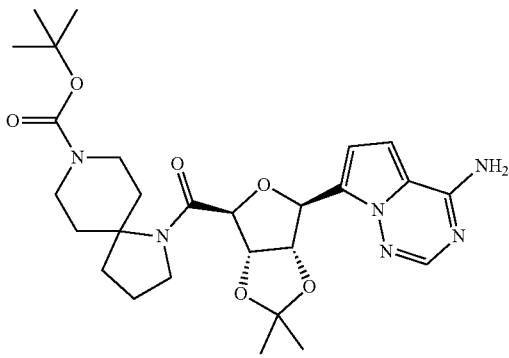 [SMILES: CC(C)(C)OC(=O)N1CCC2(CCCN2C(=O)[C@H]2O[C@@H](c3ccc4c(N)ncnn34)[C@@H]3OC(C)(C)O[C@@H]32)CC1]

To a solution of intermediate 349 (120 mg, 375 µmol, 1 eq), tert-butyl 1,8-diazaspiro[4.5]decane-8-carboxylate, (110 mg, 458 µmol, 1.22 eq) and DIPEA (150 mg, 1.16 mmol, 3.1 eq) in DMF (5 mL) was added HBTU (175 mg, 462 µmol, 1.23 eq) at 20° C. The mixture was stirred at 25° C. for 16 hours. The reaction mixture was purified by preparative HPLC (Column: Phenomenex Synergi C18 150*30 mm, 4 um; Mobile phase: from 29% MeCN in water to 59% MeCN in water, 0.1% TFA; Gradient Time: 8 min; Flow Rate: 30 m/min; Wavelength: 220 nm). The fractions contain desired product were combined and lyophilized to afford intermediate 350 (180 mg, 260 µmol, 69.5% yield) as pale yellow solid.

Below intermediates were prepared by an analogous reaction protocol as was used for the preparation of Intermediate 350 using the appropriate starting materials (Table 12).

Table 12:

TABLE 12

| Int. | Structure | Starting materials |
|---|---|---|
| 351 | 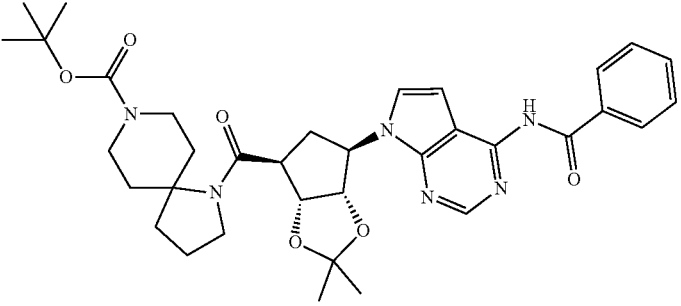 [SMILES: CC(C)(C)OC(=O)N1CCC2(CCCN2C(=O)[C@H]2C[C@@H](n3ccc4c(NC(=O)c5ccccc5)ncnc43)[C@@H]3OC(C)(C)O[C@@H]32)CC1] | Intermediate 347<br>Tert-butyl 1,8-diazaspiro[4.5]decane-8-carboxylate |
| 352 | 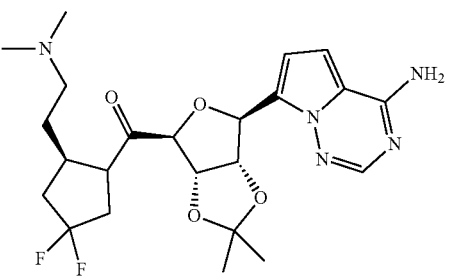 [SMILES: CN(C)CC[C@@H]1CC(F)(F)CC1C(=O)[C@H]1O[C@@H](c2ccc3c(N)ncnn23)[C@@H]2OC(C)(C)O[C@@H]21] | Intermediate 349<br>(R)-2-(4,4-difluoropyrrolidin-2-yl)-N,N-dimethylethanamine |

Example A37

Method A

Preparation of Intermediate 353

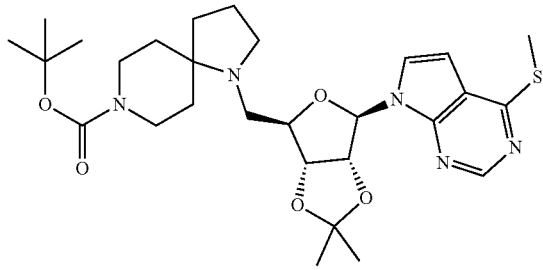 [SMILES: CSc1ncnc2c1ccn2[C@@H]1O[C@H](CN2CCCC23CCN(C(=O)OC(C)(C)C)CC3)[C@H]2OC(C)(C)O[C@H]21]

To a stirred solution of tert-butyl 1,8-diazaspiro[4.5]decane-8-carboxylate (110 mg, 458 μmol, 1 eq) in CH$_2$C12 (8 mL) was added a solution of AcOH (28 mg, 466 μmol, 1.03 eq) in CH$_2$Cl$_2$ (1 mL) at 0° C. NaBH(OAc)$_3$ (195 mg, 920 μmol, 2 eq) was added to the above solution. A solution of intermediate 37 (152 mg, 453 μmol, 1 eq) in CH$_2$C12 (6 mL) was added drop wise to the reaction mixture at 25° C. over a period of 1 hour. The mixture was stirred at 25° C. for further 1.5 hours. The reaction mixture was poured into saturated NaHCO$_3$ aqueous solution then extracted with CH$_2$C1$_{-2}$ (3 times 25 mL). The combined organic layers were washed with brine (50 mL), dried over MgSO$_4$, filtered and concentrated under reduced pressure. The residue was purified by preparative TLC (silica gel, CH$_2$C12: EtOAc 3:1) to afford desired intermediate 353 (199 mg, 352 μmol, 77.7% yield) as yellow gum.

Method B

Preparation of Intermediate 354

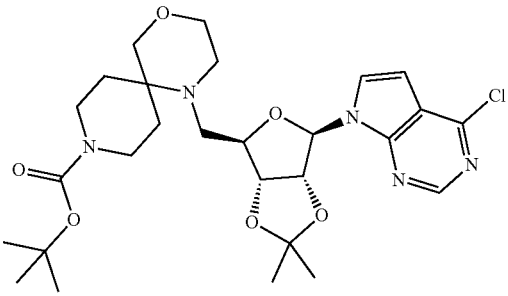 [SMILES: CC(C)(C)OC(=O)N1CCC2(CC1)COCCN2C[C@H]1O[C@@H](n2ccc3c(Cl)ncnc32)[C@@H]2OC(C)(C)O[C@@H]21]

To a mixture of tert-butyl 4-oxa-1,9-diazaspiro[5.5]undecane-9-carboxylate HCl salt (406 mg, 1.39 mmol, 0.9 eq) in CH$_2$C1$_{-2}$ (20 mL) was added Et$_3$N (140 mg, 1.39 mmol, 0.9 eq) at 0° C. under N$_2$. The mixture was stirred at 0° C. for 5 min, then warmed to 25° C. NaBH(OAc)$_3$ (653 mg, 3.08 mmol, 2 eq) was added in one portion, then intermediate 29 (500 mg, 1.54 mmol, 1 eq) in DCM (10 mL) was added drop wise very slowly. The mixture was stirred at 25° C. for 16 hours. Saturated NaHCO$_3$ (20 mL) was added and stirred for 10 mins. The aqueous phase was extracted with ethyl acetate (3 times 20 mL). The combined organic phase was washed with saturated brine (two times 20 mL), dried with anhydrous MgSO$_4$, filtered and concentrated in vacuum. The residue was purified by silica gel chromatography (column height: 250 mm, diameter: 20 mm, 100-200 mesh silica gel, CH$_2$Cl$_2$/Ethyl acetate=6/1, 2/1) to afford the product, which was further purification by preparative HPLC (Column: Gemini 150*25 mm, 5um; Mobile phase: from 50% MeCN in water to 80% MeCN in water, 0.5% NH₃; Gradient Time: 12 min; Flow Rate: 25 ml/min; Wavelength: 220 nm) to afford desired Intermediate 354 (160 mg, 265 μmol, 17.2% yield) as light yellow oil.

Below intermediates were prepared by an analogous reaction protocol as was used for the preparation of intermediate 354 or intermediate 353 using the appropriate starting materials (Table 13).

TABLE 13

| Int. | Structure | starting materials | Method |
|---|---|---|---|
| 355 | 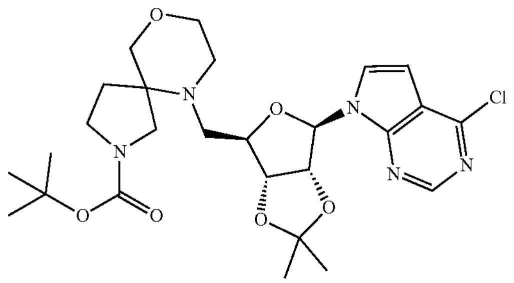 [SMILES: CC(C)(C)OC(=O)N1CCC2(COCCN2C[C@H]2O[C@@H](n3ccc4c(Cl)ncnc43)[C@@H]3OC(C)(C)O[C@@H]32)C1] | intermediate 29<br>tert-butyl 9-oxa-2,6-diazaspiro[4.5]decane-2-carboxylate | Method A |
| 356 | 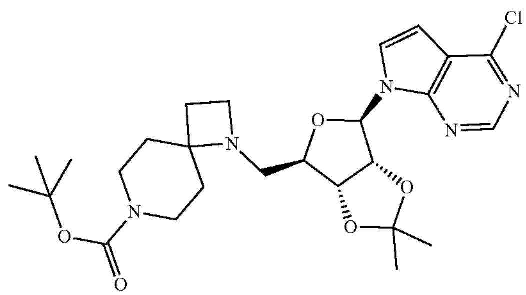 [SMILES: CC(C)(C)OC(=O)N1CCC2(CC1)CCN2C[C@H]1O[C@@H](n2ccc3c(Cl)ncnc32)[C@@H]2OC(C)(C)O[C@@H]21] | intermediate 29<br>tert-butyl 1,7-diazaspiro[3.5]nonane-7-carboxylate | Method A |
| 357 | 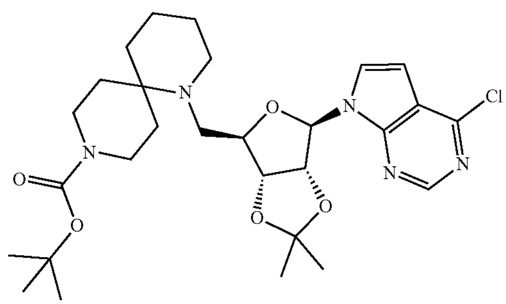 [SMILES: CC(C)(C)OC(=O)N1CCC2(CCCCN2C[C@H]2O[C@@H](n3ccc4c(Cl)ncnc43)[C@@H]3OC(C)(C)O[C@@H]32)CC1] | intermediate 29<br>tert-butyl 1,9-diazaspiro[5.5]undecane-9-carboxylate | Method A |
| 358 | 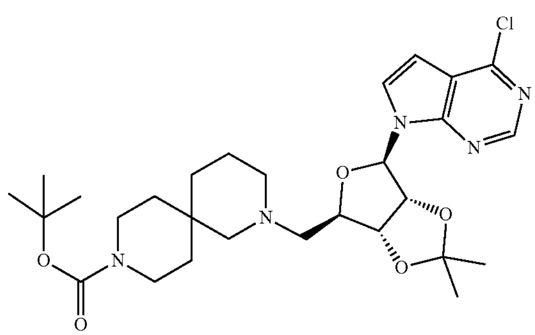 [SMILES: CC(C)(C)OC(=O)N1CCC2(CCCN(C[C@H]3O[C@@H](n4ccc5c(Cl)ncnc54)[C@@H]4OC(C)(C)O[C@@H]43)C2)CC1] | intermediate 29<br>tert-butyl 2,9-diazaspiro[5.5]undecane-9-carboxylate | Method A |
| 359 | 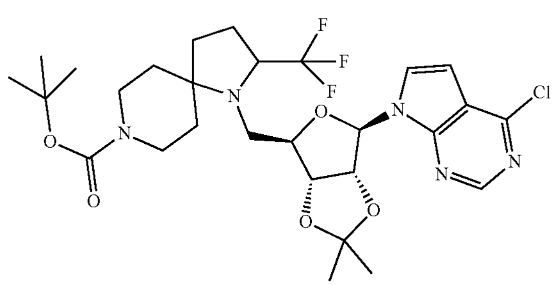 [SMILES: CC(C)(C)OC(=O)N1CCC2(CCC(C(F)(F)F)N2C[C@H]2O[C@@H](n3ccc4c(Cl)ncnc43)[C@@H]3OC(C)(C)O[C@@H]32)CC1] | intermediate 29<br>2-trifluoromethyl-1,8-diaza-spiro[4.5]decane-8-carboxylic acid tert-butyl ester | Method A |

TABLE 13-continued

| Int. | Structure | starting materials | Method |
|---|---|---|---|
| 360 | 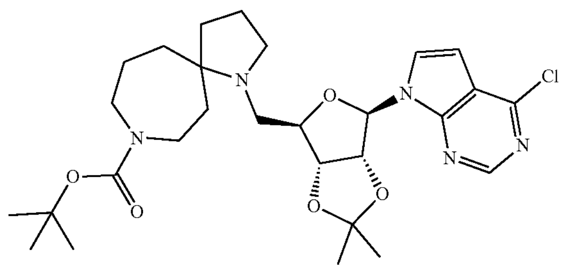 [SMILES: CC(C)(C)OC(=O)N1CCCC2(CCCN2C[C@H]2O[C@@H](n3ccc4c(Cl)ncnc43)[C@@H]3OC(C)(C)O[C@@H]32)CC1] | intermediate 29 tert-butyl 1,8-diazaspiro[4.6]undecane-8-carboxylate | Method A |
| 361 | 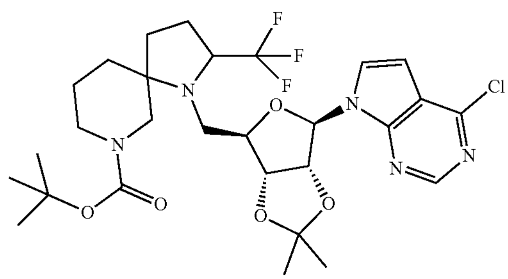 [SMILES: CC(C)(C)OC(=O)N1CCCC2(CCC(C(F)(F)F)N2C[C@H]2O[C@@H](n3ccc4c(Cl)ncnc43)[C@@H]3OC(C)(C)O[C@@H]32)C1] | intermediate 29 tert-butyl 1,7-diazaspiro[4.5]decane-7-carboxylate | Method A |
| 362 | 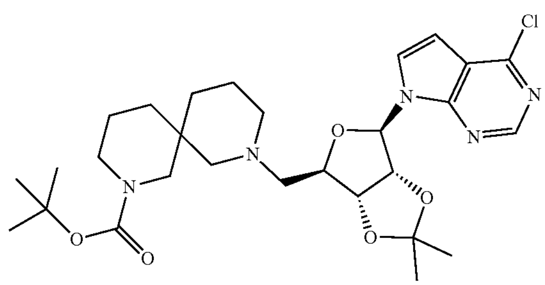 [SMILES: CC(C)(C)OC(=O)N1CCCC2(CCCN(C[C@H]3O[C@@H](n4ccc5c(Cl)ncnc54)[C@@H]4OC(C)(C)O[C@@H]43)C2)C1] | intermediate 29 tert-butyl 2,8-diazaspiro[5.5]undecane-2-carboxylate | Method A |
| 363 | 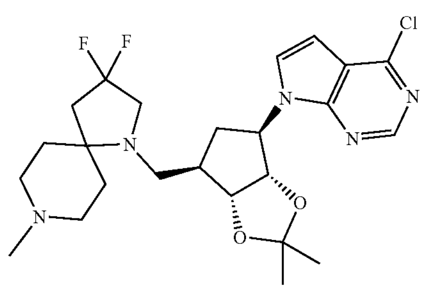 [SMILES: CN1CCC2(CC1)CC(F)(F)CN2C[C@H]1C[C@@H](n2ccc3c(Cl)ncnc32)[C@@H]2OC(C)(C)O[C@H]12] | intermediate 36, 3,3-difluoro-8-methyl-1,8-diazaspiro[4.5]decane 2hcl salt | Method B |
| 364 | 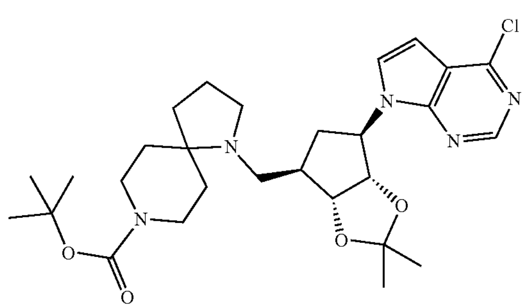 [SMILES: CC(C)(C)OC(=O)N1CCC2(CCCN2C[C@H]2C[C@@H](n3ccc4c(Cl)ncnc43)[C@@H]3OC(C)(C)O[C@H]23)CC1] | intermediate 36 tert-butyl 1,8-diazaspiro[4.5]decane-8-carboxylate | Method A |

TABLE 13-continued

| Int. | Structure | starting materials | Method |
|---|---|---|---|
| 365 | 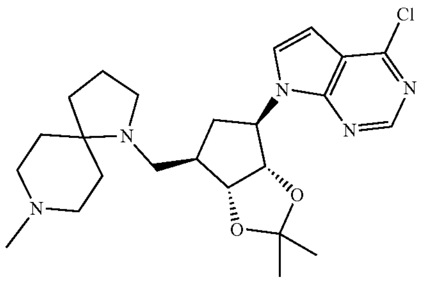 [SMILES: CN1CCC2(CCCN2C[C@H]2C[C@@H](n3ccc4c(Cl)ncnc43)[C@@H]3OC(C)(C)O[C@H]23)CC1] | intermediate 36<br>8-methyl-1,8-diazaspiro[4.5]decane | Method A |
| 366 | 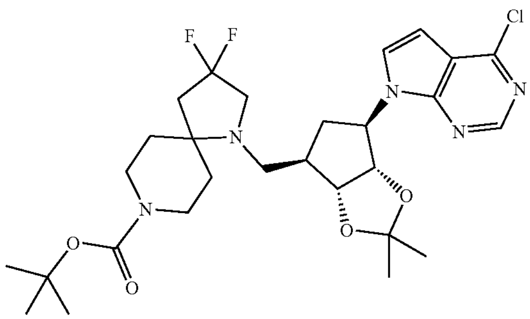 [SMILES: CC(C)(C)OC(=O)N1CCC2(CC1)CC(F)(F)CN2C[C@H]1C[C@@H](n2ccc3c(Cl)ncnc32)[C@@H]2OC(C)(C)O[C@H]12] | intermediate 36<br>tert-butyl 3,3-difluoro-1,8-diaza-spiro[4.5]decane-8-carboxylate | Method A |
| 367 | 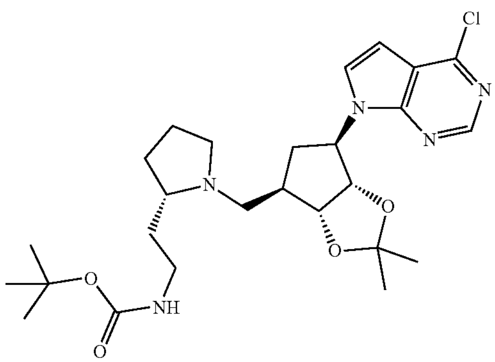 [SMILES: CC(C)(C)OC(=O)NCC[C@@H]1CCCN1C[C@H]1C[C@@H](n2ccc3c(Cl)ncnc32)[C@@H]2OC(C)(C)O[C@H]12] | intermediate 36<br>(S)-tert-butyl 2-(pyrrolidin-2-yl)ethylcarbamate | Method A |
| 368 | 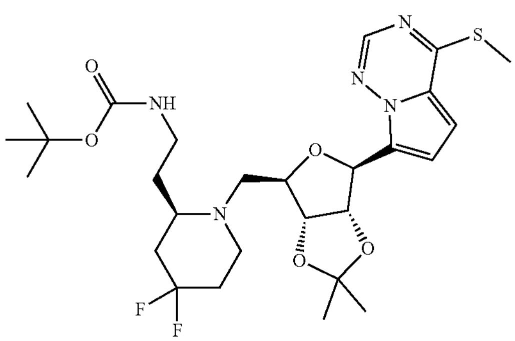 [SMILES: CSc1ncnn2c([C@@H]3O[C@H](CN4CCC(F)(F)C[C@H]4CCNC(=O)OC(C)(C)C)[C@H]4OC(C)(C)O[C@H]43)ccc12] | intermediate 37<br>(R)-tert-butyl (2-(4,4-difluoropiperidin-2-yl)ethyl)carbamate TFA salt | Method B |
| 369 | 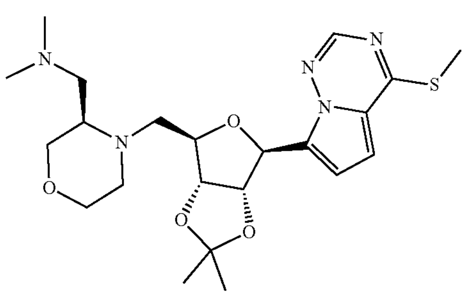 | intermediate 37<br>(R)-N,N-dimethyl-1-(morpholin-3-yl)methanamine 2hcl salt | Method B |

TABLE 13-continued

| Int. | Structure | starting materials | Method |
|---|---|---|---|
| 370 | 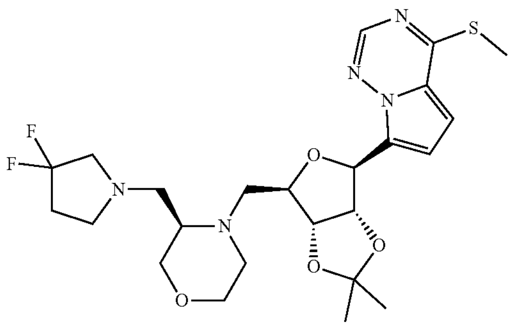 [SMILES: CSc1ncnn2c([C@@H]3O[C@H](CN4CCOC[C@H]4CN4CCC(F)(F)C4)[C@H]4OC(C)(C)O[C@H]43)ccc12] | intermediate 37<br>R)-3-((3,3-difluoropyrrolidin-1-yl)methyl)morpholine | Method A |
| 371 | 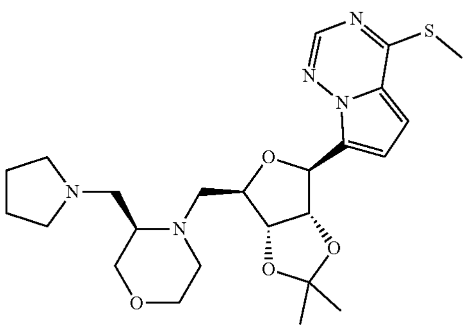 [SMILES: CSc1ncnn2c([C@@H]3O[C@H](CN4CCOC[C@H]4CN4CCCC4)[C@H]4OC(C)(C)O[C@H]43)ccc12] | intermediate 37<br>(R)-3-(pyrrolidin-1-ylmethyl)morpholine | Method A |
| 372 | 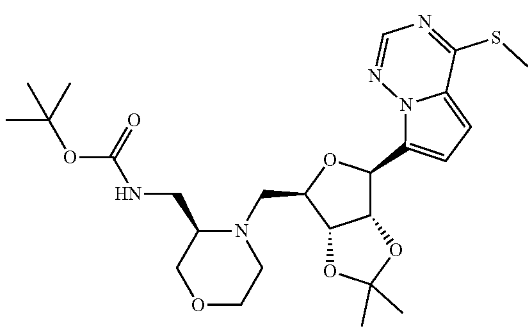 [SMILES: CSc1ncnn2c([C@@H]3O[C@H](CN4CCOC[C@H]4CNC(=O)OC(C)(C)C)[C@H]4OC(C)(C)O[C@H]43)ccc12] | intermediate 37<br>R)-tert-butyl (morpholin-3-ylmethyl)carbamate | Method A |
| 373 | 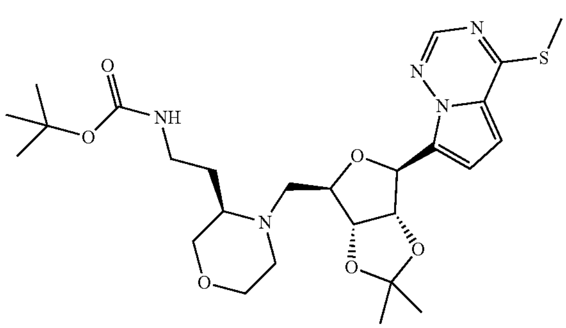 [SMILES: CSc1ncnn2c([C@@H]3O[C@H](CN4CCOC[C@H]4CCNC(=O)OC(C)(C)C)[C@H]4OC(C)(C)O[C@H]43)ccc12] | intermediate 37<br>(R)-tert-butyl (2-(morpholin-3-yl)ethyl)carbamate | Method A |
| 374 | 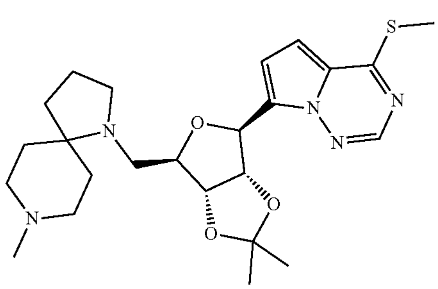 [SMILES: CSc1ncnn2c([C@@H]3O[C@H](CN4CCCC45CCN(C)CC5)[C@H]4OC(C)(C)O[C@H]43)ccc12] | intermediate 37<br>8-methyl-1,8-diazaspiro[4.5]decane | Method A |

TABLE 13-continued

| Int. | Structure | starting materials | Method |
|---|---|---|---|
| 375 | 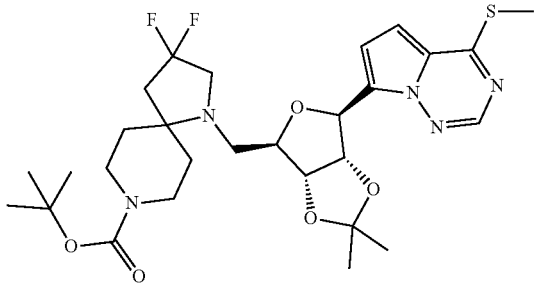 [SMILES: CSc1ncnn2c([C@@H]3O[C@H](CN4CC(F)(F)CC45CCN(C(=O)OC(C)(C)C)CC5)[C@H]4OC(C)(C)O[C@H]43)ccc12] | intermediate 37<br>tert-butyl 3,3-difluoro-<br>1,8-diaza-<br>spiro[4.5]decane-8-<br>carboxylate | Method A |
| 376 | 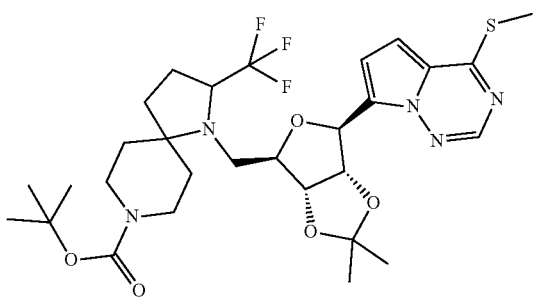 [SMILES: CSc1ncnn2c([C@@H]3O[C@H](CN4C(C(F)(F)F)CCC45CCN(C(=O)OC(C)(C)C)CC5)[C@H]4OC(C)(C)O[C@H]43)ccc12] | intermediate 37<br>2-trifluoromethyl-1,8-<br>diaza-spiro[4.5]decane-<br>8-carboxylic acid tert-<br>butyl ester, | Method A |
| 377 | 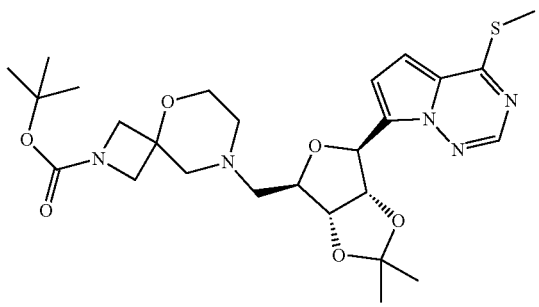 [SMILES: CSc1ncnn2c([C@@H]3O[C@H](CN4CCOC5(C4)CN(C(=O)OC(C)(C)C)C5)[C@H]4OC(C)(C)O[C@H]43)ccc12] | intermediate 37<br>tert-butyl 5-oxa-2,8-<br>diazaspiro[3.5]nonane-2-<br>carboxylate | Method A |
| 378 | 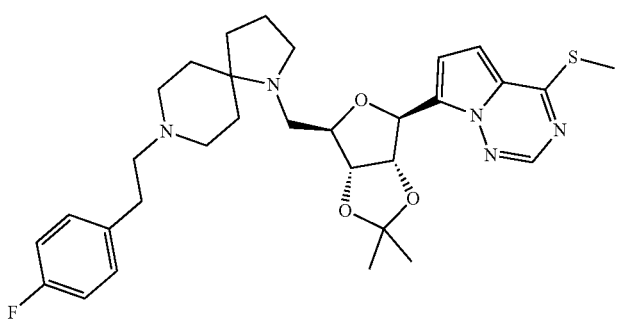 [SMILES: CSc1ncnn2c([C@@H]3O[C@H](CN4CCCC45CCN(CCc4ccc(F)cc4)CC5)[C@H]4OC(C)(C)O[C@H]43)ccc12] | intermediate 37<br>8-(4-fluorophenethyl)-1,8-<br>diazaspiro[4.5]decane 2HCl<br>salt | Method B |
| 379 | 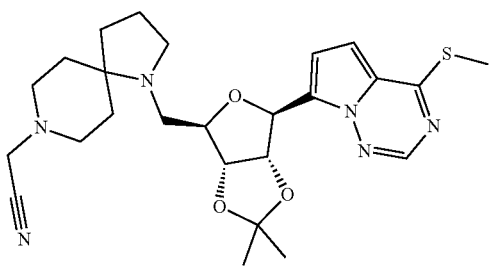 [SMILES: CSc1ncnn2c([C@@H]3O[C@H](CN4CCCC45CCN(CC#N)CC5)[C@H]4OC(C)(C)O[C@H]43)ccc12] | intermediate 37<br>2-(1,8-<br>diazaspiro[4.5]decan-8-<br>yl)acetonitrile 2HCl<br>salt | Method B |

TABLE 13-continued

| Int. | Structure | starting materials | Method |
|---|---|---|---|
| 380 | 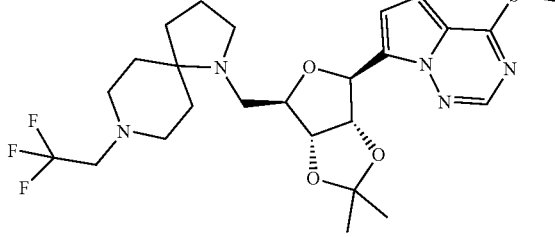 | intermediate 37<br>8-(2,2,2-trifluoroethyl)-1,8-diazaspiro[4.5]decane, 2HCl salt | Method B |
| 381 | 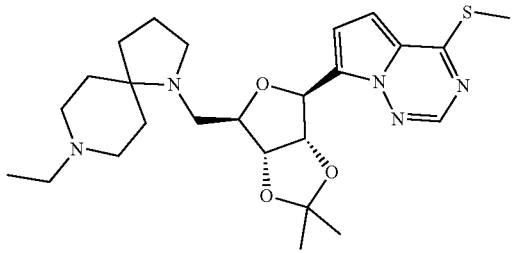 [SMILES: CCN1CCC2(CCCN2C[C@H]2O[C@@H](c3ccc4c(SC)ncnn34)[C@@H]3OC(C)(C)O[C@@H]32)CC1] | intermediate 37<br>8-ethyl-1,8-diazaspiro[4.5]decane 2HCl salt | Method B |
| 382 | 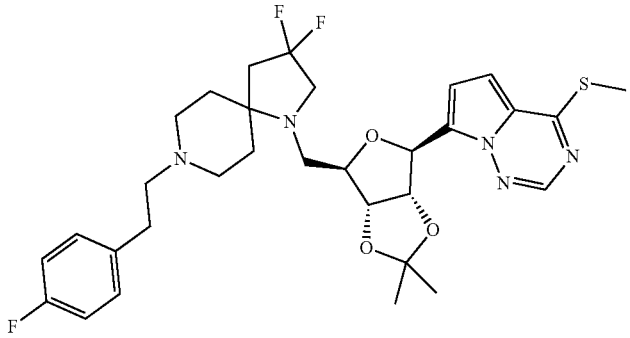 [SMILES: CSc1ncnn2c([C@@H]3O[C@H](CN4CC(F)(F)CC45CCN(CCc4ccc(F)cc4)CC5)[C@H]4OC(C)(C)O[C@H]43)ccc12] | intermediate 37<br>3,3-difluoro-8-(4-fluorophenethyl)-1,8-diazaspiro[4.5]decane | Method A |
| 383 | 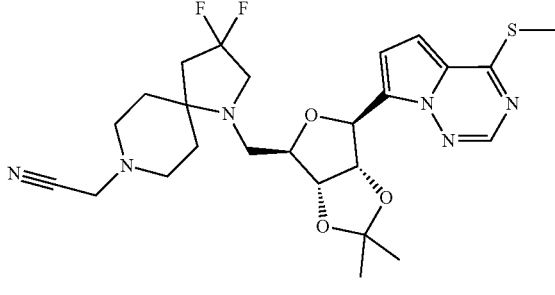 [SMILES: CSc1ncnn2c([C@@H]3O[C@H](CN4CC(F)(F)CC45CCN(CC#N)CC5)[C@H]4OC(C)(C)O[C@H]43)ccc12] | intermediate 37<br>2-(3,3-difluoro-1,8-diazaspiro[4.5]decan-8-yl)acetonitrile | Method A |
| 384 | 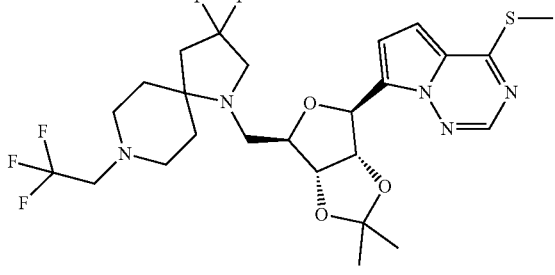 | intermediate 37<br>3,3-difluoro-8-(2,2,2-trifluoroethyl)-1,8-diazaspiro[4.5]decane 2HCl salt | Method B |

TABLE 13-continued

| Int. | Structure | starting materials | Method |
|---|---|---|---|
| 385 | 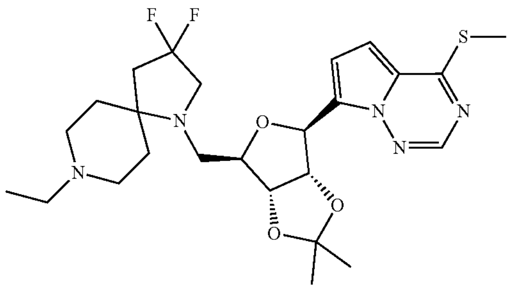 [SMILES: CCN1CCC2(CC1)CC(F)(F)CN2C[C@H]1O[C@@H](c2ccc3c(SC)ncnn23)[C@@H]2OC(C)(C)O[C@@H]21] | intermediate 37<br>8-ethyl-3,3-difluoro-1,8-diazaspiro[4.5]decane | Method A |
| 386 | 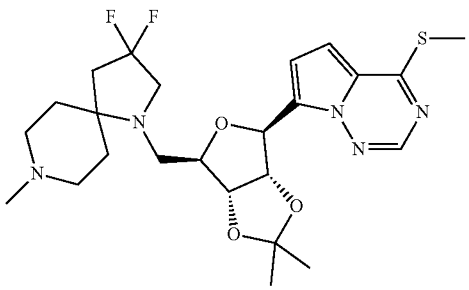 | intermediate 37<br>3,3-difluoro-8-methyl-1,8-diazaspiro[4.5]decane 2HCl salt | Method B |
| 387 | 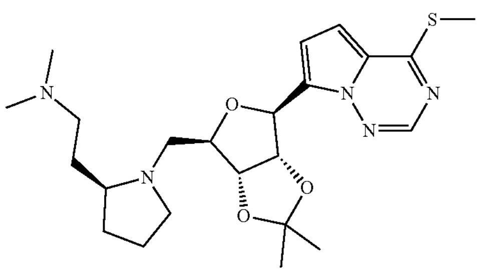 | intermediate 37<br>(S)-N,N-dimethyl-2-(pyrrolidin-2-yl)ethanamine 2hcl salt | Method B |
| 389 | 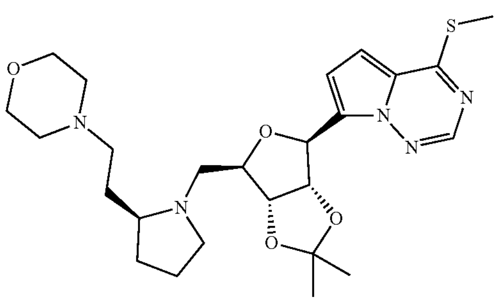 [SMILES: CSc1ncnn2c([C@@H]3O[C@H](CN4CCC[C@H]4CCN4CCOCC4)[C@H]4OC(C)(C)O[C@H]43)ccc12] | intermediate 37<br>(S)-4-(2-(pyrrolidin-2-yl)ethyl)morpholine 2HCl salt | Method B |
| 390 | 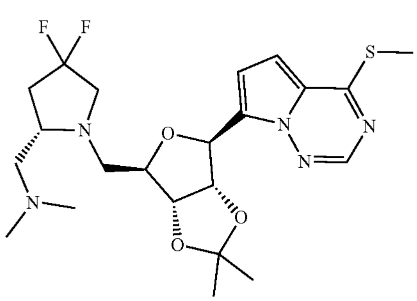 | intermediate 37<br>(S)-1-(4,4-difluoropyrrolidin-2-yl)-N,N-dimethylmethanamine 2HCl salt | Method B |

TABLE 13-continued

| Int. | Structure | starting materials | Method |
|---|---|---|---|
| 391 | 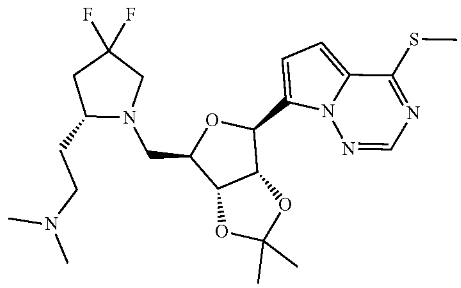 | intermediate 37<br>(R)-2-(4,4-difluoropyrrolidin-2-yl)-N,N-dimethylethanamine 2HCl salt | Method B |
| 393 | 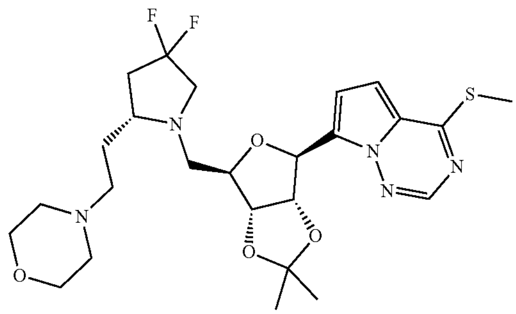 [SMILES: CSc1ncnn2c([C@@H]3O[C@H](CN4CC(F)(F)C[C@H]4CCN4CCOCC4)[C@H]4OC(C)(C)O[C@H]43)ccc12] | intermediate 37<br>(R)-4-(2-(4,4-difluoropyrrolidin-2-yl)ethyl)morpholine 2HCl salt | Method B |
| 394 | 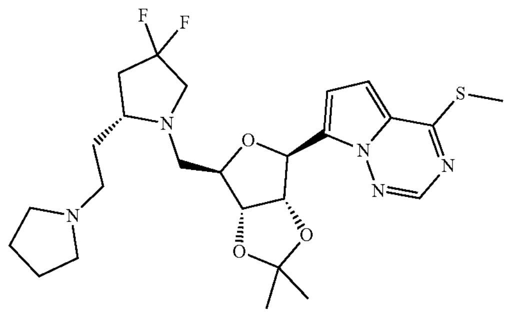 [SMILES: CSc1ncnn2c([C@@H]3O[C@H](CN4CC(F)(F)C[C@H]4CCN4CCCC4)[C@H]4OC(C)(C)O[C@H]43)ccc12] | intermediate 37<br>(R)-4,4-difluoro-2-(2-(pyrrolidin-1-yl)ethyl)pyrrolidine 2HCl salt | Method B |
| 395 | 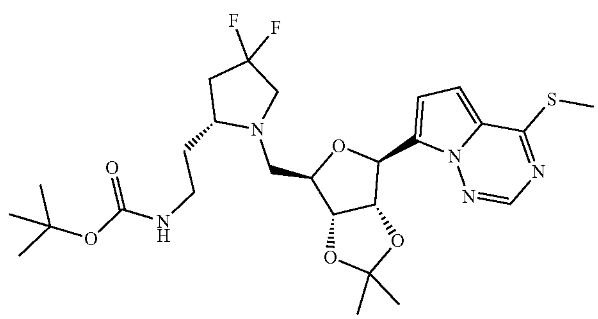 [SMILES: CSc1ncnn2c([C@@H]3O[C@H](CN4CC(F)(F)C[C@H]4CCNC(=O)OC(C)(C)C)[C@H]4OC(C)(C)O[C@H]43)ccc12] | intermediate 37<br>(R)-tert-butyl (2-(4,4-difluoropyrrolidin-2-yl)ethyl)carbamate | Method A |
| 396 | 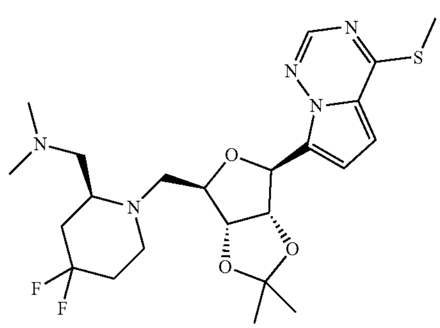 | intermediate 37<br>(S)-1-(4,4-difluoropiperidin-2-yl)-N,N-dimethylmethanamine 2HCl salt | Method B |

TABLE 13-continued

| Int. | Structure | starting materials | Method |
|---|---|---|---|
| 398 | 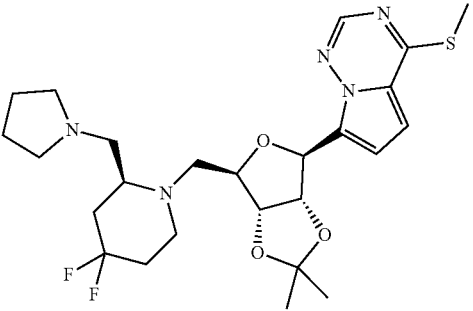 [SMILES: CSc1ncnn2c([C@@H]3O[C@H](CN4CCC(F)(F)C[C@H]4CN4CCCC4)[C@H]4OC(C)(C)O[C@H]43)ccc12] | intermediate 37<br>(S)-4,4-difluoro-2-(pyrrolidin-1-ylmethyl)piperidine 2HCl salt | Method B |
| 399 | 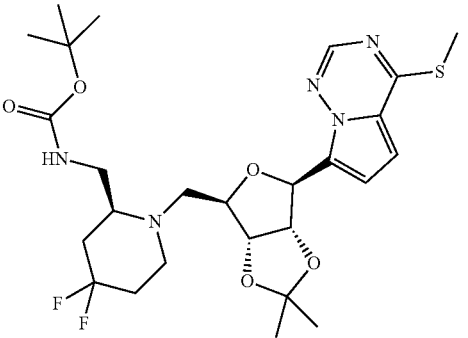 [SMILES: CSc1ncnn2c([C@@H]3O[C@H](CN4CCC(F)(F)C[C@H]4CNC(=O)OC(C)(C)C)[C@H]4OC(C)(C)O[C@H]43)ccc12] | intermediate 37<br>(S)-tert-butyl ((4,4-difluoropiperidin-2-yl)methyl)carbamate | Method A |

Example A38

Preparation of Intermediate 400

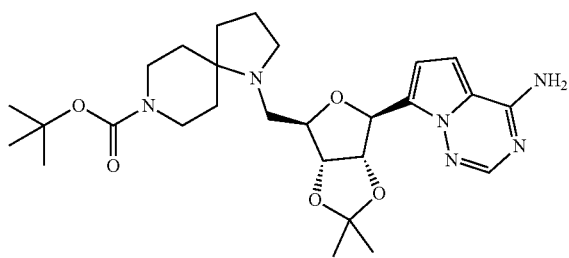 [SMILES: CC(C)(C)OC(=O)N1CCC2(CCCN2C[C@H]2O[C@@H](c3ccc4c(N)ncnn34)[C@@H]3OC(C)(C)O[C@@H]32)CC1]

A solution of Intermediate 353 (199 mg, 355.5 µmol, 1 eq) in THF (1.5 mL) and $^i$PrOH (2.5 mL) was taken up into a sealed tube. NH$_4$OH (4.55 g, 32.5 mmol, 91.2 eq) was added to the mixture and the resulting suspension was heated at 80° C. for 3 days. The reaction mixture was concentrated under reduced pressure. The crude was purified by preparative TLC (silica gel, 100% EtOAc) to afford desired Intermediate 400 (150 mg, 272.4 µmol, 76.6% yield) as yellow solid.

Below intermediates were prepared by ananalogous reaction protocol as was used for the preparation of intermediate 499 using the appropriate starting materials (Table 14).

TABLE 14

| Int. | Structure | Starting materials |
|---|---|---|
| 401 | 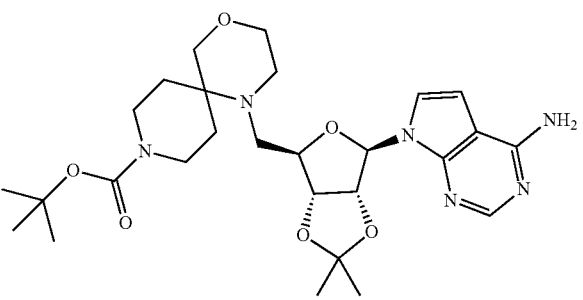 [SMILES: CC(C)(C)OC(=O)N1CCC2(CC1)COCCN2C[C@H]1O[C@@H](n2ccc3c(N)ncnc32)[C@@H]2OC(C)(C)O[C@@H]21] | Intermediate 354 |

TABLE 14-continued

| Int. | Structure | Starting materials |
|---|---|---|
| 402 | 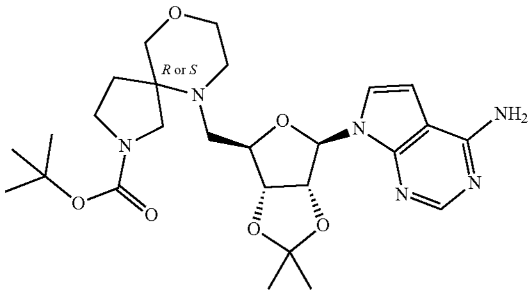 [SMILES: CC(C)(C)OC(=O)N1CCC2(COCCN2C[C@H]2O[C@@H](n3ccc4c(N)ncnc43)[C@@H]3OC(C)(C)O[C@@H]32)C1] | Intermediate 355 |
| 403 | 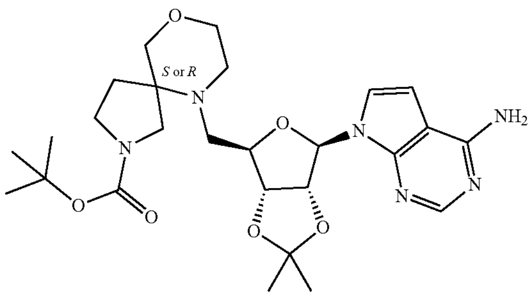 [SMILES: CC(C)(C)OC(=O)N1CCC2(COCCN2C[C@H]2O[C@@H](n3ccc4c(N)ncnc43)[C@@H]3OC(C)(C)O[C@@H]32)C1] | Intermediate 355 |
| 404 | 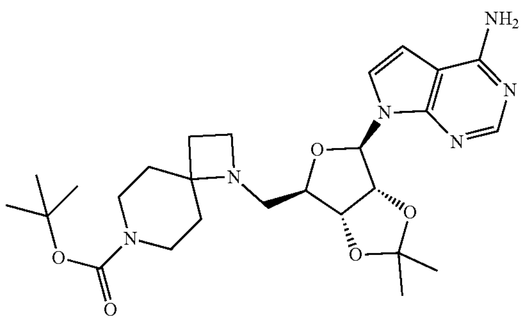 [SMILES: CC(C)(C)OC(=O)N1CCC2(CC1)CCN2C[C@H]1O[C@@H](n2ccc3c(N)ncnc32)[C@@H]2OC(C)(C)O[C@@H]21] | Intermediate 356 |
| 405 | 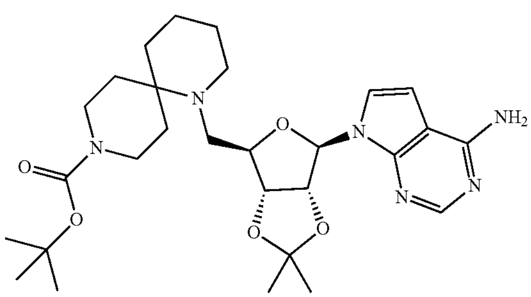 [SMILES: CC(C)(C)OC(=O)N1CCC2(CCCCN2C[C@H]2O[C@@H](n3ccc4c(N)ncnc43)[C@@H]3OC(C)(C)O[C@@H]32)CC1] | Intermediate 357 |
| 406 | 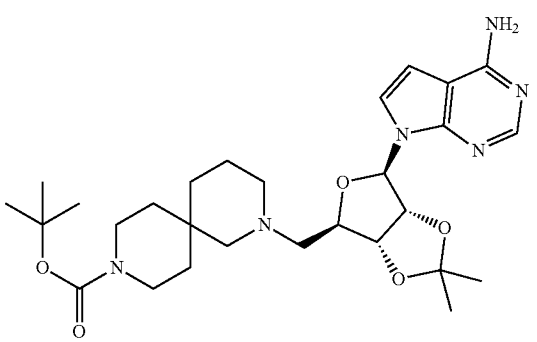 [SMILES: CC(C)(C)OC(=O)N1CCC2(CCCN(C[C@H]3O[C@@H](n4ccc5c(N)ncnc54)[C@@H]4OC(C)(C)O[C@@H]43)C2)CC1] | Intermediate 358 |

TABLE 14-continued
| Int. | Structure | Starting materials |
|---|---|---|
| 407 | 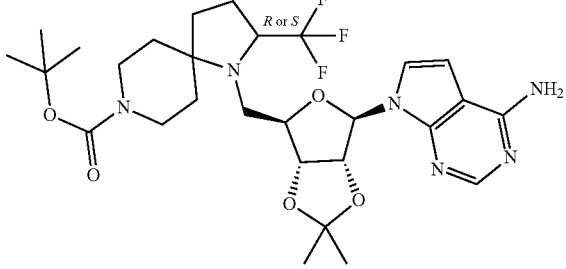 | Intermediate 359 |
| 408 | 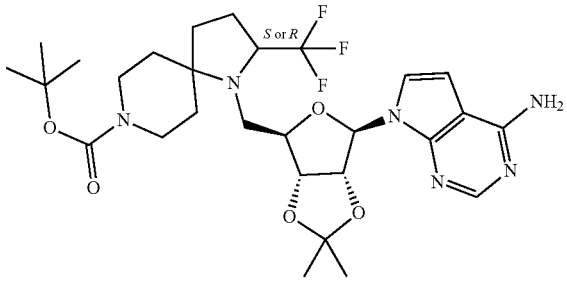 [SMILES: CC(C)(C)OC(=O)N1CCC2(CCC(C(F)(F)F)N2C[C@H]2O[C@@H](n3ccc4c(N)ncnc43)[C@@H]3OC(C)(C)O[C@@H]32)CC1] | Intermediate 359 |
| 409 | 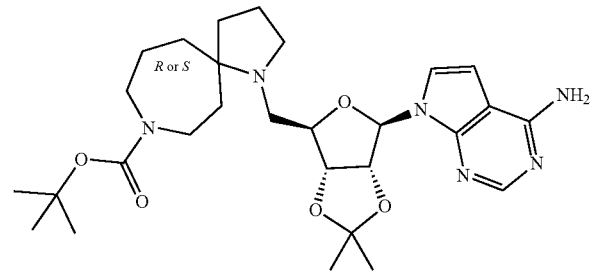 [SMILES: CC(C)(C)OC(=O)N1CCCC2(CCCN2C[C@H]2O[C@@H](n3ccc4c(N)ncnc43)[C@@H]3OC(C)(C)O[C@@H]32)CC1] | Intermediate 360 |
| 410 | 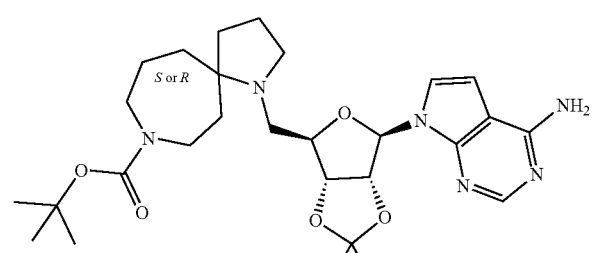 | Intermediate 360 |
| 411 | 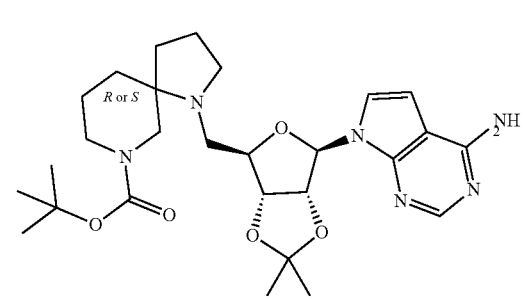 [SMILES: CC(C)(C)OC(=O)N1CCCC2(CCCN2C[C@H]2O[C@@H](n3ccc4c(N)ncnc43)[C@@H]3OC(C)(C)O[C@@H]32)C1] | Intermediate 361 |

TABLE 14-continued

| Int. | Structure | Starting materials |
|---|---|---|
| 412 | 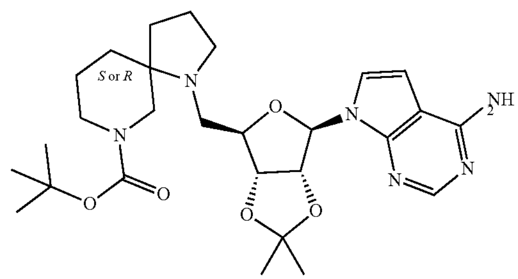 [SMILES: CC(C)(C)OC(=O)N1CCCC2(CCCN2C[C@H]2O[C@@H](n3ccc4c(N)ncnc43)[C@@H]3OC(C)(C)O[C@@H]32)C1] | Intermediate 361 |
| 413 | 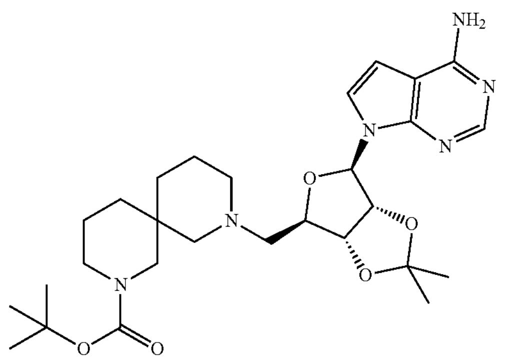 [SMILES: CC(C)(C)OC(=O)N1CCCC2(CCCN(C[C@H]3O[C@@H](n4ccc5c(N)ncnc54)[C@@H]4OC(C)(C)O[C@@H]43)C2)C1] | Intermediate 362 |
| 414 | 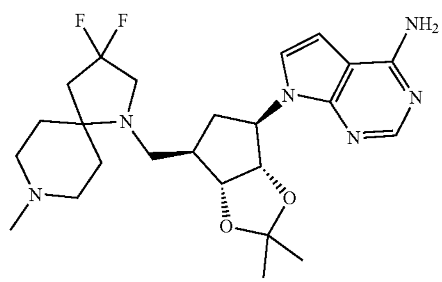 [SMILES: CN1CCC2(CC1)CC(F)(F)CN2C[C@H]1C[C@@H](n2ccc3c(N)ncnc32)[C@@H]2OC(C)(C)O[C@H]12] | Intermediate 363 |
| 415 | 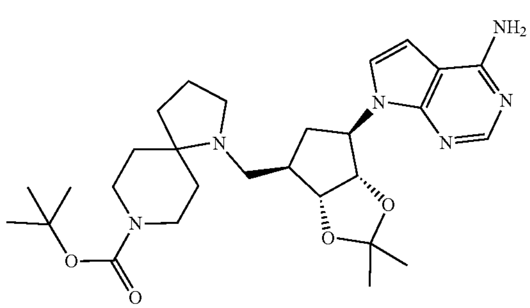 [SMILES: CC(C)(C)OC(=O)N1CCC2(CCCN2C[C@H]2C[C@@H](n3ccc4c(N)ncnc43)[C@@H]3OC(C)(C)O[C@H]23)CC1] | Intermediate 364 |
| 416 | 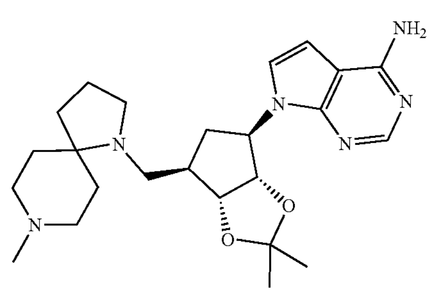 [SMILES: CN1CCC2(CCCN2C[C@H]2C[C@@H](n3ccc4c(N)ncnc43)[C@@H]3OC(C)(C)O[C@H]23)CC1] | Intermediate 365 |

TABLE 14-continued

| Int. | Structure | Starting materials |
|---|---|---|
| 417 | 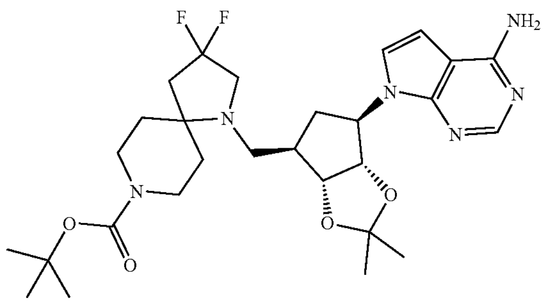 [SMILES: CC(C)(C)OC(=O)N1CCC2(CC1)CC(F)(F)CN2C[C@H]1C[C@@H](n2ccc3c(N)ncnc32)[C@@H]2OC(C)(C)O[C@H]12] | Intermediate 366 |
| 418 | 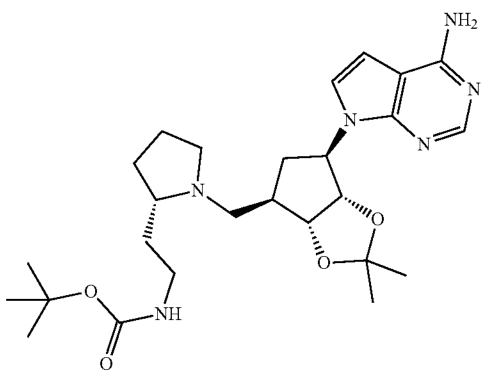 [SMILES: CC(C)(C)OC(=O)NCC[C@@H]1CCCN1C[C@H]1C[C@@H](n2ccc3c(N)ncnc32)[C@@H]2OC(C)(C)O[C@H]12] | Intermediate 367 |
| 419 | 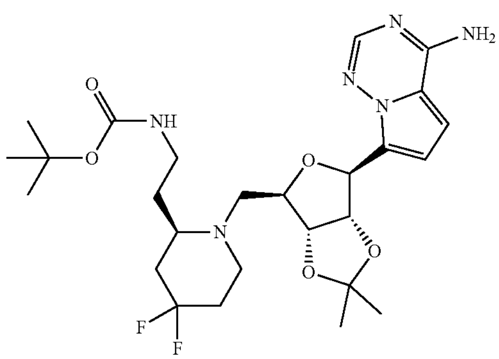 [SMILES: CC(C)(C)OC(=O)NCC[C@@H]1CC(F)(F)CCN1C[C@H]1O[C@@H](c2ccc3c(N)ncnn23)[C@@H]2OC(C)(C)O[C@@H]21] | Intermediate 368 |
| 420 | 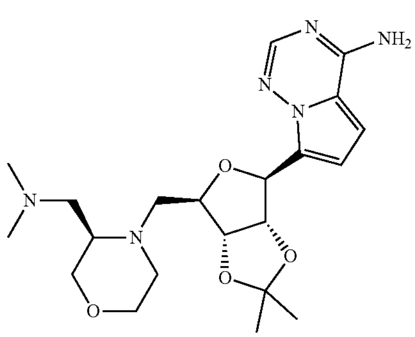 [SMILES: CN(C)C[C@@H]1COCCN1C[C@H]1O[C@@H](c2ccc3c(N)ncnn23)[C@@H]2OC(C)(C)O[C@@H]21] | Intermediate 369 |

TABLE 14-continued

| Int. | Structure | Starting materials |
|---|---|---|
| 421 | 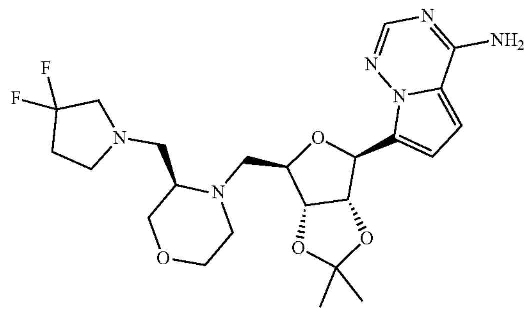 [SMILES: CC1(C)O[C@@H]2[C@H](O1)[C@@H](CN1CCOC[C@H]1CN1CCC(F)(F)C1)O[C@H]2c1ccc2c(N)ncnn12] | Intermediate 370 |
| 422 | 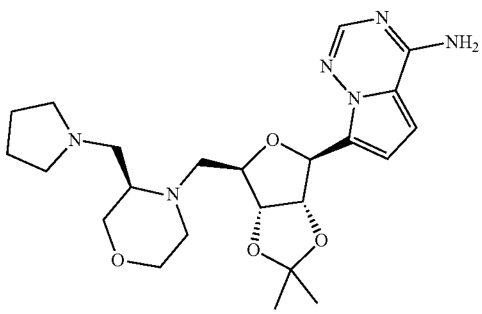 [SMILES: CC1(C)O[C@@H]2[C@H](O1)[C@@H](CN1CCOC[C@H]1CN1CCCC1)O[C@H]2c1ccc2c(N)ncnn12] | Intermediate 371 |
| 423 | 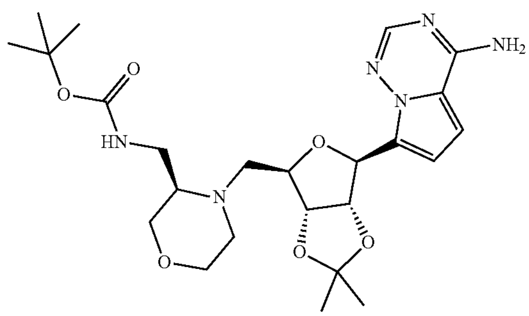 [SMILES: CC(C)(C)OC(=O)NC[C@@H]1COCCN1C[C@H]1O[C@@H](c2ccc3c(N)ncnn23)[C@@H]2OC(C)(C)O[C@@H]21] | Intermediate 372 |
| 424 | 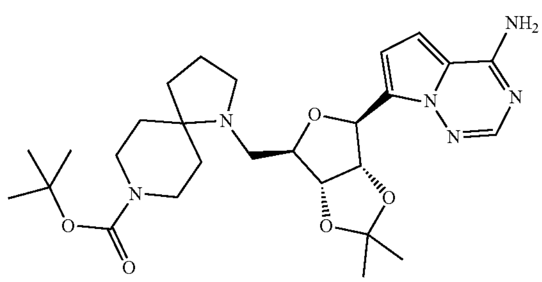 [SMILES: CC(C)(C)OC(=O)N1CCC2(CCCN2C[C@H]2O[C@@H](c3ccc4c(N)ncnn34)[C@@H]3OC(C)(C)O[C@@H]32)CC1] | Intermediate 353 |
| 425 | 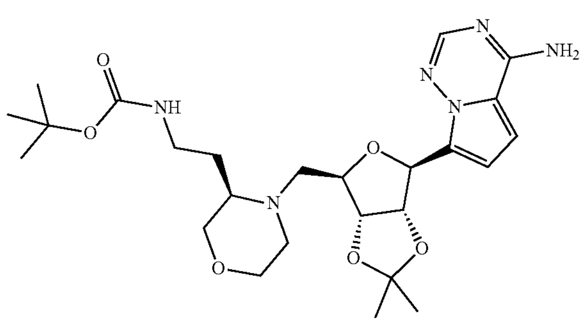 [SMILES: CC(C)(C)OC(=O)NCC[C@@H]1COCCN1C[C@H]1O[C@@H](c2ccc3c(N)ncnn23)[C@@H]2OC(C)(C)O[C@@H]21] | Intermediate 373 |

TABLE 14-continued

| Int. | Structure | Starting materials |
|---|---|---|
| 426 | 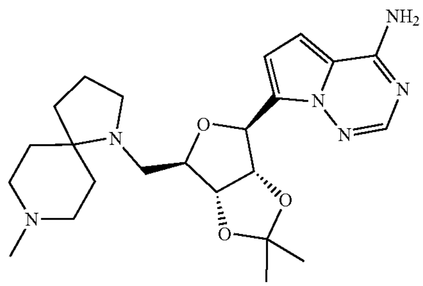 [SMILES: CN1CCC2(CCCN2C[C@H]2O[C@@H](c3ccc4c(N)ncnn34)[C@@H]3OC(C)(C)O[C@@H]32)CC1] | Intermediate 374 |
| 427 | 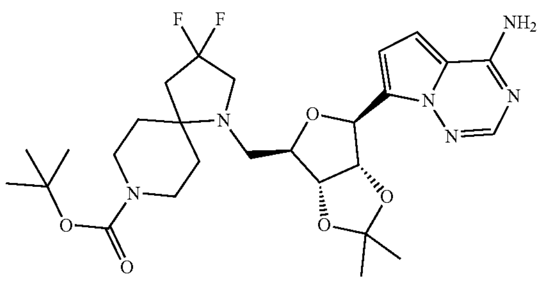 [SMILES: CC(C)(C)OC(=O)N1CCC2(CC1)CC(F)(F)CN2C[C@H]1O[C@@H](c2ccc3c(N)ncnn23)[C@@H]2OC(C)(C)O[C@@H]21] | Intermediate 375 |
| 428 | 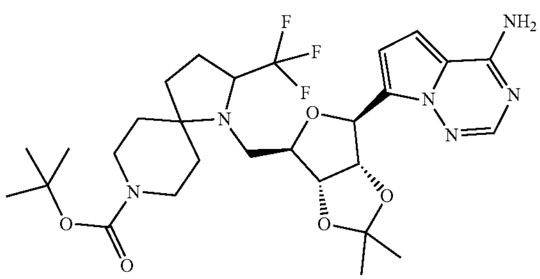 [SMILES: CC(C)(C)OC(=O)N1CCC2(CCC(C(F)(F)F)N2C[C@H]2O[C@@H](c3ccc4c(N)ncnn34)[C@@H]3OC(C)(C)O[C@@H]32)CC1] | Intermediate 376 |
| 429 | 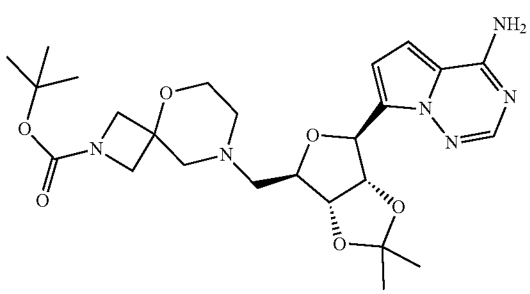 [SMILES: CC(C)(C)OC(=O)N1CC2(CN(C[C@H]3O[C@@H](c4ccc5c(N)ncnn45)[C@@H]4OC(C)(C)O[C@@H]43)CCO2)C1] | Intermediate 377 |
| 430 | 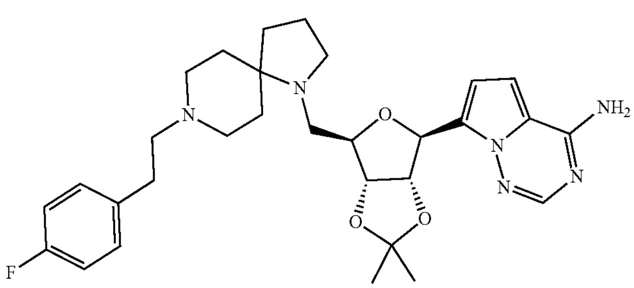 [SMILES: CC1(C)O[C@@H]2[C@H](O1)[C@@H](CN1CCCC13CCN(CCc1ccc(F)cc1)CC3)O[C@H]2c1ccc2c(N)ncnn12] | Intermediate 378 |

TABLE 14-continued
| Int. | Structure | Starting materials |
|---|---|---|
| 431A | 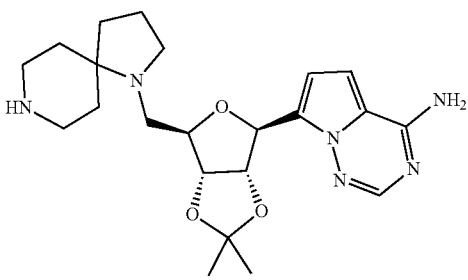 [SMILES: CC1(C)O[C@@H]2[C@H](O1)[C@@H](CN1CCCC13CCNCC3)O[C@H]2c1ccc2c(N)ncnn12] | Intermediate 379 |
| 432 | 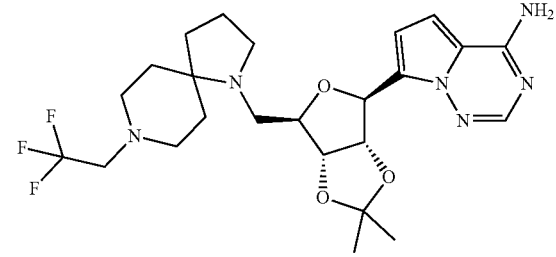 [SMILES: CC1(C)O[C@@H]2[C@H](O1)[C@@H](CN1CCCC13CCN(CC(F)(F)F)CC3)O[C@H]2c1ccc2c(N)ncnn12] | Intermediate 380 |
| 433 | 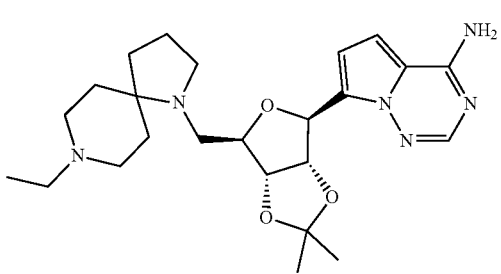 [SMILES: CCN1CCC2(CCCN2C[C@H]2O[C@@H](c3ccc4c(N)ncnn34)[C@@H]3OC(C)(C)O[C@@H]32)CC1] | Intermediate 381 |
| 434 | 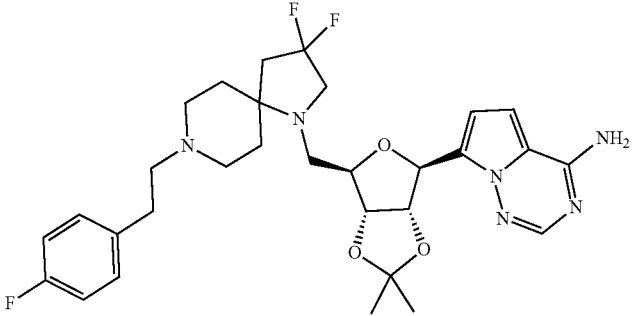 [SMILES: CC1(C)O[C@@H]2[C@H](O1)[C@@H](CN1CC(F)(F)CC13CCN(CCc1ccc(F)cc1)CC3)O[C@H]2c1ccc2c(N)ncnn12] | Intermediate 382 |
| 435A | 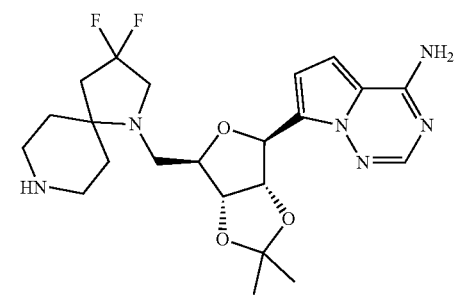 [SMILES: CC1(C)O[C@@H]2[C@H](O1)[C@@H](CN1CC(F)(F)CC13CCNCC3)O[C@H]2c1ccc2c(N)ncnn12] | Intermediate 383 |

TABLE 14-continued

| Int. | Structure | Starting materials |
|---|---|---|
| 436 | 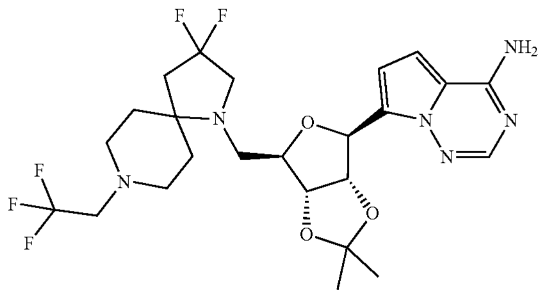 [SMILES: CC1(C)O[C@@H]2[C@H](O1)[C@@H](CN1CC(F)(F)CC13CCN(CC(F)(F)F)CC3)O[C@H]2c1ccc2c(N)ncnn12] | Intermediate 384 |
| 437 | 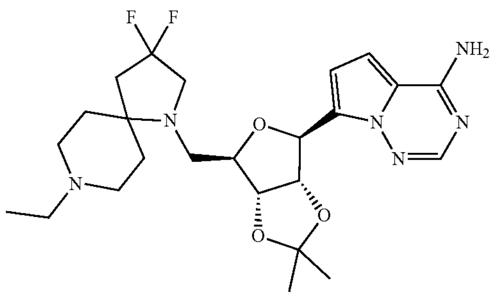 [SMILES: CCN1CCC2(CC1)CC(F)(F)CN2C[C@H]1O[C@@H](c2ccc3c(N)ncnn23)[C@@H]2OC(C)(C)O[C@@H]21] | Intermediate 385 |
| 438 | 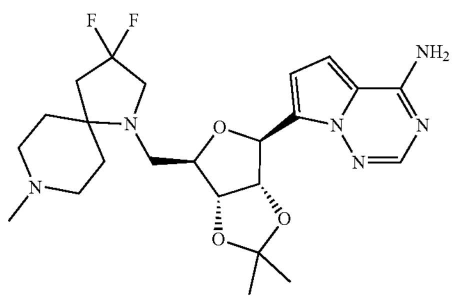 [SMILES: CN1CCC2(CC1)CC(F)(F)CN2C[C@H]1O[C@@H](c2ccc3c(N)ncnn23)[C@@H]2OC(C)(C)O[C@@H]21] | Intermediate 386 |
| 439 | 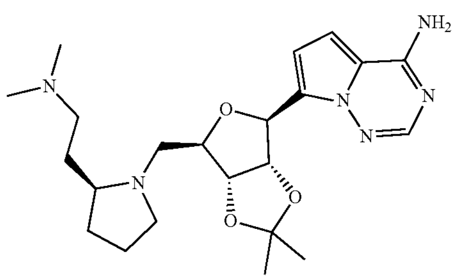 [SMILES: CN(C)CC[C@@H]1CCCN1C[C@H]1O[C@@H](c2ccc3c(N)ncnn23)[C@@H]2OC(C)(C)O[C@@H]21] | Intermediate 387 |
| 441 | 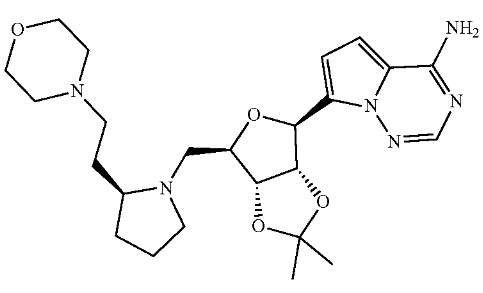 [SMILES: CC1(C)O[C@@H]2[C@H](O1)[C@@H](CN1CCC[C@H]1CCN1CCOCC1)O[C@H]2c1ccc2c(N)ncnn12] | Intermediate 389 |

TABLE 14-continued

| Int. | Structure | Starting materials |
|---|---|---|
| 442 | 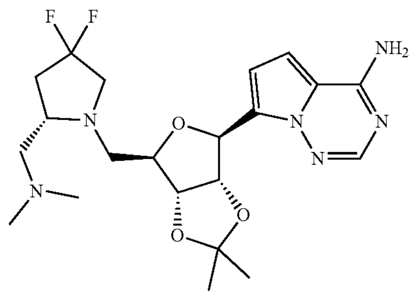 [SMILES: CN(C)C[C@@H]1CC(F)(F)CN1C[C@H]1O[C@@H](c2ccc3c(N)ncnn23)[C@@H]2OC(C)(C)O[C@@H]21] | Intermediate 390 |
| 443 | 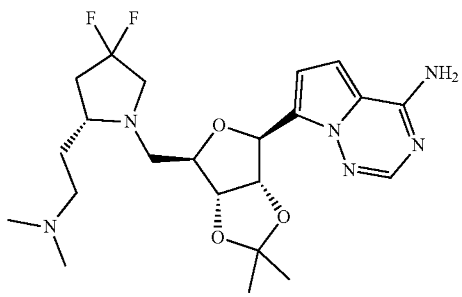 [SMILES: CN(C)CC[C@@H]1CC(F)(F)CN1C[C@H]1O[C@@H](c2ccc3c(N)ncnn23)[C@@H]2OC(C)(C)O[C@@H]21] | Intermediate 391 |
| 445 | 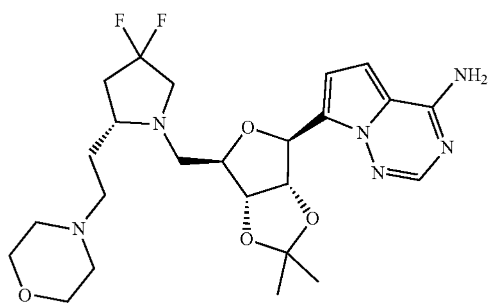 [SMILES: CC1(C)O[C@@H]2[C@H](O1)[C@@H](CN1CC(F)(F)C[C@H]1CCN1CCOCC1)O[C@H]2c1ccc2c(N)ncnn12] | Intermediate 393 |
| 446 | 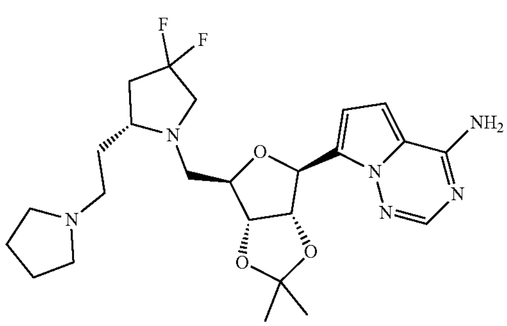 [SMILES: CC1(C)O[C@@H]2[C@H](O1)[C@@H](CN1CC(F)(F)C[C@H]1CCN1CCCC1)O[C@H]2c1ccc2c(N)ncnn12] | Intermediate 394 |
| 447 | 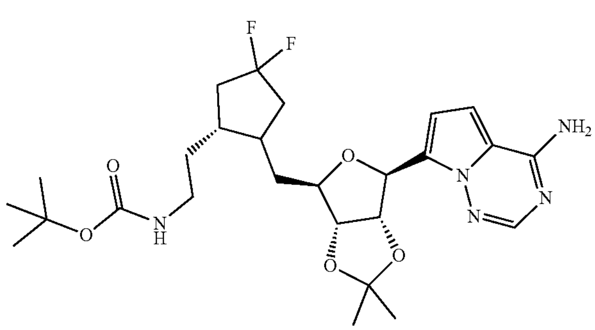 [SMILES: CC(C)(C)OC(=O)NCC[C@@H]1CC(F)(F)CC1C[C@H]1O[C@@H](c2ccc3c(N)ncnn23)[C@@H]2OC(C)(C)O[C@@H]21] | Intermediate 395 |

TABLE 14-continued

| Int. | Structure | Starting materials |
|---|---|---|
| 448 | 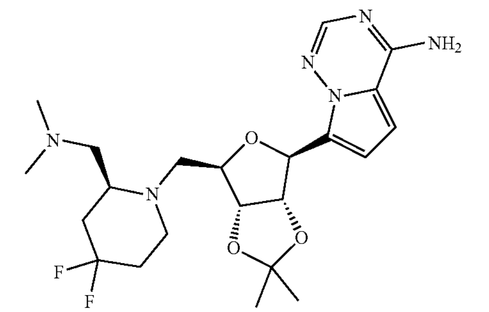 [SMILES: CN(C)C[C@@H]1CC(F)(F)CCN1C[C@H]1O[C@@H](c2ccc3c(N)ncnn23)[C@@H]2OC(C)(C)O[C@@H]21] | Intermediate 396 |
| 450 | 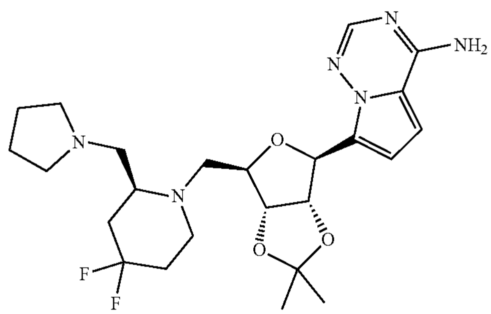 [SMILES: CC1(C)O[C@@H]2[C@H](O1)[C@@H](CN1CCC(F)(F)C[C@H]1CN1CCCC1)O[C@H]2c1ccc2c(N)ncnn12] | Intermediate 398 |
| 451 | 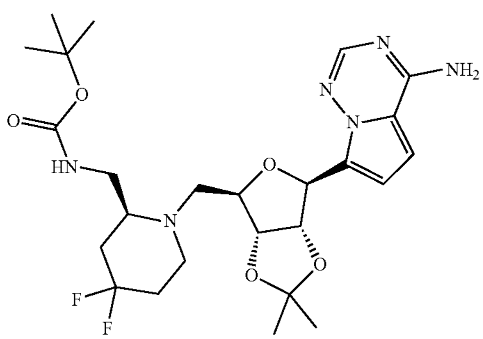 [SMILES: CC(C)(C)OC(=O)NC[C@@H]1CC(F)(F)CCN1C[C@H]1O[C@@H](c2ccc3c(N)ncnn23)[C@@H]2OC(C)(C)O[C@@H]21] | Intermediate 399 |

Example A39

Preparation of Intermediate 452

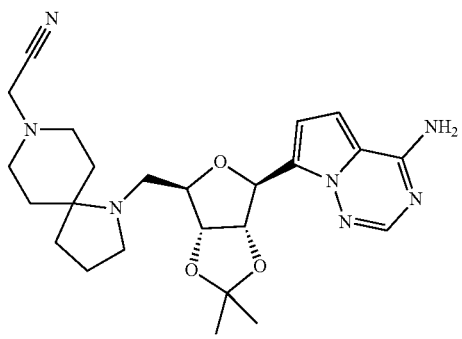 [SMILES: CC1(C)O[C@@H]2[C@H](O1)[C@@H](CN1CCCC13CCN(CC#N)CC3)O[C@H]2c1ccc2c(N)ncnn12]

To a mixture of Intermediate 431A (110 mg, 256.7 μmol, 1 eq) in $CH_2Cl_2$ (20 mL) was added $Et_3N$ (77.9 mg, 770 μmol, 3 eq) and 2-chloroacetonitrile (23.26 mg, 308 μmol, 1.20 eq). The mixture was stirred at 25° C. for 16 h. The mixture was concentrated in vacuum. The residue was purified by preparative HPLC (Column: Gemini 150*25 mm, Sum; Mobile phase: from 25% MeCN in water to 45% MeCN in water, 0.5% $NH_3$; Gradient Time: 12 min; Flow Rate: 25 m/min; Wavelength: 220 nm). Intermediate 452 (70 mg, 143.1 μmol, 55.7% yield) was obtained as a white solid.

Below intermediates were prepared by an analogous reaction protocol as was used for the preparation of intermediate 452 using the appropriate starting materials (Table 15).

TABLE 15

| Int. | Structure | Starting materials |
|---|---|---|
| 453 | 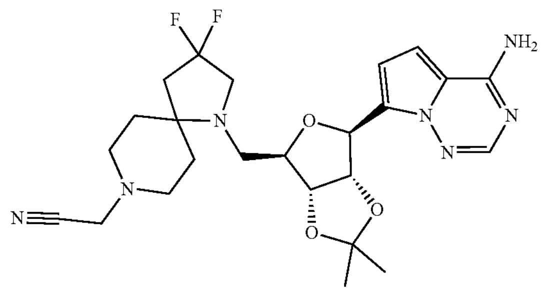 [SMILES: CC1(C)O[C@@H]2[C@H](O1)[C@@H](CN1CC(F)(F)CC13CCN(CC#N)CC3)O[C@H]2c1ccc2c(N)ncnn12] | Intermediate 435A |

Example A40

Preparation of Intermediate 454

Example A41

Preparation of Intermediate 457

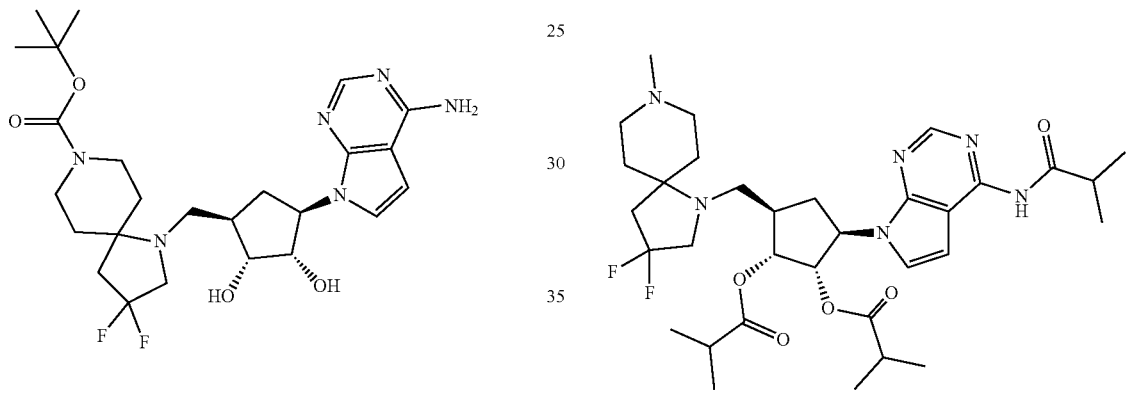

To a mixture of Intermediate 417 (360 mg, 639.8 mol, 1 eq) in MeOH (30 mL) was added PPTS (225 mg, 896 μmol, 1.4 eq) in one portion at 25° C. The mixture was stirred at 50° C. for 10 days. The mixture was concentrated in vacuum to afford Intermediate 454 (450 mg, crude) as a yellow solid, which directly used in next step without further purification.

Below intermediates were prepared by an analogous reaction protocol as was used for the preparation of Intermediate 454 using the appropriate starting materials (Table 16).

To a mixture of compound 123 (60 mg, 137.5 μmol, 1 eq) in pyridine (3 mL) was added isobutyric anhydride (217.5 mg, 1.37 mmol, 10 eq) in one portion at 25° C. The mixture was stirred at 25° C. for 20 h. The mixture was concentrated in vacuum. The residue was purified by preparative TLC (DCM:MeOH=10:1 to afford intermediate 457 (41 mg, 61.2 μmol, 44.5% yield) as white solid.

TABLE 16

| Int. | Structure | Starting materials |
|---|---|---|
| 455 | 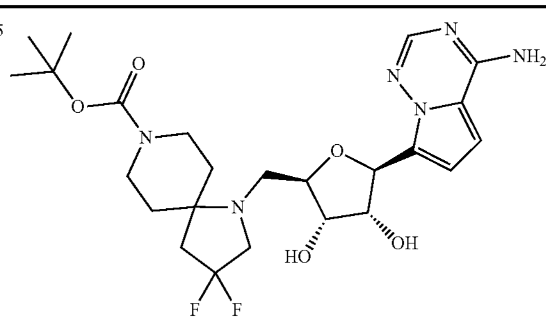 | Intermediate 427 |

Below intermediates were prepared by an analogous reaction protocol as was used for the preparation of intermediate 457 using the appropriate starting materials (Table 17).

TABLE 17

| Int. | Structure | Starting materials |
|---|---|---|
| 458 | 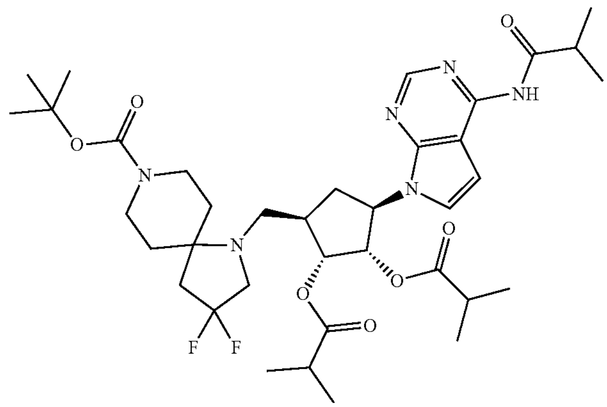 [SMILES: CC(C)C(=O)Nc1ncnc2c1ccn2[C@@H]1C[C@H](CN2CC(F)(F)CC23CCN(C(=O)OC(C)(C)C)CC3)[C@@H](OC(=O)C(C)C)[C@H]1OC(=O)C(C)C] | Intermediate 454 |
| 459 | 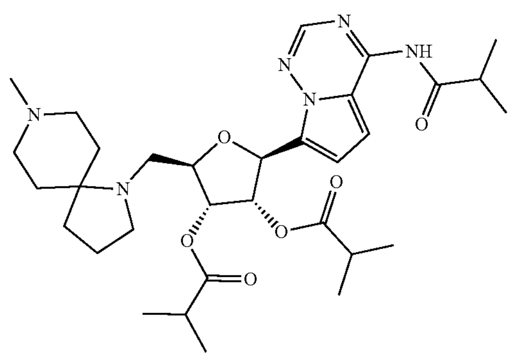 [SMILES: CC(C)C(=O)Nc1ncnn2c([C@@H]3O[C@H](CN4CCCC45CCN(C)CC5)[C@@H](OC(=O)C(C)C)[C@H]3OC(=O)C(C)C)ccc12] | compound 135 |
| 461 | 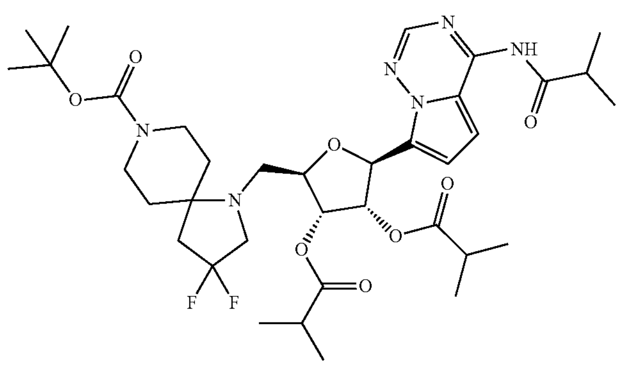 [SMILES: CC(C)C(=O)Nc1ncnn2c([C@@H]3O[C@H](CN4CC(F)(F)CC45CCN(C(=O)OC(C)(C)C)CC5)[C@@H](OC(=O)C(C)C)[C@H]3OC(=O)C(C)C)ccc12] | intermediate 455 |
| 462 | 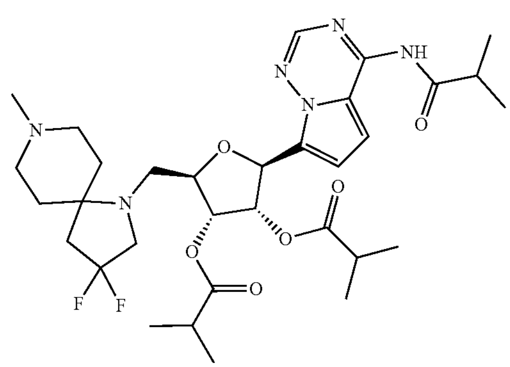 [SMILES: CC(C)C(=O)Nc1ncnn2c([C@@H]3O[C@H](CN4CC(F)(F)CC45CCN(C)CC5)[C@@H](OC(=O)C(C)C)[C@H]3OC(=O)C(C)C)ccc12] | compound 147 |

Example A42

Preparation of Intermediate 464

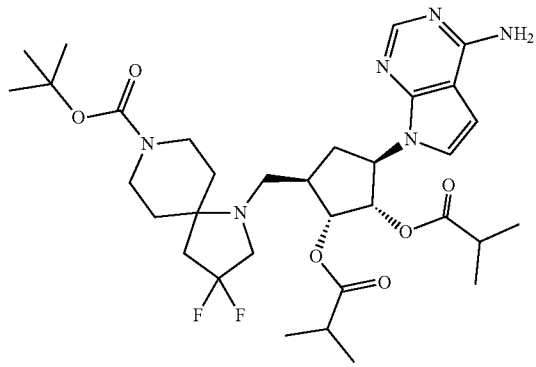 [SMILES: CC(C)C(=O)O[C@@H]1[C@@H](CN2CC(F)(F)CC23CCN(C(=O)OC(C)(C)C)CC3)C[C@@H](n2ccc3c(N)ncnc32)[C@@H]1OC(=O)C(C)C]

A mixture of intermediate 458 (250 mg, 341.1 μmol, 1 eq) in MeOH (500 uL) was stirred at 120° C. for 5 h in sealed tube. The mixture was concentrated in vacuum. The crude product was purified by TLC (DCM/Ethyl acetate=1/2 to afford intermediate 464 (143 mg, 210.6 μmol, 61.7% yield) as a white solid.

Below final compounds were prepared by an analogous reaction protocol as was used for the preparation of intermediate 464 using the appropriate starting materials (Table 18).

TABLE 18

| Int. | Structure | Starting materials |
|---|---|---|
| 465 | 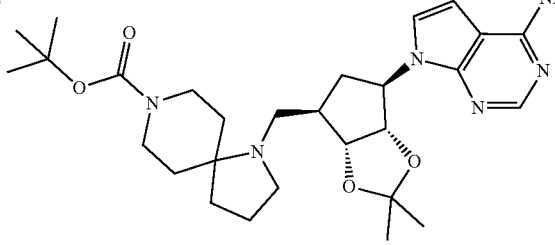 | Intermediate 351 |

Example A43

Synthesis of Intermediate 525

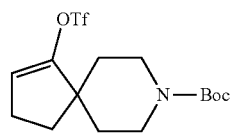 [SMILES: CC(C)(C)OC(=O)N1CCC2(CCC=C2OS(=O)(=O)C(F)(F)F)CC1]

A solution of 1M LiHMDS in THF (63 mL, 63 mmol, 2.0 eq) was added dropwise to a solution of I-oxo-8-Azaspiro[4.5]decane-8-carboxylic acid, 1,1-dimethylethyl ester (8.0 g, 31.6 mmol, 1.0 eq) in anhydrous THF (200 mL) at −78° C. The reaction mixture was stirred for 2 h at −78° C., then a solution of N,N-bis(trifluoromethylsulfonyl)aniline (22.6 g, 63.0 mmol, 2.0 eq) in anhydrous THF (60 mL) was added dropwise. After complete addition, the cooling bath was replaced with a bath at 0° C. and the reaction was maintained at 0° C. overnight. The reaction was quenched with sat. Na$_2$CO$_3$ and then was added diethyl ether, water and brine. The organic phase was separated, washed twice with sat. Na$_2$CO$_3$, once with brine, dried over MgSO$_4$, filtered and concentrated in vacuo to afford the crude product. The crude product was purified by normal phase flash chromatography (330 g SiO$_2$) using EtOAc containing 1% Et$_3$N and Heptane containing 1% Et$_3$N as eluent (gradient: 0% to 10% EtOAc containing 1% Et$_3$N; isocratic: 10% EtOAc containing 1% Et$_3$N), to afford intermediate 525 as white solid (9.4 g, 24 mmol, yield: 78%)

Synthesis of Intermediate 526

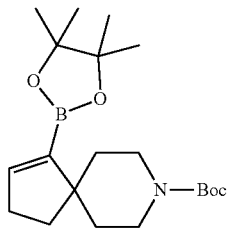 [SMILES: CC(C)(C)OC(=O)N1CCC2(CCC=C2B2OC(C)(C)C(C)(C)O2)CC1]

A suspension of intermediate 525 (9.4 g, 25.5 mmol, 1 eq), bis(pinacolato)diboron (6.8 g, 26.9 mmol, 1.1 eq), sodium phenoxide (4.3 g, 36.7 mmol, 1.5 eq), KBr (4.4 g, 36.7 mmol, 1.5 eq) and triphenylphosphine (1.3 g, 4.9 mmol, 0.2 eq) in anhydrous toluene (200 mL) was stirred and flushed with N$_2$ for 20 min. To the flushed solution was added bis(triphenylphosphine)palladium(II) dichloride (1.7 g, 2.5 mmol, 0.1 eq). The reaction mixture was flushed again for 5 min with N$_2$ and then heated at 50° C. After stirring for 20 hours, the reaction mixture was filtered over celite and the filter was washed with EtOAc. The filtrate was subsequently washed with water (3×), 1M NaOH solution (2×), and brine (1×), dried over MgSO$_4$, filtered and concentrated in vacuo to afford the crude Intermediate 526 as a dark oil. The crude product was stirred in diisopropyl ether, the precipitate (mainly triphenylphosphine oxide and unknown product) was removed by filtration. The filtrate was concentrated in vacuo and the obtained residue purified by normal phase flash chromatography (SiO$_2$) using EtOAc and heptane as eluent (isocratic: 0% EtOAc gradient: 0% to 12%, to afford intermediate 526 as white solid product (5.6 g, 15.3 mmol, yield 62%).

Synthesis of Intermediate 527a

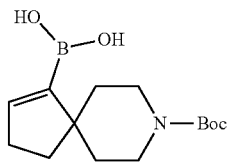 [SMILES: CC(C)(C)OC(=O)N1CCC2(CCC=C2B(O)O)CC1]

Boronate ester Intermediate 526 (5.7 g, 15.3 mmol, 1 eq) was dissolved in a mixture of acetone (200 mL) and water (50 mL). To this mixture was then added NH$_4$OAc (7.1 g, 91.8 mmol, 6.0 eq) and sodium periodate (19.6 g, 91.8 mmol, 6.0 eq), the obtained suspension was stirred for one week at r.t. The reaction mixture was diluted with EtOAc, the remaining precipitate was filtered off. The organic phase was separated, washed three times with brine, dried over MgSO$_4$, filtered and concentrated in vacuo to afford the crude product. The crude product was recrystallized in EtOAc to afford a first batch of Intermediate 527a as a white solid (1.36 g, 4.8 mmol) The filtrate was concentrated, and the obtained impure product was recrystallized in diisopropyl ether with addition of EtOAc to afford a second batch of intermediate 527a as white solid (0.8 g, 2.8 mmol) The impure product was further purified by trituration in diisopropyl ether, this was carried out twice to afford intermediate 527a as white solid (0.6 g, 2.1 mmol). The filtrates were concentrated and the remaining impure product was purified by normal phase flash chromatography (SiO$_2$) using DCM, EtOAc and heptane as eluent (isocratic: 100% DCM), followed by gradient elution: start 70:30 EtOAc: Heptane to 100% EtOAc to afford Intermediate 527a as solid product (0.7 g, 2.4 mmol) In total 3.4 g of boronic acid intermediate 527a (12.2 mmol, yield 79%) was obtained.

Synthesis of Intermediate 527b

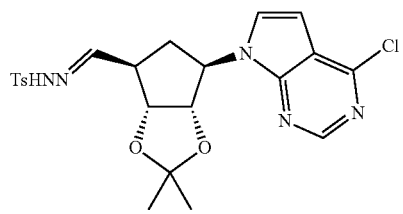

A solution of intermediate 14 (3.07 g, 9.5 mmol, 1.0 eq) in anhydrous DCM (45 mL) was added dropwise to a suspension of Dess-Martin periodinane (4.80 g, 11.40 mmol, 1.2 eq) in anhydrous DCM (45 mL) at 0° C. After the addition, the reaction mixture was allowed to warm to room temperature, stirred for two hours, and then additional Dess-Martin periodinane (0.20 g, 0.48 mmol, 0.05 eq) was added. The reaction mixture was stirred for another half hour, then MeOH (about 50 mL) and p-toluenesulfon hydrazide (2.30 g, 12.34 mmol, 1.3 eq) was added. After 2.5 hours stirring, diluted saturated Na$_2$CO$_3$/water (50/50) was added, the organic layer was separated and the aqueous layer was extracted once with EtOAc. The organic phases were combined, washed with saturated Na$_2$CO$_3$ and brine, dried over Na$_2$SO$_4$, filtered and concentrated in vacuo. The crude product was purified by normal phase flash chromatography using DCM and MeOH as eluent (SiO$_2$ column, gradient: 0% MeOH to 1.5% MeOH, isocratic: 1.5% MeOH) to afford intermediate 527b as a yellow/white crystal (4.16 g, 8.49 mmol, yield: 89%).

Synthesis of Intermediate 528 and Intermediate 529

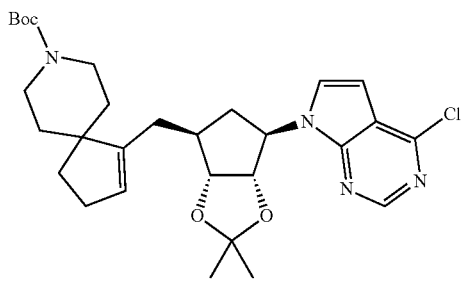 [SMILES: CC(C)(C)OC(=O)N1CCC2(CCC=C2C[C@H]2C[C@@H](n3ccc4c(Cl)ncnc43)[C@@H]3OC(C)(C)O[C@H]23)CC1]

Intermediate 528

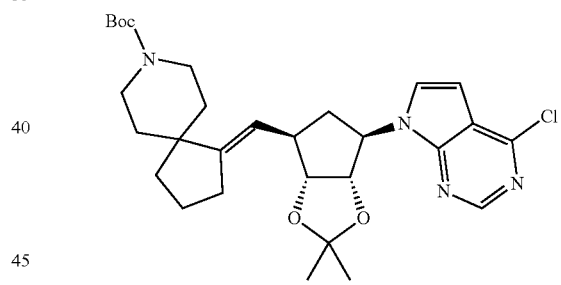

Intermediate 529

A reaction mixture of Intermediate 527b (5.6 g, 11.4 mmol, 1.0 eq), intermediate 527a (3.2 g, 11.4 mmol, 1.0 eq), K$_2$CO$_3$ (4.7 g, 34.1 mmol, 3.0 eq) and 1,4-dioxane (60 mL) was heated at 110° C. and stirred for six hours. To the reaction mixture was added EtOAc, then it was washed three times with diluted sat. Na$_2$CO$_3$/water (50:50), once with brine, dried over MgSO$_4$, filtered and concentrated in vacuo. The crude mixture was purified with normal phase flash chromatography using heptane and EtOAc as eluent (SiO$_2$ column, gradient: 20% to 30% EtOAc to afford a mayor fraction of a mixture of 87% intermediate 528 and 13% intermediate 529 (2.3 g, yield: 36%) and a minor fraction of pure intermediate 529 was obtained (246 mg, yield: 4%).

Synthesis of Intermediate 530 and Intermediate 531

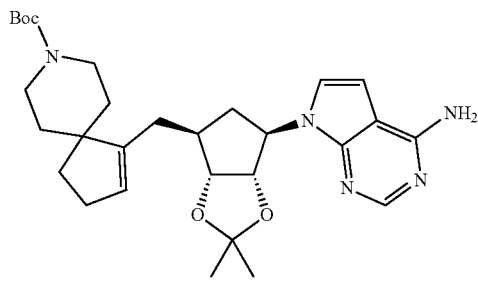 [SMILES: CC(C)(C)OC(=O)N1CCC2(CCC=C2C[C@H]2C[C@@H](n3ccc4c(N)ncnc43)[C@@H]3OC(C)(C)O[C@H]23)CC1]

Intermediate 530

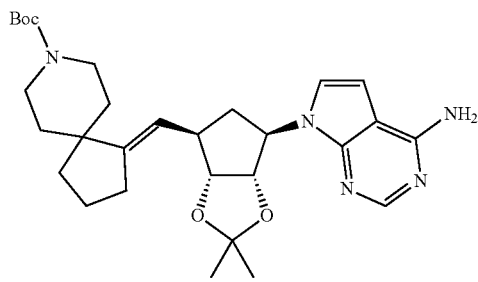 [SMILES: CC(C)(C)OC(=O)N1CCC2(CCC/C2=C\[C@H]2C[C@@H](n3ccc4c(N)ncnc43)[C@@H]3OC(C)(C)O[C@@H]32)CC1]

Intermediate 531

A solution of mixture of intermediate 528 and intermediate 529 (ratio: 87:13, 2.3 g, 4.3 mmol) in THF (20 mL) and ammonia in water (25% w/t, 20 mL) was stirred in an autoclave at 100° C. until complete conversion (four days). After complete conversion, the reaction mixture was concentrated in vacuo. The residue was dissolved in MeOH and the obtained solution was concentrated again to afford the crude mixture of intermediate 530 and intermediate 531 which was used in the next step without any purification.

B. Preparation of Final Compounds

Example B1

Synthesis of Final Compound 1

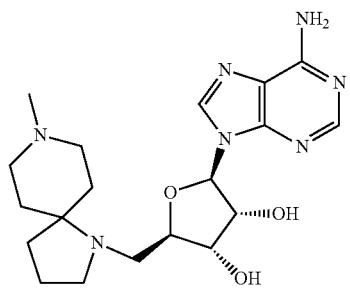 [SMILES: CN1CCC2(CCCN2C[C@H]2O[C@@H](n3cnc4c(N)ncnc43)[C@H](O)[C@@H]2O)CC1]

Intermediate 159 (0.18 g, 0.278 mmol), formaldehyde solution 37 wt. % in $H_2O$ (0.023 mL, 0.305 mmol) and sodium acetate were dissolved in THF (5 mL) and the mixture was stirred 30 min. Then sodium triacetoxyborohydride (0.088 g, 0.42 mmol) was added and the solution was stirred at room temperature overnight. The solvents were evaporated to dryness and to the residue in MeOH (3.4 mL) was added ammonia solution 7 N in MeOH (17 mL). The mixture was stirred at room temperature for 4 days. The solvent was evaporated to dryness and the residue was then dissolved in trifluoroacetic acid (16 mL) and water (0.9 mL) and stirred at room temperature overnight. The solvents were evaporated to dryness and the product was purified by reverse phase (Aqueous phase: 25 mM $NH_4HCO_3$ Organic phase: MeCN: 1:1 gradient 95% [Aqueous phase]—5% [Organic phase] to 63% [Aqueous phase]—37% [Organic phase] to give final compound 1 (0.037 gr, yield: 31%).

Below final compounds were prepared by an analogous reaction protocol as was used for the preparation of final compound 1 using the appropriate starting materials (Table 19).

TABLE 19

| Co. | Structure | Starting materials |
|---|---|---|
| 2 | 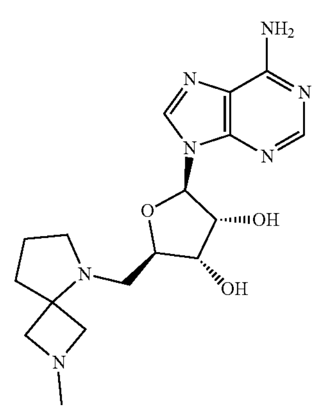 [SMILES: CN1CC2(CCCN2C[C@H]2O[C@@H](n3cnc4c(N)ncnc43)[C@H](O)[C@@H]2O)C1] | a) Intermediate 174 |

TABLE 19-continued
| Co. | Structure | Starting materials |
|---|---|---|
| 3 | 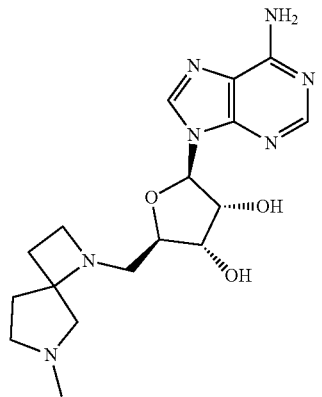 [SMILES: CN1CCC2(CCN2C[C@H]2O[C@@H](n3cnc4c(N)ncnc43)[C@H](O)[C@@H]2O)C1] | a) Intermediate 173 |
| 4 | 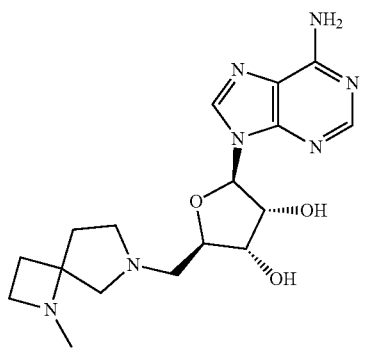 [SMILES: CN1CCC12CCN(C[C@H]1O[C@@H](n3cnc4c(N)ncnc43)[C@H](O)[C@@H]1O)C2] | a) Intermediate 171 |
| 5 | 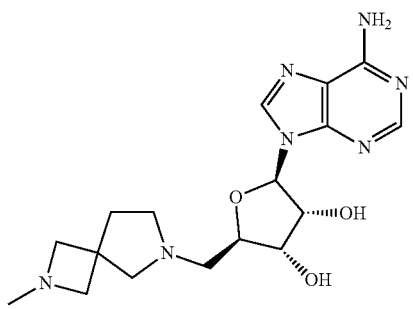 [SMILES: CN1CC2(CCN(C[C@H]3O[C@@H](n4cnc5c(N)ncnc54)[C@H](O)[C@@H]3O)C2)C1] | a) Intermediate 172 |
| 6 | 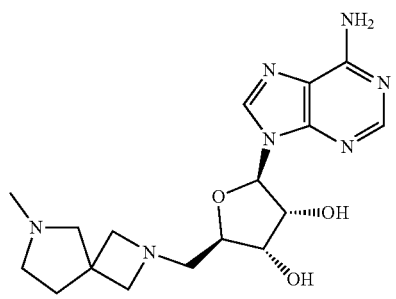 [SMILES: CN1CCC2(C1)CN(C[C@H]1O[C@@H](n3cnc4c(N)ncnc43)[C@H](O)[C@@H]1O)C2] | a) Intermediate 170 |

TABLE 19-continued

| Co. | Structure | Starting materials |
|---|---|---|
| 7 | 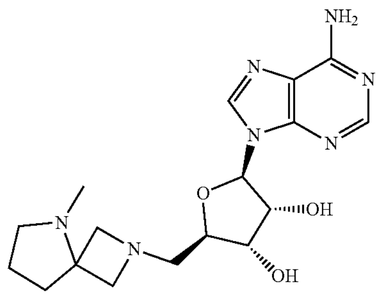 [SMILES: CN1CCCC12CN(C[C@H]1O[C@@H](n3cnc4c(N)ncnc43)[C@H](O)[C@@H]1O)C2] | a) Intermediate 169 |
| 8 | 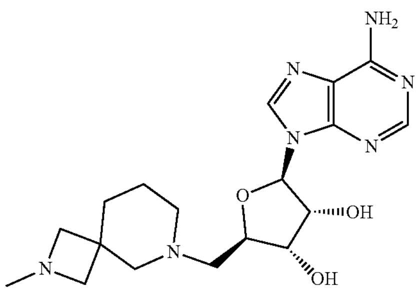 [SMILES: CN1CC2(CCCN(C[C@H]3O[C@@H](n4cnc5c(N)ncnc54)[C@H](O)[C@@H]3O)C2)C1] | a) Intermediate 168 |
| 9 | 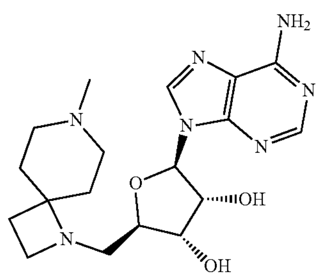 [SMILES: CN1CCC2(CC1)CCN2C[C@H]1O[C@@H](n2cnc3c(N)ncnc32)[C@H](O)[C@@H]1O] | a) Intermediate 167 |
| 10 | 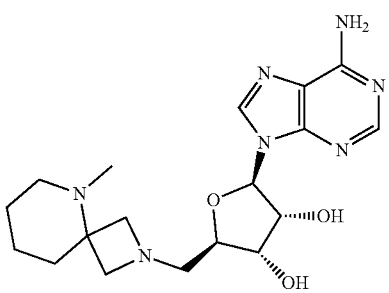 [SMILES: CN1CCCCC12CN(C[C@H]1O[C@@H](n3cnc4c(N)ncnc43)[C@H](O)[C@@H]1O)C2] | a) Intermediate 166 |
| 11 | 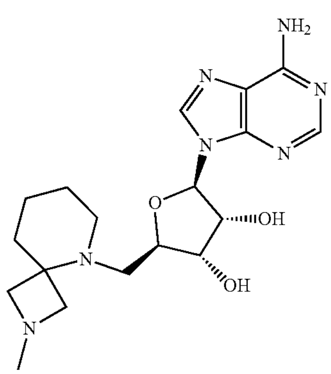 [SMILES: CN1CC2(CCCCN2C[C@H]2O[C@@H](n3cnc4c(N)ncnc43)[C@H](O)[C@@H]2O)C1] | a) Intermediate 165 |

TABLE 19-continued

| Co. | Structure | Starting materials |
|---|---|---|
| 12 | 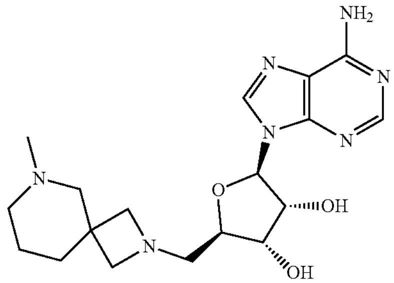 [SMILES: CN1CCCC2(C1)CN(C[C@H]1O[C@@H](n3cnc4c(N)ncnc43)[C@H](O)[C@@H]1O)C2] | a) Intermediate 164 |
| 13 | 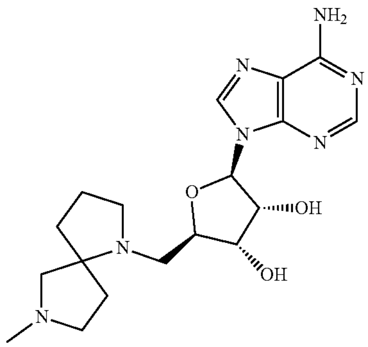 [SMILES: CN1CCC2(CCCN2C[C@H]2O[C@@H](n3cnc4c(N)ncnc43)[C@H](O)[C@@H]2O)C1] | a) Intermediate 161 |
| 14 | 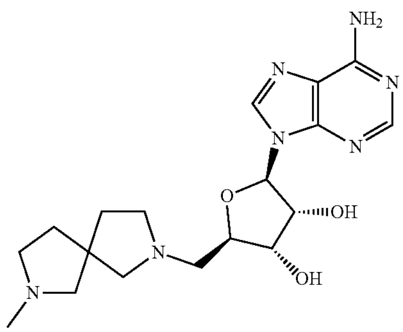 [SMILES: CN1CCC2(CCN(C[C@H]3O[C@@H](n4cnc5c(N)ncnc54)[C@H](O)[C@@H]3O)C2)C1] | a) Intermediate 163 |
| 15 | 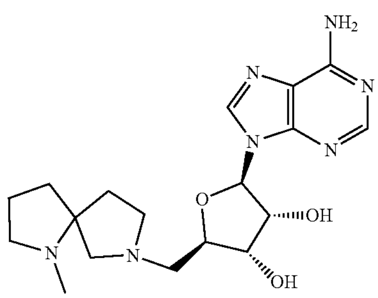 [SMILES: CN1CCCC12CCN(C[C@H]1O[C@@H](n3cnc4c(N)ncnc43)[C@H](O)[C@@H]1O)C2] | a) Intermediate 162 |
| 16 | 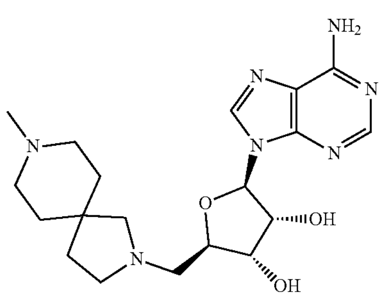 [SMILES: CN1CCC2(CC1)CCN(C[C@H]1O[C@@H](n3cnc4c(N)ncnc43)[C@H](O)[C@@H]1O)C2] | a) Intermediate 160 |

TABLE 19-continued

| Co. | Structure | Starting materials |
|---|---|---|
| 17 | 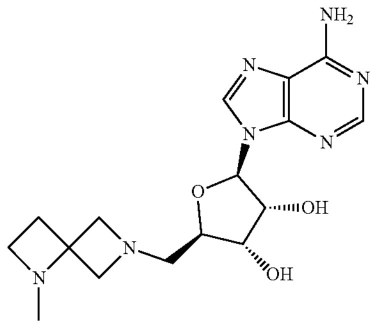 [SMILES: CN1CCC12CN(C[C@H]1O[C@@H](n3cnc4c(N)ncnc43)[C@H](O)[C@@H]1O)C2] | a) Intermediate 175 |
| 18 | 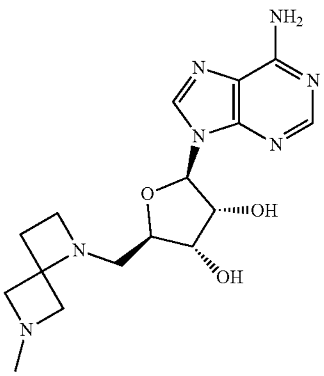 [SMILES: CN1CC2(CCN2C[C@H]2O[C@@H](n3cnc4c(N)ncnc43)[C@H](O)[C@@H]2O)C1] | a) Intermediate 176 |

Example B2

Preparation of Final Compound 19 and Intermediate 210

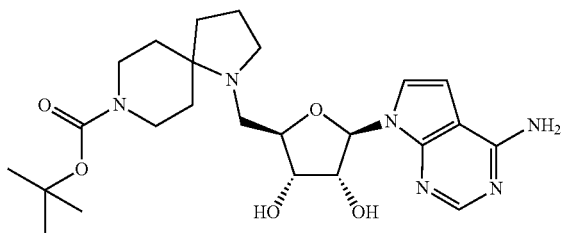 [SMILES: CC(C)(C)OC(=O)N1CCC2(CCCN2C[C@H]2O[C@@H](n3ccc4c(N)ncnc43)[C@H](O)[C@@H]2O)CC1]

Intermediate 210

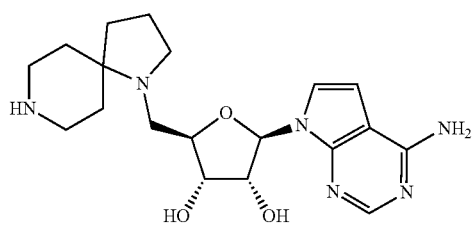

final compound 19

Final Compound 19

HCl (104 mL, 416 mmol, 4 M in dioxane) was added to a stirred solution of intermediate 114 (22.7 g, 41.6 mmol) in MeOH (1800 mL) at room temperature. The reaction mixture was stirred at room temperature for 18 hours. The reaction mixture was poured out into 4 L DIPE. The resulting suspension was stirred for 10 minutes at room temperature. The precipitate was filtered off and washed with DIPE to give precipitate 1 and filtrate 1. The precipitate 1 was dissolved in MeOH and slightly alkalized with a 7N solution of $NH_3$ in MeOH. Then the solvents were evaporated yielding 16.51 g of crude final compound 19. A purification was performed via Prep HPLC (Stationary phase: Uptisphere C18 ODB—10 µm, 200 g, 5 cm, Mobile phase: 0.25% $NH_4HCO_3$ solution in water, $CH_3CN$) to give final compound 19 (9.18 g, 23.631 mmol, 56.8% yield). The filtrate 1 was slightly alkalized with a 7N solution of $NH_3$ in MeOH upon with precipitation occurred. The precipitate was filtered off and the solvents of the filtrate were evaporated yielding 10.7 g of crude Intermediate 210. A purification was performed via Prep HPLC (Stationary phase: Uptisphere C18 ODB—10 µm, 200 g, 5 cm, Mobile phase: 0.25% $NH_4HCO_3$ solution in water, $CH_3CN$) to give Intermediate 210 (2.11 g, 10.4% yield).

Example B3

Preparation of Final Compound 20

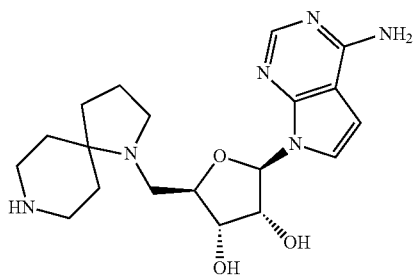 [SMILES: Nc1ncnc2c1ccn2[C@@H]1O[C@H](CN2CCCC23CCNCC3)[C@@H](O)[C@H]1O]

HCl (86.5 mL, 345.8 mmol, 4 M in dioxane) was added to a stirred solution of intermediate 114 (18.28 g, 34.6 mmol) in MeOH (1500 mL) at room temperature. The reaction mixture was stirred at room temperature, for 5 days. The reaction mixture was poured into 2 L DIPE. The resulting suspension was stirred for 10 minutes at room temperature. The solvents were decanted off so that the sticky precipitate remained. This residue was dissolved in MeOH and slightly alkalized with a 7N solution of $NH_3$ in MeOH. Then the solvents were evaporated yielding final compound 20 as HCl salt. (17.40 g).

Below final compounds were prepared by an analogous reaction protocol as was used for the preparation of final compound 20 using the appropriate starting materials (Table 20).

TABLE 20

| Co. | Structure | Starting materials and conditions |
|---|---|---|
| 76 | 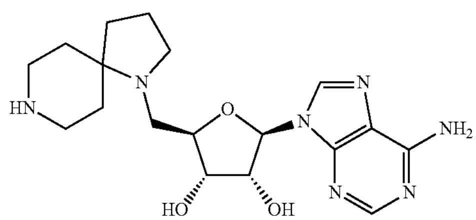 [SMILES: Nc1ncnc2c1ncn2[C@@H]1O[C@H](CN2CCCC23CCNCC3)[C@@H](O)[C@H]1O] | a) Intermediate 115<br>b) HCl (4 M in dioxane) in MeOH |
| 24 | 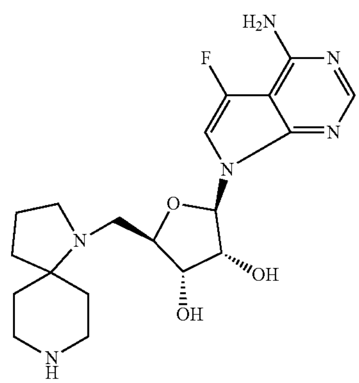 | a) Intermediate 117<br>b) HCl (4 M in dioxane) in MeOH |
| 25 | 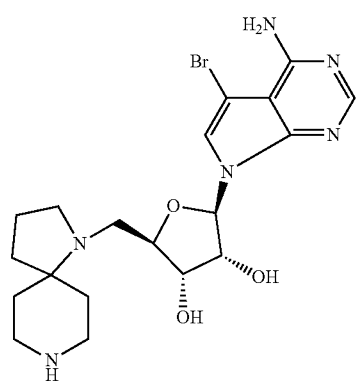 [SMILES: Nc1ncnc2c1c(F)cn2[C@@H]1O[C@H](CN2CCCC23CCNCC3)[C@@H](O)[C@H]1O] | a) Intermediate 118<br>b) HCl (4 M in dioxane) in MeOH<br>HCl salt (eq not determined) |

TABLE 20-continued

| Co. | Structure | Starting materials and conditions |
|---|---|---|
| 26 | 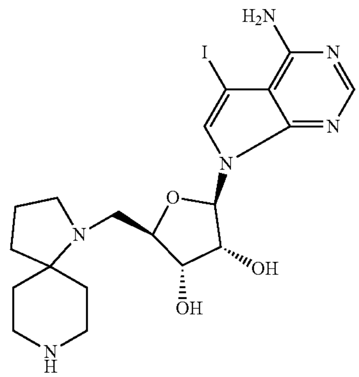 [SMILES: Nc1ncnc2c1c(I)cn2[C@@H]1O[C@H](CN2CCCC23CCNCC3)[C@@H](O)[C@H]1O] | a) Intermediate 119<br>b) HCl (4 M in dioxane) in MeOH |
| 27 | 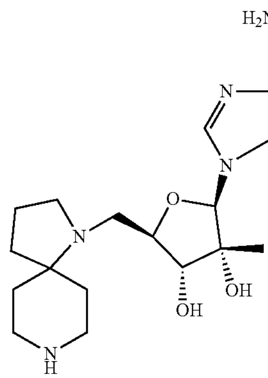 | a) Intermediate 120<br>b) HCl (4 M in dioxane) in MeOH |
| 28 | 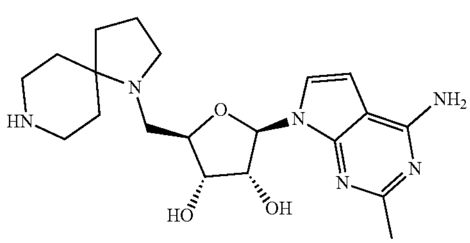 [SMILES: Cc1nc(N)c2ccn([C@@H]3O[C@H](CN4CCCC45CCNCC5)[C@@H](O)[C@H]3O)c2n1] | a) Intermediate 121<br>b) HCl in MeOH |
| 29 | 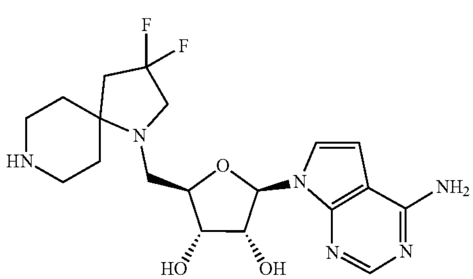 [SMILES: Nc1ncnc2c1ccn2[C@@H]1O[C@H](CN2CC(F)(F)CC23CCNCC3)[C@@H](O)[C@H]1O] | a) Intermediate 122<br>b) HCl (4 M in dioxane) in MeOH |
| 30 | 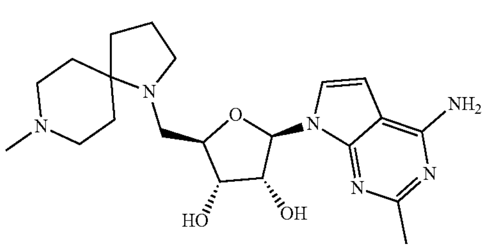 [SMILES: Cc1nc(N)c2ccn([C@@H]3O[C@H](CN4CCCC45CCN(C)CC5)[C@@H](O)[C@H]3O)c2n1] | a) Intermediate 123<br>b) HCl in MeOH |

TABLE 20-continued

| Co. | Structure | Starting materials and conditions |
|---|---|---|
| 31 | 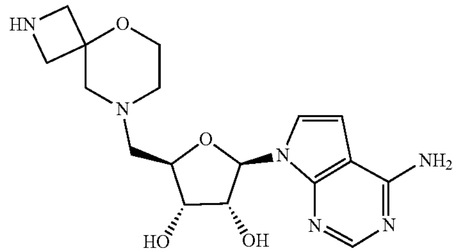 [SMILES: Nc1ncnc2c1ccn2[C@@H]1O[C@H](CN2CCOC3(CNC3)C2)[C@@H](O)[C@H]1O] | a) Intermediate 124<br>b) HCl (4 M in dioxane) in MeOH |
| 32 | 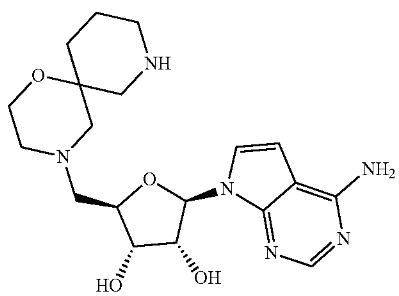 [SMILES: Nc1ncnc2c1ccn2[C@@H]1O[C@H](CN2CCOC3(CCCNC3)C2)[C@@H](O)[C@H]1O] | a) Intermediate 125<br>b) HCl in MeOH |
| 33 | 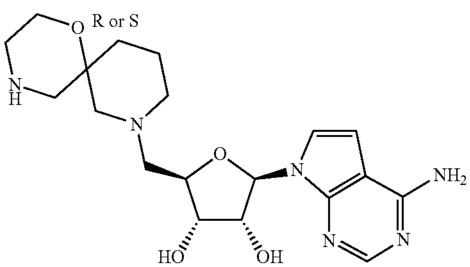 [SMILES: Nc1ncnc2c1ccn2[C@@H]1O[C@H](CN2CCCC3(CNCCO3)C2)[C@@H](O)[C@H]1O] | a) Intermediate 126<br>b) HCl (4 M in dioxane) in MeOH |
| 34 | 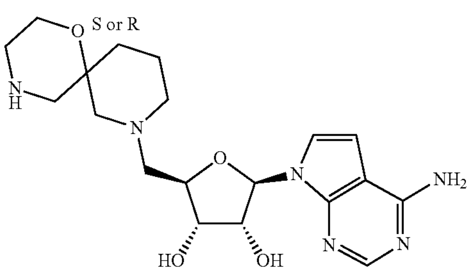 [SMILES: Nc1ncnc2c1ccn2[C@@H]1O[C@H](CN2CCCC3(CNCCO3)C2)[C@@H](O)[C@H]1O] | a) Intermediate 126<br>b) HCl (4 M in dioxane) in MeOH |
| 35 | 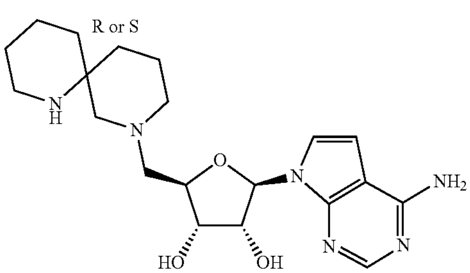 [SMILES: Nc1ncnc2c1ccn2[C@@H]1O[C@H](CN2CCCC3(CCCCN3)C2)[C@@H](O)[C@H]1O] | a) Intermediate 127<br>b) HCl (4 M in dioxane) in MeOH |

TABLE 20-continued

| Co. | Structure | Starting materials and conditions |
|---|---|---|
| 36 | [Structure: 2,8-diazaspiro[5.5]undecane (S or R) attached via CH₂ to 5'-position of a ribose bearing 7-deazaadenine (4-amino-7H-pyrrolo[2,3-d]pyrimidine)] | a) Intermediate 128<br>b) HCl (4 M in dioxane) in MeOH |
| 37 | [Structure: oxa-diazaspiro system attached via CH₂ to 5'-position of a ribose bearing 7-deazaadenine] | a) Intermediate 129<br>b) HCl (4 M in dioxane) in MeOH |
| 38 | [Structure: difluoro-diazaspiro[4.5]decane attached via CH₂ to 5'-position of a ribose bearing 7-deazaadenine] | a) Intermediate 130<br>b) HCl/MeOH in MeOH |
| 39 | [Structure: 1,7-diazaspiro[4.5]decane attached via CH₂ to 5'-position of a ribose bearing 7-deazaadenine]<br>HCl salt (eq not determined) | a) Intermediate 131<br>b) HCl (4 M in dioxane) in MeOH |
| 40 | [Structure: 2,8-diazaspiro[4.5]decane attached via CH₂ to 5'-position of a ribose bearing 7-deazaadenine] | a) Intermediate 132<br>b) HCl (4 M in dioxane) in MeOH |

TABLE 20-continued

| Co. | Structure | Starting materials and conditions |
|---|---|---|
| 41 | 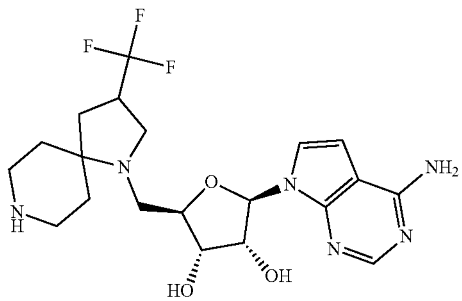 [SMILES: Nc1ncnc2c1ccn2[C@@H]1O[C@H](CN2CC(C(F)(F)F)CC23CCNCC3)[C@@H](O)[C@H]1O] | a) Intermediate 133<br>b) HCl (4 M in dioxane) in MeOH |
| 42 | 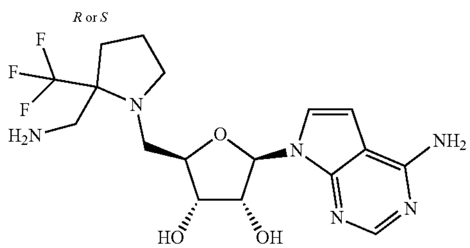 [SMILES: NCC1(C(F)(F)F)CCCN1C[C@H]1O[C@@H](n2ccc3c(N)ncnc32)[C@H](O)[C@@H]1O] | a) Intermediate 134<br>b) HCl in MeOH |
| 43 | 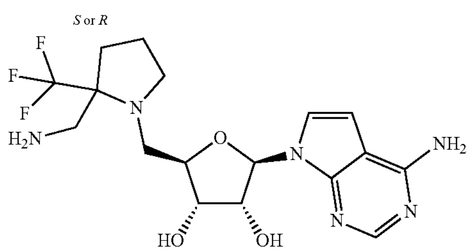 [SMILES: NCC1(C(F)(F)F)CCCN1C[C@H]1O[C@@H](n2ccc3c(N)ncnc32)[C@H](O)[C@@H]1O] | a) Intermediate 134<br>b) HCl in MeOH |
| 44 | 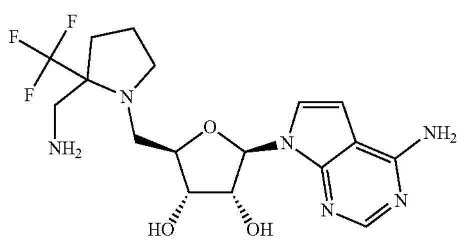 [SMILES: NCC1(C(F)(F)F)CCCN1C[C@H]1O[C@@H](n2ccc3c(N)ncnc32)[C@H](O)[C@@H]1O] | a) Intermediate 134<br>b) HCl in MeOH |
| 45 | 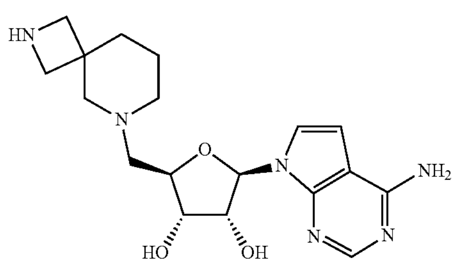 | a) Intermediate 135<br>b) HCl (4 M in dioxane) |
| 47 | 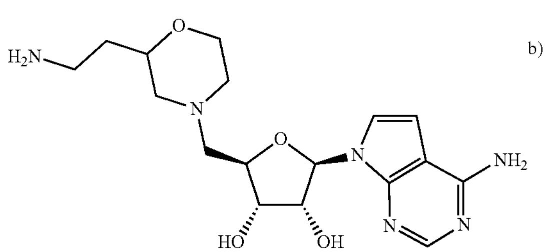 | a) Intermediate 138<br>b) HCl (4 M in dioxane) in MeOH |

TABLE 20-continued

| Co. | Structure | Starting materials and conditions |
|---|---|---|
| 48 | 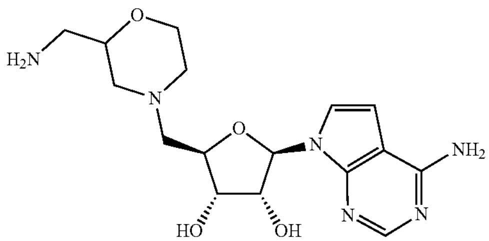 [SMILES: NCC1CN(C[C@H]2O[C@@H](n3ccc4c(N)ncnc43)[C@H](O)[C@@H]2O)CCO1] | a) Intermediate 139
b) HCl (4 M in dioxane) in MeOH |
| 49 | | a) Intermediate 140
b) HCl (4 M in dioxane) in MeOH |
| 50 | | a) Intermediate 182
b) HCl (4 M in dioxane) in MeOH |
| 51 | | a) Intermediate 144
b) HCl (4 M in dioxane) in MeOH |
| 52 | | a) Intermediate 145
b) HCl (4 M in dioxane) in MeOH |
| 53 | | a) Intermediate 146
b) HCl (4 M in dioxane) in MeOH |

TABLE 20-continued

| Co. | Structure | Starting materials and conditions |
|---|---|---|
| 54 | [structure] | a) Intermediate 148<br>b) HCl (4 M in dioxane) in MeOH |
| 55 | [structure] | a) Intermediate 149<br>b) HCl (4 M in dioxane) in MeOH |
| 56 | [structure] | a) Intermediate 151<br>b) HCl (4 M in dioxane) in MeOH |
| 57 | [structure] | a) Intermediate 152<br>b) HCl (4 M in dioxane) in MeOH |
| 58 | [structure] | a) Intermediate 153a<br>b) HCl (4 M in dioxane) in MeOH |
| 59 | [structure] | c) Intermediate 153b<br>d) HCl (4 M in dioxane) in MeOH |

TABLE 20-continued

| Co. | Structure | Starting materials and conditions |
|---|---|---|
| 60 | 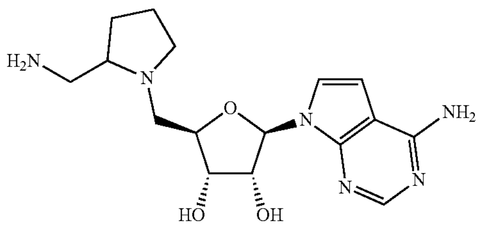 [SMILES: NCC1CCCN1C[C@H]1O[C@@H](n2ccc3c(N)ncnc32)[C@H](O)[C@@H]1O] | a) Intermediate 154<br>b) HCl (4 M in dioxane) in MeOH |
| 61 | 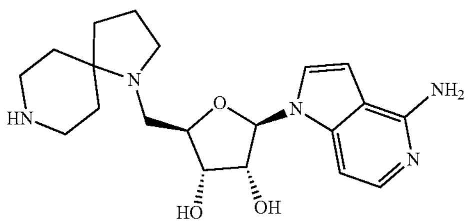 [SMILES: Nc1nccc2c1ccn2[C@@H]1O[C@H](CN2CCCC23CCNCC3)[C@@H](O)[C@H]1O] | a) Intermediate 155<br>b) HCl in MeOH |
| 62 | 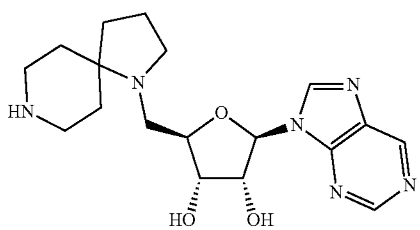 [SMILES: O[C@@H]1[C@H](O)[C@@H](CN2CCCC23CCNCC3)O[C@H]1n1cnc2cncnc21] | a) Intermediate 157<br>b) HCl (4 M in dioxane) in MeOH |
| 63 | 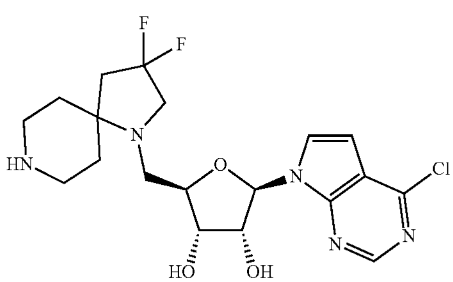 [SMILES: O[C@@H]1[C@H](O)[C@@H](CN2CC(F)(F)CC23CCNCC3)O[C@H]1n1ccc2c(Cl)ncnc21] | a) Intermediate 59<br>b) TFA in DCM |
| 64 | 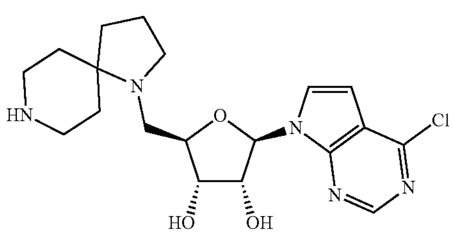 [SMILES: O[C@@H]1[C@H](O)[C@@H](CN2CCCC23CCNCC3)O[C@H]1n1ccc2c(Cl)ncnc21] | a) Intermediate 48<br>b) HCl (4 M in dioxane) |
| 65 | 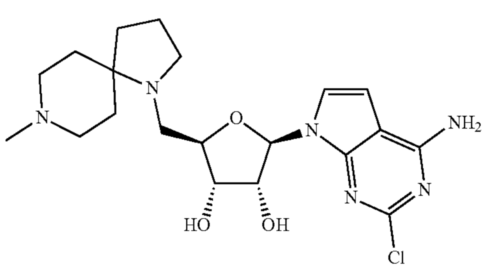 [SMILES: CN1CCC2(CCCN2C[C@H]2O[C@@H](n3ccc4c(N)nc(Cl)nc43)[C@H](O)[C@@H]2O)CC1] | a) Intermediate 61<br>b) HCl in MeOH |

TABLE 20-continued

| Co. | Structure | Starting materials and conditions |
|---|---|---|
| 66 | 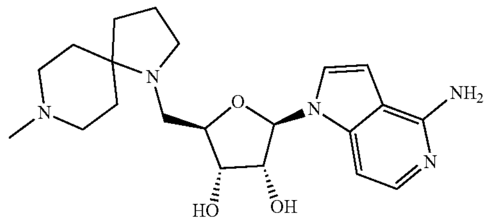 [SMILES: CN1CCC2(CCCN2C[C@H]2O[C@@H](n3ccc4c(N)nccc43)[C@H](O)[C@@H]2O)CC1] | a) Intermediate 156<br>b) HCl in MeOH |
| 67 | 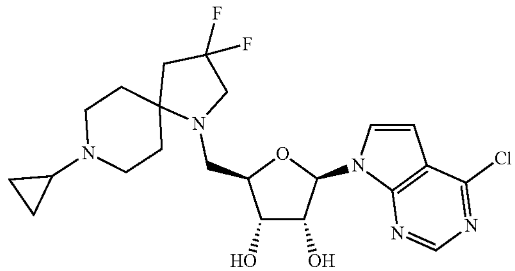 [SMILES: O[C@@H]1[C@H](O)[C@@H](CN2CC(F)(F)CC23CCN(C2CC2)CC3)O[C@H]1n1ccc2c(Cl)ncnc21] | a) Intermediate 186<br>b) HCl (4 M in dioxane)in MeOH |
| 68 | 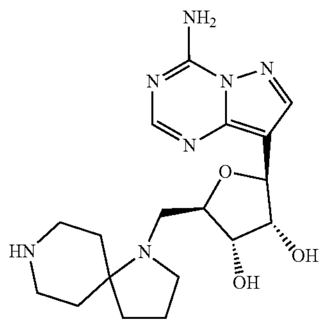 [SMILES: Nc1ncnc2c([C@@H]3O[C@H](CN4CCCC45CCNCC5)[C@@H](O)[C@H]3O)cnn12] | a) Intermediate 187<br>b) HCl (4 M in dioxane)in MeOH |
| 270 | 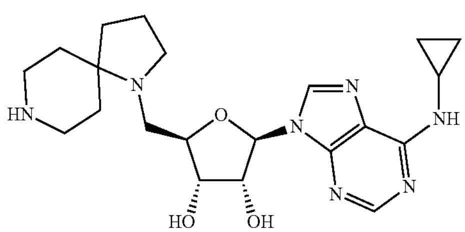 [SMILES: O[C@@H]1[C@H](O)[C@@H](CN2CCCC23CCNCC3)O[C@H]1n1cnc2c(NC3CC3)ncnc21] | a) Intermediate 158<br>b) HCl (4 M in dioxane)in MeOH |

Example B4

Preparation of Final Compound 71a and 71b

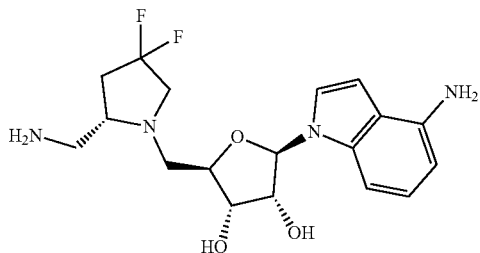 [SMILES: NC[C@@H]1CC(F)(F)CN1C[C@H]1O[C@@H](n2ccc3c(N)cccc32)[C@H](O)[C@@H]1O]

HO HCl (Co. 71a), free base (Co. 71b)

HCl (5.37 mL, 21.5 mmol, 4 M in dioxane) was added to a stirred solution of intermediate 147 (1.15 g, 2.15 mmol) in MeOH (90 mL) at room temperature. The reaction mixture was stirred at room temperature for 3 days after which the mixture was poured out into a beaker with 200 mL DIPE. The resulting suspension was stirred for 10 minutes at room temperature. The solvents were decanted off so that the sticky precipitate remained. This residue was dissolved in MeOH and slightly alkalized with a 7N solution of $NH_3$ in MeOH. Then the solvents were evaporated to give final compound 71a (mono HCl salt) (1.037 g).

50 mg was purified with Prep HPLC (Stationary phase: RP XBridge Prep C18 OBD-10 µm, 30×150 mm, mobile phase: 0.25% $NH_4HCO_3$ solution in water, MeOH yielding 25.0 mg final compound 71b as free base.

Example B5

Preparation of Final Compound 72

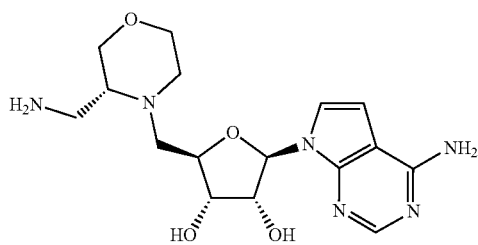 [SMILES: NC[C@@H]1COCCN1C[C@H]1O[C@@H](n2ccc3c(N)ncnc32)[C@H](O)[C@@H]1O]

HCl (0.106 mL, 0.4 mmol, 4 M in dioxane) was added to a stirred solution of intermediate 141 (24 mg, 0.04 mmol) in MeOH (5 mL) at room temperature. The reaction mixture was stirred at room temperature for 2 days. The reaction mixture was diluted with DIPE to 15 mL. The mixture was stirred for 1 hour at room temperature. The solvents were decanted from the formed sticky precipitate. The precipitate was dissolved in 10 mL MeOH and then the solvents were evaporated to give final compound 72 (15 mg, 0.0374 mmol, 88.4% yield) as mono HCl salt.

Example B6

Preparation of Final Compound 73a and 73b

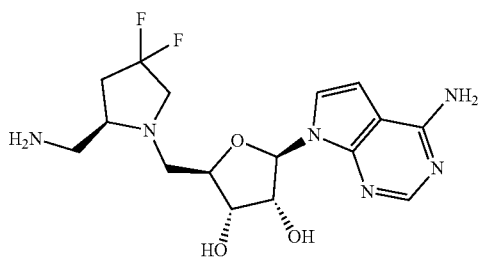 [SMILES: NC[C@H]1CC(F)(F)CN1C[C@H]1O[C@@H](n2ccc3c(N)ncnc32)[C@H](O)[C@@H]1O]

HCl (Co. 73a), free base (Co. 73b)

HCl (5.1 mL, 4 M, 20.4 mmol) was added to a stirred solution of intermediate 150 (1.09 g, 2.04 mmol) in MeOH (85 mL) at room temperature. The reaction mixture was stirred at room temperature for 18 hours after which the mixture was poured out into 200 mL DIPE. The resulting suspension was stirred for 10 minutes at room temperature. The solvents were decanted off so that the sticky precipitate remained. This residue was dissolved in MeOH and the solvents were evaporated to give final compound 73a (0.93 g, 103.9% yield) as mono HCl salt. 50 mg was purified with Prep HPLC (Stationary phase: RP XBridge Prep C18 OBD-10 µm, 30×150 mm, Mobile phase: 0.25% $NH_4HCO_3$ solution in water and MEOH yielding 29.9 mg final compound 73b as free base.

Example B7

Preparation of Final Compound 74

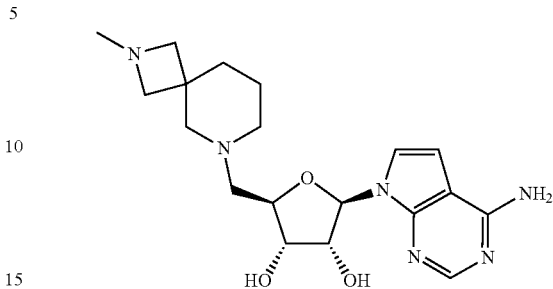

To a solution of Intermediate 177 (120.6 mg) in MeOH (7.8 mL) was added formaldehyde (0.066 mL) at r.t. The reaction mixture was stirred at room temperature for 15 minutes. Then $NaBH_3CN$ (73.15 mg) was added into the reaction mixture. The reaction mixture was stirred at room temperature for 2 hours. Then the mixture was diluted with water to be 20 mL of mixture of water and MeOH. The reaction mixture was then stirred at room temperature overnight.

A purification was performed via Prep HPLC (Stationary phase: RP SunFire Prep C18 OBD-10 µm, 30×150 mm, Mobile phase: 0.25% $NH_4HCO_3$ solution in water, MeOH).

A second purification was performed via Prep SFC (Stationary phase: Chiralpak Diacel AD 20×250 mm, Mobile phase: $CO_2$, MeOH with 0.4% $iPrNH_2$) yielding 49 mg of final compound 74

Example B8

Preparation of Final Compound 75

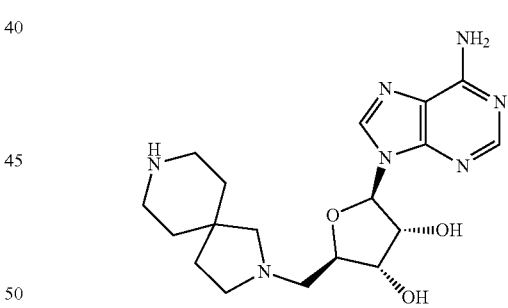

Intermediate 169 (100 mg, 0.154 mmol) was dissolved in MeOH (1.5 mL) and ammonia solution 7 N in MeOH (6 mL) was added. The solution was stirred at room temperature overnight. The solvents were evaporated to dryness and the residue was then dissolved in a mixture of TFA (5 mL) and water (0.3 mL) and stirred at room temperature overnight. The solvents were evaporated to dryness and the product was purified by reverse phase gradient 90% [$NH_4OH$ 0.4% in water]—10% [MeOH]54% [$NH_4OH$ 0.4% in water]—46% [MeOH] to give final compound 75 (16 mg, yield: 26%).

Below intermediates were prepared by an analogous reaction protocol as was used for the preparation of final compound 75 using the appropriate starting materials (Table 21).

TABLE 21

| Co. | Structure | Starting materials and conditions |
|---|---|---|
| 76 | 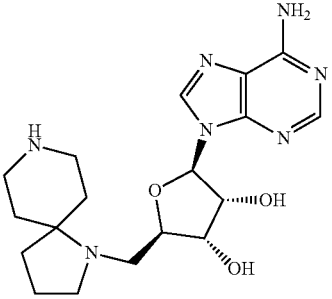 [SMILES: Nc1ncnc2c1ncn2[C@@H]1O[C@H](CN2CCCC23CCNCC3)[C@@H](O)[C@H]1O] | a) intermediate 159<br>b) Ammonia solution 7N in MeOH<br>c) TFA in water |
| 77 | 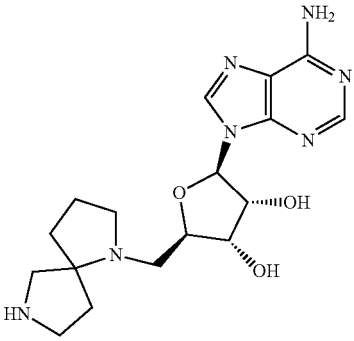 [SMILES: Nc1ncnc2c1ncn2[C@@H]1O[C@H](CN2CCCC23CCNC3)[C@@H](O)[C@H]1O] | a) Intermediate 161<br>b) Ammonia solution 7N in MeOH<br>c) TFA in water |
| 78 | 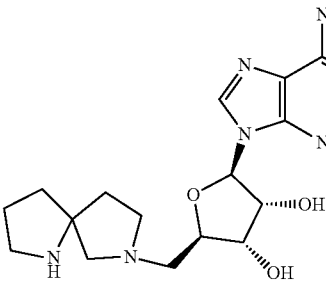 | a) Intermediate 162<br>b) Ammonia solution 7N in MeOH<br>c) TFA in water |
| 79 | 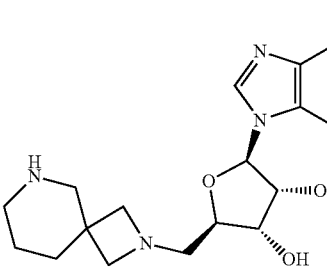 | a) Intermediate 164<br>b) Ammonia solution 7N in MeOH<br>c) TFA in water |
| 80 | 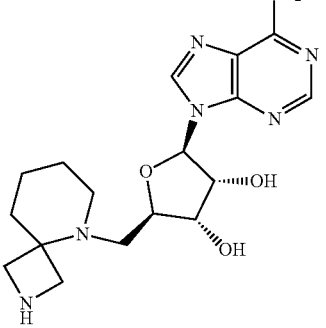 | a) Intermediate 165<br>b) Ammonia solution 7N in MeOH<br>c) TFA in water |

TABLE 21-continued

| Co. | Structure | Starting materials and conditions |
|---|---|---|
| 81 | 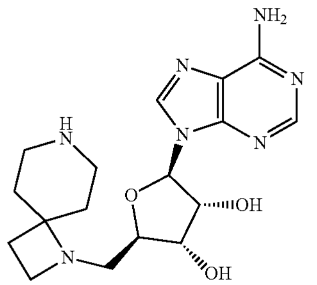 [SMILES: Nc1ncnc2c1ncn2[C@@H]1O[C@H](CN2CCC23CCNCC3)[C@@H](O)[C@H]1O] | a) Intermediate 167<br>b) Ammonia solution 7N in MeOH<br>c) TFA in water |
| 82 | 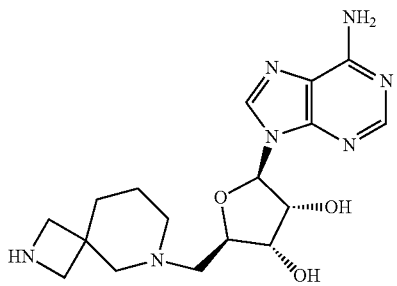 [SMILES: Nc1ncnc2c1ncn2[C@@H]1O[C@H](CN2CCCC3(CNC3)C2)[C@@H](O)[C@H]1O] | a) Intermediate 168<br>b) Ammonia solution 7N in MeOH<br>c) TFA in water |
| 83 | 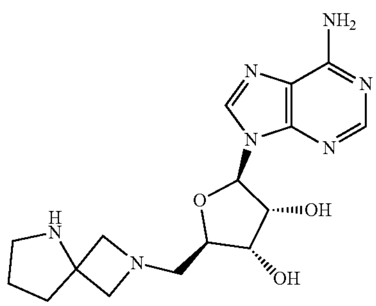 [SMILES: Nc1ncnc2c1ncn2[C@@H]1O[C@H](CN2CC3(CCCN3)C2)[C@@H](O)[C@H]1O] | a) Intermediate 169<br>b) Ammonia solution 7N in MeOH<br>c) TFA in water |
| 84 | 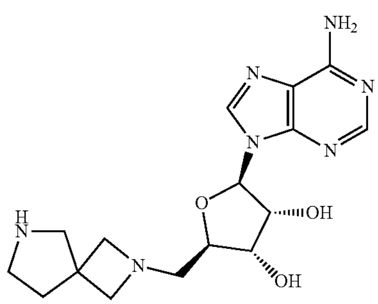 [SMILES: Nc1ncnc2c1ncn2[C@@H]1O[C@H](CN2CC3(CCNC3)C2)[C@@H](O)[C@H]1O] | a) Intermediate 170<br>b) Ammonia solution 7N in MeOH<br>c) TFA in water |
| 85 | 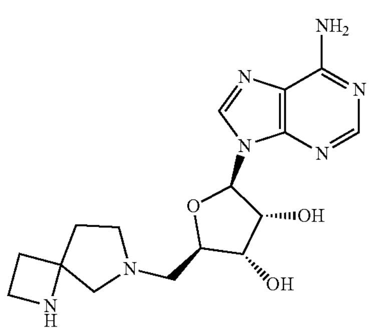 [SMILES: Nc1ncnc2c1ncn2[C@@H]1O[C@H](CN2CCC3(CCN3)C2)[C@@H](O)[C@H]1O] | a) Intermediate 171<br>b) Ammonia solution 7N in MeOH<br>c) TFA in water |

TABLE 21-continued
| Co. | Structure | Starting materials and conditions |
|---|---|---|
| 86 | 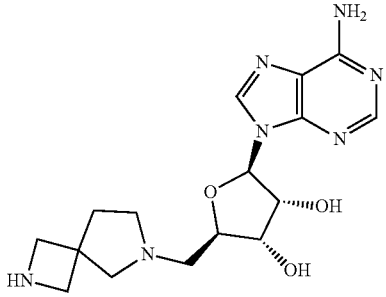 [SMILES: Nc1ncnc2c1ncn2[C@@H]1O[C@H](CN2CCC3(CNC3)C2)[C@@H](O)[C@H]1O] | a) Intermediate 172<br>b) Ammonia solution 7N in MeOH<br>c) TFA in water |
| 87 | 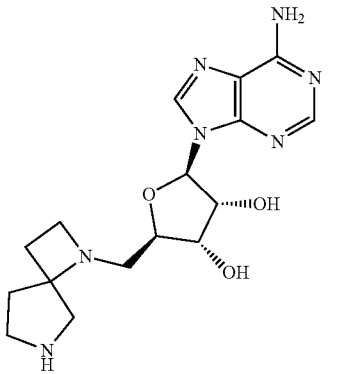 [SMILES: Nc1ncnc2c1ncn2[C@@H]1O[C@H](CN2CCC23CCNC3)[C@@H](O)[C@H]1O] | a) Intermediate 173<br>b) Ammonia solution 7N in MeOH<br>c) TFA in water |
| 88 | 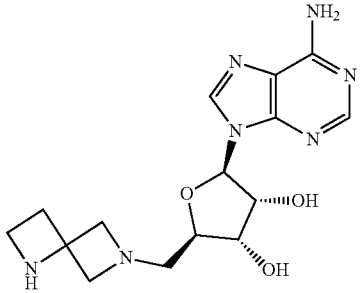 [SMILES: Nc1ncnc2c1ncn2[C@@H]1O[C@H](CN2CC3(CCN3)C2)[C@@H](O)[C@H]1O] | a) Intermediate 175<br>b) Ammonia solution 7N in MeOH<br>c) TFA in water |
| 89 | 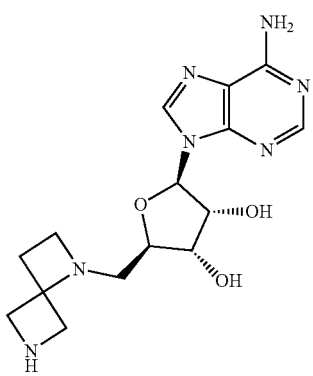 [SMILES: Nc1ncnc2c1ncn2[C@@H]1O[C@H](CN2CCC23CNC3)[C@@H](O)[C@H]1O] | a) Intermediate 176<br>b) Ammonia solution 7N in MeOH<br>c) TFA in water |

Example B9

Preparation of Final Compound 90

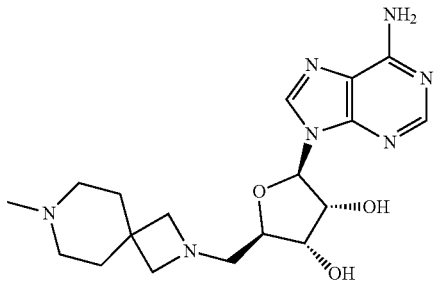 [SMILES: CN1CCC2(CC1)CN(C[C@H]1O[C@@H](n3cnc4c(N)ncnc43)[C@H](O)[C@@H]1O)C2]

Intermediate 45 (396 mg, 0.93 mmol), Intermediate 190 (273 mg, 1.02 mmol) and sodium acetate (79.2 mg, 0.97 mmol) were dissolved in dichloroethane (9 mL) and the mixture was stirred 30 min. Then sodium triacetoxyborohydride (295 mg, 1.39 mmol) was added and the solution was stirred at room temperature overnight. The mixture was diluted with DCM (20 mL) and washed with $Na_2CO_3$ 1M (20 mL). The organic layer was dried over $MgSO_4$ and filtered. The solvents were evaporated to dryness and to the residue was added an ammonia solution 7 N in MeOH (50 mL). The mixture was stirred at room temperature overnight. The solvents were evaporated to dryness and the residue was then dissolved in water (2.5 mL) and trifluoroacetic acid (47 mL) and stirred at 0° C. for 5 h. The solvents were evaporated to dryness and the product was purified by reverse phase three times 90% [$NH_4OH$ 0.4% in water]—10% [MeOH] 54% [$NH_4OH$ 0.4% in water]—46% [MeOH] The product was triturated in ACN to give final compound 99 (4 mg, 1% yield).

Example B10

Preparation of Final Compound 91

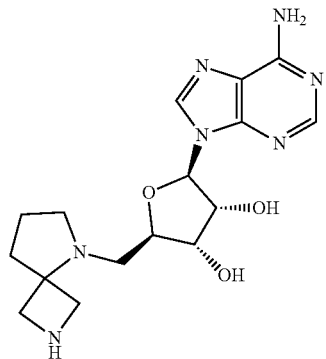 [SMILES: Nc1ncnc2c1ncn2[C@@H]1O[C@H](CN2CCCC23CNC3)[C@@H](O)[C@H]1O]

Intermediate 174 (45 mg, 0.097 mmol) in MeOH (1 mL) was added an ammonia solution 7 N in MeOH (6 mL). The mixture was stirred at room temperature overnight. The solvents were evaporated to dryness and the product was purified by reverse phase 90% [$NH_4OH$ 0.4% in water]—10% [MeOH] 54% [$NH_4OH$ 0.4% in water]—46% [MeOH] to give final compound 91 (6 mg, yield: 16%).

Example B11

Preparation of Final Compound 92

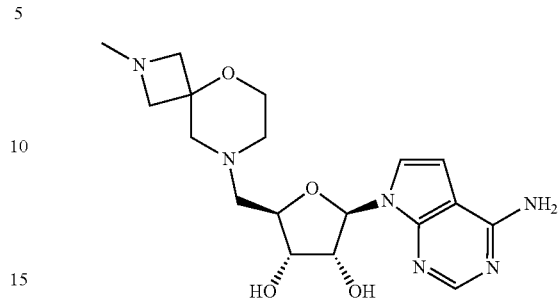

To a solution of Intermediate 178 (120.6 mg, 0.29 mmol) in MeOH (5 mL) was added formaldehyde (0.0435 mL, 0.579 mmol 37%) at room temperature and the reaction mixture was stirred for 15 minutes. Then $NaBH_3CN$ (36.4 mg, 0.58 mmol) was added and the reaction mixture was stirred at room temperature for 2 hours. Then molecular sieves were added and the reaction mixture was stirred overnight at room temperature The solid was removed by filtration after which HCl in dioxane (0.0724 mL, 0.29 mmol, 4M) was added and the mixture was stirred for another 2 hours. DIPE was used to precipitate the product's salt. The solid was dried and purified by RP-HPLC to give final compound 92 (52 mg, yield: 46%).

Example B12

Preparation of Final Compound 93

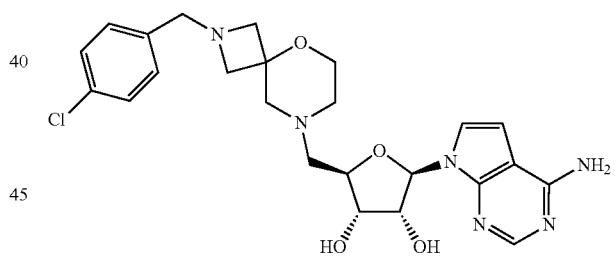

To a solution of intermediate 178 (120.6 mg, 0.29 mmol) in MeOH (5 mL) was added 4-chlorobenzaldehyde (0.041 g, 0.29 mmol) at room temperature. The reaction mixture was stirred at room temperature for 15 minutes. Then $NaBH_3CN$ (36.4 mg, 0.58 mmol) was added into the reaction mixture. The reaction mixture was stirred at room temperature for 2 hours. Molecular sieves were added and the reaction mixture was stirred at room temperature overnight. The solid was removed by filteration. 4N HCl in dioxane was added into the reaction mixture after which the mixture was stirred at room temperature for 2 hours. DIPE was used to precipitate the product's salt. The solid was dried and a purification was performed via Prep HPLC (Stationary phase: RP XBridge Prep C18 ODB—5 µm, 30×250 mm, Mobile phase: 0.25% $NH_4HCO_3$ solution in water, $CH_3CN$) to give final compound 93 (73 mg, yield: 50.3%).

Preparation of Final Compound 94

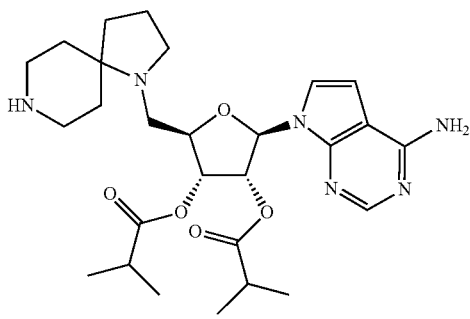 [SMILES: CC(C)C(=O)O[C@@H]1[C@H](OC(=O)C(C)C)[C@@H](CN2CCCC23CCNCC3)O[C@H]1n1ccc2c(N)ncnc21]

Final Compound 96

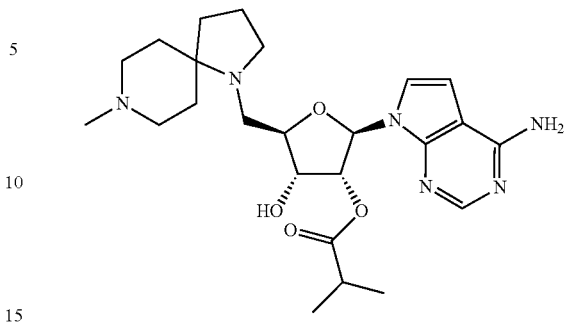

HCl (4M in dioxane) (2.31 mL, 4 M, 9.2 mmol) was added to a stirred solution of intermediate 325 (0.58 g, 0.92 mmol) in MeOH (50 mL) at room temperature. The reaction mixture was stirred at room temperature for 4 days. The reaction mixture was poured out into 60 mL DIPE. The resulting suspension was stirred for 10 minutes at room temperature. The solvents were decanted off so that the sticky precipitate remained. This residue was dissolved in MeOH and then the solvents were evaporated. The residue was dissolved in MeOH and $SiO_2$-gel was added. The solvents were evaporated and the residue was used in a solid load plunger to be purified over a $SiO_2$ column, type Grace Reveleris SRC, 12 g, Si 40, on an Armen Spot II Ultimate purification system using DCM and MeOH as eluens in a gradient starting from 100% DCM and ending with 60% MeOH and 40% DCM. The fractions containing product were combined and the solvents were evaporated yielding final compound 94 (154 mg, yield: 29.5%) as mono HC salt.

Preparation of Final Compound 95a, 95b, 96 and 97

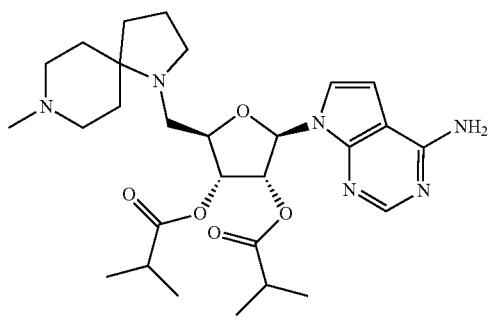 [SMILES: CC(C)C(=O)O[C@@H]1[C@H](OC(=O)C(C)C)[C@@H](CN2CCCC23CCN(C)CC3)O[C@H]1n1ccc2c(N)ncnc21]

HCl (Co. 95a), free base (Co. 95b)

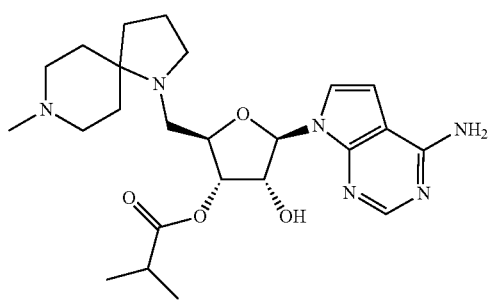 [SMILES: CC(C)C(=O)O[C@H]1[C@@H](O)[C@H](n2ccc3c(N)ncnc32)O[C@@H]1CN1CCCC12CCN(C)CC2]

Final Compound 97

A solution of intermediate 327 (16.5 g, 26.4 mmol) and isobutyric acid (24.5 mL, 263.9 mmol) in MeOH (250 mL) was stirred and heated at 110° C. in a stainless steel autoclave for 4 hours. The solvents were evaporated. The residue was dissolved in DCM and purified over a $SiO_2$ column, type Grace Reveleris SRC, 120 g, Si 40, on a Grace Reveleris $X^2$ purification system using DCM and MeOH as eluens in a gradient starting from 100% DCM to 40% MeOH and 60% DCM. The fractions containing product were combined and the solvents were evaporated yielding 12.18 g crude final compound 95a fraction 1 and 1.9 g crude final compound 96 fraction 1.

The crude final compound 95a fraction 1 was dissolved in DCM and purified over a $SiO_2$ column, type Grace Reveleris SRC, 120 g, Si 40, on a Grace Reveleris $X^2$ purification system using DCM and MeOH as eluens in a gradient starting from 100% DCM to 40% MeOH and 60% DCM. The fractions containing product were combined and the solvents were evaporated yielding 4.55 g crude final compound 95a fraction 2 and 5.43 g crude final compound 95a fraction 3.

400 mL DIPE was added to fraction crude final compound 95a fraction 2 which caused a sticky suspension. The mixture was stirred and HCl (6M in iPrOH) (1.4 mL, 6 M, 8.4 mmol) was added. The mixture was stirred at room temperature for 18 hour resulting in a fine solid suspension. The suspension was filtered and the residue was washed with DIPE. The solid material was dried in vacuo at 30° C. The residue was dissolved in DCM and purified over a $SiO_2$ column, type Grace Reveleris SRC, 40 g, Si 40, on a Grace Reveleris $X^2$ purification system using DCM and MeOH as eluens in a gradient starting from 100% DCM to 40% MeOH and 60% DCM. The fractions containing product were combined and the solvents were evaporated yielding 2.24 g of pure final compound 95a fraction 1 as mono HCl salt.

400 mL DIPE was added to fraction crude final compound 95a fraction 3 resulting in a fine solid suspension. The mixture was stirred at room temperature for 18 hours. The suspension was filtered and the residue was washed with DIPE. The solid material was dried in vacuo at 30° C. yielding 2.85 g final compound 95a fraction 2 as monoHCl salt.

The solvents of the filtrate of final compound 95a fraction 2 were evaporated. The residue was co-evaporated with DIPE. The solid material was dried in vacuo at 30° C. yielding 2.22 g final compound 95b fraction 3 as free base.

Fraction crude final compound 96 fraction 1 was dissolved in DCM and purified over a $SiO_2$ column, type Grace Reveleris SRC, 80 g, Si 40, on a Grace Reveleris $X^2$ purification system using DCM and MeOH as eluens in a gradient starting from 100% DCM to 40% MeOH and 60% DCM. The fractions containing product were combined and the solvents were evaporated yielding 0.46 g. A mixture of 70% final compound 96 as a free base and 30% final compound 97 as a free base.

Example B13

Preparation of Final Compound 98, 99 and 100

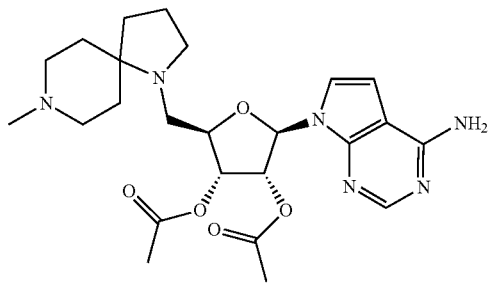 [SMILES: CC(=O)O[C@@H]1[C@H](OC(C)=O)[C@@H](CN2CCCC23CCN(C)CC3)O[C@H]1n1ccc2c(N)ncnc21]

HCl
Final Compound 98

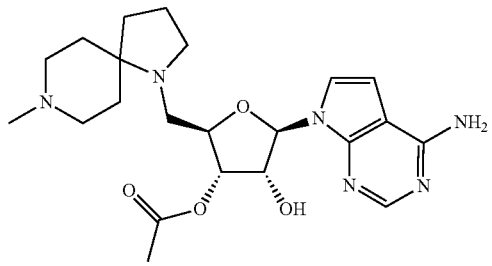 [SMILES: CC(=O)O[C@H]1[C@@H](O)[C@H](n2ccc3c(N)ncnc32)O[C@@H]1CN1CCCC12CCN(C)CC2]

HCl
Final Compound 99

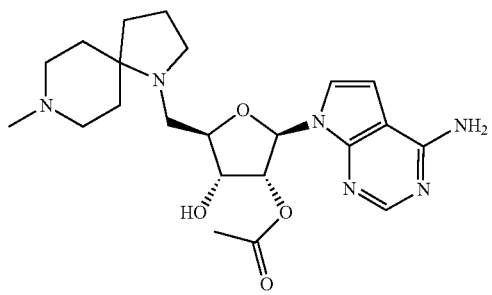 [SMILES: CC(=O)O[C@@H]1[C@H](O)[C@@H](CN2CCCC23CCN(C)CC3)O[C@H]1n1ccc2c(N)ncnc21]

HCl
Final Compound 100

A solution of Intermediate 329 (27 g, 49.5 mmol) and isobutyric acid (45.9 mL, 495 mmol) in MeOH (450 mL) was stirred and heated in a stainless steel autoclave at 90° C. for 4 hour. The solvents were evaporated. The residue was triturated in 400 mL DIPE. HCl (6M in iPrOH)(19.8 mL, 6 M, 119 mmol) was added and the mixture was stirred at room temperature for 18 hours which resulted in a suspension together with some sticky material. This mixture was filtered and washed with DIPE. The residue was combined with the remaining sticky material in the flask, dissolved in DCM and purified over a $SiO_2$ column, type Grace Reveleris SRC, 330 g, Si 40, on a Armen Spot II Ultimate purification system using DCM and MeOH as eluens in a gradient starting from 100% DCM and ending with 20% MeOH and 80% DCM. The fractions containing product were combined and the solvents were evaporated yielding 0.936 g of final compounds 98 as mono HCl salt and 1.97 g of crude mixture of final compounds 99 and 100. The crude mixture of final compounds 99 and 100 were dissolved in DCM and purified over a $SiO_2$ column, type Grace Reveleris SRC, 80 g, Si 40, on a Armen Spot II Ultimate purification system using DCM and MeOH as eluens in a gradient starting from 100% DCM for 5 CV's and ending with 20% MeOH and 80% DCM over 15 CV's. The fractions containing product were combined and the solvents were evaporated yielding 1.41 g of a mixture of 65% final compound 99 and 35% final compound 100 as mono HCl salt.

Example B14

Preparation of Final Compound 101

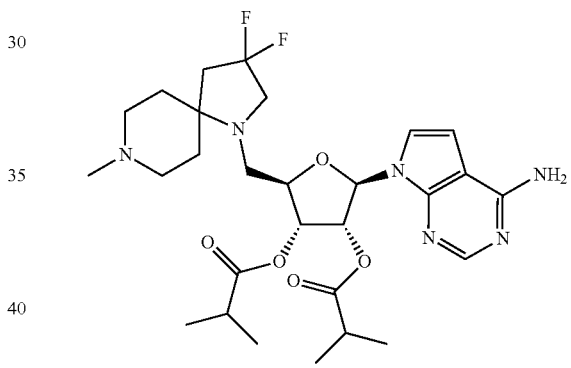

Ammonium fluoride (0.64 g, 17.4 mmol) was added to a stirred solution of intermediate 333 (1.1 g, 1.74 mmol) in MeOH, anhydrous (50 mL) and molecular sieve (2.5 g). The reaction mixture was stirred and refluxed for 5 hours. The reaction mixture was allowed to cool down to room temperature and was then diluted with 50 mL MeOH and 25 mL DCM. The resulting suspension was filtered over a pad of Celite. The pad was washed two times with DCM. The combined solvents of the filtrate were evaporated. The residue was purified with Prep HPLC (Stationary phase: RP XBridge Prep C18 OBD—10 μm, 30×150 mm, Mobile phase: 0.25% $NH_4HCO_3$ solution in water, $CH_3CN$) after which it was again purified with Prep HPLC (Stationary phase: RP XBridge Prep C18 OBD-10 μm, 30×150 mm, Mobile phase: 0.25% $NH_4HCO_3$ solution in water, $CH_3CN$). The residue was again not pure and was purified for a third time with Prep HPLC (Stationary phase: RP XBridge Prep C18 OBD-10 μm, 30×150 mm, Mobile phase: 0.5% $NH_4OAc$ solution in water+10% $CH_3CN$, $CH_3CN$) to give final compound 101 (1.8 mg, 0.00308 mmol, yield: 0.18%)

Example B15

Preparation of Final Compound 101

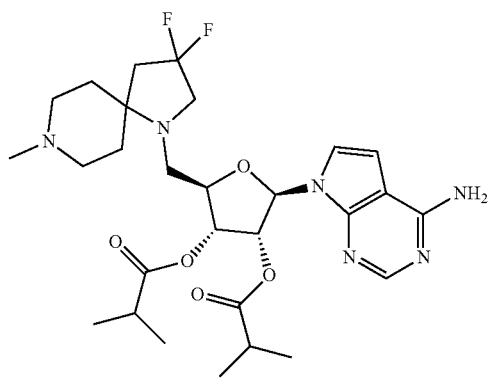 [SMILES: CC(C)C(=O)O[C@@H]1[C@H](OC(=O)C(C)C)[C@@H](CN2CC(F)(F)CC23CCN(C)CC3)O[C@H]1n1ccc2c(N)ncnc21]

A solution of intermediate 335 (0.71 g, 1.0 mmol) in MeOH (10 mL) was stirred and heated at 110° C. using microwave irradiation for 19 hours. The solvents were evaporated after which the residue was dissolved in DCM and purified over a SiO$_2$ column, type Grace Reveleris SRC, 12 g, Si 40, on a Grace Reveleris X$^2$ purification system using DCM and MeOH as eluens in a gradient starting from 100% DCM to 15% MeOH and 85% DCM. The fractions containing product were combined and the solvents were evaporated to give final compound 101 (0.34 g).

Example B16

Preparation of Final Compound 103

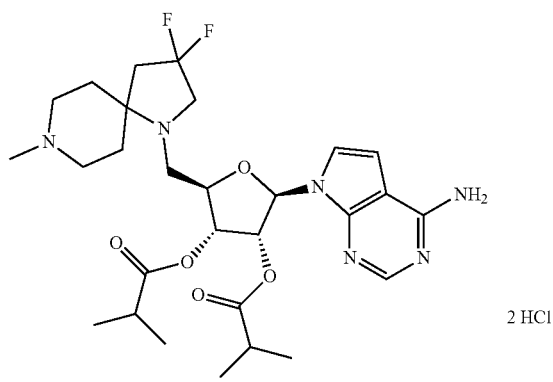 [SMILES: CC(C)C(=O)O[C@@H]1[C@H](OC(=O)C(C)C)[C@@H](CN2CC(F)(F)CC23CCN(C)CC3)O[C@H]1n1ccc2c(N)ncnc21]

2 HCl

A solution of intermediate 335 (17.9 g, 20.6 mmol) and SOCl$_2$ (1.5 mL, 20.6 mmol) in MeOH (260 mL) was stirred and heated at 110° C. in a sealed stainless steel autoclave for 5 hours. The solvents were evaporated and the residue was dissolved in DCM with some MeOH and purified over a SiO$_2$ column, type Grace Reveleris SRC, 330 g, Si 40, on a Armen Spot II Ultimate purification system using DCM and MeOH as eluens in a gradient starting with 100% DCM and going to 40% MeOH and 60% DCM. The fractions containing product were combined and the solvents were evaporated yielding 9.77 g crude final compound 103 fraction 1. Crude final compound 103 fraction 1 was dissolved in DCM with some MeOH and purified over a SiO$_2$ column, type Grace Reveleris SRC, 120 g, Si 40, on a Armen Spot II Ultimate purification system using DCM and MeOH as eluens in a gradient starting with 100% DCM and going to 40% MeOH and 60% DCM. The fractions containing product were combined and the solvents were evaporated yielding 7.22 g of a light brown solid. This residue was recrystallized in ACN yielding a white precipitate which was filtered off, washed with ACN and then dried in vacuo at 40° C. yielding 3.57 g pure final compound 103 fraction as bis HCl salt.

The solvents of the filtrate of pure final compound 103 fraction were evaporated. The residue was triturated in DIPE. The precipitate was filtered off and dried on the air yielding 2.75 g crude final compound 103 fraction 2. Crude final compound 103 fraction 2 was dissolved in ACN. Water was added and 1 equivalent of NaHCO$_3$ (0.35 g, 4.2 mmol). The residue was stirred at room temperature, for 25 minutes. DCM was added and the product was extracted from the mixture. The organic layer was separated, dried with MgSO$_4$, filtered and the solvents of the filtrate evaporated. The residue was triturated in DIPE. The precipitate was filtered off. The solvents of the filtrate were evaporated yielding 1.90 g of crude final compound 103 fraction 3. Crude final compound 103 fraction 3 was dissolved in a mixture of 200 mL DIPE and 5 mL ACN. A solution of 1.64 mL 2M HCl (3.28 mmol) in diethylether was added. Immediately a white precipitate was formed. The mixture was stirred at room temperature for 30 minutes. The precipitate was filtered off and washed with DIPE. The remaining residue was recrystallized in ACN yielding a white precipitate which was filtered off, washed with cold ACN and then dried in vacuo at 40° C. yielding 1.24 g of pure final compound 103 fraction 2 as bis HCl salt. The filtrate of pure final compound 103 fraction 2 was evaporated, dissolved in DCM and washed three times with a saturated aqueous NaHCO$_3$ solution to obtain the product as free base after separation of the organic layer, drying with MgSO$_4$ and evaporating off the solvents. The residue was dissolved in a mixture of 200 mL DIPE and 25 mL ACN and then acidified with 1 equivalent of HCl using a 2M solution of HCl in Et$_2$O. The formed white precipitate was filtered off, washed with DIPE and dried. The resulting solid material was recrystallized in 40 mL ACN. The precipitate was filtered off and dried in vacuo at 45° C. yielding 196.2 mg pure final compound 103 fraction 3 as bis HCl salt.

Example B17

Preparation of Final Compound 104

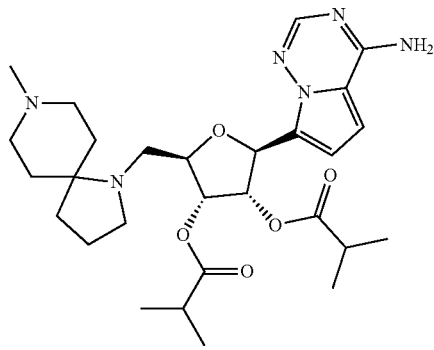 [SMILES: CC(C)C(=O)O[C@@H]1[C@H](OC(=O)C(C)C)[C@@H](CN2CCCC23CCN(C)CC3)O[C@H]1c1ccc2c(N)ncnn12]

A mixture of intermediate 459 (177 mg, 289 μmol, 1 eq) in MeOH (5 mL) was heated at 110° C. for 3 hours. The mixture was concentrated under reduced pressure. The residue was purified by preparative HPLC (Column: Gemini 150*25 mm, 5um; Mobile phase: from 45% MeCN in water to 65% MeCN in water, 0.5% $NH_3$; Gradient Time: 12 min; Flow Rate: 25 m/min; Wavelength: 220 nm). The fractions containing desired product were combined and lyophilized to afford final compound 104 (78 mg, 140.9 μmol, 48.8% yield) as a white solid.

Below final compounds were prepared by an analogous reaction protocol as was used for the preparation of final compound 104 using the appropriate starting materials (Table 22).

TABLE 22

| Co. | Structure | Starting materials |
|---|---|---|
| 105 | 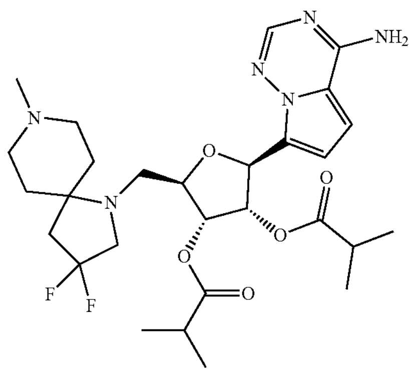 [SMILES: CC(C)C(=O)O[C@@H]1[C@H](OC(=O)C(C)C)[C@@H](CN2CC(F)(F)CC23CCN(C)CC3)O[C@H]1c1ccc2c(N)ncnn12] | Intermediate 462 |
| 106 | 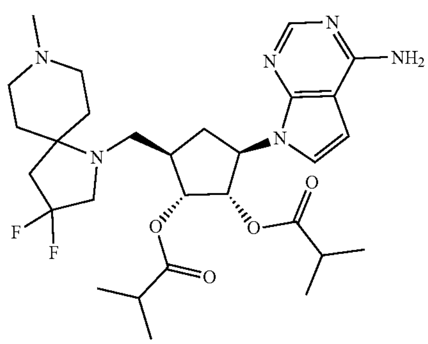 [SMILES: CC(C)C(=O)O[C@@H]1[C@@H](CN2CC(F)(F)CC23CCN(C)CC3)C[C@@H](n2ccc3c(N)ncnc32)[C@@H]1OC(=O)C(C)C] | Intermediate 457 |
| 107 | 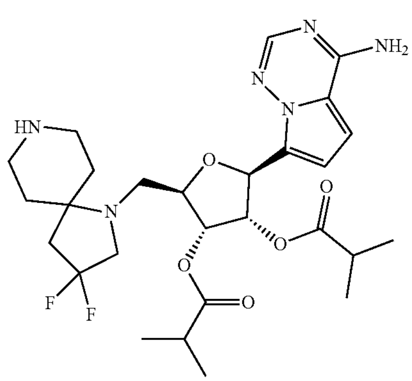 [SMILES: CC(C)C(=O)O[C@@H]1[C@H](OC(=O)C(C)C)[C@@H](CN2CC(F)(F)CC23CCNCC3)O[C@H]1c1ccc2c(N)ncnn12] | Intermediate 461 |

Example B18

Method A

Preparation of Final Compound 108

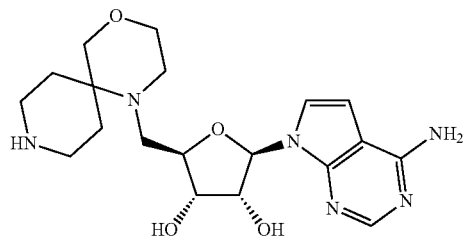 [SMILES: Nc1ncnc2c1ccn2[C@@H]1O[C@H](CN2CCOCC23CCNCC3)[C@@H](O)[C@H]1O]

To a solution of Intermediate 401 (100 mg, 183.6 μmol, 1 eq) in MeOH (2 mL) was added HCl/dioxane (2 mL) and the mixture was stirred at 25° C. for 16 h. The solvent was removed and the residue was dissolved in MeOH (5 mL) and the basified to pH=8 by 25% aqueous ammonia. The crude was purified by preparative HPLC (Column: Gemini 150*25 mm, 5um; Mobile phase: from 5% MeCN in water to 30. MeCN in water, 0.5% $NH_3$; Gradient Time: 12 min; Flow Rate: 25 ml/min; Wavelength: 220 nm). The fractions contain desired product were combined and lyophilized to give final compound 108 (41.14 mg, 100.9 μmol, 54.9% yield) as a white solid.

Method B

Preparation of Final Compound 109

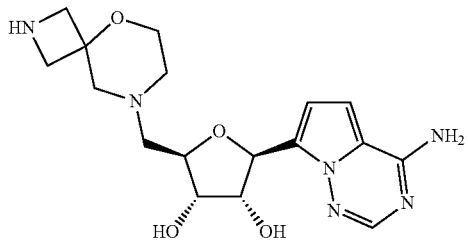 [SMILES: Nc1ncnn2c([C@@H]3O[C@H](CN4CCOC5(CNC5)C4)[C@@H](O)[C@H]3O)ccc12]

To a stirred solution of intermediate 429 (142 mg, 275 μmol, 1 eq) in $CH_2C12$ (6 mL) was added TFA (1.5 mL) at 25° C. The mixture was stirred at 25° C. for 16 hours. The reaction mixture was concentrated under reduced pressure. The solvent was removed and the residue was dissolved in MeOH (5 mL) and the basified to pH=8 by 25% aqueous ammonia. The crude was purified by preparative HPLC (Column:Gemini15025 mm, 5 um; Mobile phase: from 5% MeCN in water to 25% MeCN in water, 0.5% $NH_3$; Gradient Time: 12 min; Flow Rate: 25 ml/min; Wavelength: 220 nm). The fractions containing desired product were combined and lyophilized to afford final compound 19 (58 mg, 147.92 μmol, 53.8% yield) as a white solid.

Below final compounds were prepared by ananalogous reaction protocol as was used for the preparation of final compound 108 or final final compound 19 using the appropriate starting materials (Table 23).

TABLE 23

| Co. | Structure | Starting materials | Method |
|---|---|---|---|
| 110 | (structure) | Intermediate 402 | Method A |
| 111 | (structure) | Intermediate 403 | Method A |
| 112 | (structure) | Intermediate 404 | Method B |
| 113 | (structure) | Intermediate 405 | Method A |
| 114 | (structure) | Intermediate 406 | Method A |
| 115 | (structure) | Intermediate 407 | Method A |

TABLE 23-continued

| Co. | Structure | Starting materials | Method |
|---|---|---|---|
| 116 | 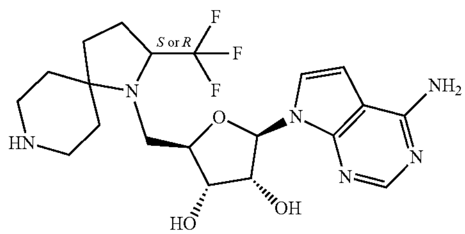 [SMILES: Nc1ncnc2c1ccn2[C@@H]1O[C@H](CN2C(C(F)(F)F)CCC23CCNCC3)[C@@H](O)[C@H]1O] | Intermediate 408 | Method A |
| 117 | 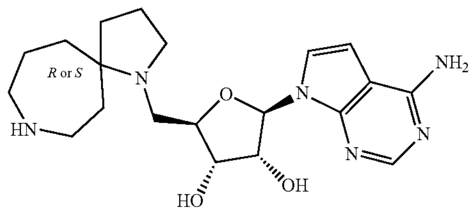 [SMILES: Nc1ncnc2c1ccn2[C@@H]1O[C@H](CN2CCCC23CCCNCC3)[C@@H](O)[C@H]1O] | Intermediate 409 | Method A |
| 118 | 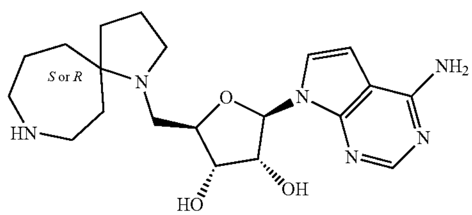 [SMILES: Nc1ncnc2c1ccn2[C@@H]1O[C@H](CN2CCCC23CCCNCC3)[C@@H](O)[C@H]1O] | Intermediate 410 | Method A |
| 119 | 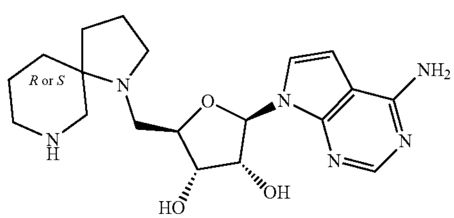 [SMILES: Nc1ncnc2c1ccn2[C@@H]1O[C@H](CN2CCCC23CCCNC3)[C@@H](O)[C@H]1O] | Intermediate 411 | Method A |
| 120 | 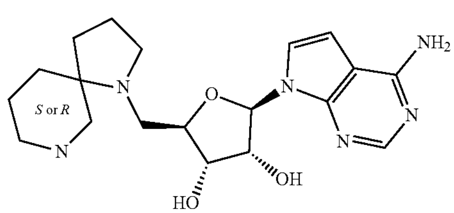 [SMILES: Nc1ncnc2c1ccn2[C@@H]1O[C@H](CN2CCCC23CCCNC3)[C@@H](O)[C@H]1O] | Intermediate 412 | Method A |
| 121 | 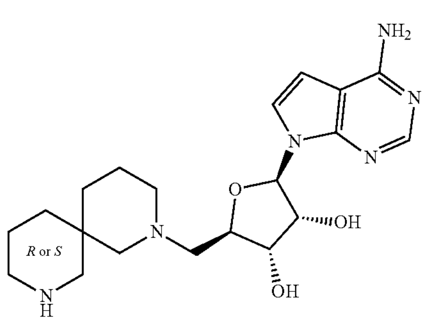 [SMILES: Nc1ncnc2c1ccn2[C@@H]1O[C@H](CN2CCCC3(CCCNC3)C2)[C@@H](O)[C@H]1O] | Intermediate 413 | Method A |

TABLE 23-continued
| Co. | Structure | Starting materials | Method |
|---|---|---|---|
| 122 | 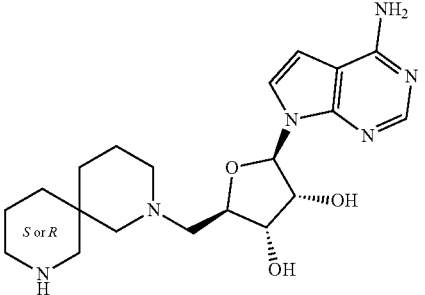 [SMILES: Nc1ncnc2c1ccn2[C@@H]1O[C@H](CN2CCCC3(CCCNC3)C2)[C@@H](O)[C@H]1O] | Intermediate 413 | Method A |
| 123 | 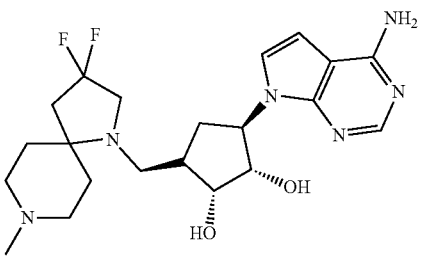 | Intermediate 414 | Method A |
| 124 | 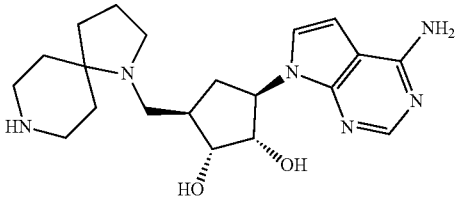 [SMILES: Nc1ncnc2c1ccn2[C@@H]1C[C@H](CN2CCCC23CCNCC3)[C@@H](O)[C@H]1O] | Intermediate 415 | Method A |
| 125 | 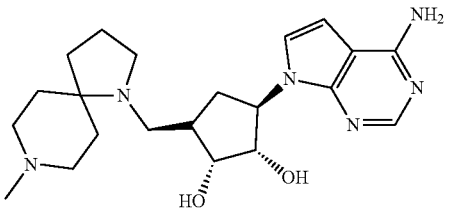 | Intermediate 416 | Method A |
| 126 | 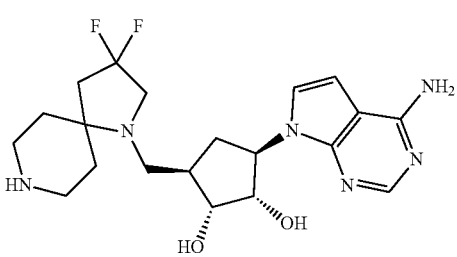 [SMILES: Nc1ncnc2c1ccn2[C@@H]1C[C@H](CN2CC(F)(F)CC23CCNCC3)[C@@H](O)[C@H]1O] | Intermediate 417 | Method A |
| 127 | 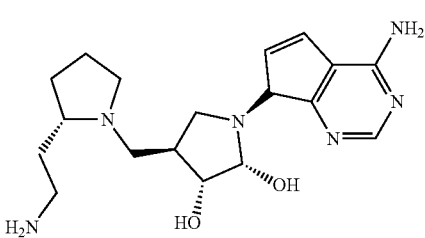 | Intermediate 418 | Method A |

TABLE 23-continued

| Co. | Structure | Starting materials | Method |
|---|---|---|---|
| 128 | 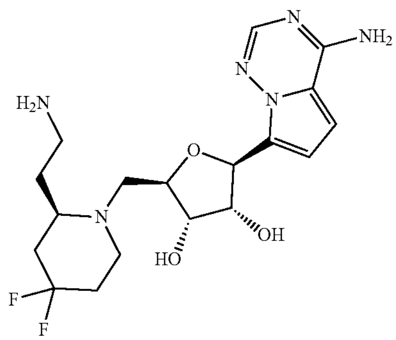 [SMILES: NCC[C@@H]1CC(F)(F)CCN1C[C@H]1O[C@@H](c2ccc3c(N)ncnn23)[C@H](O)[C@@H]1O] | Intermediate 419 | Method A |
| 129 | 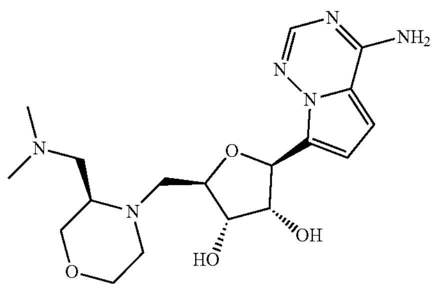 [SMILES: CN(C)C[C@@H]1COCCN1C[C@H]1O[C@@H](c2ccc3c(N)ncnn23)[C@H](O)[C@@H]1O] | Intermediate 420 | Method A |
| 130 | 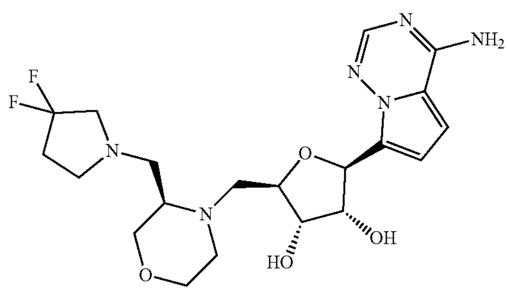 [SMILES: Nc1ncnn2c([C@@H]3O[C@H](CN4CCOC[C@H]4CN4CCC(F)(F)C4)[C@@H](O)[C@H]3O)ccc12] | Intermediate 421 | Method A |
| 131 | 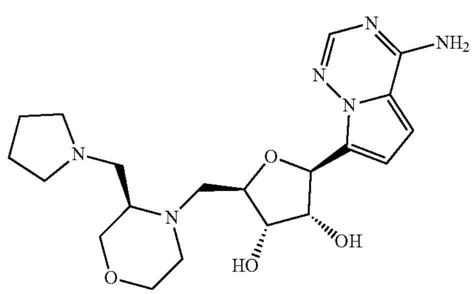 [SMILES: Nc1ncnn2c([C@@H]3O[C@H](CN4CCOC[C@H]4CN4CCCC4)[C@@H](O)[C@H]3O)ccc12] | Intermediate 422 | Method A |
| 132 | 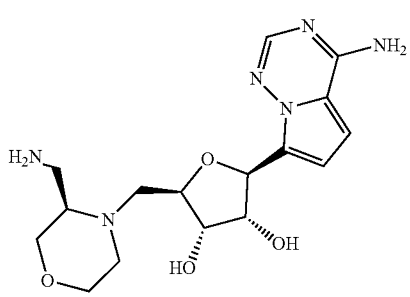 [SMILES: NC[C@@H]1COCCN1C[C@H]1O[C@@H](c2ccc3c(N)ncnn23)[C@H](O)[C@@H]1O] | Intermediate 423 | Method A |

TABLE 23-continued
| Co. | Structure | Starting materials | Method |
|---|---|---|---|
| 133 | 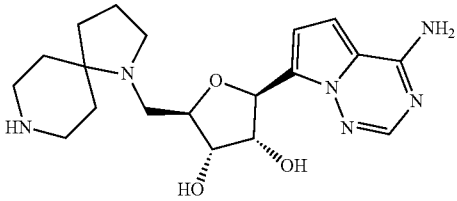 [SMILES: Nc1ncnn2c([C@@H]3O[C@H](CN4CCCC45CCNCC5)[C@@H](O)[C@H]3O)ccc12] | Intermediate 424 | Method A |
| 134 | 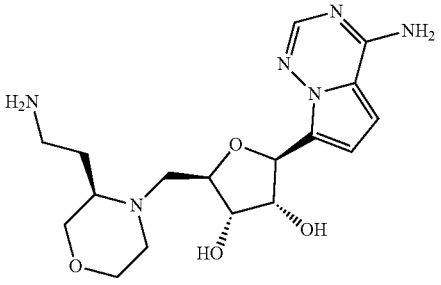 [SMILES: NCC[C@@H]1COCCN1C[C@H]1O[C@@H](c2ccc3c(N)ncnn23)[C@H](O)[C@@H]1O] | Intermediate 425 | Method A |
| 135 | 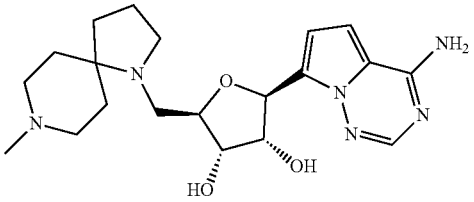 [SMILES: CN1CCC2(CCCN2C[C@H]2O[C@@H](c3ccc4c(N)ncnn34)[C@H](O)[C@@H]2O)CC1] | Intermediate 426 | Method A |
| 136 | 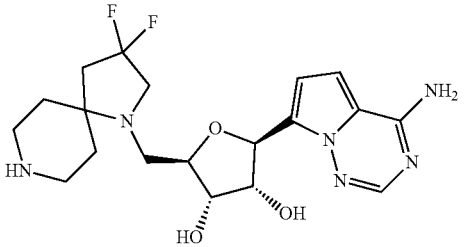 [SMILES: Nc1ncnn2c([C@@H]3O[C@H](CN4CC(F)(F)CC45CCNCC5)[C@@H](O)[C@H]3O)ccc12] | Intermediate 427 | Method A |
| 137 | 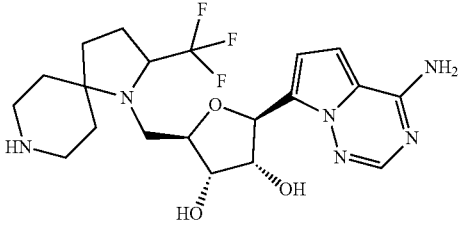 [SMILES: Nc1ncnn2c([C@@H]3O[C@H](CN4C(C(F)(F)F)CCC45CCNCC5)[C@@H](O)[C@H]3O)ccc12] | Intermediate 428 | Method A |
| 139 | 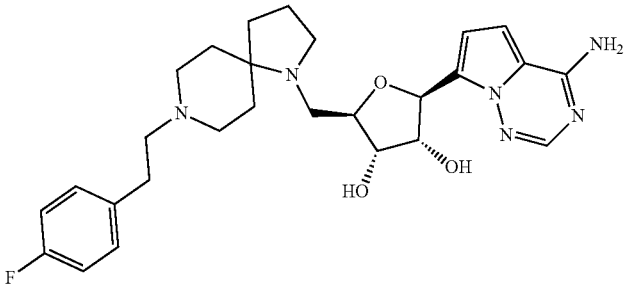 [SMILES: Nc1ncnn2c([C@@H]3O[C@H](CN4CCCC45CCN(CCc4ccc(F)cc4)CC5)[C@@H](O)[C@H]3O)ccc12] | Intermediate 430 | Method A |

TABLE 23-continued

| Co. | Structure | Starting materials | Method |
|---|---|---|---|
| 140 | 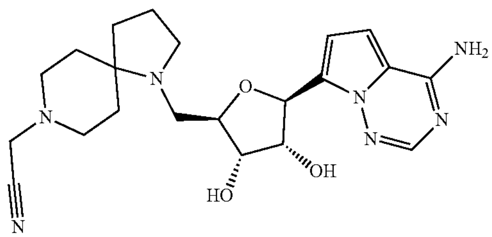 [SMILES: N#CCN1CCC2(CCCN2C[C@H]2O[C@@H](c3ccc4c(N)ncnn34)[C@H](O)[C@@H]2O)CC1] | Intermediate 431 | Method B |
| 141 | 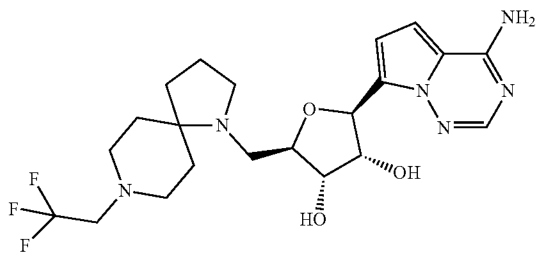 [SMILES: Nc1ncnn2c([C@@H]3O[C@H](CN4CCCC45CCN(CC(F)(F)F)CC5)[C@@H](O)[C@H]3O)ccc12] | Intermediate 432 | Method A |
| 142 | 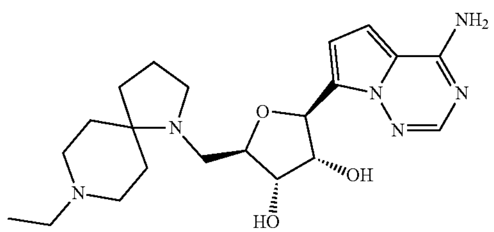 [SMILES: CCN1CCC2(CCCN2C[C@H]2O[C@@H](c3ccc4c(N)ncnn34)[C@H](O)[C@@H]2O)CC1] | Intermediate 433 | Method A |
| 143 | 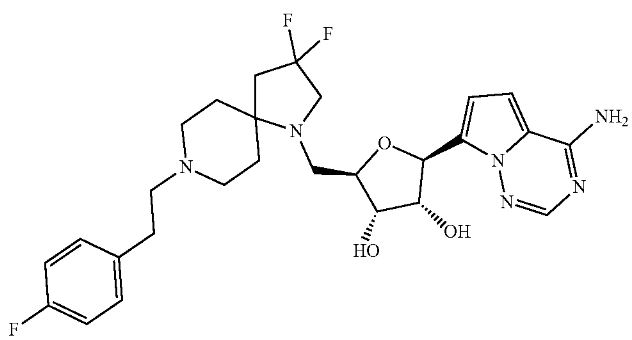 [SMILES: Nc1ncnn2c([C@@H]3O[C@H](CN4CC(F)(F)CC45CCN(CCc4ccc(F)cc4)CC5)[C@@H](O)[C@H]3O)ccc12] | Intermediate 434 | Method A |
| 144 | 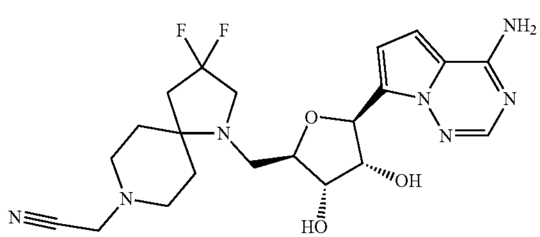 [SMILES: N#CCN1CCC2(CC1)CC(F)(F)CN2C[C@H]1O[C@@H](c2ccc3c(N)ncnn23)[C@H](O)[C@@H]1O] | Intermediate 435 | Method B |
| 145 | 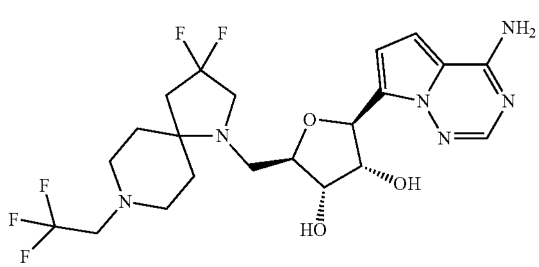 [SMILES: Nc1ncnn2c([C@@H]3O[C@H](CN4CC(F)(F)CC45CCN(CC(F)(F)F)CC5)[C@@H](O)[C@H]3O)ccc12] | Intermediate 436 | Method A |

TABLE 23-continued

| Co. | Structure | Starting materials | Method |
|---|---|---|---|
| 146 | 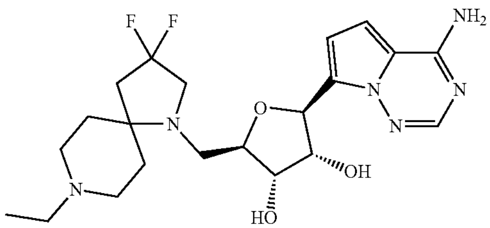 [SMILES: CCN1CCC2(CC1)CC(F)(F)CN2C[C@H]1O[C@@H](c2ccc3c(N)ncnn23)[C@H](O)[C@@H]1O] | Intermediate 437 | Method A |
| 147 | 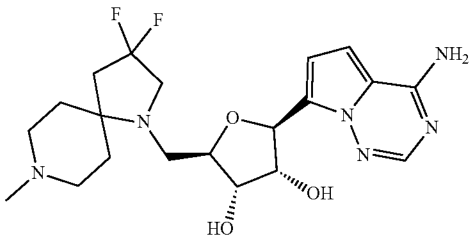 [SMILES: CN1CCC2(CC1)CC(F)(F)CN2C[C@H]1O[C@@H](c2ccc3c(N)ncnn23)[C@H](O)[C@@H]1O] | Intermediate 438 | Method A |
| 148 | 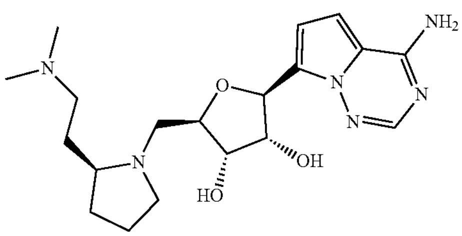 [SMILES: CN(C)CC[C@@H]1CCCN1C[C@H]1O[C@@H](c2ccc3c(N)ncnn23)[C@H](O)[C@@H]1O] | Intermediate 439 | Method A |
| 150 | 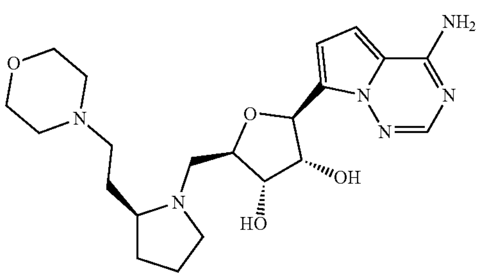 [SMILES: Nc1ncnn2c([C@@H]3O[C@H](CN4CCC[C@H]4CCN4CCOCC4)[C@@H](O)[C@H]3O)ccc12] | Intermediate 441 | Method A |
| 151 | 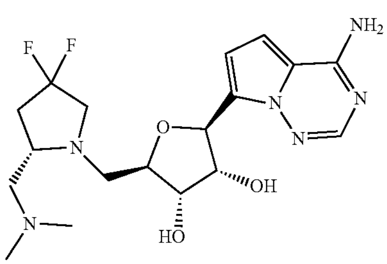 [SMILES: CN(C)C[C@@H]1CC(F)(F)CN1C[C@H]1O[C@@H](c2ccc3c(N)ncnn23)[C@H](O)[C@@H]1O] | Intermediate 442 | Method A |
| 152 | 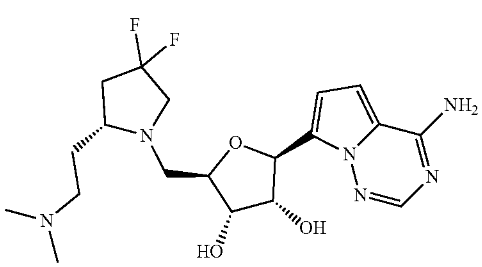 [SMILES: CN(C)CC[C@@H]1CC(F)(F)CN1C[C@H]1O[C@@H](c2ccc3c(N)ncnn23)[C@H](O)[C@@H]1O] | Intermediate 443 | Method A |

TABLE 23-continued

| Co. | Structure | Starting materials | Method |
|---|---|---|---|
| 154 | 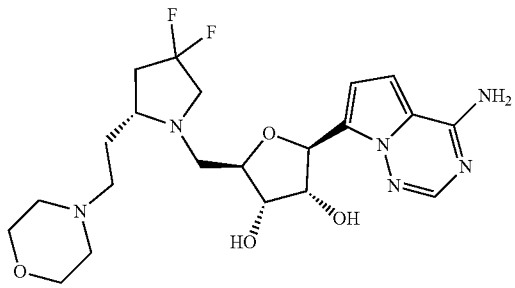 [SMILES: Nc1ncnn2c([C@@H]3O[C@H](CN4CC(F)(F)C[C@H]4CCN4CCOCC4)[C@@H](O)[C@H]3O)ccc12] | Intermediate 445 | Method A |
| 155 | 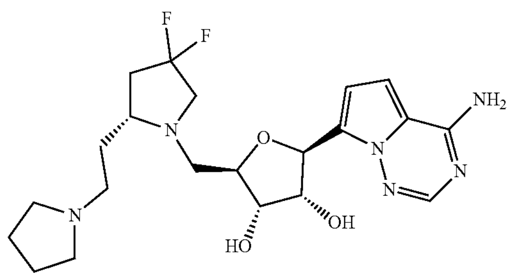 [SMILES: Nc1ncnn2c([C@@H]3O[C@H](CN4CC(F)(F)C[C@H]4CCN4CCCC4)[C@@H](O)[C@H]3O)ccc12] | Intermediate 446 | Method A |
| 156 | 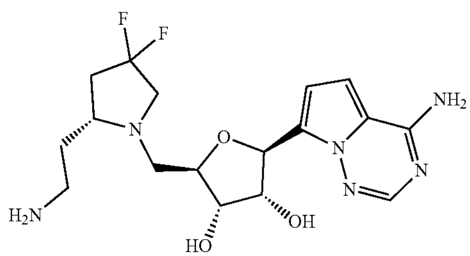 [SMILES: NCC[C@@H]1CC(F)(F)CN1C[C@H]1O[C@@H](c2ccc3c(N)ncnn23)[C@H](O)[C@@H]1O] | Intermediate 447 | Method A |
| 157 | 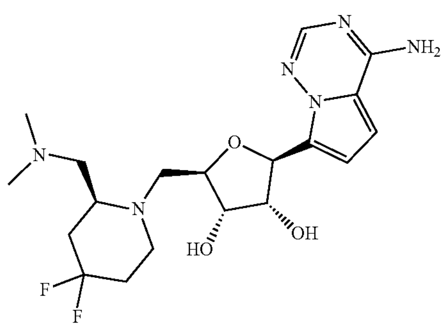 [SMILES: CN(C)C[C@@H]1CC(F)(F)CCN1C[C@H]1O[C@@H](c2ccc3c(N)ncnn23)[C@H](O)[C@@H]1O] | Intermediate 448 | Method A |
| 159 | 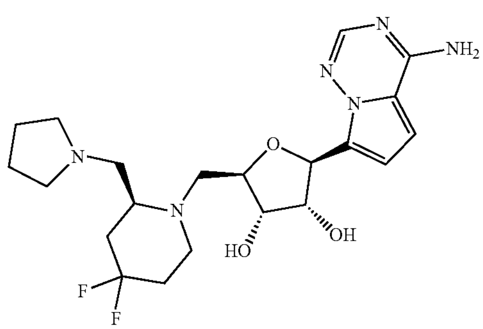 [SMILES: Nc1ncnn2c([C@@H]3O[C@H](CN4CCC(F)(F)C[C@H]4CN4CCCC4)[C@@H](O)[C@H]3O)ccc12] | Intermediate 450 | Method A |

TABLE 23-continued

| Co. | Structure | Starting materials | Method |
|---|---|---|---|
| 160 | 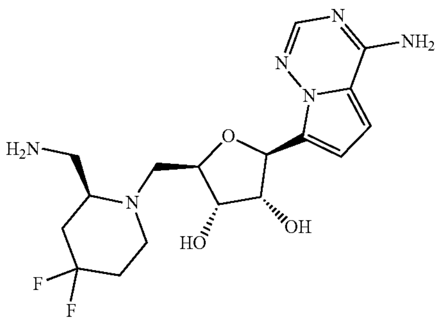 [SMILES: NC[C@@H]1CC(F)(F)CCN1C[C@H]1O[C@@H](c2ccc3c(N)ncnn23)[C@H](O)[C@@H]1O] | Intermediate 451 | Method A |
| 161 | 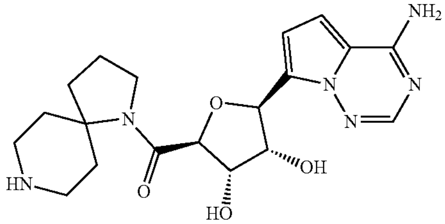 [SMILES: Nc1ncnn2c([C@@H]3O[C@H](C(=O)N4CCCC45CCNCC5)[C@@H](O)[C@H]3O)ccc12] | Intermediate 350 | Method A |
| 162 | 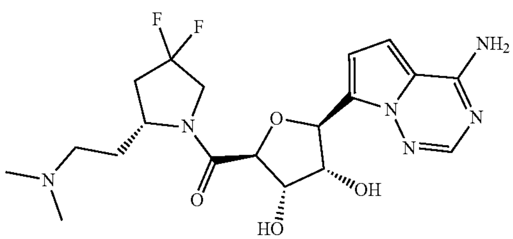 [SMILES: CN(C)CC[C@@H]1CC(F)(F)CN1C(=O)[C@H]1O[C@@H](c2ccc3c(N)ncnn23)[C@H](O)[C@@H]1O] | Intermediate 352 | Method B |
| 163 | 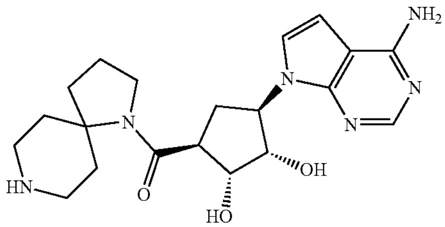 [SMILES: Nc1ncnc2c1ccn2[C@@H]1C[C@H](C(=O)N2CCCC23CCNCC3)[C@@H](O)[C@H]1O] | Intermediate 462 | Method B |
| 164 | 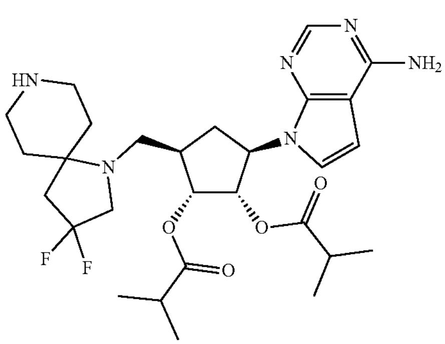 [SMILES: CC(C)C(=O)O[C@@H]1[C@@H](CN2CC(F)(F)CC23CCNCC3)C[C@@H](n2ccc3c(N)ncnc32)[C@@H]1OC(=O)C(C)C] | Intermediate 461 | Method B |

TABLE 23-continued

| Co. | Structure | Starting materials | Method |
|---|---|---|---|
| 165 | 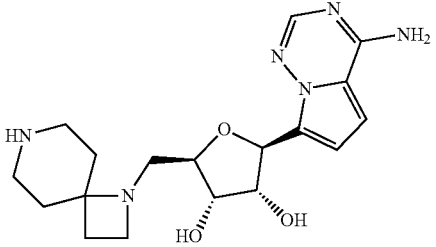 [SMILES: Nc1ncnn2c([C@@H]3O[C@H](CN4CCC45CCNCC5)[C@@H](O)[C@H]3O)ccc12] | Intermediate 452 | Method A |

Example B19

Synthesis of Final Compound 166 and Final Compound 167

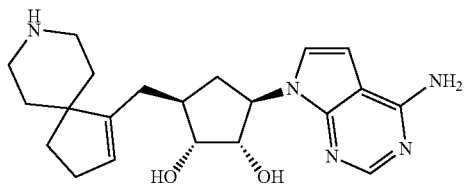 [SMILES: Nc1ncnc2c1ccn2[C@@H]1C[C@H](CC2=CCCC23CCNCC3)[C@@H](O)[C@H]1O]

Final Compound 166

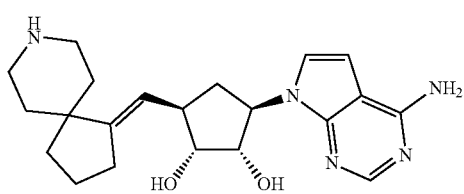 [SMILES: Nc1ncnc2c1ccn2[C@@H]1C[C@H](/C=C2\CCCC23CCNCC3)[C@@H](O)[C@H]1O]

Final Compound 167

To a solution of a crude mixture of intermediate 530 and Intermediate 531 in EtOH (50 mL) was added 1M HCl in water (54 mL, 54 mmol, 12 eq) at room temperature. After stirring overnight, the reaction mixture was heated to 40° C. and additional 1M HCl in water (23 mL, 23 mmol, 5 eq) was added. The reaction mixture was stirred for 12 hours at 40° C. to afford complete conversion, then neutralised with ammonia in water (25% w/t) and concentrated in vacuo. The crude product was triturated in water with few drops of EtOH and the obtained suspension was filtered leaving the product as residue. The filtrate was concentrated in vacuo and triturated with again with water and the suspension was filtered. The residues were combined and purified by preparative reversed phase flash chromatography (Stationary phase: Uptisphere C18 ODB—10 μm, 200 g, 5 cm, Mobile phase: 0.25% NH$_4$HCO$_3$ solution in water, CH$_3$CN) to afford a pure fraction of final compound 166 (354 mg, 0.92 mmol, yield over two steps: 21%) and a fraction of crude final compound 167 The crude final compound 167 was further purified with preparative reversed phase flash chromatography (Stationary phase: RP XBridge Prep C18 ODB—5 μm, 30×250 mm, Mobile phase: 0.25% NH$_4$HCO$_3$ solution in water, MeOH) to afford final compound 167 (16 mg, 40 μmol, yield over two steps: 1%).

C. Conversions of Final Compounds

Example C1

Preparation of Final Compound 168

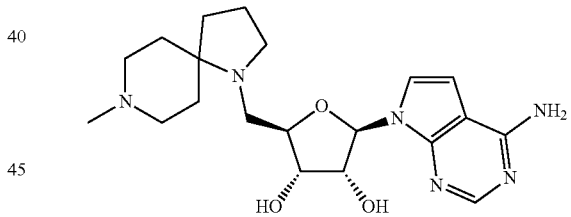

Sodium cyanoborohydride (17.04 g, 271 mmol) was added to a stirred solution of compound 19 (60 g, 135.5 mmol) and formaldehyde (14.2 mL, 190 mmol) in MeOH (3000 mL) at room temperature. After addition the reaction mixture was stirred at room temperature for 1 hour. The reaction was quenched by the addition of 10 mL water and mL of a saturated aqueous NaHCO$_3$ solution and then filtered over a pad of Celite. The pad was washed two times with MeOH. The solvents of the filtrate were evaporated and co-evaporated with toluene yielding final compound 168 (64.4 g, yield: 110.9%).

Below final compounds were prepared by an analogous reaction protocol as was used for the preparation of final compound 168 using the appropriate starting materials (Table 24).

TABLE 24

| Compound Structure | | Starting materials and methods |
|---|---|---|
| 169 | (structure) | a) Compound 19<br>b) 3,3,3-trifluoropropanal<br>c) Acetic acid, NaBH₃CN in MeOH |
| 170 | (structure) | a) Compound 19<br>b) Benzeneacetaldehyde, 4-fluoro-Acetic acid,<br>c) NaBH₃CN in MeOH |
| 171 | (structure) | a) Compound 19<br>b) 4-fluorobenzaldehyde<br>c) Acetic acid, NaBH₃CN in MeOH |
| 172 | (structure) | a) Compound 19<br>b) 3-Pyridinecarboxaldehyde<br>c) Acetic acid, NaBH(OAc)₃, DCM, MeOH |
| 173 | (structure) | a) Compound 19<br>b) 2-(4-fluorophenoxy)acetyldehyde<br>c) Acetic acid, NaBH(OAc)₃, DCM, MeOH |
| 174 | (structure) | a) Compound 19<br>b) (1-ethoxycyclopropoxy)<br>c) Acetic acid, NaBH₃CN in MeOH |

TABLE 24-continued

| Compound Structure | Starting materials and methods |
|---|---|
| 175 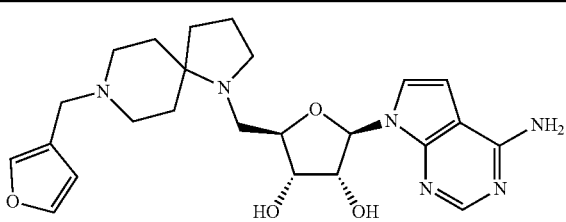 | a) Compound 19<br>b) 3-furaldehyde<br>c) Acetic acid, NaBH(OAc)$_3$, DCM, MeOH |
| 176 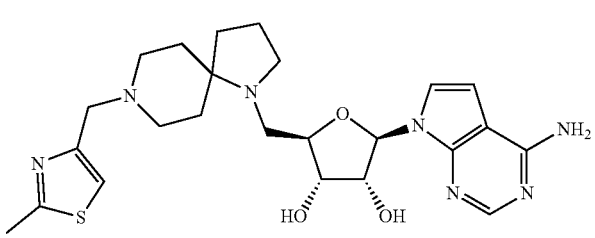 [SMILES: Cc1nc(CN2CCC3(CCCN3C[C@H]3O[C@@H](n4ccc5c(N)ncnc54)[C@H](O)[C@@H]3O)CC2)cs1] | a) Compound 19<br>b) 4-formyl-2-methylthiazole<br>c) Acetic acid, NaBH(OAc)$_3$, DCM, MeOH |
| 177 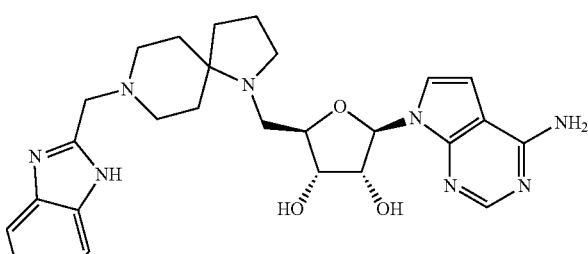 | a) Compound 19<br>b) 1H-benzoimidazole-2-carboxaldehyde<br>c) Acetic acid, NaBH(OAc)$_3$, DCM, MeOH |
| 178 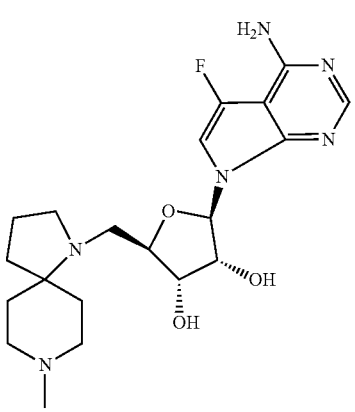 [SMILES: CN1CCC2(CCCN2C[C@H]2O[C@@H](n3cc(F)c4c(N)ncnc43)[C@H](O)[C@@H]2O)CC1] | a) Compound 24<br>b) paraformaldehyde<br>c) potassium acetate, NaBH$_3$CN in MeOH |
| 179 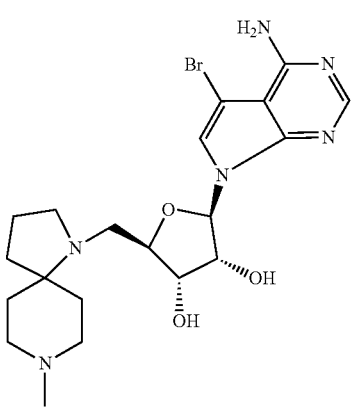 [SMILES: CN1CCC2(CCCN2C[C@H]2O[C@@H](n3cc(Br)c4c(N)ncnc43)[C@H](O)[C@@H]2O)CC1] | a) Compound 25<br>b) paraformaldehyde<br>c) potassium acetate, NaBH$_3$CN in MeOH |

TABLE 24-continued
| Compound Structure | Starting materials and methods |
|---|---|
| 180 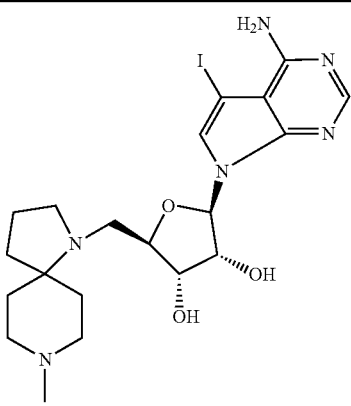 | a) Compound 26<br>b) Paraform<br>c) potassium acetate, NaBH₃CN in MeOH |
| 181 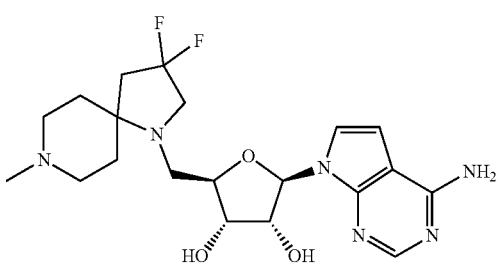 [SMILES: CN1CCC2(CC1)CC(F)(F)CN2C[C@H]1O[C@@H](n2ccc3c(N)ncnc32)[C@H](O)[C@@H]1O] | a) Compound 29<br>b) formaldehyde<br>c) NaBH₃CN in MeOH |
| 182 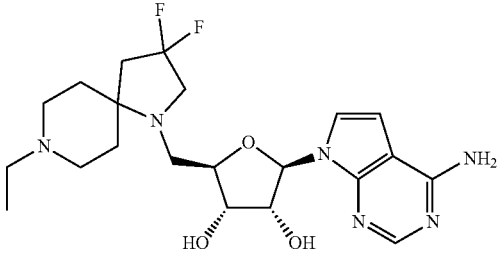 [SMILES: CCN1CCC2(CC1)CC(F)(F)CN2C[C@H]1O[C@@H](n2ccc3c(N)ncnc32)[C@H](O)[C@@H]1O] | a) Compound 29<br>b) Acetaldehyde<br>c) NaBH₃CN in MeOH |
| 183 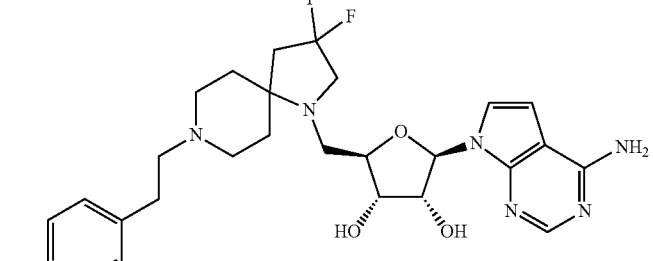 | a) Compound 29<br>b) (4-fluoro-phenyl)-acetaldehyde<br>c) NaBH₃CN in MeOH |
| 184 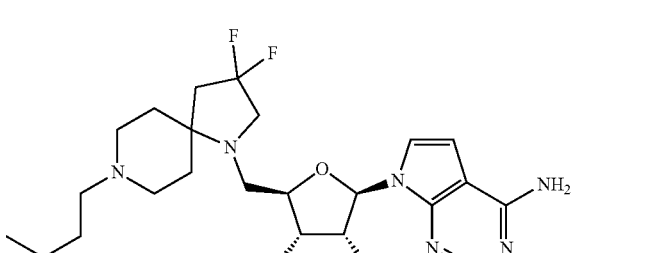 | a) Compound 29<br>b) isovaleraldehyde<br>c) NaBH₃CN in MeOH |

TABLE 24-continued
| Compound Structure | Starting materials and methods |
|---|---|
| 185 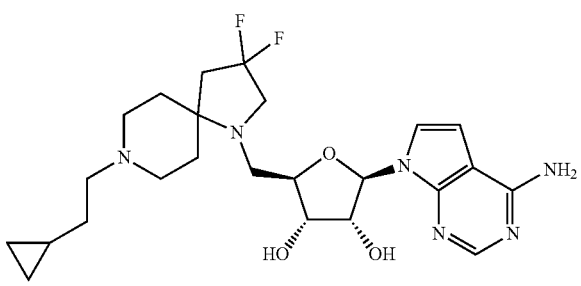 [SMILES: Nc1ncnc2c1ccn2[C@@H]1O[C@H](CN2CC(F)(F)CC23CCN(CCC2CC2)CC3)[C@@H](O)[C@H]1O] | a) Compound 29<br>b) 2-cyclopropylacetaldehyde: 50% (w/w) in toluene<br>c) NaBH$_3$CN in MeOH |
| 186 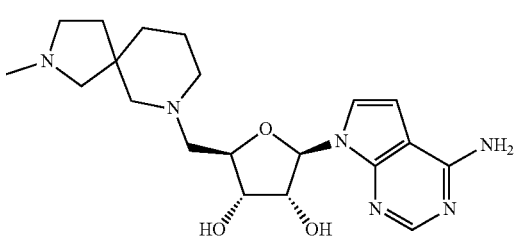 [SMILES: CN1CCC2(CCCN(C[C@H]3O[C@@H](n4ccc5c(N)ncnc54)[C@H](O)[C@@H]3O)C2)C1] | a) Compound 40<br>b) formaldehyde<br>c) NaBH$_3$CN in MeOH |
| 187 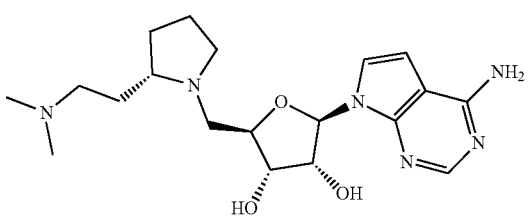 [SMILES: CN(C)CC[C@@H]1CCCN1C[C@H]1O[C@@H](n2ccc3c(N)ncnc32)[C@H](O)[C@@H]1O] | a) compound 57<br>b) Formaldehyde<br>c) NaBH$_3$CN in MeOH |
| 208 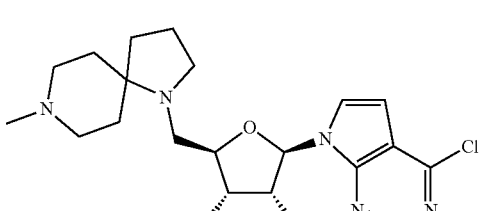 | a) Compound 64<br>b) Formaldehyde<br>c) NaBH$_3$CN in MeOH |
| 188 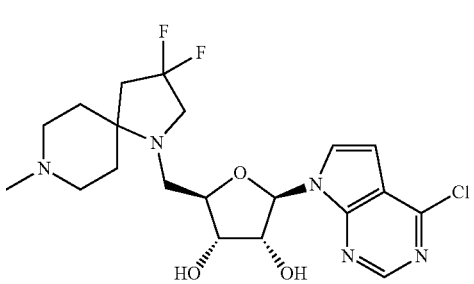 [SMILES: CN1CCC2(CC1)CC(F)(F)CN2C[C@H]1O[C@@H](n2ccc3c(Cl)ncnc32)[C@H](O)[C@@H]1O] | a) compound 63<br>b) Formaldehyde<br>c) NaBH$_3$CN in MeOH |

Example C2

Preparation of Final Compound 189

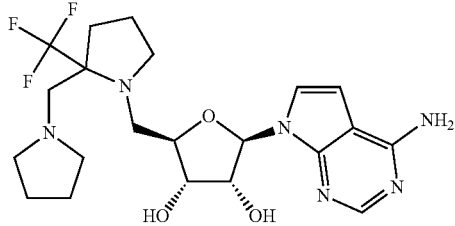 [SMILES: Nc1ncnc2c1ccn2[C@@H]1O[C@H](CN2CCCC2(CN2CCCC2)C(F)(F)F)[C@@H](O)[C@H]1O]

A mixture of compound 236 (210 mg, 0.46 mmol) 1,4-dibromobutane (119 mg, 0.55 mmol) and $K_2CO_3$ (317 mg, 2.3 mmol) in 20 ml of ACN was stirred at 66° C. for 24 hours. The solid was filtered off, the filtrate was concentrated under reduced pressure. The residue was purified by prep. HPLC, column: Waters Xbridge 150*25 5 u, gradient: $CH_3CN$/10 mM $NH_4HCO_3$ 20%-50%; Gradient Time: 12 min; FlowRate: 25 ml/min to afford final compound 189 (14.7 mg, 5% yield) as a white solid.

Example C3

Preparation of Final Compound 168

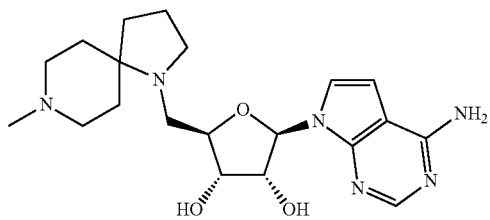 [SMILES: CN1CCC2(CCCN2C[C@H]2O[C@@H](n3ccc4c(N)ncnc43)[C@H](O)[C@@H]2O)CC1]

$Pd/C_{10\%}$ (50 mg, 0.047 mmol) was suspended in MeOH (40 mL) under nitrogen atmosphere. Thiophene 0.4% solution in DIPE (1 mL), final compound 19 (0.5 g, 1.29 mmol) and paraformaldehyde (0.116 g, 3.86 mmol) were added. The reaction was hydrogenated under hydrogen gas 1 atmosphere at 50° C. The catalyst was filtered off over a pad of Celite and washed several times with MeOH. The solvents of the filtrate were evaporated to give final compound 168 (0.52 g, yield: 94.3%).

Below final compounds were prepared by an analogous reaction protocol as was used for the preparation of final compound 168 using the appropriate starting materials (Table 25).

Example C4

Preparation of Final Compound 192

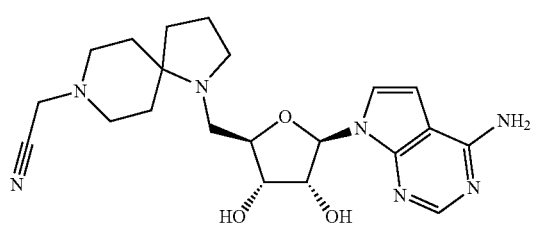 [SMILES: N#CCN1CCC2(CCCN2C[C@H]2O[C@@H](n3ccc4c(N)ncnc43)[C@H](O)[C@@H]2O)CC1]

A mixture of final compound 19 (0.1 g, 0.26 mmol), chloroacetonitrile (0.019 g, 0.26 mmol) and $Na_2CO_3$ (0.03 g, 0.28 mmol) in ACN (5 mL) was stirred and heated at 80° C. for 3 hours. The solvents were evaporated. The residue was dissolved in 20 mL MeOH and then filtered. The filtrate was purified with Prep HPLC (Stationary phase: RP XBridge Prep C18 OBD-10 μm, 30×150 mm, Mobile phase: 0.25% $NH_4HCO_3$ solution in water, MeOH) to give final compound 192 (35 mg, 0.082 mmol, yield: 31.8%).

Below final compounds were prepared by an analogous reaction protocol as was used for the preparation of final compound 192 using the appropriate starting materials (Table 26).

TABLE 25

| Compound | Structure | Starting materials and methods |
|---|---|---|
| 191 | (structure shown) | a) compound 62<br>b) formaldehyde |

TABLE 26

| Compound | Structure | Starting materials and conditions |
|---|---|---|
| 193 | 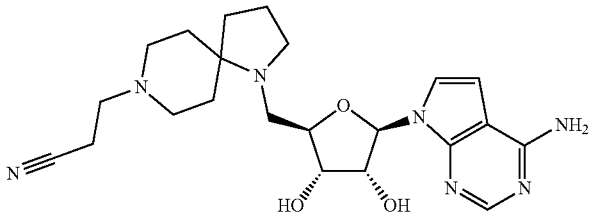 [SMILES: N#CCCN1CCC2(CCCN2C[C@H]2O[C@@H](n3ccc4c(N)ncnc43)[C@H](O)[C@@H]2O)CC1] | a) compound 19<br>b) Acrylonitrile<br>c) sodium carbonate, acetonitrile |
| 194 | 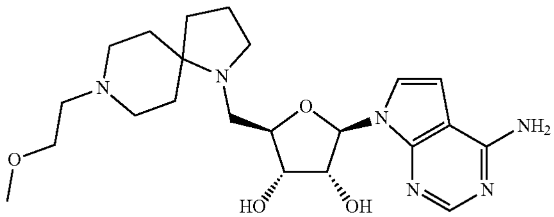 [SMILES: COCCN1CCC2(CCCN2C[C@H]2O[C@@H](n3ccc4c(N)ncnc43)[C@H](O)[C@@H]2O)CC1] | a) compound 19<br>b) 2-bromoethyl methyl ether<br>c) sodium carbonate, acetonitrile |
| 195 | 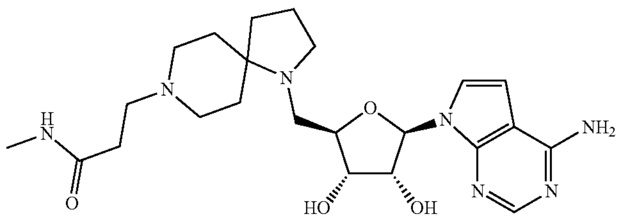 [SMILES: CNC(=O)CCN1CCC2(CCCN2C[C@H]2O[C@@H](n3ccc4c(N)ncnc43)[C@H](O)[C@@H]2O)CC1] | a) compound 19<br>b) 3-chloro-N-methylpropanamide<br>c) sodium carbonate, acetonitrile |
| 196 | 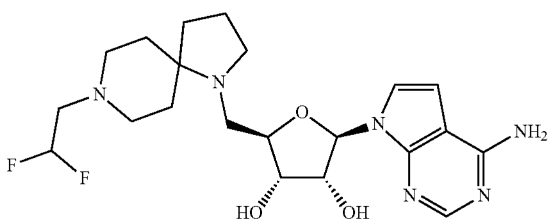 [SMILES: Nc1ncnc2c1ccn2[C@@H]1O[C@H](CN2CCCC23CCN(CC(F)F)CC3)[C@@H](O)[C@H]1O] | a) compound 19<br>b) 2-iodo-1,1-difluoroethane<br>c) sodium carbonate, acetonitrile |
| 197 | 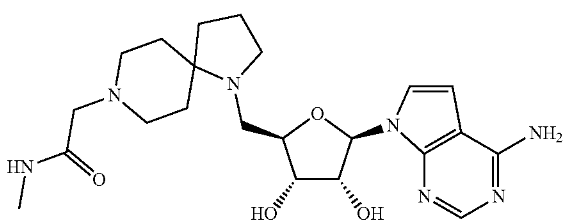 [SMILES: CNC(=O)CN1CCC2(CCCN2C[C@H]2O[C@@H](n3ccc4c(N)ncnc43)[C@H](O)[C@@H]2O)CC1] | a) compound 19<br>b) 2-chloro-N-methylacetamide<br>c) sodium carbonate, acetonitrile |
| 198 | 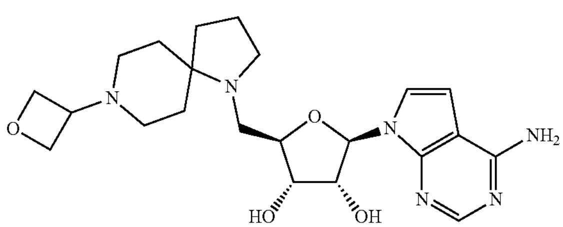 [SMILES: Nc1ncnc2c1ccn2[C@@H]1O[C@H](CN2CCCC23CCN(C2COC2)CC3)[C@@H](O)[C@H]1O] | a) compound 19<br>b) 3-bromooxetane<br>c) sodium carbonate, acetonitrile |
| 199 | 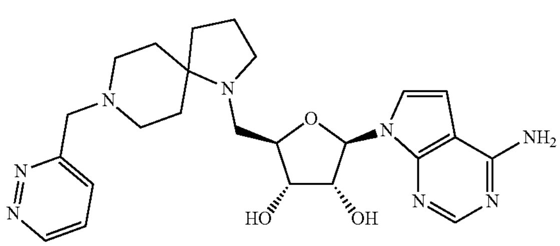 [SMILES: Nc1ncnc2c1ccn2[C@@H]1O[C@H](CN2CCCC23CCN(Cc2cccnn2)CC3)[C@@H](O)[C@H]1O] | a) compound 19<br>b) 3-(bromomethyl) pyridazine hydrobromide<br>c) sodium carbonate, acetonitrile |

TABLE 26-continued

| Compound | Structure | Starting materials and conditions |
|---|---|---|
| 200 | 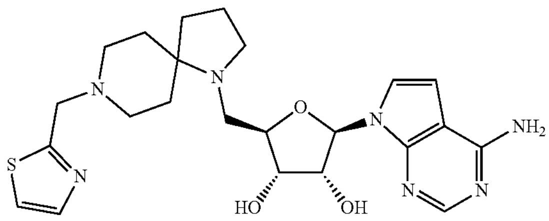 [SMILES: Nc1ncnc2c1ccn2[C@@H]1O[C@H](CN2CCCC23CCN(Cc2nccs2)CC3)[C@@H](O)[C@H]1O] | a) compound 19<br>b) 2-(chloromethyl) thiazole<br>c) sodium carbonate, acetonitrile |
| 201 | 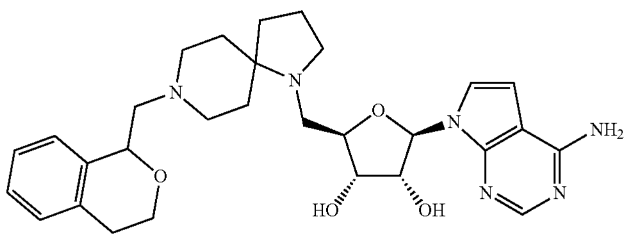 [SMILES: Nc1ncnc2c1ccn2[C@@H]1O[C@H](CN2CCCC23CCN(CC2OCCc4ccccc42)CC3)[C@@H](O)[C@H]1O] | a) compound 19<br>b) 1-(bromomethyl)-3,4-dihydro-1H-2-<br>c) sodium carbonate, acetonitrile |

Example C5

Preparation of Final Compound 202

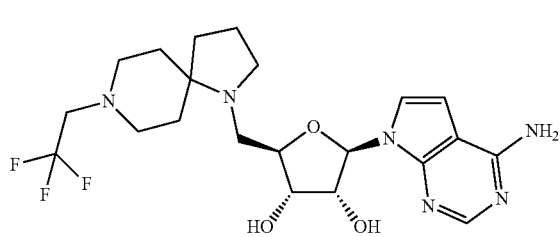 [SMILES: Nc1ncnc2c1ccn2[C@@H]1O[C@H](CN2CCCC23CCN(CC(F)(F)F)CC3)[C@@H](O)[C@H]1O]

2,2,2-trifluoroethyl methanesulfonate (0.46 g, 2.57 mmol) was added to a stirred solution of compound 19 (125 mg, 0.32 mmol) and Et$_3$N (0.36 mL, 2.57 mmol) in THF (5 mL) at room temperature. After addition the reaction mixture was stirred at room temperature for 2 days. The solvents were evaporated. The residue was dissolved in 10 mL MeOH and then purified with Prep HPLC (Stationary phase: RP XBridge Prep C18 OBD-10 μm, 30×150 mm, Mobile phase: 0.25% NH$_4$HCO$_3$ solution in water, MeOH yielding final compound 202 (1 mg, 0.0021 mmol, yield: 0.65%).

Example C6

Preparation of Final Compound 203

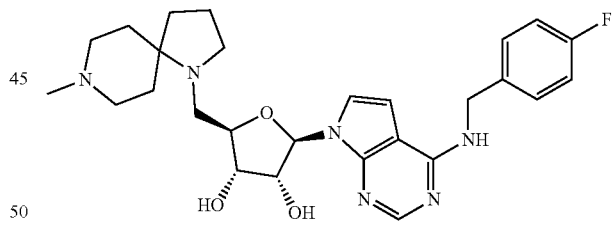

Compound 205 (100 mg, 0.24 mmol) and 4-fluorobenzylamine (29.7 mg, 0.24 mmol) in EtOH (5 mL) was stirred at 120° C. for 2 h. The reaction mixture was concentrated to dryness. A purification was performed via Prep HPLC (Stationary phase: RP SunFire Prep C18 OBD-10 μm, 30×150 mm, Mobile phase: 0.25% NH$_4$HCO$_3$ solution in water and MeCN) to give final compound 293 (27 mg, 22% yield).

Below final compounds were prepared by an analogous reaction protocol as was used for the preparation of final compound 203 using the appropriate starting materials (Table 27).

TABLE 27

| Compound | Structure | Starting materials and conditions |
|---|---|---|
| 204 | 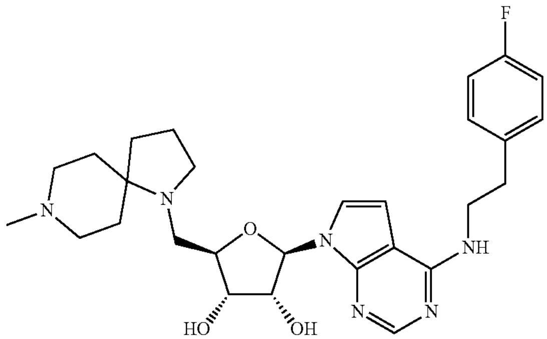 [SMILES: CN1CCC2(CCCN2C[C@H]2O[C@@H](n3ccc4c(NCCc5ccc(F)cc5)ncnc43)[C@H](O)[C@@H]2O)CC1] | a) Compound 208<br>b) 4-flurophenethylamine |
| 205 | 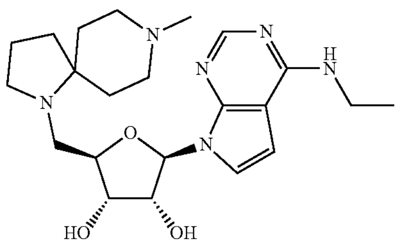 [SMILES: CCNc1ncnc2c1ccn2[C@@H]1O[C@H](CN2CCCC23CCN(C)CC3)[C@@H](O)[C@H]1O] | a) Compound 208<br>b) ethylamine |

Example C7

Synthesis of Final Compound 206 and Final Compound 207

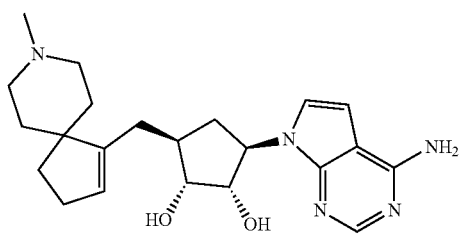 [SMILES: CN1CCC2(CCC=C2C[C@H]2C[C@@H](n3ccc4c(N)ncnc43)[C@H](O)[C@@H]2O)CC1]

Final Compound 206

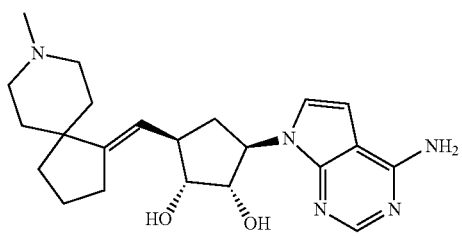 [SMILES: CN1CCC2(CCC/C2=C\[C@H]2C[C@@H](n3ccc4c(N)ncnc43)[C@H](O)[C@@H]2O)CC1]

Final Compound 207

NaBH(OAc)₃ (432.182 mg, 2.039 mmol) was added to a solution of a mixture of final compound 166 and final compound 167 (391 mg, 1 mmol), formaldehyde (0.107 mL, 1.43 mmol), AcOH (0.058 mL, 1 mmol) in MeOH (22 mL). The solution was stirred at room temperature for 2 h. Again NaBH(OAc)₃ (216 mg, 1 mmol) was added to the solution and the reaction was stirred overnight. Again NaBH(OAc)₃ (216 mg, 1 mmol) and formaldehyde (0.038 mL, 0.5 mmol) were added to the solution and the reaction was stirred overnight. The reaction was quenched with water/sat NaHCO₃ (50/50). The mixture was concentrated in vacuo. The residue was purified via Prep HPLC (Stationary phase: RP XBridge Prep C18 OBD-10 μm, 50×150 mm, Mobile phase: 0.25% NH₄HCO₃ solution in water, CH₃CN) yielding final compound 206 (220 mg, 54.3%) and final compound 297 (18.5 mg 4.6%)

Analytical Part

LCMS (Liquid chromatography/Mass spectrometry)

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times ($R_t$) and ions. If not specified differently in the table of data, the reported molecular ion corresponds to the [M+H]⁺ (protonated molecule) and/or [M−H]⁻ (deprotonated molecule). In case the compound was not directly ionizable the type of adduct is specified (i.e. [M+NH₄]⁺, [M+HCOO]⁻, etc. . . . ). For molecules with multiple isotopic patterns (Br, Cl), the reported value is the one obtained for the lowest isotope mass. All results were obtained with experimental uncertainties that are commonly associated with the method used.

Hereinafter, "SQD" means Single Quadrupole Detector, "MSD" Mass Selective Detector, "RT" r.t., "BEH" bridged ethylsiloxane/silica hybrid, "DAD" Diode Array Detector, "HSS" High Strength silica, "Q-Tof" Quadrupole Time-of-flight mass spectrometers, "CLND", ChemiLuminescent Nitrogen Detector, "ELSD" Evaporative Light Scanning Detector,

TABLE

LCMS Method codes (Flow expressed in mL/min; column temperature (T) in °C.; Run time in minutes).

| Method code | Instrument | column | mobile phase | gradient | Flow Col T | Run time |
|---|---|---|---|---|---|---|
| 1 | Waters: Acquity® UPLC® DAD and SQD | Waters: BEH C18 (1.7 μm, 2.1 * 50 mm) | A: 10 mM CH$_3$COONH$_4$ in 95% H$_2$O + 5% CH$_3$CN B: CH$_3$CN | From 95% A to 5% A in 1.3 min, held for 0.2 min, to 95% A in 0.2 min held for 0.1 min | 0.7 70 | 1.8 |
| 2 | Waters: Acquity® UPLC® - DAD and SQD | Waters: BEH C18 (1.7 μm, 2.1 * 50 mm) | A: 10 mM CH$_3$COONH$_4$ in 95% H$_2$O + 5% CH$_3$CN B: CH$_3$CN | From 95% A to 5% A in 1.3 min, held for 0.2 min, to 95% A in 0.2 min held for 0.1 min | 0.7 70 | 1.8 |
| 3 | Waters: Acquity® UPLC® - DAD and SQD | Waters: HSS T3 (1.8 μm, 2.1 * 100 mm) | A: 10 mM CH$_3$COONH$_4$ in 95% H$_2$O + 5% CH$_3$CN B: CH$_3$CN | From 100% A to 5% A in 2.10 min, to 0% A in 0.90 min, to 5% A in 0.5 min | 0.7 55 | 3.5 |
| 4 | Waters: Acquity® UPLC® - DAD and SQD | Waters: HSS T3 (1.8 μm, 2.1 * 100 mm) | A: 0.2% NH$_4$HCO$_3$ B: CH$_3$CN | From 96% A to 60% A in 2.10 min, to 0% A in 0.4 min, hold 0.8 min. to 95% A in 0.2 min | 0.6 55 | 3.5 |
| 5 | Waters: Acquity® UPLC® - DAD and SQD | BEH C18 column (1.7 μm, 2.1 × 50 mm; Waters Acquity) | A: 10 mM ammonium acetate in H$_2$O/acetonitrile 95/5; B: acetonitrile | 95% A and 5% B to 5% A and 95% B in 1.3 minutes and hold for 0.7 minutes | 0.8 55 | 2 |
| 6 | Waters: Acquity® UPLC® - DAD and SQD | Waters: HSS T3 (1.8 μm, 2.1 * 100 mm) | A: 10 mM CH$_3$COONH$_4$ in 95% H$_2$O + 5% CH$_3$CN B: CH$_3$CN | From 100% A to 5% A in 2.10 min, to 0% A in 0.90 min, to 5% A in 0.5 min | 0.7 55 | 3.5 |
| 7 | Agilent 1100/1200 - DAD and MSD | Waters: Atlantis® HILIC Silica (5 μm, 4.6 × 150 mm) | A: CF$_3$COOH 0.1% in water, B: CF$_3$COOH 0.05% in CH$_3$CN | 10% A for 10 min. | 0.8 50 | 10 |
| 8 | Agilent 1100/1200 - DAD and MSD | Waters: Atlantis® HILIC Silica (5 μm, 4.6 × 150 mm) | A: CF$_3$COOH 0.1% in water, B: CF$_3$COOH 0.05% in CH$_3$CN | 20% A for 10 min. | 0.8 50 | 10 |
| 9 | Agilent 1100/1200 - DAD and MSD | Agilent: TC-C18 (5 μm, 2.1 × 50 mm) | A: CF$_3$COOH 0.1% in water, B: CF$_3$COOH 0.05% in CH$_3$CN | 100% A for 1 min, to 40% A in 4 min, to 15% A in 2.5 min, back to 100% A in 2 min. | 0.8 50 | 10.5 |
| 10 | Agilent 1100/1200 - DAD and MSD | Waters: XBridge™ Shield RP18 (5 μm, 2.1 × 50 mm) | A: NH$_4$OH 0.05% in water, B: CH$_3$CN | 100% A for 1 min, to 40% A in 4 min, held for 2.5 min, back to 100% A in 2 min. | 0.8 40 | 10.5 |
| 11 | Agilent 1100-DAD and MSD | YMC: Pack ODS-AQ (3 μm, (4.6 × 50 mm) | A: HCOOH 0.1% in water B: CH$_3$CN | 95% A to 5% A in 4.8 min, held for 1 min, back to 95% A in 0.2 min. | 2.6 35 | 6 |
| 12 | Agilent 1290 Infinity DAD TOF-LC/MS G6224A | YMC-pack ODS-AQ C18 (50 × 4.6 mm, 3 μm) | A: 0.1% HCOOH in H$_2$O B: CH$_3$CN | ISET 2V1.0 Emulated Agilent Pump G1312A V1.0 From 94.51% A to 5% A in 4.8 min, held for 1.0 min, to 95% A in 0.2 min | 2.6 35 | 6.0 |
| 13 | Waters: Acquity® UPLC® - DAD and SQD | Waters: HSS T3 (1.8 μm, 2.1 * 100 mm) | A: 10 mM CH$_3$COONH$_4$ in 95% H$_2$O + 5% CH$_3$CN B: CH$_3$CN | From 100% A to 5% A in 2.10 min, to 0% A in 0.90 min, to 5% A in 0.5 min | 0.7 55 | 3.5 |

TABLE

Co. No. means compound number; Retention time ($R_t$) in min; n.d. means not determined.

| Co. No. | $R_t$ | [M+H]+ | LCMS Method | Co. No. | $R_t$ | [M+H]+ | LCMS Method |
|---|---|---|---|---|---|---|---|
| 91 | 0.33 | 362 | 11 | 31 | 1.11 | 377 | 4 |
| 14 | 0.25 | 390 | 12 | 92 | 1.34 | 391 | 4 |
| 2 | 0.35 | 376 | 11 | 93 | 1.42 | 501 | 3 |
| 84 | 0.22 | 362 | 11 | 57 | 1.27 | 363 | 4 |
| 88 | 0.24 | 348 | 12 | 29 | 0.90 | 425 | 3 |
| 89 | 0.27 | 348 | 12 | 67 | 0.97 | 484 | 5 |
| 1 | 0.24 | 404 | 11 | 170 | 1.42 | 511 | 3 |
| 78 | 0.24 | 376 | 11 | 174 | 2.42 | 429 | 4 |
| 13 | 0.28 | 390 | 11 | 169 | 1.36 | 485 | 3 |
| 6 | 0.25 | 376 | 12 | 187 | 0.79 | 391 | 6 |
| 17 | 0.24 | 362 | 11 | 171 | 1.00 | 497 | 2 |
| 76 | 1.21 | 390 | 4 | 270 | 0.91 | 430 | 6 |
| 11 | 0.33 | 390 | 11 | 56 | 1.02 | 349 | 4 |
| 12 | 0.22 | 390 | 11 | 191 | 0.82 | 389 | 6 |
| 3 | 0.85 | 376 | 11 | 54 | 0.98 | 335 | 4 |
| 5 | 0.22 | 376 | 11 | 53 | 1.15 | 349 | 4 |
| 86 | 0.26 | 362 | 11 | 48 | 0.73 | 365 | 6 |
| 75 | 0.22 | 390 | 11 | 49 | 1.03 | 365 | 4 |
| 83 | 0.29 | 362 | 11 | 52 | 1.38 | 363 | 4 |
| 9 | 0.23 | 390 | 11 | 60 | 0.78 | 349 | 6 |
| 79 | 0.22 | 376 | 11 | 47 | 0.97 | 379 | 4 |
| 4 | 0.24 | 376 | 11 | 55 | 1.08 | 363 | 4 |
| 16 | 0.23 | 404 | 11 | 51 | 1.21 | 363 | 4 |
| 7 | 0.26 | 376 | 11 | 15 | 0.26 | 390 | 11 |
| 81 | 0.27 | 376 | 12 | 77 | 0.27 | 376 | 12 |
| 80 | 0.33 | 376 | 12 | 201 | 2.76 | 535 | 4 |
| 82 | 0.26 | 376 | 12 | 197 | 1.77 | 460 | 4 |
| 8 | 0.23 | 390 | 11 | 195 | 1.70 | 474 | 4 |
| 87 | 0.26 | 362 | 12 | 193 | 2.04 | 442 | 4 |
| 18 | 0.30 | 362 | 12 | 199 | 1.81 | 481 | 4 |
| 90 | 0.27 | 390 | 11 | 173 | 2.77 | 527 | 4 |
| 10 | 0.28 | 390 | 11 | 177 | 2.23 | 519 | 4 |
| 58 | 0.35 | 364 | 2 | 175 | 2.52 | 469 | 4 |
| 59 | 1.17 | 364 | 4 | 176 | 2.35 | 500 | 4 |
| 62 | 0.87 | 375 | 6 | 172 | 2.20 | 480 | 4 |
| 19 | 0.81 | 389 | 3 | 192 | 1.07 | 428 | 3 |
| 20 | 0.80 | 389 | 3 | 196 | 1.20 | 453 | 3 |
| 168 | 0.39 | 403 | 5 | 200 | 1.14 | 486 | 3 |
| 74 | 1.41 | 389 | 4 | 194 | 0.75 | 447 | 3 |
| 45 | 1.23 | 375 | 4 | 72 | 0.78 | 365 | 3 |
| 27 | 0.78 | 404 | 6 | 113 | 4.37 | 403 | 10 |
| 208 | 1.21 | 422 | 3 | 147 | 3.59 | 439 | 10 |
| 95b | 1.60 | 543 | 3 | 156 | 2.28 | 399 | 9 |
| 95a | 1.60 | 543 | 3 | 145 | 4.25 | 507 | 10 |
| 203 | 0.92 | 511 | 2 | 139 | 2.62 | 511 | 9 |
| 205 | 2.23 | 431 | 4 | 154 | 3.37 | 469 | 10 |
| 204 | 1.56 | 525 | 3 | 152 | 2.43 | 427 | 9 |
| 114 | 4.37 | 403 | 8 | 137 | 3.60 | 457 | 10 |
| 198 | 1.00 | 445 | 3 | 71b | 0.86 | 385 | 3 |
| 24 | 0.83 | 407 | 6 | 71a | 0.85 | 385 | 3 |
| 179 | 1.02 | 481 | 6 | 73b | 0.84 | 385 | 3 |
| 202 | 0.68 | 471 | 5 | 73a | 0.83 | 385 | 3 |
| 112 | 5.09 | 375 | 10 | 146 | 2.57 | 453 | 9 |
| 28 | 4.00 | 403 | 10 | 143 | 3.29 | 547 | 9 |
| 122 | 2.31 | 403 | 7 | 161 | 3.70 | 403 | 10 |
| 121 | 2.30 | 403 | 7 | 150 | 3.32 | 433 | 10 |
| 133 | 3.38 | 389 | 10 | 65 | 3.84 | 437 | 10 |
| 188 | 1.34 | 458 | 3 | 115 | 2.88 | 457 | 9 |
| 30 | 3.58 | 417 | 10 | 141 | 3.91 | 471 | 10 |
| 63 | 1.23 | 444 | 6 | 142 | 3.79 | 417 | 10 |
| 110 | 2.76 | 391 | 10 | 116 | 2.89 | 457 | 9 |
| 111 | 2.74 | 391 | 10 | 105 | 3.98 | 579 | 9 |
| 108 | 3.06 | 405 | 10 | 107 | 3.95 | 565 | 9 |
| 178 | 0.94 | 421 | 3 | 148 | 0.34 | 391 | 1 |
| 38 | 3.40 | 425 | 10 | 155 | 2.52 | 453 | 9 |
| 181 | 1.00 | 439 | 3 | 118 | 4.90 | 403 | 10 |
| 32 | 3.61 | 405 | 10 | 117 | 4.76 | 403 | 10 |
| 68 | 0.78 | 390 | 6 | 42 | 3.46 | 417 | 10 |
| 127 | 4.46 | 361 | 10 | 43 | 3.59 | 417 | 10 |
| 124 | 3.98 | 387 | 10 | 164 | 3.94 | 563 | 9 |
| 136 | 3.61 | 425 | 10 | 144 | 3.52 | 464 | 10 |
| 135 | 3.46 | 403 | 10 | 140 | 3.26 | 428 | 10 |
| 119 | 3.40 | 389 | 10 | 180 | 0.65 | 529 | 1 |
| 125 | 3.61 | 401 | 10 | 123 | 3.75 | 437 | 10 |
| 120 | 3.47 | 389 | 10 | 162 | 2.33 | 441 | 10 |
| 109 | 2.88 | 377 | 10 | 40 | 0.86 | 389 | 6 |
| 126 | 3.99 | 423 | 10 | 39 | 0.40 | 389 | 5 |
| 101 | 1.84 | 579 | 3 | 98 | 0.57 | 487 | 5 |
| 103 | 1.82 | 579 | 6 | 106 | 3.79 | 577 | 9 |
| 50 | 0.99 | 399 | 3 | 94 | 0.79 | 529 | 5 |
| 66 | 3.95 | 402 | 10 | 37 | 0.34 | 405 | 5 |
| 61 | 4.19 | 388 | 10 | 33 | 1.36 | 405 | 4 |
| 151 | 3.24 | 413 | 10 | 34 | 1.36 | 405 | 4 |
| 104 | 3.29 | 543 | 9 | 129 | 2.81 | 393 | 10 |
| 131 | 3.06 | 419 | 10 | 189 | 4.15 | 471 | 10 |
| 186 | 0.43 | 403 | 5 | 35 | 0.94 | 403 | 6 |
| 182 | 1.01 | 453 | 6 | 36 | 0.95 | 403 | 6 |
| 183 | 1.60 | 547 | 6 | 41 | 1.07 | 457 | 6 |
| 184 | 1.39 | 495 | 6 | 163 | 4.07 | 401 | 10 |
| 185 | 1.30 | 493 | 6 | 128 | 3.99 | 413 | 10 |
| 160 | 3.26 | 399 | 10 | 134 | 3.19 | 379 | 10 |
| 132 | 2.58 | 365 | 10 | 166 | 0.99 | 384 | 6 |
| 130 | 3.09 | 455 | 10 | 167 | 1.03 | 384 | 3 |
| 96 | 0.56 | 473 | 5 | 207 | 1.01 | 398 | 6 |
| 99 | 0.42 | 445 | 5 | 206 | 1.09 | 398 | 3 |
| 157 | 3.51 | 427 | 10 | 85 | 0.81 | 362 | 6 |
| 159 | 4.16 | 453 | 10 | | | | |

Melting Points

Values are peak values, and are obtained with experimental uncertainties that are commonly associated with this analytical method.

DSC823e

For a number of compounds, melting points were determined with a DSC823e (Mettler-Toledo). Melting points were measured with a temperature gradient of 10° C./minute. Maximum temperature was 300° C.

Co 183: 132.73° C.

Mettler Toledo MP50 Apparatus

For a number of compounds, m.p. were determined in open capillary tubes on a Mettler Toledo MP50 apparatus. M.p. were measured with a temperature ranging from 50° C. to 300° C., using a gradient of 10° C./minute. The m.p. value was read from a digital display.

Co. 84: 115.1° C.; Co. 78: 132.4° C.; Co. 13: 121.6° C.; Co. 12: 109.8° C.; Co. 5: 219.8° C.; Co. 1: 140.1° C.; Co. 83: 127.0° C.; Co. 9: 219.0° C.; Co. 79: 172.8° C.; Co. 4: 107.7° C.; Co. 16: 106.0° C.; Co. 7: 181.3° C.; Co. 81: 115.8° C.; Co. 80: 102.8° C.; Co. 82: 240.2° C.; Co. 8: 118.9° C.; Co. 77: 223.9° C.

NMR

For a number of compounds, $^1$H NMR spectra were recorded on a Bruker DPX-400 spectrometer operating at 400 MHz, on a Bruker DPX-360 operating at 360 MHz, on a Bruker Avance 600 spectrometer operating at 600 MHz. As solvents CHLOROFORM-d (deuterated chloroform, $CDCl_3$) or DMSO-$d_6$ (deuterated DMSO, dimethyl-d6 sulfoxide) were used. Chemical shifts (δ) are reported in parts per million (ppm) relative to tetramethylsilane (TMS), which was used as internal standard.

Co. 166: $^1$H NMR (600 MHz, DMSO-$d_6$) δ ppm 1.24 (dq, J=13.6, 2.3 Hz, 1H) 1.30 (br dq, J=13.6, 2.3 Hz, 1H) 1.42 (ddd, J=12.9, 10.4, 8.5 Hz, 1H) 1.75-1.83 (m, 2H) 1.83-1.90 (m, 2H) 1.97 (brdd, J=15.7, 8.9 Hz, 1H) 2.11-2.17 (m, 1H) 2.17-2.21 (m, 2H) 2.21-2.25 (m, 1H) 2.25-2.30 (m, 1H) 2.87 (tt, J=13.1, 2.9 Hz, 2H) 3.15-3.21 (m, 2H) 3.69 (br t, J=4.5 Hz, 1H) 4.30 (br t, J=6.7 Hz, 1H) 4.66 (br s, 1H) 4.79 (dt, J-=10.3, 8.4 Hz, 1H) 4.85 (br s, 1H) 5.46 (t, J=1.8 Hz, 1H) 6.53 (d, J=3.5 Hz, 1H) 6.90 (br s, 2H) 7.22 (d, J=3.5 Hz, 1H) 8.03 (s, 1H).

Co. 167: $^1$H NMR (600 MHz, DMSO-$d_6$) δ ppm 1.19-1.31 (m, 2H) 1.35-1.49 (m, 2H) 1.49-1.68 (m, 5H) 2.20-2.32 (m, 2H) 2.35-2.41 (m, 1H) 2.52-2.60 (m, 2H) 2.64 (qd, J=8.7, 4.8 Hz, 1H) 2.79 (br t, J=12.9 Hz, 2H) 3.72 (t, J=5.2 Hz, 1H) 4.20 (dd, J=7.3, 5.9 Hz, 1H) 4.68 (br s, 1H) 4.78-4.88 (m, 2H) 5.27 (dt, J=9.0, 2.5 Hz, 1H) 6.54 (d, J=3.5 Hz, 1H) 6.90 (br s, 2H) 7.25 (d, J=3.5 Hz, 1H) 8.03 (s, 1H).

Co. 29: $^1$H NMR (360 MHz, DMSO-$d_6$) δ ppm 1.31 (br t, J=10.6 Hz, 2H) 1.45-1.63 (m, 2H) 2.10-2.32 (m, 2H) 2.42 (br t, J=12.1 Hz, 2H) 2.61 (dd, J=13.7, 5.7 Hz, 1H) 2.78-2.96 (m, 3H) 3.05-3.25 (m, 2H) 3.84 (q, J=5.1 Hz, 1H) 4.05 (br s, 1H) 4.35 (br s, 1H) 5.13 (br s, 1H) 5.34 (br s, 1H) 6.03 (d, J=5.1 Hz, H) 6.60 (d, J=3.7 Hz, 1H) 7.02 (br s, 2H) 7.28 (d, J=3.7 Hz, 1H) 8.06 (s, 1H).

Co. 95b: $^1$H NMR (360 MHz, CHLOROFORM-d) δ ppm 1.10 (dd, J=15.4, 7.0 Hz, 6H) 1.20 (dd, J=7.0, 1.1 Hz, 6H) 1.27-1.37 (m, 2H) 1.56-1.77 (m, 6H) 2.00 (br t, J=11.2 Hz, 2H) 2.27 (s, 3H) 2.46-2.67 (m, 2H) 2.70-2.90 (m, 6H) 4.26 (q, J=4.6 Hz, 1H) 5.13 (s, 2H) 5.52 (t, J=5.3 Hz, 1H) 5.67 (t, J=5.5 Hz, 1H) 6.39-6.47 (m, 2H) 7.18 (d, J=4.0 Hz, 1H) 8.34 (s, 1H).

Co. 94: $^1$H NMR (360 MHz, DMSO-$d_6$) δ ppm 0.98 (d, J=7.0 Hz, 3H) 1.03 (d, J=7.0 Hz, 3H) 1.12 (dd, J=6.8, 5.7 Hz, 6H) 1.35 (br d, J=13.5 Hz, 2H) 1.61-1.91 (m, 6H) 2.53-2.66 (m, 2H) 2.67-2.92 (m, 6H) 3.25 (br t, J=12.1 Hz, 2H) 4.14 (q, J=5.1 Hz, 1H) 5.51 (t, J=5.3 Hz, 1H) 5.74 (t, J=5.7 Hz, 1H) 6.21 (d, J=5.5 Hz, 1H) 6.65 (d, J=3.7 Hz, 1H) 7.14 (br s, 2H) 7.34 (d, J=3.7 Hz, 1H) 8.10 (s, 1H) 8.91 (br s, 2H).

Co. 207: $^1$H NMR (400 MHz, DMSO-$d_6$) δ ppm 1.14-1.39 (m, 2H) 1.48-1.63 (m, 7H) 1.87-2.02 (m, 2H) 2.15 (s, 3H) 2.20-2.42 (m, 3H) 2.57-2.68 (m, 3H) 3.71 (t, J=5.2 Hz, 1H) 4.19 (dd, J=7.5, 5.7 Hz, 1H) 4.64-4.90 (m, 1H) 5.23-5.32 (m, 1H) 6.54 (d, J=3.5 Hz, 1H) 6.88 (br s, 2H) 7.25 (d, J=3.5 Hz, 1H) 8.03 (s, 1H). Co. 19: $^1$H NMR (360 MHz, DMSO-$d_6$) δ ppm 1.08-1.19 (m, 2H) 1.39 (td, J=12.5, 4.6 Hz, 1H) 1.46-1.73 (m, 5H) 2.40-2.48 (m, 2H) 2.52-2.57 (m, 1H) 2.61-2.72 (m, 1H) 2.75-2.93 (m, 4H) 3.79-3.89 (m, 1H) 4.03 (t, J=4.6 Hz, 1H) 4.37 (t, J=5.3 Hz, 1H) 5.11 (br s, 1H) 5.32 (br s, 1H) 6.04 (d, J=5.9 Hz, 1H) 6.60 (d, J=3.7 Hz, 1H) 7.02 (br s, 2H) 7.33 (d, J=3.7 Hz, 1H) 8.07 (s, 1H).

Co. 206: $^1$H NMR (400 MHz, DMSO-$d_6$) δ ppm 1.02-1.15 (m, 2H) 1.32-1.43 (m, 1H) 1.63-1.79 (m, 4H) 1.87-2.00 (m, 3H) 2.05-2.31 (m, 8H) 2.61-2.70 (m, 2H) 3.61-3.74 (m, 1H) 4.27 (dd, J=8.1, 5.5 Hz, 1H) 4.41-5.00 (m, 3H) 5.38 (br s, 1H) 6.53 (d, J=3.5 Hz, 1H) 6.88 (br s, 2H) 7.24 (d, J=3.5 Hz, 1H) 8.02 (s, 1H).

Co. 181: $^1$H NMR (360 MHz, DMSO-$d_6$) δ ppm 1.32 (br t, J=11.2 Hz, 2H) 1.59-1.81 (m, 2H) 1.81-1.92 (m, 2H) 1.98-2.25 (m, 5H) 2.58 (dd, J=13.5, 5.5 Hz, 1H) 2.73 (br d, J=11.3 Hz, 2H) 2.85 (dd, J=13.4, 4.9 Hz, 1H) 2.97-3.26 (m, 2H) 3.84 (q, J=5.1 Hz, 1H) 4.04 (t, J=4.8 Hz, 1H) 4.13 (br s, 1H) 4.36 (t, J=5.3 Hz, 1H) 5.47 (br s, 1H) 6.03 (d, J=5.5 Hz, 1H) 6.60 (d, J=3.7 Hz, 1H) 7.02 (br s, 2H) 7.31 (d, J=3.7 Hz, 1H) 8.05 (s, 1H).

Co. 101: $^1$H NMR (600 MHz, CHLOROFORM-d) δ ppm 1.09 (d, J=7.0 Hz, 3H) 1.13 (d, J=7.0 Hz, 3H) 1.19 (d, J=7.0 Hz, 3H) 1.20 (d, J=6.9 Hz, 3H) 1.49-1.57 (m, 1H) 1.50-1.60 (m, 1H) 1.78 (br s, 1H) 1.92 (br t, J=11.2 Hz, 1H) 1.99-2.08 (m, 2H) 2.09-2.19 (m, 1H) 2.27-2.32 (m, 1H) 2.33 (s, 3H) 2.48-2.56 (m, 1H) 2.56-2.63 (m, 1H) 2.76 (dd, J=14.2, 3.6 Hz, 1H) 2.93 (br t, J=13.6 Hz, 2H) 2.98 (dd, J=14.4, 3.4 Hz, 1H) 3.08 (td, J=15.1, 11.6 Hz, 1H) 3.34-3.41 (m, 1H) 4.20-4.23 (m, 1H) 5.21 (s, 2H) 5.52 (t, J=5.4 Hz, 1H) 5.66 (t, J=5.9 Hz, 1H) 6.43 (d, J=5.9 Hz, 1H) 6.45 (d, J=3.7 Hz, 1H) 7.17 (d, J=3.8 Hz, 1H) 8.35 (s, 1H).

Co. 179: $^1$H NMR (360 MHz, DMSO-$d_6$) δ ppm 1.15 (br t, J=11.7 Hz, 2H) 1.47-1.73 (m, 6H) 1.85-1.96 (m, 2H) 2.15 (s, 3H) 2.45-2.48 (m, 1H) 2.58-2.68 (m, 1H) 2.72 (br d, J=10.6 Hz, 2H) 2.76-2.88 (m, 2H) 3.86 (dt, J=6.3, 4.3 Hz, 1H) 4.02 (br q, J=4.0 Hz, 1H) 4.34 (q, J=5.1 Hz, 1H) 5.08 (br d, J=4.4 Hz, 1H) 5.32 (d, J=6.2 Hz, 1H) 6.07 (d, J=5.5 Hz, 1H) 6.78 (br s, 2H) 7.78 (s, 1H) 8.11 (s, 1H).

Co. 168: $^1$H NMR (360 MHz, DMSO-$d_6$) δ ppm 1.10-1.20 (m, 2H) 1.50-1.76 (m, 6H) 1.87-1.98 (m, 2H) 2.16 (s, 3H) 2.44-2.48 (m, 1H) 2.59-2.86 (m, 5H) 3.80-3.89 (m, 1H) 3.98-4.07 (m, 1H) 4.37 (t, J=5.3 Hz, 1H) 5.08 (br s, 1H) 5.27 (br s, 1H) 6.04 (d, J=5.9 Hz, 1H) 6.60 (d, J=3.7 Hz, 1H) 7.01 (br s, 2H) 7.35 (d, J=3.7 Hz, 1H) 8.06 (s, 1H).

Co. 108: $^1$H NMR (400 MHz, METHANOL-$d_4$) δ ppm 1.57-1.81 (m, 4H) 2.68 (br t, J=12.3 Hz, 2H) 2.74-2.91 (m, 4H) 2.96 (br d, J=13.1 Hz, 2H) 3.67 (br d, J=4.8 Hz, 4H) 4.00 (q, J=5.5 Hz, 1H) 4.27 (t, J=5.6 Hz, 1H) 4.40 (t, J=4.8 Hz, 1H) 6.15 (d, J=4.3 Hz, 1H) 6.65 (d, J=3.8 Hz, 1H) 7.36 (d, J=3.8 Hz, 1H) 8.09 (s, 1H).

Co. 74: $^1$H NMR (360 MHz, DMSO-$d_6$) δ ppm 1.31-1.53 (m, 4H) 2.20 (s, 3H) 2.30 (br s, 2H) 2.44 (br dd, J=13.4, 6.4 Hz, 3H) 2.64 (dd, J=13.4, 4.2 Hz, 1H) 2.76 (t, J=6.4 Hz, 2H) 2.91-2.98 (m, 2H) 3.87-3.98 (m, 1H) 4.02 (t, J=5.3 Hz, 1H) 4.29 (t, J=5.1 Hz, 1H) 5.16 (br s, 1H) 5.34 (br s, 1H) 6.03 (d, J=4.8 Hz, 1H) 6.60 (d, J=3.7 Hz, 1H) 7.03 (br s, 2H) 7.30 (d, J=3.7 Hz, 1H) 8.06 (s, 1H).

EXPERIMENTAL PROCEDURES IN VITRO ASSAY (ASSAY 1)

Reagents.

PRMT5-MEP50 enzyme was purchased from Charles River (Argenta). The enzyme complex was produced in insect cells (Sf9) infected simultaneously with two baculoviruses. One virus expresses full length human PRMT5 with Flag-tag at N-terminus, the second virus expresses full length MEP50 with His6-TEV cleavage at N-terminus. The protein was affinity purified using anti-Flag (M2) beads eluted with 3×FLAG peptide, followed by His-Select eluted with 0.5M imidazole. Eluted protein was then dialysed against tris-buffered saline (TBS) (pH 8.0) containing 20% glycerol and 3 mM dithiothreitol (DTT).

Full-length untagged human recombinant histone H2A (residues 1-130, Genbank Accession #NM_021052, MW=14.1 kDa) expressed in *E. coli* was purchased from Reaction Biology Corporation, Cat #HMT-11-146. Reagents used for making reaction buffer or stopping reaction were purchased including Tris base (Sigma Cat #T-1503), NaCl (Sigma Cat #RGF-3270), $MgCl_2$ (Sigma Cat #M0250), DTT (Invitrogen Cat #15508-013) and Formic Acid (Riedel deHaen, Cat #33015)

High Throughput Mass Spectrometer Assay

PRMT5 catalyzes the sequential methylations of the terminal nitrogen atoms on the guanidine groups of arginine residues within proteins using co-substrate S-adenosyl-L-methionine (AdoMet, SAM), forming mono-methyl (MMA), symmetric-dimethyl arginine (sDMA) and S-adenosyl-L-homocysteine (AdoHcy, SAH). The enzyme activity was determined by following the product SAH formation using high throughput mass spectrometry (Agilent Rapidfire 300 System coupled to a Sciex 4000 series QTrapm triple-quad MS/MS). The reaction buffer was 20 mM Tris-HC, pH 8.5, 50 mM NaCl, 5 mM $MgCl_2$ and 1 mM DTT. The reaction activity was stopped using 1% formic acid (final concentration).

Inhibition Studies.

The $IC_{50}$ Studies were performed using eleven point dosing series made for each compound by serially diluted 1:2 in dimethyl sulfoxide (DMSO), with point 12 being a DMSO control. Compounds were first spotted to plates, and followed by addition of 2 µM SAM and 0.6 µM H2A (histone H2A) solution mixture. The same volume of enzyme solution was added to initiate the enzymatic reactions. The final concentrations of the reaction are at 1 µM SAM, 0.3 µM H2A and 10 nM enzyme. The reaction was incubated at 30° C. for 60 minutes (min) and then quenched by addition of formic acid to a final concentration of 1%. The inhibitions of SAH formation in the presence of compounds were calculated as a percentage of the control relative to the uninhibited reaction as a function of inhibitor concentration. The data were fit as follows:

$$Y = \text{Bottom} + (Top - \text{Bottom})/(1+10^{\wedge}((\log IC_{50}-X)*h))$$

where $IC_{50}$ is the inhibitor concentration (same unit as X) at 50% inhibition and h is the Hill slope. Y is percent of inhibition, X is log of compound concentration. Bottom and Top are the plateaus in same units as Y.

EXPERIMENTAL PROCEDURE PD ASSAY
(ASSAY 2)

Reagents

A549 cells (ATCC, Cat #CCL-185) were cultured in Dulbecco's Modified Eagle's Medium (DMEM) (Sigma, Cat #D5796), supplemented with 10% Fetal Calf Serum (FCS)(HyClone™, Cat #SV30160.03), 100 mM Sodium Pyruvate (Sigma, Cat #S8636), 200 mM L-Glutamine (Sigma, Cat #G7513) and 50 mg/mL Gentamycing (Gibco, Cat #15750-037).

Reagents used for buffers were purchased: Dulbecco's phosphate buffered saline (DPBS) without Ca/Mg (Sigma, Cat #D8537), phosphate buffered saline (PBS) 10× (Roche, Cat #11 666 789 001), Formalin solution 10% (Sigma, HT50-1-128-4L), MeOH 100% (Sigma, Cat #32213-2.5L), Triton X-100 (Acros, Cat #215680010), Bovine Serum Albumin (BSA) (Sigma, Cat #A2153), Alexa fluor 488 goat anti-rabbit antibody (Life Technologies, Cat #A11034), HCS CellMask Deep Red Stain (Life Technologies, Cat #H32721), Hoechst Stain (Life Technologies, Cat #33258), Anti-dimethyl-Arginine, sym (SYM10) antibody (Millipore, 07-412).

Immunohistochemistry Procedure

Cells were plated at 400 cells/40 µL/well in 384 well black plates µclear bottom (Perkin Elmer) and overnight incubated at 37° C., 5% $CO_2$. The $IC_{50}$ Studies were performed using nine point dosing series ranging from 10 µM to 1 µM for each compound. 80 nL of the respective dilution of the compounds was added using the Labcyte POD 810 (Labcyte) reaching a final DMSO concentration of 0.2% in cell culture. After an incubation period of 48 h at 37° C. and 5% $CO_2$, cells were fixed in 10% formalin solution for 15 min at r.t. and 20 min in ice-cold MeOH, after which they were washed 3× in DPBS. Subsequently, the cells were blocked for 1 h in blocking buffer (PBS+1% BSA and 0.5% Triton X-100) and incubated overnight at 4° C. with the SYM10 antibody diluted 1/2000 in blocking buffer. The cells were washed 3× with washing buffer (PBS+0.1% Triton X-100) and incubated with the Alexa fluor 488 goat anti-rabbit antibody diluted 1/200 in blocking buffer for 1 h at r.t. Subsequently, they were washed 3× with washing buffer and incubated for 30 min at r.t. with PBS containing a 1/5000 dilution of Hoechst Stain and a 1/5000 dilution of the HCS CellMask Deep Red Stain. After a final wash with PBS, the plates were imaged using the 10×W lens of the Opera® system (Perkin Elmer Life Sciences) using following settings (values in nm):

| laser | Filter camera | Primary dichrome | Detect dichrome |
|---|---|---|---|
| 488 | 540/75 | 405/488/561/635 | 510 |
| 405 | 450/50 | 405/488/561/635 | 510 |
| 635 | 690/50 | 405/488/561/635 | 510 |

Analyses:

The inhibition of nuclear symmetric Arginine dimethylation in the presence of compounds (% effect) was calculated as the "median nuclear SYM10 intensity"/"median cytoplasmic SYM10 intensity", normalized by below equation:

$$\text{normalized} = 100 - \frac{\text{raw} - \text{lowMedian}}{\text{highMedian} - \text{lowMedian}} * 100$$

In the above equations, the following variable names are use:

| | |
|---|---|
| normalized | The normalized feature value |
| raw | The raw feature value |
| lowMedian | The median of the raw values of the low control wells |
| highMedian | The median of the raw values of the high control wells |

In the above equations, the following controls were used for normalization:

Low control: minimum level of symmetrically dimethylated Arginines (cells treated with reference compound at 10 µM).

High control: maximum level of symmetrically dimethylated Arginines (DMSO treated cells).

$IC_{50}$ and $pIC_{50}$ ($-\log IC_{50}$) values were calculated using the appropriate software.

$pIC_{50}$ values (Co. No. means compound number; n.d. means not determined). In case several measurements were done on the same compound, all individual measurements are shown in the Table below.

| Co. No. | $pIC_{50}$ Assay 1 | $pIC_{50}$ Assay 2 |
|---|---|---|
| 1 | 6.66 | 5.14 |
| 2 | 6.11 | <5 |
| 3 | 5.78 | <5 |
| 4 | 5.64 | <5 |
| 5 | 5.09 | <5 |
| 6 | <4 | n.d. |
| 7 | 4.18 | <5 |
| 8 | 6.81 | 5.82 |
| 9 | 6.11 | <5 |
| 10 | 4.41 | <5 |
| 10 | 4.61 | <5 |
| 11 | 4.91 | <5 |
| 12 | 4.17 | <5 |
| 13 | 6.02 | <5 |
| 14 | 6.01 | <5 |
| 15 | 4.53 | <5 |
| 16 | 4.65 | <5 |
| 17 | <4 | n.d. |
| 18 | 5.07 | <5 |
| 19 | 7.36 | 6.93 |
| 19 | 7.94 | 7.24 |

| Co. No. | pIC$_{50}$ Assay 1 | pIC$_{50}$ Assay 2 |
|---|---|---|
| 24 | 7.93 | ~7.17 |
| 27 | 5.87 | <5 |
| 28 | 7.58 | 5.94 |
| 29 | 7.99 | ~7.22 |
| 29 | 8.12 | ~7.35 |
| 30 | 6.70 | 5.76 |
| 31 | 7.40 | ~5.84 |
| 32 | 5.35 | 5.04 |
| 33 | 6.62 | 4.92 |
| 34 | 5.40 | <4.7 |
| 35 | 6.98 | ~5.21 |
| 36 | 5.72 | ~5.13 |
| 37 | 6.77 | 5.27 |
| 38 | 5.79 | 5.41 |
| 39 | 7.17 | 4.95 |
| 40 | 8.20 | 6.39 |
| 41 | 5.24 | <5 |
| 42 | 7.22 | ~6.22 |
| 43 | 5.47 | <4.7 |
| 45 | 7.08 | ~6.13 |
| 47 | 6.16 | <5 |
| 48 | 6.84 | ~5.59 |
| 49 | 6.92 | ~5.29 |
| 50 | 7.35 | 5.82 |
| 51 | 7.67 | 6.00 |
| 52 | 7.99 | ~5.95 |
| 53 | 7.54 | 6.05 |
| 54 | 5.81 | <5 |
| 55 | 6.51 | 5.21 |
| 56 | 6.73 | ~5 |
| 57 | 7.95 | 6.80 |
| 58 | 6.14 | ~5.16 |
| 59 | 7.35 | 5.62 |
| 60 | 7.54 | 5.94 |
| 61 | 6.89 | <5 |
| 62 | 6.30 | <5 |
| 65 | 7.25 | 6.02 |
| 66 | 6.22 | 5.17 |
| 67 | 5.73 | ~5.21 |
| 68 | 6.64 | ~5.71 |
| 71b | 7.29 | 6.25 |
| 72 | 7.27 | ~5.45 |
| 73b | 6.68 | 5.61 |
| 74 | 7.43 | 6.43 |
| 74 | 7.45 | ~6.51 |
| 75 | 4.40 | <5 |
| 76 | 7.05 | ~5.65 |
| 76 | 7.49 | n.d. |
| 76 | 7.61 | ~5.97 |
| 78 | 5.55 | <5 |
| 79 | 4.67 | <5 |
| 80 | 5.48 | <5 |
| 81 | 6.45 | 5.09 |
| 82 | 6.90 | 5.63 |
| 83 | 4.35 | <5 |
| 84 | 4.11 | <5 |
| 86 | 6.38 | <5 |
| 87 | 5.62 | <5 |
| 88 | 4.33 | <5 |
| 89 | 5.56 | <5 |
| 90 | 4.15 | <5 |
| 91 | 5.91 | <5 |
| 92 | 6.90 | ~5.86 |
| 93 | 5.52 | ~5.61 |
| 94 | <5 | ~7.3 |
| 95b | <4 | ~7.34 |
| 95b | <5 | 7.05 |
| 95a | <5 | 6.94 |
| 95a | <5 | 6.95 |
| 96 | 6.20 | 7.69 |
| 99 | 6.76 | 6.69 |
| 101 | <5 | 7.06 |
| 101 | 6.92 | 7.08 |
| 103 | <5 | 6.46 |
| 104 | <5 | 5.80 |
| 105 | <5 | 5.18 |
| 106 | <5 | 4.71 |
| 107 | <5 | 6.90 |
| 108 | 7.59 | 6.69 |
| 109 | 5.65 | <5 |
| 110 | 5.91 | <5 |
| 111 | 6.76 | ~5.26 |
| 112 | 7.48 | ~5.75 |
| 113 | 8.09 | 6.84 |
| 114 | 7.47 | ~5.97 |
| 115 | 7.63 | ~5.78 |
| 116 | 6.82 | 5.53 |
| 117 | 7.47 | 6.30 |
| 118 | 7.45 | 6.29 |
| 119 | 6.81 | ~5.97 |
| 120 | 5.64 | <5 |
| 121 | 5.74 | <5 |
| 122 | 7.60 | 6.18 |
| 123 | 7.65 | 6.79 |
| 124 | 7.56 | 6.35 |
| 125 | 6.83 | ~6.06 |
| 126 | 7.76 | 7.35 |
| 127 | 7.21 | ~5.56 |
| 128 | 6.69 | <5 |
| 129 | <5 | <4.7 |
| 130 | <5 | <4.7 |
| 131 | <5 | <4.7 |
| 132 | 5.81 | <4.7 |
| 133 | 7.54 | ~5.98 |
| 134 | 6.70 | 5.05 |
| 135 | 6.21 | ~5.98 |
| 136 | 7.30 | ~6.58 |
| 137 | 5.94 | <5 |
| 139 | 5.49 | 5.78 |
| 140 | 6.53 | ~5.52 |
| 141 | <5 | <5 |
| 142 | 5.71 | <5 |
| 143 | 5.14 | 5.80 |
| 144 | 6.35 | ~6.03 |
| 145 | <5 | <5 |
| 146 | 5.40 | 5.33 |
| 147 | 6.73 | 6.22 |
| 148 | 5.90 | <5 |
| 150 | <5 | <5 |
| 151 | 5.26 | ~5.21 |
| 152 | 5.53 | 5.39 |
| 154 | <5 | <5 |
| 155 | 5.60 | <5 |
| 156 | 7.58 | 5.98 |
| 157 | <5 | <4.7 |
| 159 | <5 | <4.7 |
| 160 | 5.57 | <4.7 |
| 161 | 6.42 | 5.38 |
| 162 | 5.42 | <4.7 |
| 163 | 8.07 | 6.90 |
| 164 | <5 | ~5.19 |
| 165 | 6.06 | <5 |
| 166 | 8.73 | 7.41 |
| 166 | 8.80 | 7.92 |
| 166 | 9.20 | 7.87 |
| 167 | 8.50 | 7.52 |
| 167 | 8.80 | 7.68 |
| 168 | 7.58 | 6.69 |
| 168 | 7.76 | ~6.64 |
| 168 | 8.07 | ~6.7 |
| 169 | 6.56 | 6.22 |
| 170 | 7.37 | ~6.83 |
| 171 | 5.79 | ~5.39 |
| 172 | 6.51 | ~6.04 |
| 173 | 6.46 | 6.11 |
| 174 | 6.30 | ~5.64 |
| 175 | 6.23 | 5.85 |
| 176 | 5.95 | 5.22 |
| 177 | 6.72 | 6.34 |
| 178 | 7.29 | 6.92 |
| 179 | 7.50 | 7.02 |
| 180 | 7.99 | 6.57 |

-continued

| Co. No. | pIC$_{50}$ Assay 1 | pIC$_{50}$ Assay 2 |
|---|---|---|
| 181 | 7.71 | 7.18 |
| 182 | 7.81 | 6.30 |
| 183 | 7.65 | ~6.62 |
| 184 | 7.17 | ~5.83 |
| 185 | 7.60 | 6.23 |
| 186 | 7.87 | 6.21 |
| 187 | 7.20 | 5.77 |
| 188 | 6.43 | 6.15 |
| 189 | <5 | n.d. |
| 191 | 5.04 | <5 |
| 192 | 7.16 | 7.08 |
| 193 | 6.73 | 6.33 |
| 194 | 6.37 | ~5.25 |
| 195 | 6.27 | <5 |
| 196 | 5.94 | 5.49 |
| 197 | 5.19 | <5 |
| 198 | 6.36 | ~5.96 |
| 199 | 6.05 | 5.73 |
| 200 | 5.32 | <5 |
| 201 | 6.34 | ~4.99 |
| 202 | 5.70 | ~5.33 |
| 203 | 6.68 | 6.18 |
| 204 | 6.43 | 5.86 |
| 205 | 5.79 | 5.15 |
| 206 | 8.29 | 7.19 |
| 207 | 8.30 | 7.28 |
| 208 | 7.12 | 6.31 |
| 270 | 5.33 | <5 |
| 270 | 5.37 | <5 |
| 270 | 5.46 | <5 |

COMPOSITION EXAMPLES

"Active ingredient" (a.i.) as used throughout these examples relates to compounds of Formula (I), and pharmaceutically acceptable addition salts, and solvates thereof; in particular to any one of the exemplified compounds.

Typical examples of recipes for the formulation of the invention are as follows:

1. Tablets

Active ingredient 5 to 50 mg
Di-calcium phosphate 20 mg
Lactose 30 mg
Talcum 10 mg
Magnesium stearate 5 mg
Potato starch ad 200 mg 2. Suspension An aqueous suspension is prepared for oral administration so that each milliliter contains 1 to 5 mg of active ingredient, 50 mg of sodium carboxymethyl cellulose, mg of sodium benzoate, 500 mg of sorbitol and water ad 1 ml.

3. Injectable

A parenteral composition is prepared by stirring 1.5% (weight/volume) of active ingredient in 0.9% NaCl solution or in 10% by volume propylene glycol in water.

4. Ointment

Active ingredient 5 to 1000 mg
Stearyl alcohol 3 g
Lanoline 5 g
White petroleum 15 g
Water ad 100 g In this Example, active ingredient can be replaced with the same amount of any of the compounds according to the present invention, in particular by the same amount of any of the exemplified compounds.

The invention claimed is:

1. A compound of Formula (I)

wherein $R^1$ represents hydrogen or $CH_3$;

$R^2$ represents hydrogen;

$R^a$ represents hydrogen or —C(=O)—$C_{1-4}$alkyl;

$R^b$ represents hydrogen or —C(=O)—$C_{1-4}$alkyl;

Y represents —O—, —$CH_2$— or —$CF_2$—;

$R^{7a}$ represents hydrogen;

$R^{7b}$ represents hydrogen, or $C_{1-4}$alkyl optionally substituted with one or more halo atoms;

$X^1$ represents a covalent bond or —O—;

$X^2$ represents a covalent bond, —$CH_2$—, —$CF_2$—, —$CH_2CH_2$—, —$CF_2CH_2$—, or —$CH_2CF_2$—;

provided that $X^2$ represents a covalent bond, —$CH_2$— or —$CF_2$—, when $X^1$ represents —O—;

$X^3$ represents N or CH; or in case one of the dotted lines represents an additional bond, $X^3$ represents C;

$R^8$ and $R^{10}$ each independently are selected from the group consisting of hydrogen;

halo; and $C_{1-6}$alkyl optionally substituted with one or more halo atoms;

$R^9$ and $R^{10}$ each independently are selected from the group consisting of hydrogen;

halo; —$NH_2$; and $C_{1-6}$alkyl optionally substituted with one —$NR^{9a}R^{9b}$;

or $R^8$ and $R^9$ are linked together to form together with the common carbon atom to which they are attached a 4-, 5-, 6- or 7-membered saturated heterocyclyl, containing one or two N-atoms and optionally one oxygen atom; wherein said 4-, 5-, 6- or 7-membered saturated heterocyclyl is optionally substituted on one or more ring carbon atoms with one or more substituents each independently selected from the group consisting of halo, and $C_{1-6}$alkyl optionally substituted with one or more halo atoms;

and wherein said 4-, 5-, 6- or 7-membered saturated heterocyclyl is optionally substituted on one or two ring N-atoms with a substituent selected from the group consisting of $C_{1-6}$alkyl; $Het^{1a}$; $C_{3-6}$cycloalkyl; —$C_{1-6}$alkyl-C(=O)—$NR^{5a}R^{5b}$; $C_{1-4}$alkyl substituted with one or more halo atoms; and $C_{1-4}$alkyl substituted with one substituent selected from the group consisting of —$OC_{1-4}$alkyl, cyano, $C_{3-6}$cycloalkyl, $Ar^{1a}$, —O—$Ar^{1a}$, $Het^{2a}$ and —O-$Het^{2c}$;

or $R^{10}$ and $R^{11}$ are linked together to form together with the common carbon atom to which they are attached a 4-, 5-, 6- or 7-membered saturated heterocyclyl, containing one or two N-atoms and optionally one oxygen atom; wherein said 4-, 5-, 6- or 7-membered saturated heterocyclyl is optionally substituted on one or more ring carbon atoms with one or more substituents each independently selected from the group consisting of halo, and $C_{1-6}$alkyl optionally substituted with one or more halo atoms;

and wherein said 4-, 5-, 6- or 7-membered saturated heterocyclyl is optionally substituted on one or two ring N-atoms with a substituent selected from the group consisting of $C_{1-6}$alkyl; $Het^{1b}$; $C_{3-6}$cycloalkyl; $-C_{1-4}$alkyl-C(=O)-NR$^{6a}$R$^{6b}$; $C_{1-4}$alkyl substituted with one or more halo atoms; and $C_{1-4}$alkyl substituted with one substituent selected from the group consisting of $-OC_{1-4}$alkyl, cyano, $C_{3-6}$cycloalkyl, $Ar^{1b}$, $-O-Ar^{1b}$, $Het^{2b}$ and $-O-Het^{2d}$;

Z represents $-CH_2-$, $-C(=O)-$, or $-CH(C_{1-4}$alkyl)-; and in case $X^3$ represents C, Z can also represent =CH-;

the dotted lines attached to $X^3$ are optional bonds that may be present when $X^3$ represents a carbon atom, provided that maximum one of the dotted lines represents an optional bond;

in case one of the dotted lines attached to $X^3$ represents an additional bond, $X^3$ represents C, and (i) R$^{7a}$ is absent or (ii) R$^8$ is absent or (iii) Z represents =CH-;

R$^{9a}$ and R$^{9b}$ each independently are selected from the group consisting of hydrogen and $C_{1-4}$alkyl; or R$^{9a}$ and R$^{9b}$ are linked together to form together with the common nitrogen atom to which they are attached a 4-, 5-, 6- or 7-membered saturated heterocyclyl which optionally contains one oxygen atom;

R$^{5a}$ and R$^{5b}$ each independently are selected from the group consisting of hydrogen and $C_{1-4}$alkyl;

Het$^{1a}$ and Het$^{1b}$ are attached to the remainder of the molecule of Formula (I) through any available ring carbon atom;

Het$^{1a}$ and Het$^{1b}$ each independently represent a 4-, 5-, 6- or 7-membered saturated heterocyclyl, containing one or two heteroatoms each independently selected from O, S, S(=O)$_p$ and N;

Ar$^{1a}$ and Ar$^{1b}$ each independently represent phenyl optionally substituted with one or more substituents each independently selected from the group consisting of halo; cyano; and $C_{1-4}$alkyl optionally substituted with one or more halo atoms;

Het$^{2a}$ and Het$^{2b}$ each independently represent a 4-, 5-, 6- or 7-membered monocyclic aromatic or non-aromatic heterocyclyl containing at least one heteroatom each independently selected from O, S, S(=O)$_p$ and N; or a fused 8-, 9-, 10- or 11-membered bicyclic aromatic or non-aromatic heterocyclyl containing at least one heteroatom each independently selected from O, S, S(=O)$_p$ and N; said monocyclic heterocyclyl or said fused bicyclic heterocyclyl optionally being substituted with one or more substituents each independently selected from the group consisting of halo, cyano, and $C_{1-4}$alkyl optionally substituted with one or more halo atoms;

Het$^{2c}$ and Het$^{2d}$ are attached to the remainder of the molecule of Formula (I) through any available ring carbon atom;

Het$^{2c}$ and Het$^{2d}$ each independently represent a 4-, 5-, 6- or 7-membered monocyclic aromatic or non-aromatic heterocyclyl containing at least one heteroatom each independently selected from O, S, S(=O)$_p$ and N; or a fused 8-, 9-, 10- or 11-membered bicyclic aromatic or non-aromatic heterocyclyl containing at least one heteroatom each independently selected from O, S, S(=O)$_p$ and N; said monocyclic heterocyclyl or said fused bicyclic heterocyclyl optionally being substituted with one or more substituents each independently selected from the group consisting of halo, cyano, and $C_{1-4}$alkyl optionally substituted with one or more halo atoms;

R$^{6a}$ and R$^{6b}$ each independently are selected from the group consisting of hydrogen and $C_{1-4}$alkyl;

p represents 1 or 2;

Het represents a bicyclic aromatic heterocyclic ring system selected from the group consisting of (a-1), (a-2), (a-3) and (a-4):

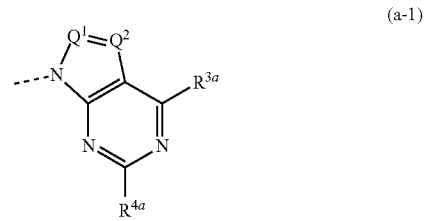

(a-1)

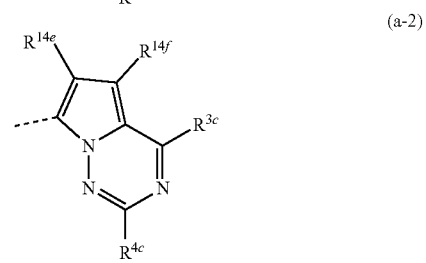

(a-2)

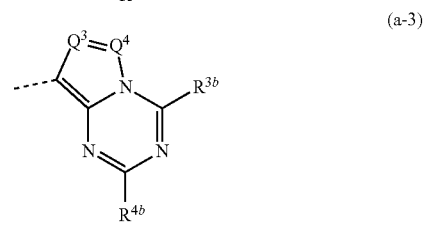

(a-3)

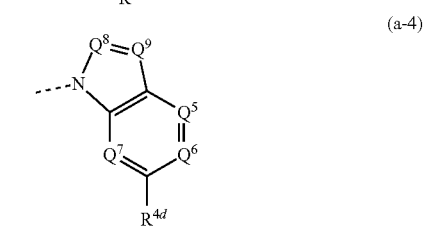

(a-4)

R$^{3a}$, R$^{3b}$, R$^{3c}$ and R$^{3d}$ each independently are selected from the group consisting of hydrogen, halo, $-NR^{12a}R^{12b}$, $C_{1-4}$alkyl, and $-O-C_{1-4}$alkyl;

R$^{12a}$ and R$^{12b}$ each independently are selected from the group consisting of hydrogen;

$C_{3-6}$cycloalkyl; $C_{1-4}$alkyl; and $C_{1-4}$alkyl substituted with one phenyl which is optionally substituted with one or more substituents selected from the group consisting of halo, cyano, $-OC_{1-4}$alkyl, $-OH$, and $C_{1-4}$alkyl optionally substituted with one or more halo atoms;

R$^{4a}$, R$^{4b}$, R$^{4c}$, R$^{4e}$ and R$^{4f}$ each independently are selected from the group consisting of hydrogen, halo, $-NR^{13a}R^{13b}$, and $C_{1-4}$alkyl;

R$^{13a}$ and R$^{3b}$ each independently are selected from the group consisting of hydrogen and $C_{1-4}$alkyl;

Q$^1$ represents N or CR$^{14a}$;
Q$^2$ represents N or CR$^{14b}$;
Q$^3$ represents N or CR$^{14c}$;

$Q^4$ represents N or $CR^{14d}$;
provided that maximum one of $Q^3$ and $Q^4$ represents N;
$Q^8$ represents N or $CR^{14g}$;
$Q^9$ represents N or $CR^{14h}$;
$Q^{10}$ represents N or $CR^{14i}$;
$Q^{11}$ represents N or $CR^{14j}$;
$Q^5$ represents $CR^{3d}$; $Q^6$ represents N; and $Q^7$ represents $CR^{4f}$; or
$Q^5$ represents $CR^{3d}$; $Q^6$ represents $CR^{4e}$; and $Q^7$ represents N; or
$Q^5$ represents N; $Q^6$ represents $CR^{4e}$; and $Q^7$ represents $CR^{4f}$; or
$Q^5$ represents N; $Q^6$ represents $CR^{4e}$; and $Q^7$ represents N; or
$Q^5$ represents N; $Q^6$ represents N; and $Q^7$ represents $CR^{4f}$; or
$Q^5$ represents N; $Q^6$ represents N; and $Q^7$ represents N;
$R^{14a}$, $R^{14b}$, $R^{14c}$, $R^{14d}$, $R^{14e}$, $R^{14f}$, $R^{14g}$, $R^{14h}$, $R^{14i}$, and $R^{14j}$ each independently are selected from the group consisting of hydrogen; halogen; $C_{1-4}$alkyl; $-NR^{15a}R^{15b}$; and $C_{1-4}$alkyl substituted with one or more halo atoms;
$R^{15a}$ and $R^{15b}$ each independently are selected from the group consisting of hydrogen and $C_{1-4}$alkyl;
provided that $R^{10}$ and $R^{11}$ may not be linked together when $R^8$ and $R^9$ are linked together;
and wherein at least one of $R^8$, $R^9$, $R^{10}$ and $R^{11}$ contains a nitrogen atom;
or a pharmaceutically acceptable addition salt or a solvate thereof.

2. The compound according to claim 1, wherein
Het represents a bicyclic aromatic heterocyclic ring system selected from the group consisting of (a-1), (a-2) and (a-3).

3. The compound according to claim 2, wherein
$R^1$ represents hydrogen;
Y represents —O— or —$CH_2$—;
$R^{7b}$ represents hydrogen, or $C_{1-4}$alkyl optionally substituted with one or more halo atoms;
$X^2$ represents a covalent bond, —$CH_2$—, —$CF_2CH_2$—, or —$CH_2CF_2$—;
provided that $X^2$ represents a covalent bond or —$CH_2$—, when $X^1$ represents —O—;
$X^3$ represents N; or in case one of the dotted lines represents an additional bond, $X^3$ represents C;
$R^8$ and $R^{10}$ each independently are selected from the group consisting of hydrogen;
halo; and $C_{1-6}$alkyl optionally substituted with one or more halo atoms;
$R^9$ and $R^{10}$ each independently are selected from the group consisting of hydrogen; halo; —$NH_2$; and $C_{1-6}$alkyl optionally substituted with one —$NR^{9a}R^{9b}$;
or $R^8$ and $R^9$ are linked together to form together with the common carbon atom to which they are attached a 4-, 5-, 6- or 7-membered saturated heterocyclyl, containing one or two N-atoms; wherein said 4-, 5-, 6- or 7-membered saturated heterocyclyl is optionally substituted on one or two ring N-atoms with a substituent selected from the group consisting of $C_{1-6}$alkyl; $Het^{1a}$; $C_{3-6}$cycloalkyl; —$C_{1-4}$alkyl-C(=O)—$NR^{5a}R^{5b}$; $C_{1-4}$alkyl substituted with one or more halo atoms; and $C_{1-4}$alkyl substituted with one substituent selected from the group consisting of —$OC_{1-4}$alkyl, cyano, $C_{3-6}$cycloalkyl, $Ar^{1a}$, —O—$Ar^{1a}$, and $Het^{2a}$;
or $R^{10}$ and $R^{11}$ are linked together to form together with the common carbon atom to which they are attached a 4-, 5-, 6- or 7-membered saturated heterocyclyl, containing one or two N-atoms and optionally one oxygen atom; wherein said 4-, 5-, 6- or 7-membered saturated heterocyclyl is optionally substituted on one or more ring carbon atoms with one or more halo substituents; and wherein said 4-, 5-, 6- or 7-membered saturated heterocyclyl is optionally substituted on one or two ring N-atoms with a substituent selected from the group consisting of $C_{1-6}$alkyl; and $C_{1-4}$alkyl substituted with one $Ar^{1b}$;
Z represents —$CH_2$— or —C(=O)—; and in case $X^3$ represents C, Z can also represent =CH—;
the dotted lines attached to $X^3$ are optional bonds that may be present when $X^3$ represents a carbon atom, provided that maximum one of the dotted lines represents an optional bond;
in case one of the dotted lines attached to $X^3$ represents an additional bond, $X^3$ represents C, and (i) $R^{7a}$ is absent or (ii) $R^8$ is absent or (iii) Z represents =CH—;
$Het^{1a}$ is attached to the remainder of the molecule of Formula (I) through any available ring carbon atom;
$Het^{1a}$ represents a 4-, 5-, 6- or 7-membered saturated heterocyclyl, containing one or two heteroatoms each independently selected from O;
$Ar^{1a}$ and $Ar^{1b}$ each independently represent phenyl optionally substituted with one or more halo substituents;
$Het^{2a}$ represents a 4-, 5-, 6- or 7-membered monocyclic aromatic or non-aromatic heterocyclyl containing at least one heteroatom each independently selected from O, S, S(=O)$_p$ and N; or a fused 8-, 9-, 10- or 11-membered bicyclic aromatic or non-aromatic heterocyclyl containing at least one heteroatom each independently selected from O, S, S(=O)$_p$ and N; said monocyclic heterocyclyl or said fused bicyclic heterocyclyl optionally being substituted with one or more $C_{1-4}$alkyl substituents;
$R^{3a}$, $R^{3b}$ and $R^{3c}$ each independently are selected from the group consisting of hydrogen, halo, and —$NR^{12a}R^{12b}$;
$R^{12a}$ and $R^{12b}$ each independently are selected from the group consisting of hydrogen;
$C_{3-6}$cycloalkyl; $C_{1-4}$alkyl; and $C_{1-4}$alkyl substituted with one phenyl which is optionally substituted with one or more halo substituents;
$R^{4a}$, $R^{4b}$ and $R^{4c}$ each independently are selected from the group consisting of hydrogen and $C_{1-4}$alkyl;
$Q^1$ represents $CR^{14a}$;
$Q^2$ represents N or $CR^{14b}$;
$Q^3$ represents $CR^{14c}$;
$Q^4$ represents N;
$R^{14a}$, $R^{14b}$, $R^{14c}$, $R^{14e}$ and $R^{14f}$ each independently are selected from the group consisting of hydrogen and halogen;
provided that $R^{10}$ and $R^{11}$ may not be linked together when $R^8$ and $R^9$ are linked together;
and wherein at least one of Re, $R^9$, $R^{10}$ and $R^{11}$ contains a nitrogen atom.

4. The compound according to claim 2, wherein
$R^1$ represents hydrogen;
Y represents —O— or —$CH_2$—;
$R^{7b}$ represents hydrogen;
$X^2$ represents a covalent bond or —$CH_2$—;
$X^3$ represents N; or in case one of the dotted lines represents an additional bond, $X^3$ represents C;
$R^8$ and $R^{10}$ each independently are selected from the group consisting of hydrogen and halo;
$R^9$ and $R^{11}$ each independently are selected from the group consisting of hydrogen and halo;

or $R^8$ and $R^9$ are linked together to form together with the common carbon atom to which they are attached a 4-, 5-, 6- or 7-membered saturated heterocyclyl, containing one N-atom; wherein said 4-, 5-, 6- or 7-membered saturated heterocyclyl is optionally substituted on one ring N-atom with $C_{1-6}$alkyl;

or $R^{10}$ and $R^{11}$ are linked together to form together with the common carbon atom to which they are attached a 4-, 5-, 6- or 7-membered saturated heterocyclyl, containing one N-atom; wherein said 4-, 5-, 6- or 7-membered saturated heterocyclyl is optionally substituted on one ring N-atom with $C_{1-6}$alkyl;

provided that $R^{10}$ and $R^{11}$, or $R^8$ and $R^9$ are linked together;

Z represents —$CH_2$—; and in case $X^3$ represents C, Z can also represent =CH—;

the dotted lines attached to $X^3$ are optional bonds that may be present when $X^3$ represents a carbon atom, provided that maximum one of the dotted lines represents an optional bond;

in case one of the dotted lines attached to $X^3$ represents an additional bond, $X^3$ represents C, and (i) $R^{7a}$ is absent or (ii) $R^8$ is absent or (iii) Z represents =CH—;

Het represents a bicyclic aromatic heterocyclic ring system selected from the group consisting of (a-1) and (a-2);

$R^{3a}$ and $R^{3c}$ represent $NH_2$;
$R^{4a}$ and $R^{4c}$ represent hydrogen;
$Q^1$ represents $CR^{14a}$;
$Q^2$ represents $CR^{14b}$;
$R^{14a}$, $R^{14b}$, $R^{14e}$ and $R^{14f}$ each independently are selected from the group consisting of hydrogen and halogen.

5. The compound according to claim 1, wherein $R^a$ and $R^b$ represent —C(=O)—$C_{1-4}$alkyl.

6. The compound according to claim 1, wherein $R^a$ and $R^b$ represent hydrogen.

7. The compound according to claim 1, wherein $R^1$ and $R^2$ represent hydrogen.

8. The compound according to claim 1, wherein $X^3$ represents C or CH.

9. The compound according to claim 1, wherein $X^3$ represents N.

10. The compound according to claim 1, wherein Het represents a bicyclic aromatic heterocyclic ring system of Formula (a-1).

11. The compound according to claim 10, wherein $R^{3a}$ represents —$NR^{12a}R^{12b}$; and $R^{12a}$ and $R^{12b}$ represent hydrogen.

12. The compound according to claim 1, wherein $R^{10}$ and $R^{11}$, or $R^8$ and $R^9$ are linked together.

13. A pharmaceutical composition comprising a pharmaceutically acceptable carrier and, as active ingredient, a therapeutically effective amount of a compound according to claim 1.

14. A method of treating a disease, syndrome, condition, or disorder selected from the group consisting of a blood disorder, metabolic disorders, autoimmune disorders, cancer, inflammatory diseases, cardiovascular diseases, neurodegenerative diseases, pancreatitis, multiorgan failure, kidney diseases, platelet aggregation, sperm motility, transplantation rejection, graft rejection, and lung injuries, comprising administering to a subject in need thereof a therapeutically effective amount of the compound of claim 1.

15. A method of treating a disease, syndrome, condition, or disorder, wherein said disease, syndrome, condition, or disorder is affected by the inhibition of PRMT5, comprising administering to a subject in need thereof a therapeutically effective amount of the compound of claim 1.

16. The method of claim 15 wherein said disease, syndrome, condition, or disorder is selected from the group consisting of a blood disorder, metabolic disorders, autoimmune disorders, cancer, inflammatory diseases, cardiovascular diseases, neurodegenerative diseases, pancreatitis, multiorgan failure, kidney diseases, platelet aggregation, sperm motility, transplantation rejection, graft rejection, and lung injuries.

17. The method of claim 16 wherein said disease, syndrome, condition, or disorder is cancer.

\* \* \* \* \*